United States Patent
Li et al.

(10) Patent No.: US 9,988,361 B2
(45) Date of Patent: Jun. 5, 2018

(54) ANTI-ENTEROVIRUS 71 THIADIAZOLIDINE DERIVATIVE

(71) Applicant: JIANGSU KANION PHARMACEUTICAL CO. LTD, Lianyungang, Jiangsu (CN)

(72) Inventors: Peng Li, Jiangsu (CN); Haiying He, Jiangsu (CN); Ning Li, Jiangsu (CN); Jian Li, Jiangsu (CN); Shuhui Chen, Jiangsu (CN); Bailing Yang, Jiangsu (CN); Wang Shen, Jiangsu (CN); Wei Xiao, Jiangsu (JP)

(73) Assignee: Jiangsu Kanion Pharmaceutical Co., Ltd., Jiangsu (CN)

( * ) Notice: Subject to any disclaimer, the term of this patent is extended or adjusted under 35 U.S.C. 154(b) by 0 days. days.

(21) Appl. No.: 15/307,710

(22) PCT Filed: Apr. 21, 2015

(86) PCT No.: PCT/CN2015/077043
§ 371 (c)(1),
(2) Date: Oct. 28, 2016

(87) PCT Pub. No.: WO2015/165340
PCT Pub. Date: Nov. 5, 2015

(65) Prior Publication Data
US 2017/0066732 A1    Mar. 9, 2017

(30) Foreign Application Priority Data

Apr. 28, 2014 (CN) .......................... 2014 1 0176161
Oct. 14, 2014 (CN) .......................... 2014 1 0543064
Apr. 16, 2015 (CN) .......................... 2015 1 0182757

(51) Int. Cl.
| C07D 285/10 | (2006.01) |
| C07D 417/04 | (2006.01) |
| C07D 498/04 | (2006.01) |
| C07D 417/14 | (2006.01) |

(52) U.S. Cl.
CPC ......... *C07D 285/10* (2013.01); *C07D 417/04* (2013.01); *C07D 417/14* (2013.01); *C07D 498/04* (2013.01)

(58) Field of Classification Search
CPC .. C07D 285/10; C07D 405/14; C07D 417/04; C07D 417/14; C07D 498/04; A61K 31/4439
USPC ...................................................... 546/274.4
See application file for complete search history.

(56) References Cited

U.S. PATENT DOCUMENTS

| 5,194,440 | A | * | 3/1993 | Pineiro | ............... | C07D 417/04 514/320 |
| 5,852,192 | A | * | 12/1998 | Himmelsbach | ...... | C07D 211/58 546/210 |
| 6,159,994 | A | * | 12/2000 | McDonald | .......... | C07D 417/06 514/362 |
| 2003/0087936 | A1 | * | 5/2003 | Shia | ..................... | C07D 233/32 514/341 |
| 2004/0116476 | A1 | * | 6/2004 | Chern | .................. | C07D 233/32 514/341 |
| 2005/0267164 | A1 | * | 12/2005 | Chern | .................. | C07D 401/04 514/341 |
| 2006/0167065 | A1 | * | 7/2006 | Wilde | .................... | A61K 31/17 514/365 |
| 2007/0049623 | A1 | * | 3/2007 | Chern | .................. | C07D 233/32 514/341 |
| 2011/0039842 | A1 | * | 2/2011 | Deadman | ............. | C07D 471/04 514/233.2 |

FOREIGN PATENT DOCUMENTS

| WO | WO 2010029048 | * | 3/2010 |
| WO | WO 2015118352 | * | 8/2015 |

OTHER PUBLICATIONS

Chen; J Biomed Sci 2008, 15, 291-300.*
Chern; Bioorganic & Medicinal Chemistry Letters 2004, 14, 5051-5056.*
Chern; Bioorganic & Medicinal Chemistry Letters 2005, 15, 4206-4211.*
De Colibus; Nature Structure and Molecular Biology 2014, 21, 282-288.*
Ke; J. Med. Chem., 2006, 49, 4517-4525.*
Ravichandran; European Journal of Medicinal Chemistry 2010, 45, 2791-2797.*
Shia; J. Med. Chem. 2002, 45, 1644-1655.*
Kang; Bioorganic & Medicinal Chemistry Letters 19 (2009) 6063-6068. (Year: 2009).*

* cited by examiner

*Primary Examiner* — Daniel R Carcanague
(74) *Attorney, Agent, or Firm* — Calfee, Halter & Griswold LLP

(57) ABSTRACT

Disclosed is a novel anti-enterovirus 71 (EV71) 1,2,5-thiadiazolidine-1,1-dioxide derivative or a pharmaceutically acceptable salt thereof, and specifically, a compound represented by formula (II) or a pharmaceutically acceptable salt thereof.

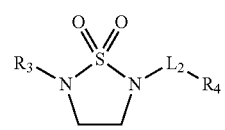

(II)

7 Claims, No Drawings

ANTI-ENTEROVIRUS 71 THIADIAZOLIDINE DERIVATIVE

CROSS-REFERENCE TO RELATED APPLICATIONS

The present application is the US national phase of PCT application PCT/CN2015/077043, filed on Apr. 21, 2015, which in turn claims priority to each of Chinese Patent Application No. 201410176161.6, filed on Apr. 28, 2014, Chinese Patent Application No. 201410543064.6, filed on Oct. 14, 2014, and Chinese Patent Application No. 201510182757.1, filed on Apr. 16, 2015 the entire contents of which are incorporated herein by reference in their entirety.

FIELD OF TECHNOLOGY

The present invention relates to a novel anti-interovirus 71 (EV71) 1,2,5-thiadiazolidine-1,1-dioxide derivative or a pharmaceutically-acceptable salt(s) thereof, specifically a compound(s) represented by Formula (II) or a pharmaceutically-acceptable salt(s) thereof.

BACKGROUND

The enterovirus 71 is a member of small RNA virus family and one of the most common etiologies of hand-foot-mouth disease. It can also cause various diseases related to nervous system such as herpes pharyngitis, aseptic meningitis, encephalitis, and poliomyelitis-like paralysis and is possibly accompanied with severe central nervous system complications or neuritic pulmonary edema.

The hand-foot-mouth disease features strong epidemic intensity, strong infectivity, and complex transmission route. There is no specific anti-enterovirus 71 medicine yet.

Although the existing technologies such as the patents of US20030087936, U.S. Pat. No. 6,706,739, US20040116476, US20050267164, and US20070049623 have disclosed a series of structures, for example the structures represented by Formula (B-I), it still needs in urgency to develop a novel compound with better activity that is more beneficial to make medicine.

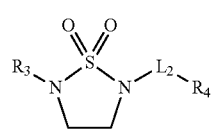
(B-1)

SUMMARY

The present invention provides a compound represented by Formula (II) or a pharmaceutically-acceptable salt(s) thereof;

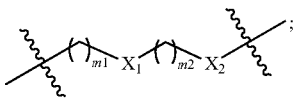
(II)

Wherein:

$R_3$ is any selected from 5-membered heterocycles, $C_{6\sim12}$ aryl groups, $C_{6\sim12}$ aralkyl groups, $C_{5\sim12}$ heteroaromatic rings and $C_{5\sim12}$ heteroaryl groups substituted with $R_{01}$;

$L_2$ is independently selected respectively from

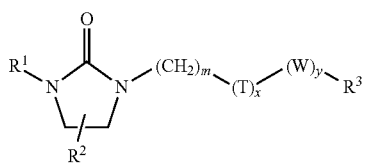

$m_1$ and $m_2$ are independently selected respectively from 0, 1, 2, 3, 4, 5 or 6;

$X_1$ and $X_2$ are independently selected respectively from single bond, —C($R_{d1}$)($R_{d2}$)—, —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, —C(=O)O—, —C(=O)—, —C(=S)—, —S(=O)— or —S(=O)$_2$;

$R_4$ is selected from 5~14-membered cyclic hydrocarbyl or heterocycloalkyl groups;

$R_{d1}$ and $R_{d2}$ are independently selected respectively from H, F, Cl, Br, I, CN, OH, SH, NH2, CHO, COOH or any selected from $C_{1-10}$ alkyl or heteroalkyl groups and $C_{3-10}$ cyclic hydrocarbyl or heterocycloalkyl groups substituted with $R_{01}$, $C_{1-10}$ alkyl or heteroalkyl groups substituted with $C_{3-10}$ hydrocarbyl or heterocycloalkyl groups;

$R_{01}$ is selected from F, Cl, Br, I, CN, OH, SH, NH$_2$, CHO, COOH and $R_{02}$;

$R_{02}$ is selected from $C_{1-10}$ alkal groups, $C_{1-10}$ alkylamino groups, N,N-di($C_{1-10}$ alkayl) amino groups, $C_{1-10}$ alkoxy groups, $C_{1-10}$ alkanoyl groups, $C_{1-10}$ alkoxycarbonyl groups, $C_{1-10}$ alkylsulfonyl groups, $C_{1-10}$ alkylsulfinyl groups, $C_{3-10}$ cycloalkyl groups, $C_{3-10}$ cycloalkylamino groups, $C_{3-10}$ heterocyclic alkyl amino groups, $C_{3-10}$ cycloalkoxy groups, $C_{3-10}$ cycloalkyl acyl groups, $C_{3-10}$ cycloalkoxy-carbonyl groups, $C_{3-10}$ cycloalkylsulfonyl groups and $C_{3-10}$ cycloalkylsulfinyl groups;

The "hetero" denotes a hetero atom or hetero atom radical selected from —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, =O, =S, —C(=O)O—, —C(=O)—, —C(=S)—, —S(=O)— and/or —S(=O)$_2$—;

$R_{d3-d7}$ is independently selected respectively from H and $R_{03}$;

$R_{03}$ is selected from $C_{1-10}$alkyl groups, $C_{1-10}$ alkanoyl groups, $C_{1-10}$ alkoxycarbonyl groups, $C_{1-10}$ alkylsulfonyl groups, $C_{1-10}$ alkylsulfinyl groups, $C_{3-10}$ cycloalkyl groups, $C_{3-10}$ cycloalkyl acyl groups, $C_{3-10}$ cycloalkoxy-carbonyl groups, $C_{3-10}$ cycloalkylsulfonyl groups and $C_{3-10}$ cycloalkylsulfinyl groups.

$R_{02}$ and $R_{03}$ are optionally substituted with $R_{001}$;

$R_{001}$ is selected from F, Cl, Br, I, CN, OH, N(CH$_3$)$_2$, NH(CH$_3$), NH$_2$, CHO, COOH, trifluoromethyl group, aminomethyl group, hydroxymethyl group, methyl group, methoxy group, formyl group, methoxycarbonyl group, methylsulfonyl group and methylsulfinyl group;

The number of $R_{01}$, $R_{001}$ and hetero atom or hetero atom radical is independently selected respectively from 0, 1, 2 or 3;

Optionally, $R_{d1}$ and $R_{d2}$ interconnects to a 3 or 4-membered carbocyclic or heterocyclic ring.

In some schemes according to the present invention, $R_3$ is any selected from substituted 5~6 membered aryl and substituted heteroaryl group.

In some schemes according to the present invention, $R_3$ is any selected from pyridyl group, phenyl group, furanyl group, pyrazolyl group, pyrrolyl group, thiazolyl group, pyridazinyl group, pyrimidinyl group, and thienyl group substituted with $R_{01}$ and the definition of $R_{01}$ is as above and the number of $R_{01}$ is selected from 0, 1, 2 or 3.

In some schemes according to the present invention, $R_{01}$ is selected from F, Cl, Br, I, CN, OH, SH, $NH_2$, CHO, COOH, Me,

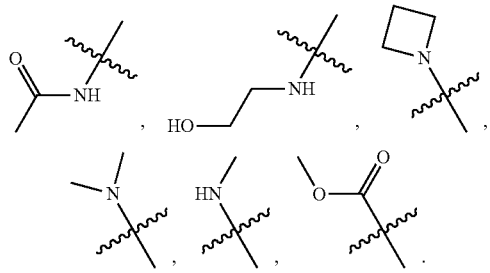

In some schemes according to the present invention, $R_3$ is selected from the following:

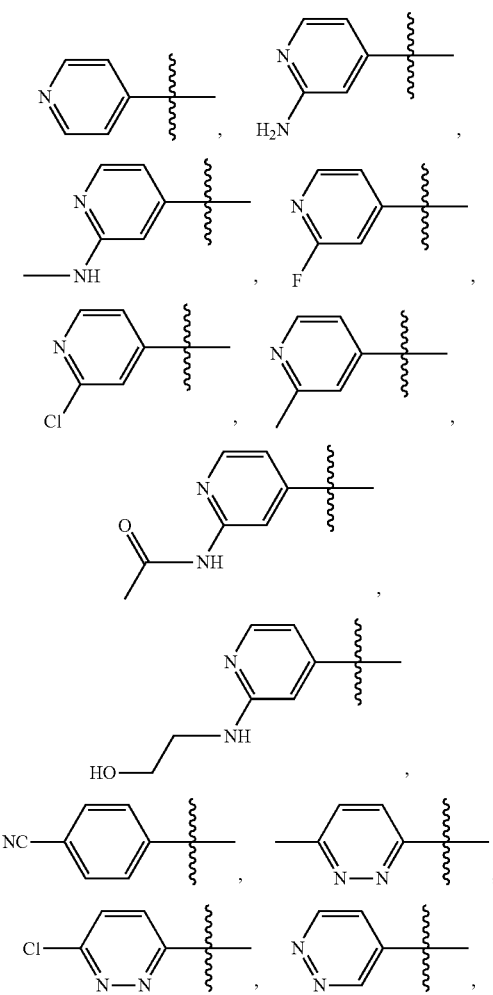

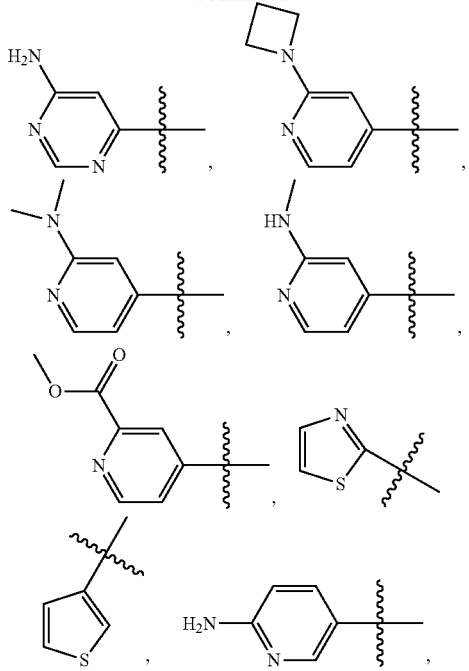

In some schemes according to the present invention, $L_2$ is selected from

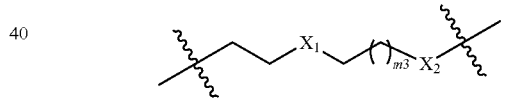

and $m_3$ is 0, 1 or 2 and other variables are defined as above.

In some schemes according to the present invention, $X_1$ and $X_2$ are independently selected respectively from single bond, —O—, —C(=O)—, —CH($CH_3$)—, —C($CH_3$)$_2$—, —$CF_2$—, —CH(F)—,

—CH(OH), —$CH_2$—, —NH— and —N($CH_3$)—.

In some schemes according to the present invention, $L_2$ is selected from the following:

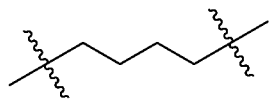

-continued

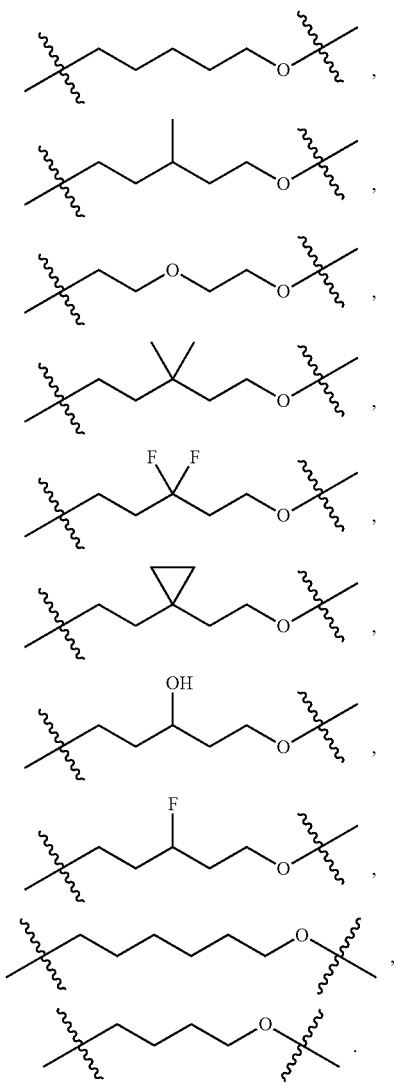

In some schemes according to the present invention, R$_4$ is selected from the following:

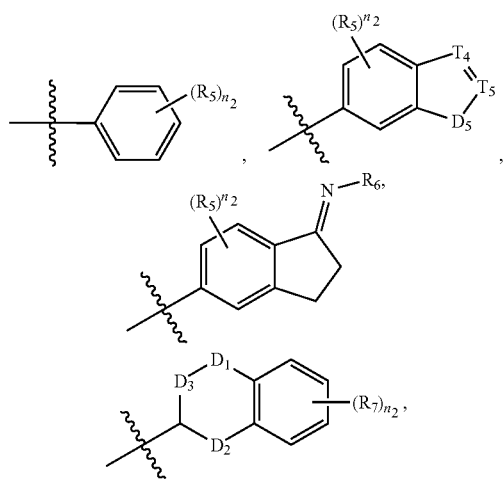

-continued

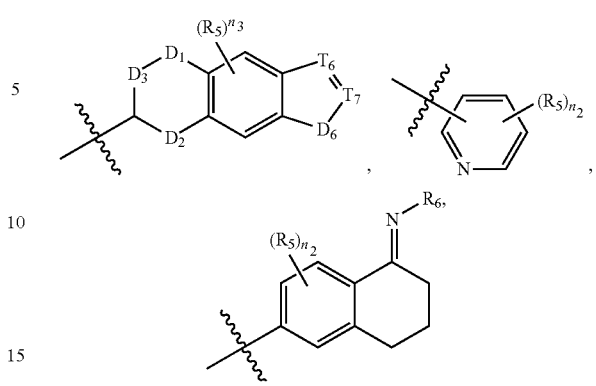

T$_{4-7}$ is independently selected respectively from N or C(R$_t$).

D$_{1-3}$, D$_5$ and D$_6$ are independently selected respectively from single bond, —C(R$_{d1}$)(R$_{d2}$)—, —C(=O)N(R$_{d3}$)—, —N(R$_{d4}$)—, —C(=NR$_{d5}$)—, —S(=O)$_2$N(R$_{d6}$)—, —S(=O)N(R$_{d7}$)—, —O—, —S—, —C(=O)O—, —C(=O)—, —C(=S)—, —S(=O)— or —S(=O)$_2$—, n$_2$ is selected from 0, 1, 2 or 3, n$_3$ is selected from 0, 1 or 2, R$_5$, R$_6$, R$_7$, R$_t$, R$_{d1}$ and R$_{d2}$ are independently selected respectively from H, F, Cl, Br, I, CN, OH, SH, NH$_2$, CHO and COOH or any selected from C$_{1-10}$ alkyl or heteroalkyl groups and C$_{3-10}$ cyclic hydrocarbyl or heterocycloalkyl groups substituted with R$_{01}$, C$_{1-10}$ alkyl or heteroalkyl groups substituted with C$_{3-10}$ hydrocarbyl or heterocycloalkyl groups. Other variables are defined as in claim 1.

In some schemes according to the present invention, R$_4$ is selected from the following:

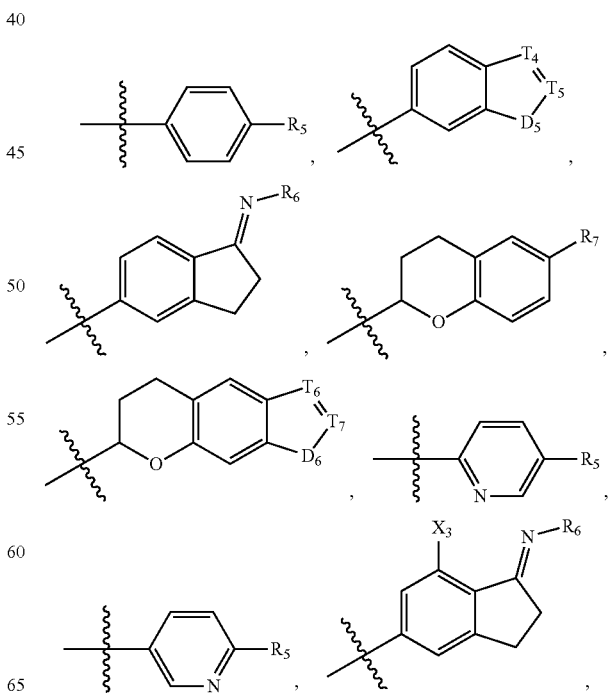

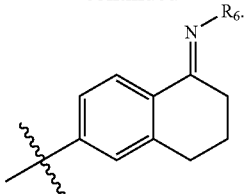

$X_3$ is selected from F, Cl, Br, I, CN, OH, SH, $NH_2$, CHO, COOH or any selected from $C_{1-10}$ alkyl or heteroalkyl groups and $C_{3-10}$ cyclic hydrocarbyl or heterocycloalkyl groups substituted with $R_{01}$, $C_{1-10}$ alkyl or heteroalkyl groups substituted with $C_{3-10}$ hydrocarbyl or heterocycloalkyl groups.

In some schemes according to the present invention, $R_{5-7}$ is independently selected respectively from the following:

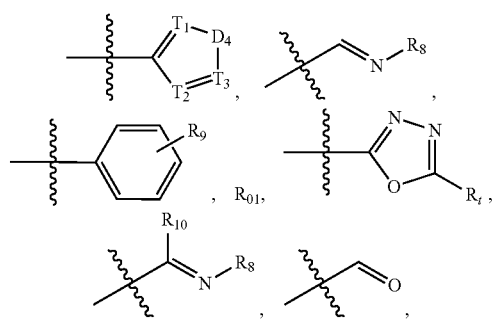

wherein:

$T_{1-3}$ is independently selected respectively from N or $C(R_t)$;

$D_4$ is selected from $-C(R_{d1})(R_{d2})-$, $-C(=O)N(R_{d3})-$, $-N(R_{d4})-$, $-C(=NR_{d5})-$, $-S(=O)_2N(R_{d6})-$, $-S(=O)N(R_{d7})-$, $-O-$, $-S-$, $-C(=O)O-$, $-C(=O)-$, $-C(=S)-$, $-S(=O)-$ or $-S(=O)_2-$;

$R_8$, $R_9$ and $R_t$ are independently selected respectively from H, F, Cl, Br, I, CN, OH, SH, $NH_2$, CHO, COOH or any selected from $C_{1-10}$ alkyl or heteroalkyl groups and $C_{3-10}$ cyclic hydrocarbyl or heterocycloalkyl groups substituted with $R_{01}$, $C_{1-10}$ alkyl or heteroalkyl groups substituted with $C_{3-10}$ hydrocarbyl or heterocycloalkyl groups;

$R_{10}$ is selected from F, Cl, Br, I, CN, OH, SH, $NH_2$, CHO, COOH or any selected from $C_{1-10}$ alkyl or heteroalkyl groups and $C_{3-10}$ cyclic hydrocarbyl or heterocycloalkyl groups substituted with $R_{01}$, $C_{1-10}$ alkyl or heteroalkyl groups substituted with $C_{3-10}$ hydrocarbyl or heterocycloalkyl groups.

In some schemes according to the present invention, $R_{5-9}$, $R_{01}$ and $R_t$ are independently selected respectively from the following:

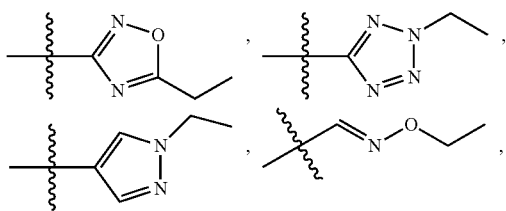

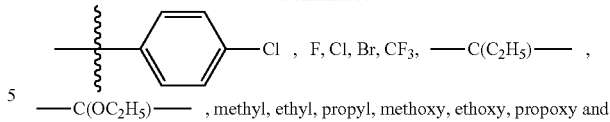, methyl, ethyl, propyl, methoxy, ethoxy, propoxy and

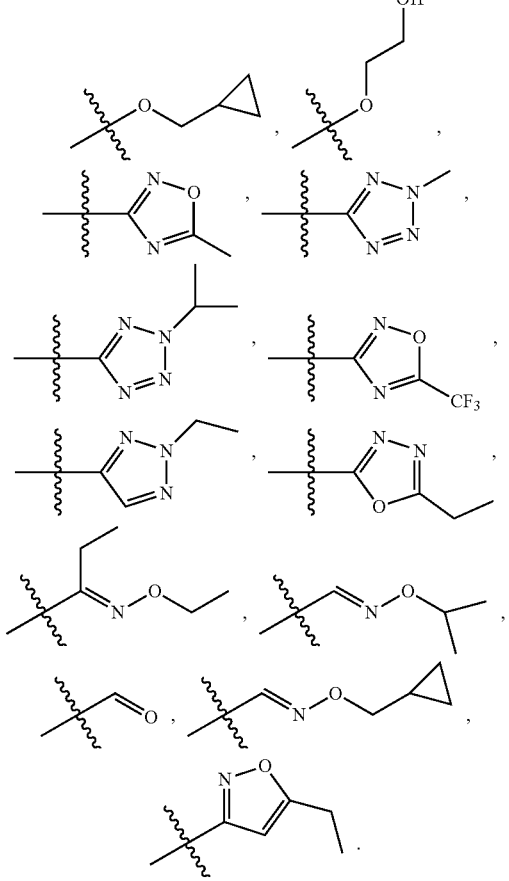

In some schemes according to the present invention, $R_4$ is selected from the following:

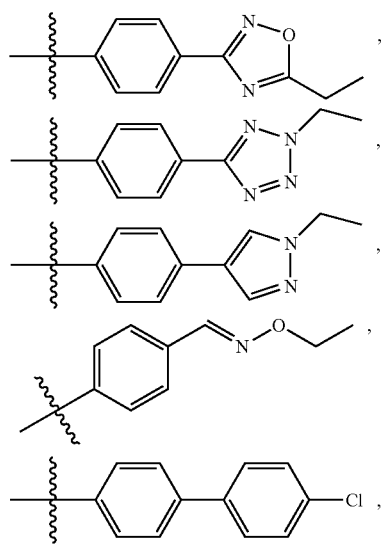

-continued
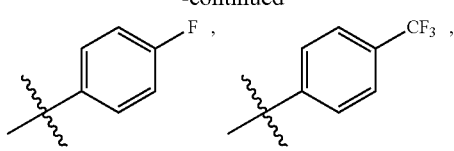
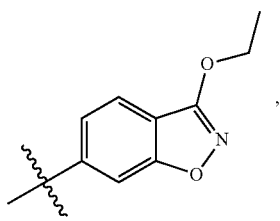
-continued
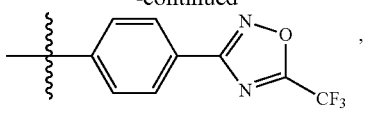
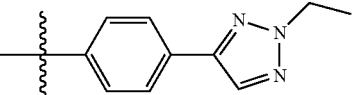
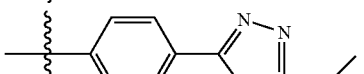
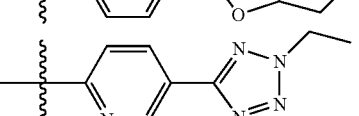
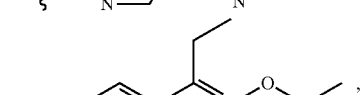
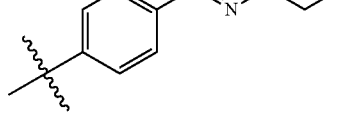
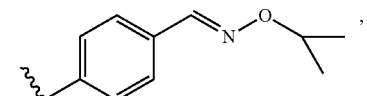
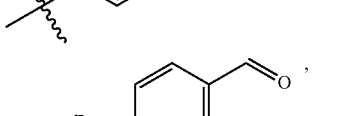
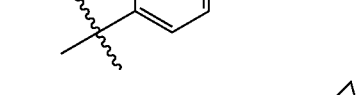
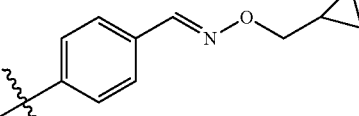
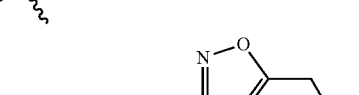
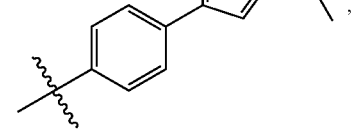
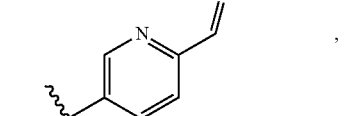
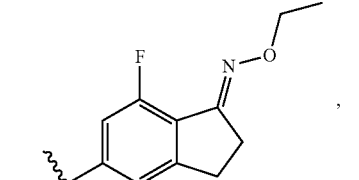

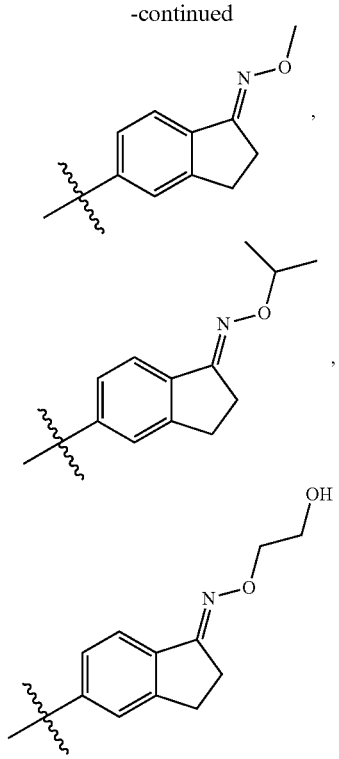
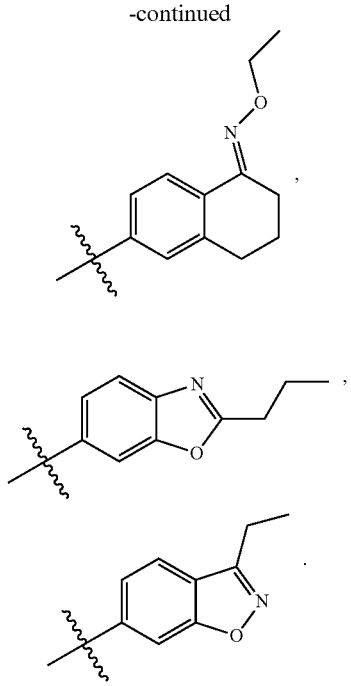
Specifically, the present invention selects it from the following:
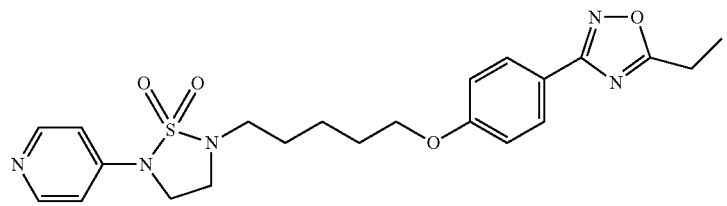
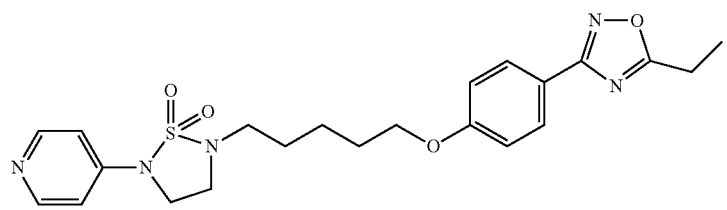
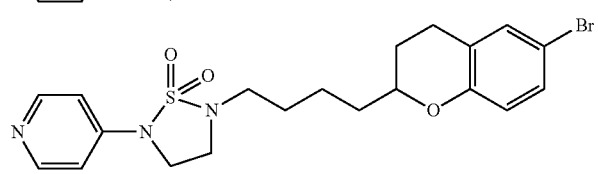
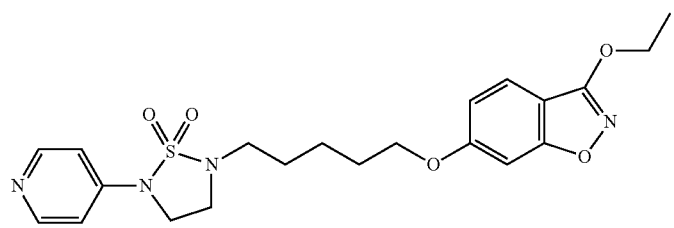

-continued
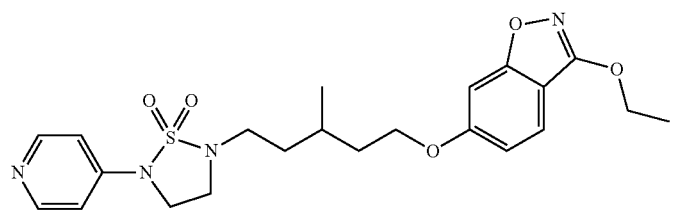
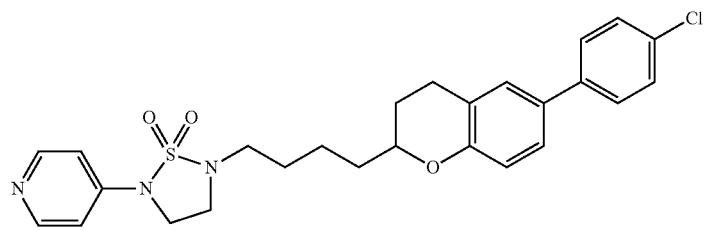
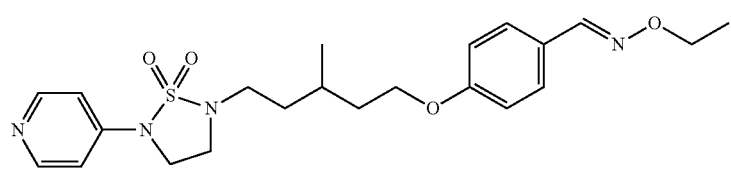
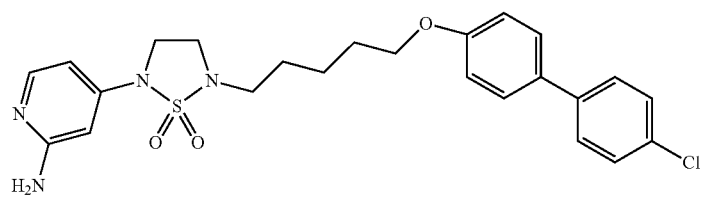
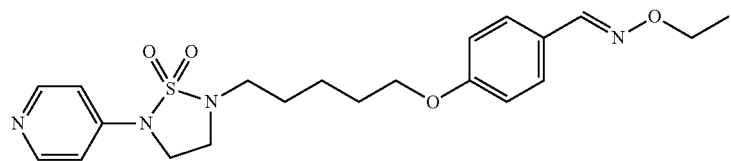
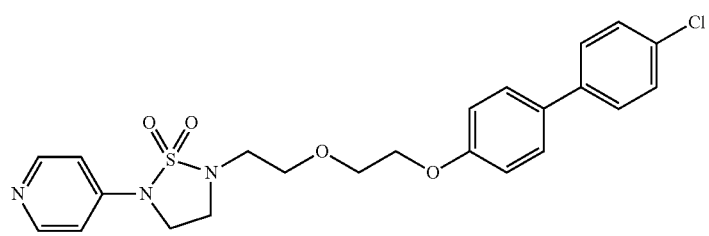
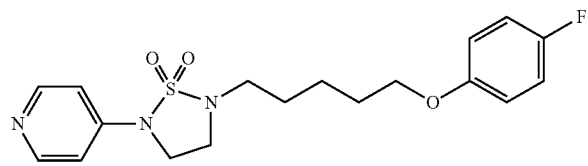
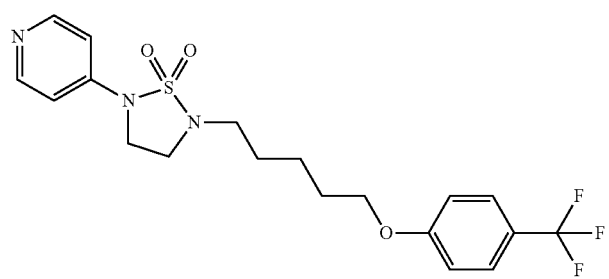

-continued
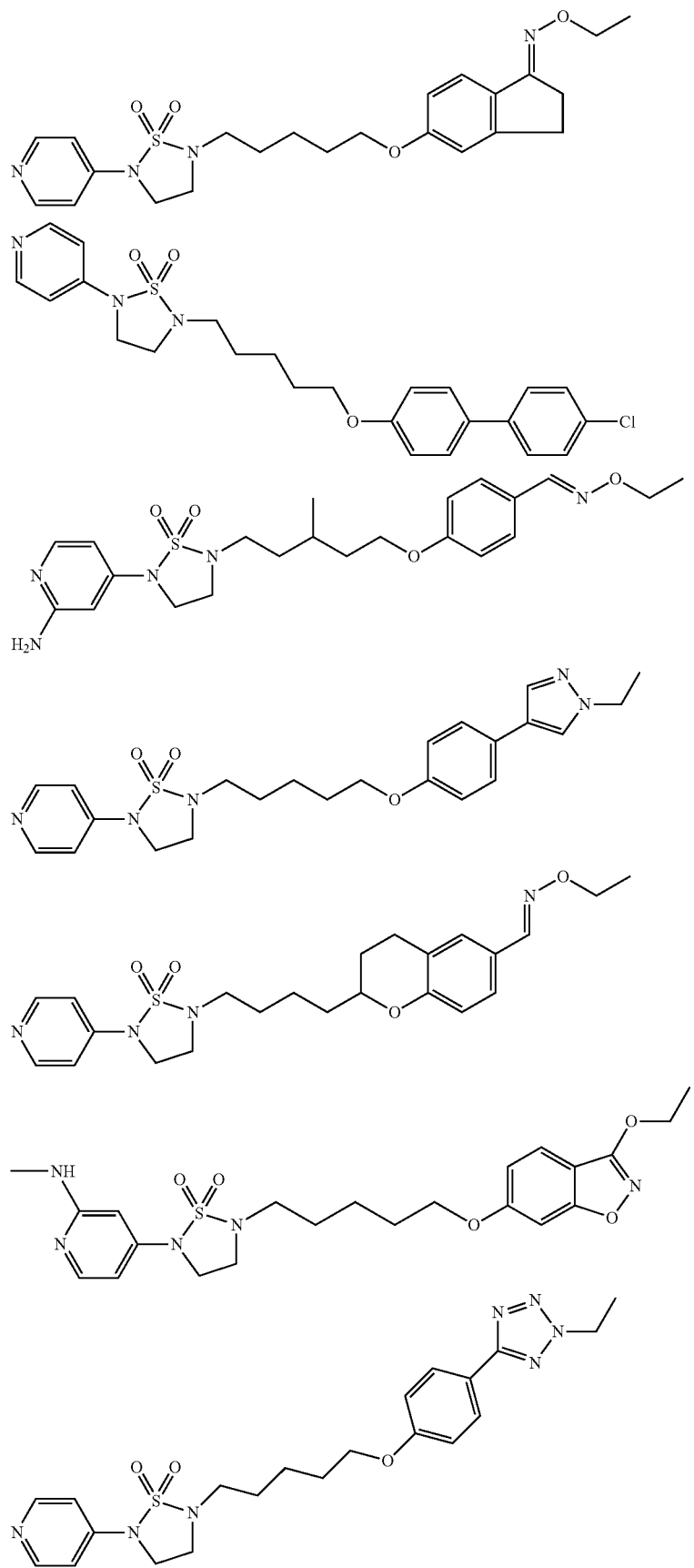

-continued
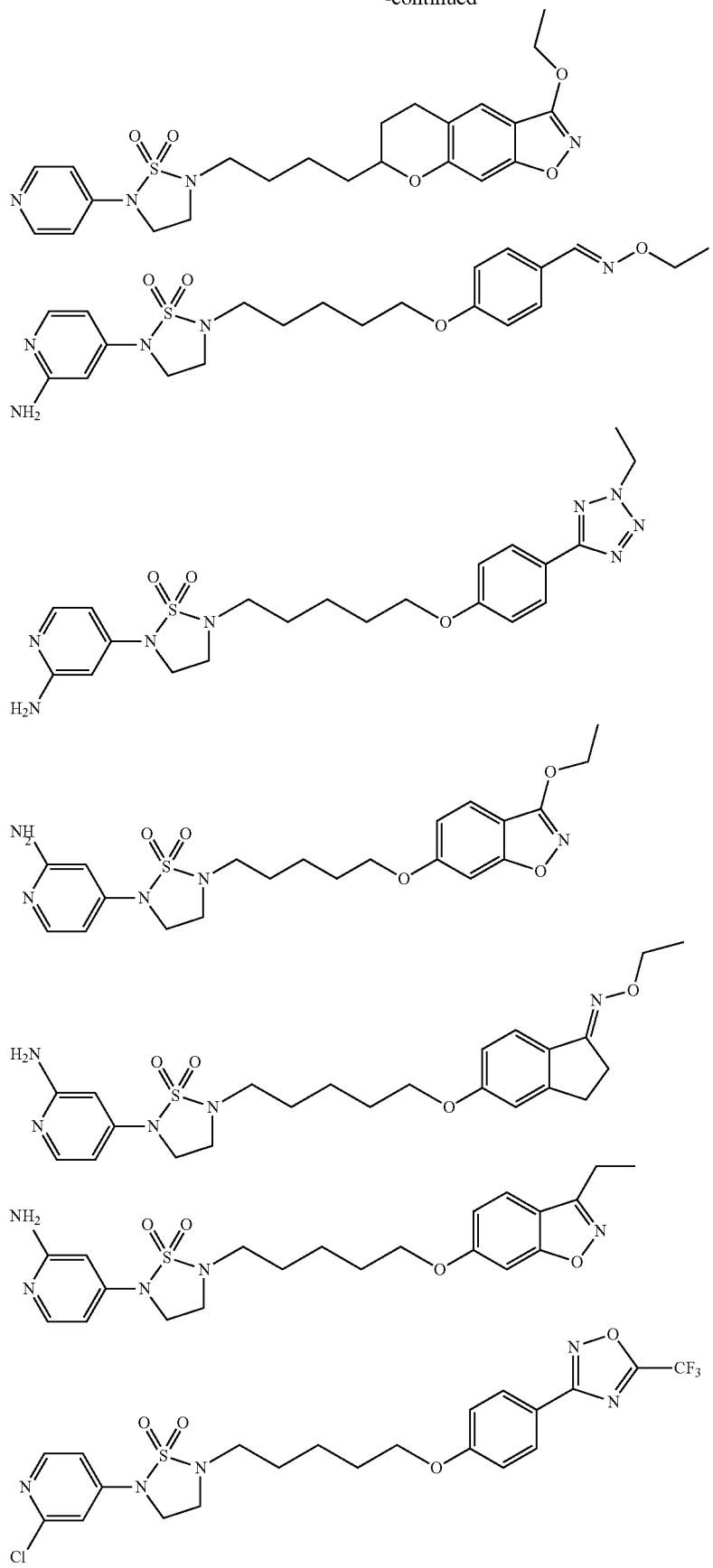

-continued
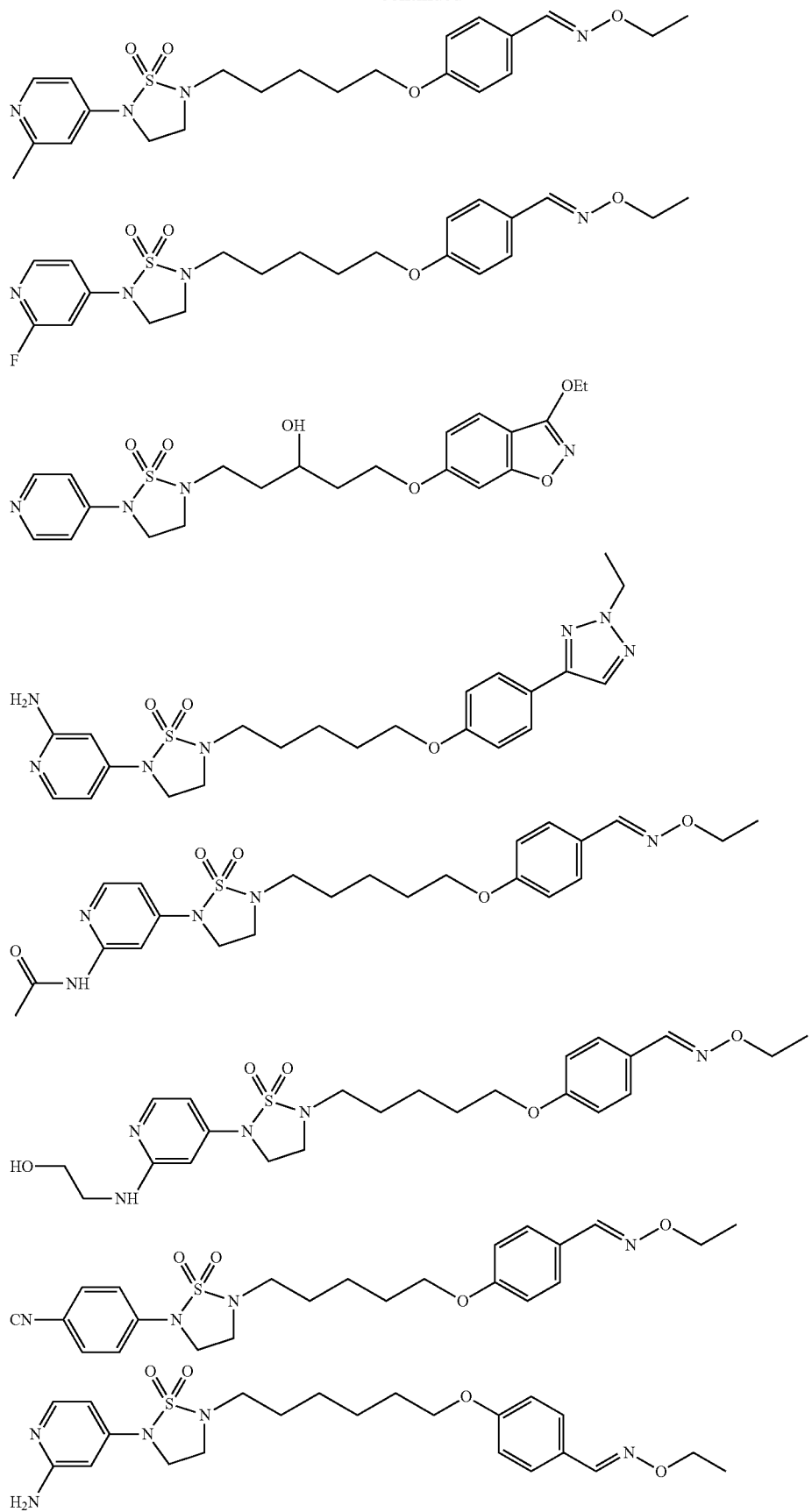

-continued
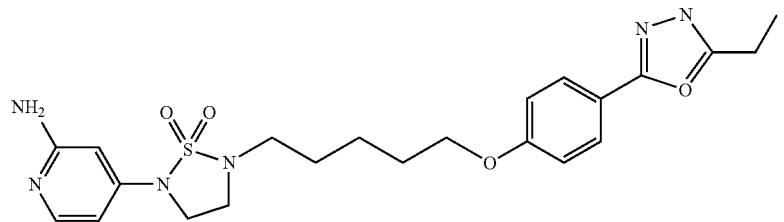
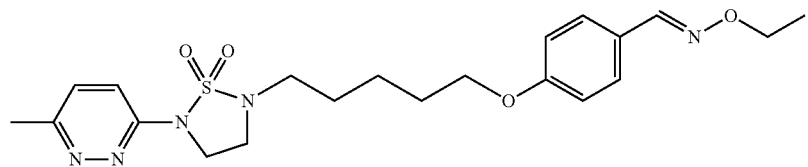
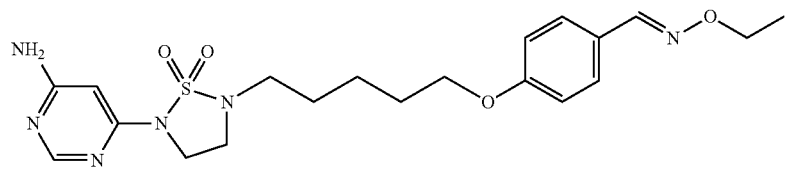
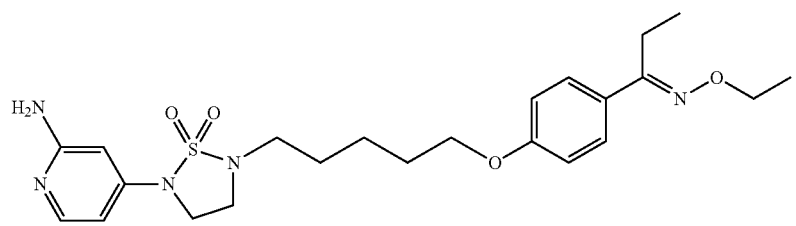
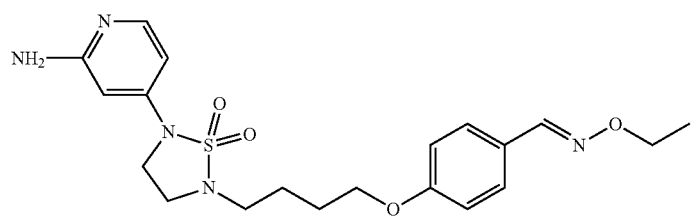
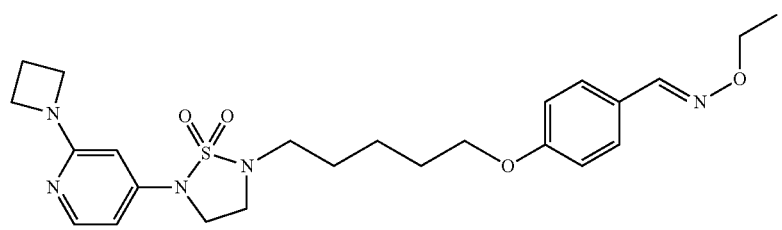
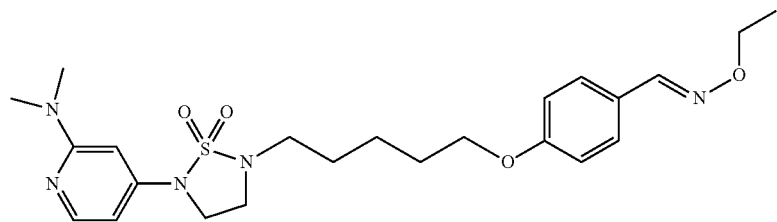

-continued
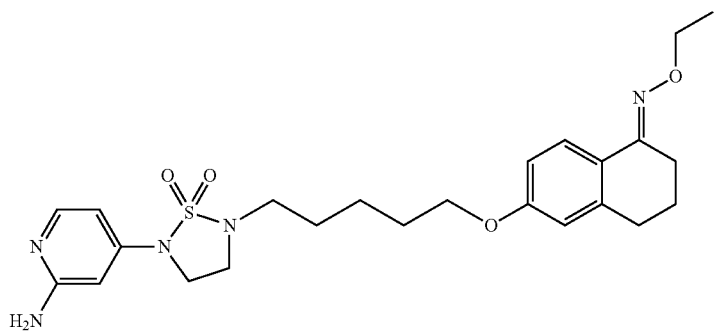
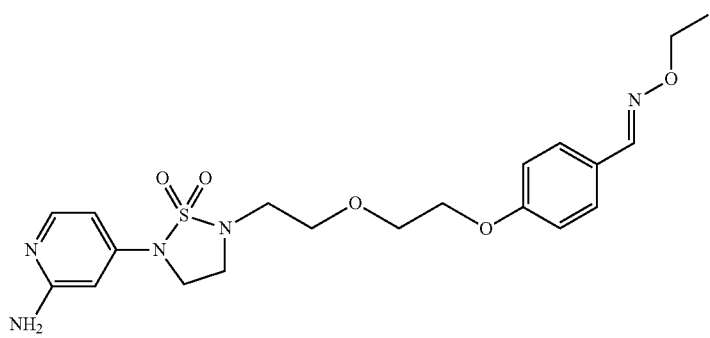
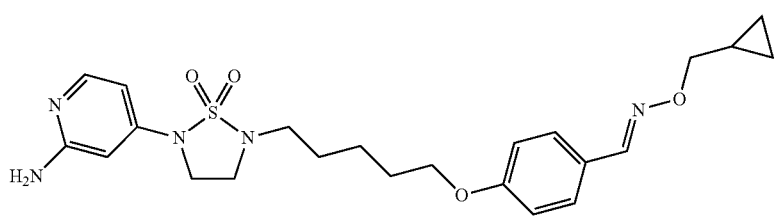
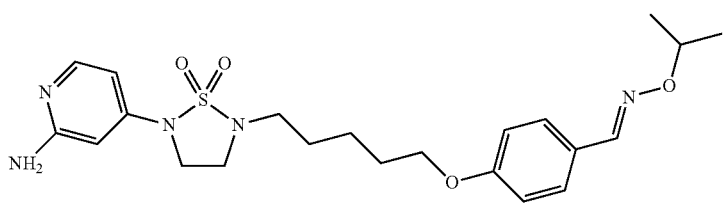
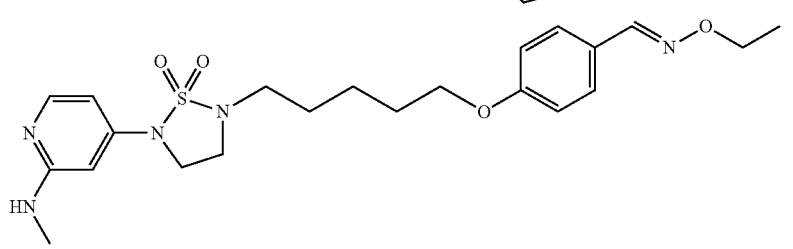
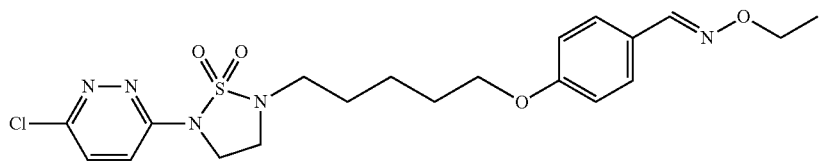
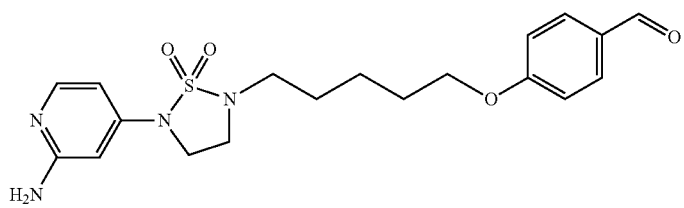

-continued
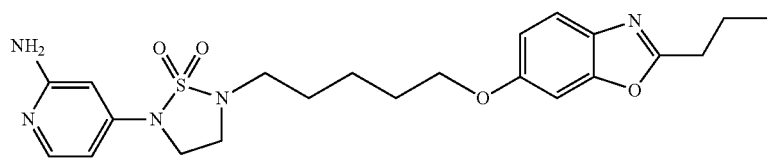
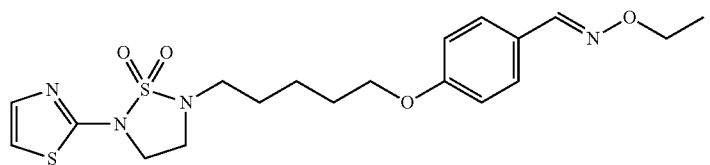
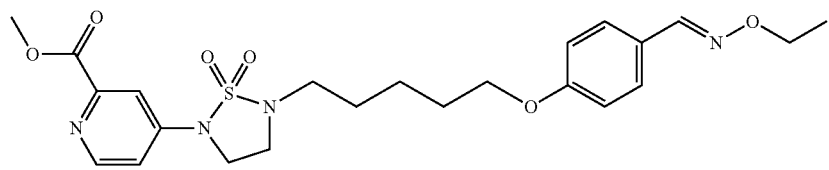
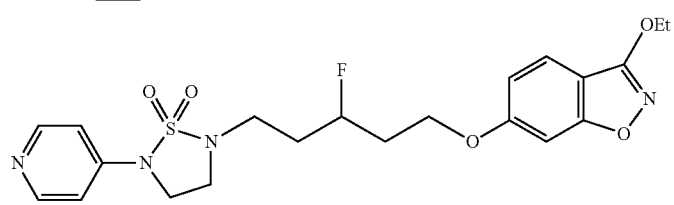
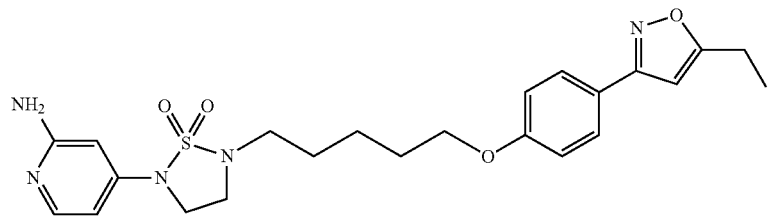
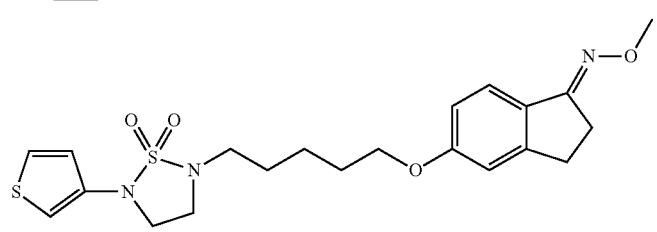
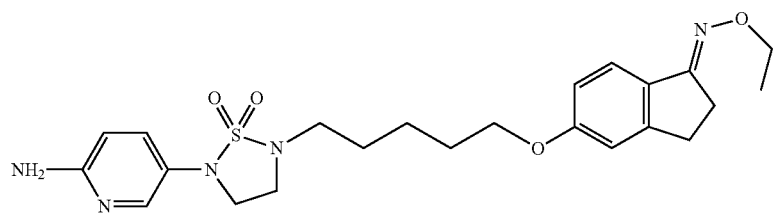
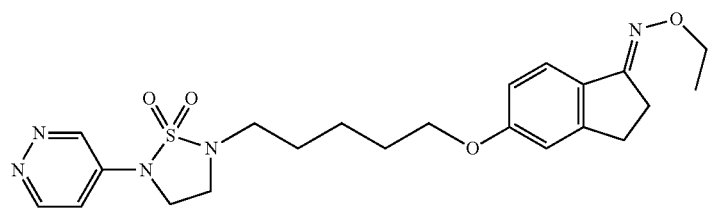

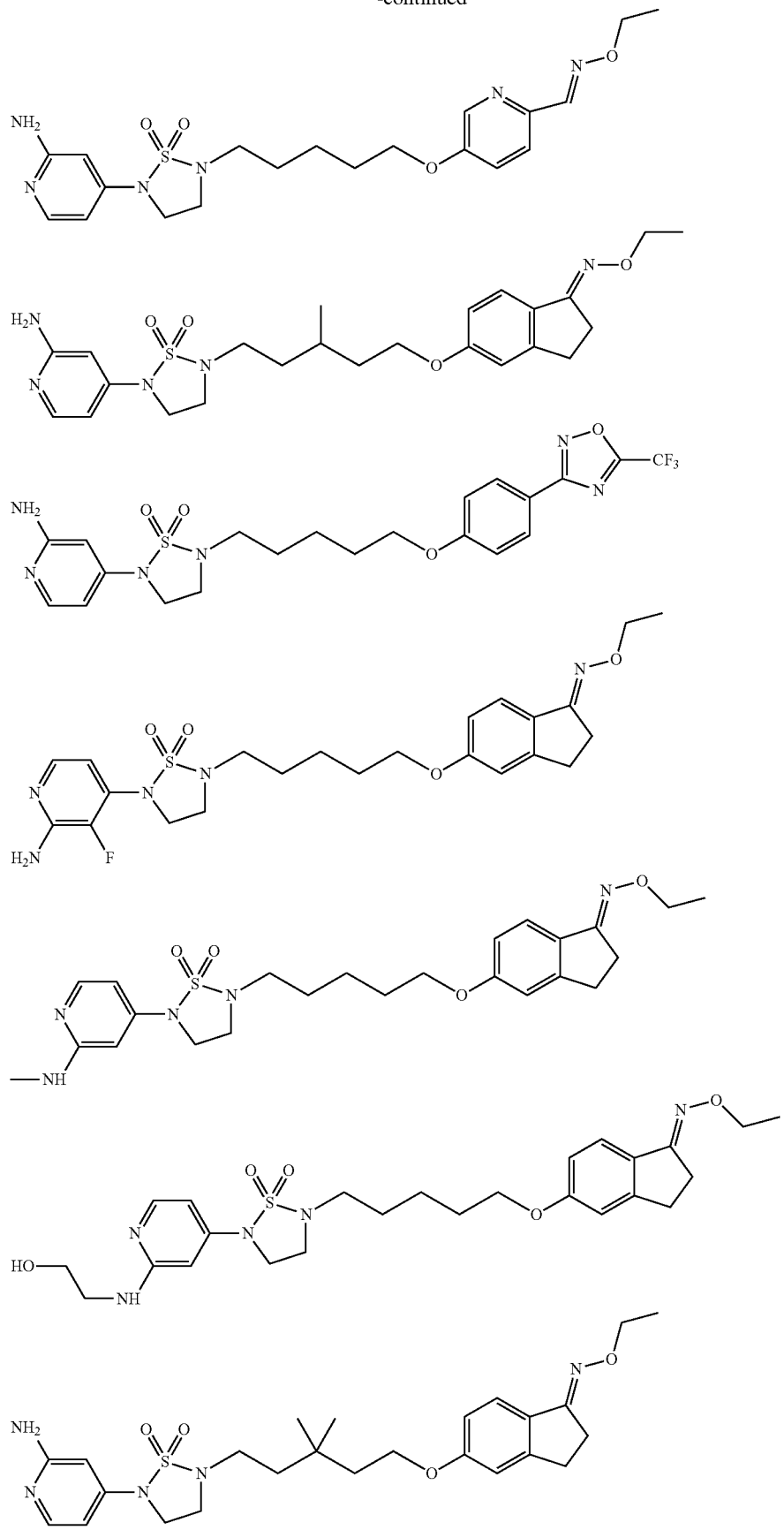

-continued
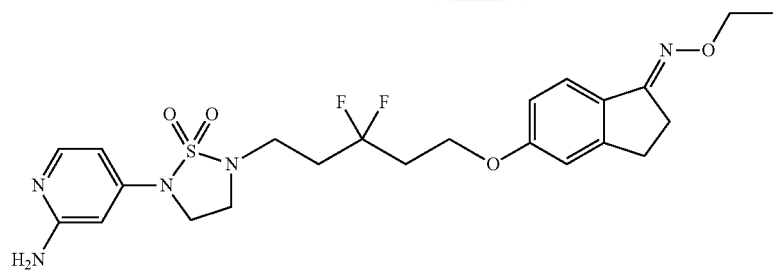
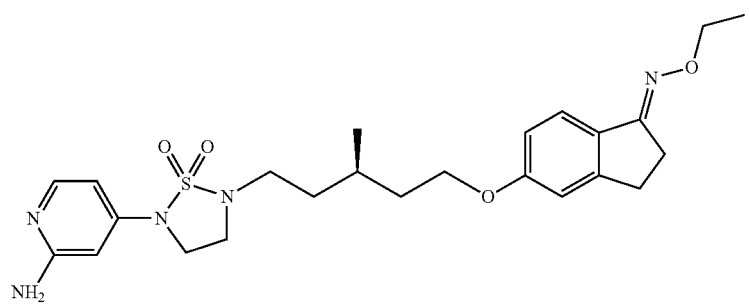
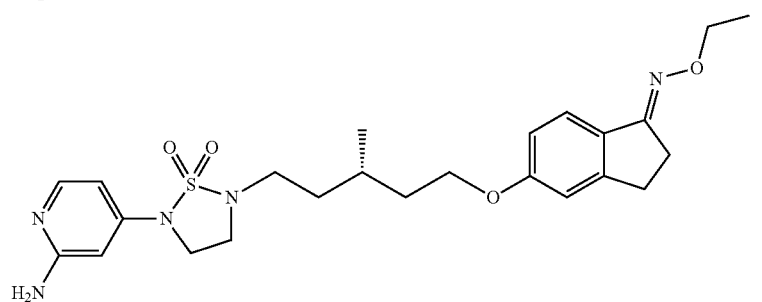
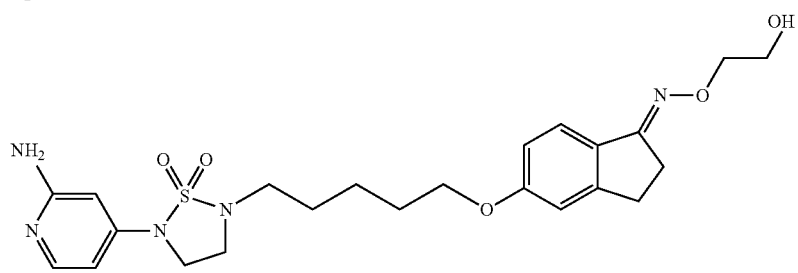
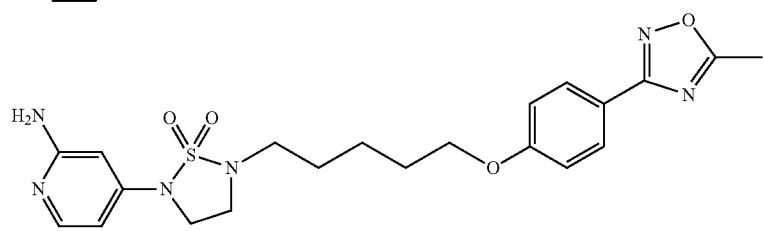
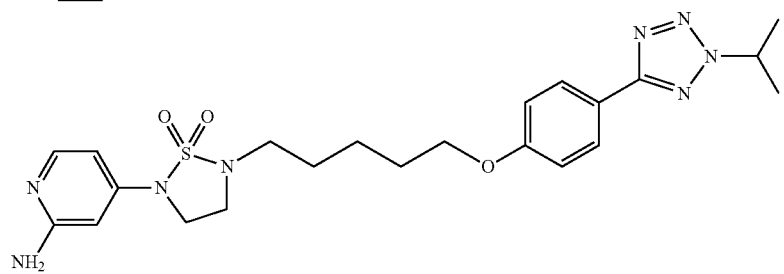

-continued
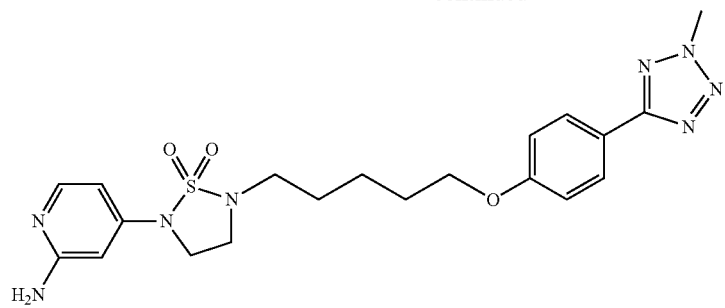
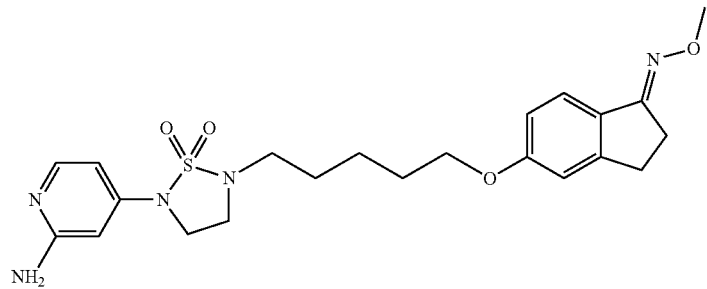
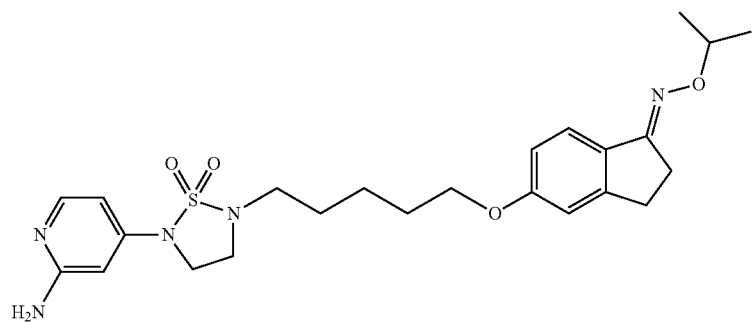
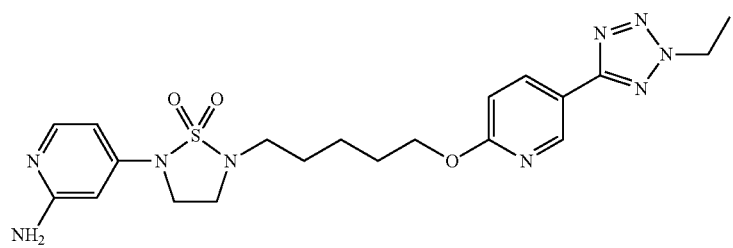
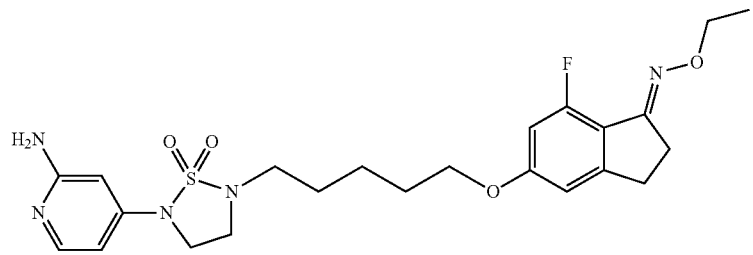
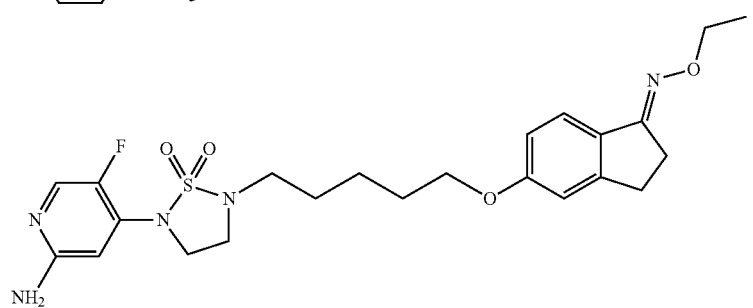

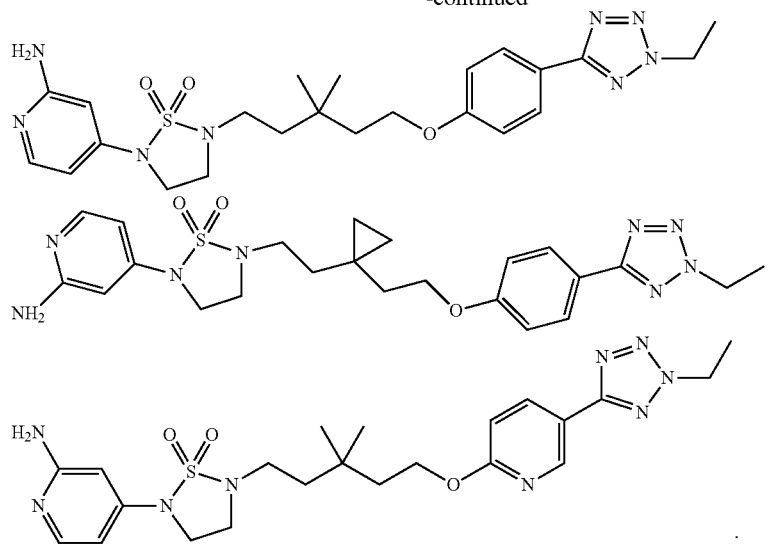

Relevant Definitions:

Unless indicated otherwise, the following terms and phrases used here are intended to have the following meanings. Any specific term or phrase without specific definition should not be regarded as uncertain or indistinctive but should be understood as its common meaning. Any trade name appearing in the present invention denotes the corresponding product it refers to or its active ingredient.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

$C_{1-12}$ alkyl or heteroalkyl group, $C_{3-12}$ cyclic or heterocycloalkyl group and $C_{1-12}$ alkyl or heteroalkyl group substituted with $C_{3-12}$ cycloalkyl or heterocycloalkyl group include but not limited to:

$C_{1-12}$ alkal groups, $C_{1-12}$ alkylamino groups, N,N-di($C_{1-12}$ alkayl) amino groups, $C_{1-12}$ alkoxy groups, $C_{1-12}$ alkanoyl groups, $C_{1-12}$ alkoxycarbonyl groups, $C_{1-12}$ alkylsulfonyl groups, $C_{1-12}$ alkylsulfinyl groups, $C_{3-12}$ cycloalkyl groups, $C_{3-12}$ cycloalkylamino groups, $C_{3-12}$ heterocyclic alkyl amino groups, $C_{3-12}$ cycloalkoxy groups, $C_{3-12}$ cycloalkyl acyl groups, $C_{3-12}$ cycloalkoxy-carbonyl groups, $C_{3-12}$ cycloalkylsulfonyl groups and $C_{3-12}$ cycloalkylsulfinyl groups, 5~12 membered aryl or heteroaryl groups and 5~12 membered aralkyl or heteroaralkyl groups;

methyl group, ethyl group, n-propyl group, isopropyl group, —CH$_2$C (CH$_3$) (CH$_3$) (OH), cyclopropyl group, cyclobutyl group, propyl methylene, cyclopropylmethyl group, benzyl group, trifluoromethyl group, aminomethyl group, hydroxymethyl group, methoxy group, formyl group, methoxycarbonyl group, methylsulfonyl group, methylsulfinyl group, ethoxy group, acetyl group, ethanesulfonyl group, ethoxycarbonyl group, dimethyl amino group, diethylamino group, dimethylamino-carbonyl group and diethyl-aminocarbonyl group; N(CH$_3$)$_2$, NH(CH$_3$), —CH$_2$CF$_3$, —CH2CH$_2$CF$_3$, —CH$_2$CH$_2$F, —CH$_2$CH$_2$S(=O)$_2$CH$_3$, —CH$_2$CH$_2$CN,

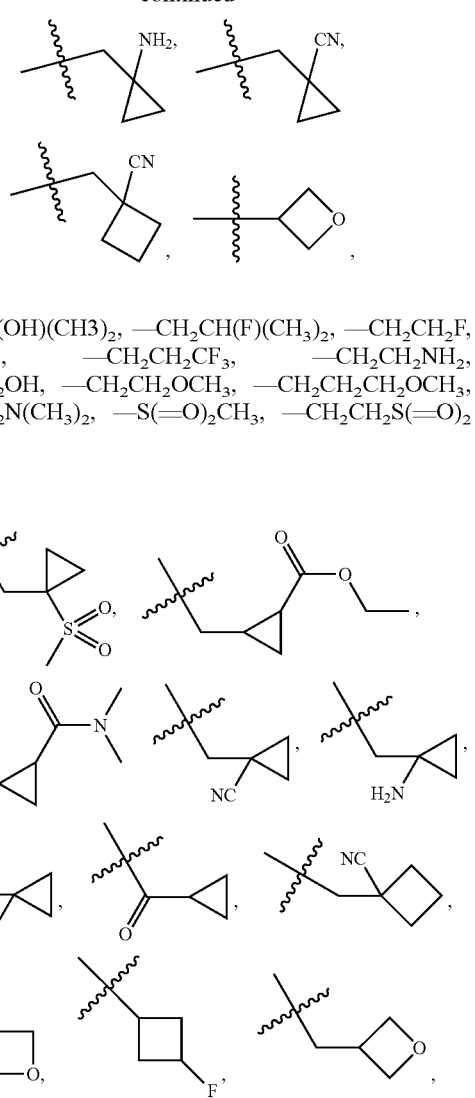

—CH$_2$CH(OH)(CH3)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$,

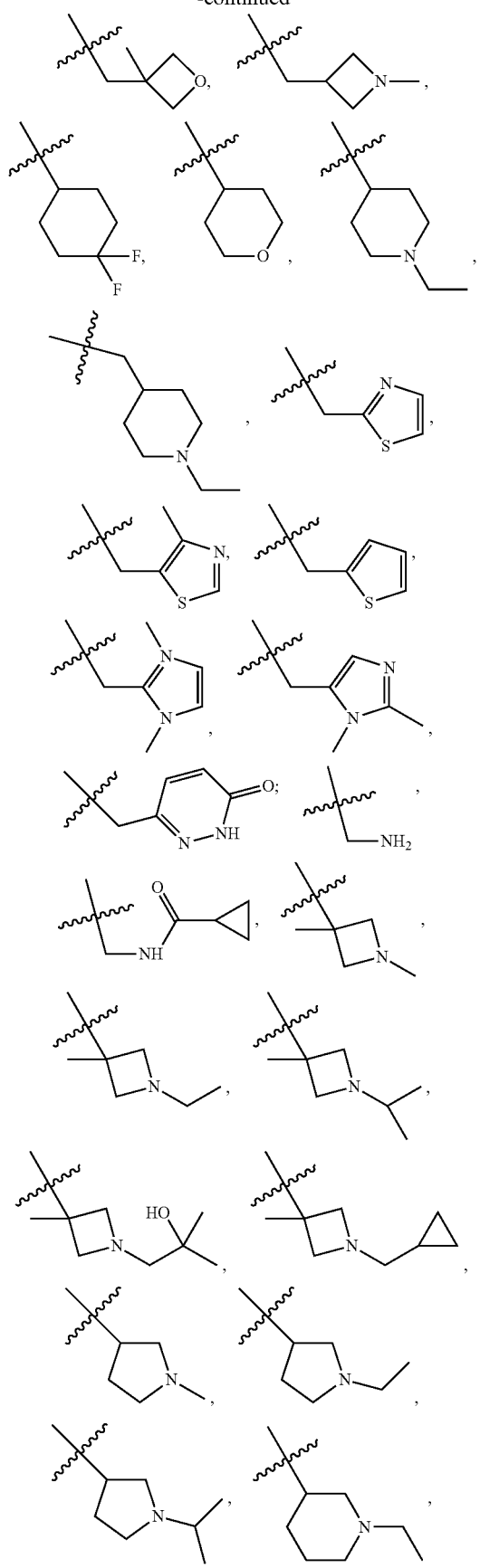
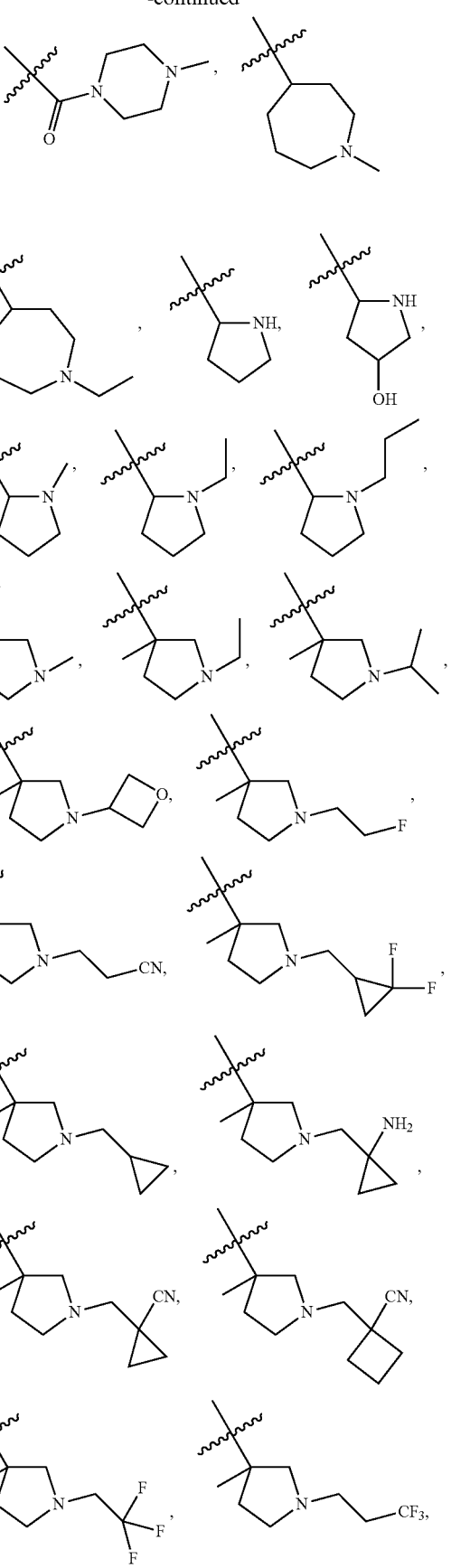

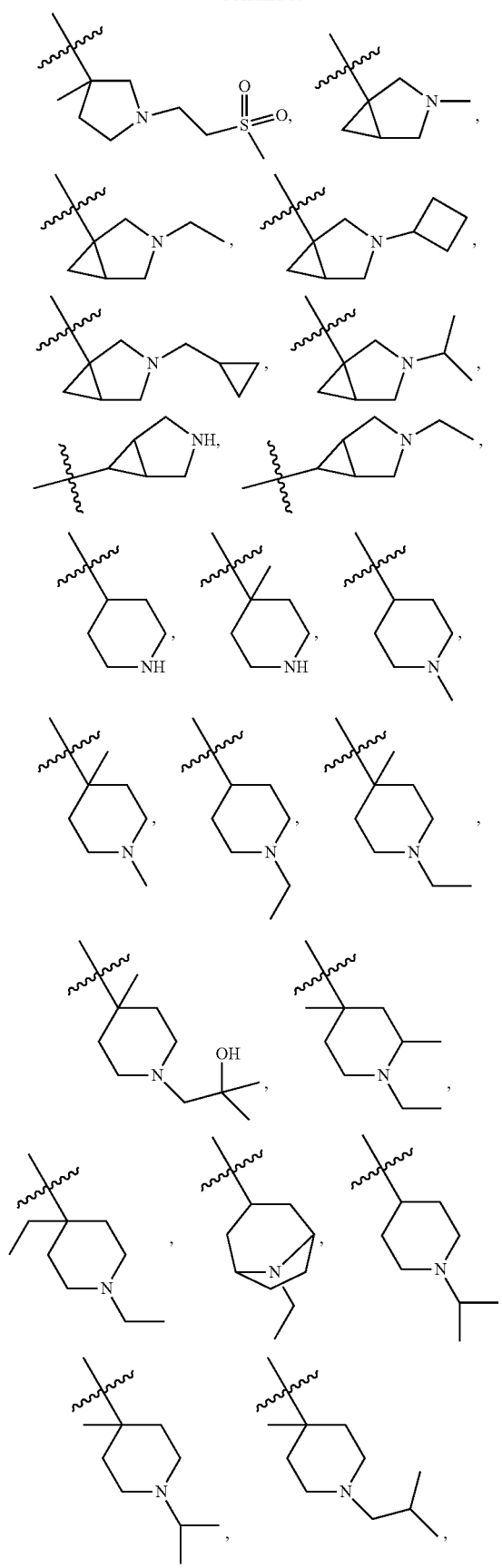
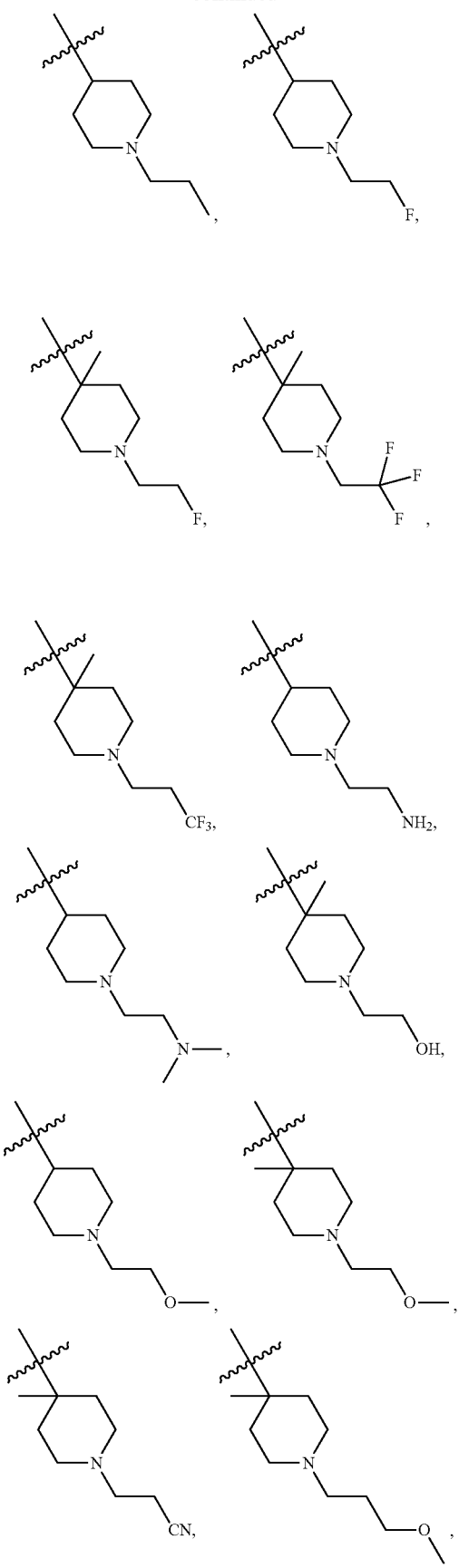

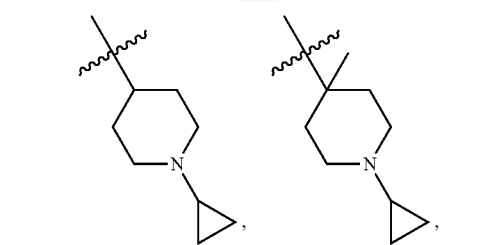
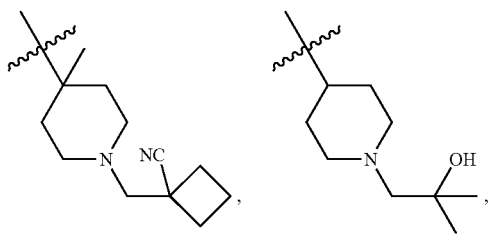
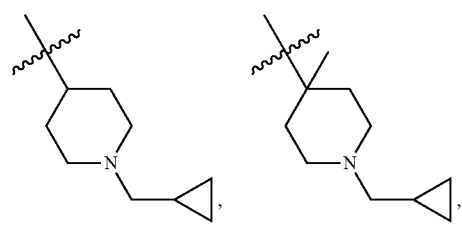
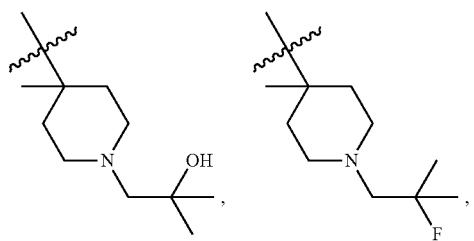
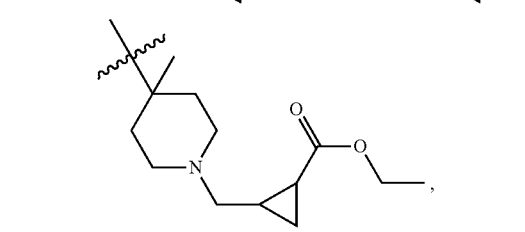
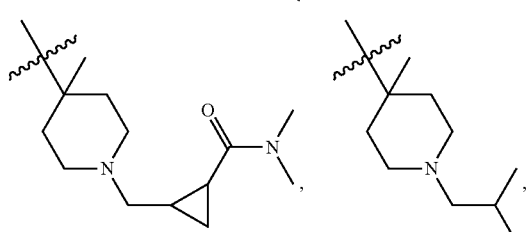
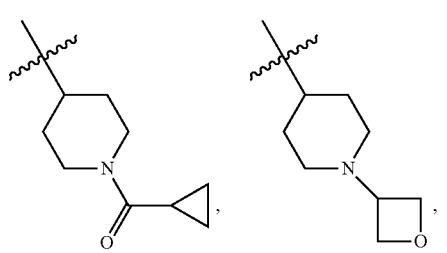
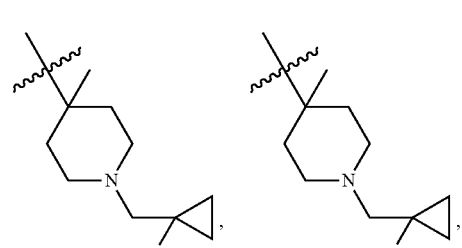
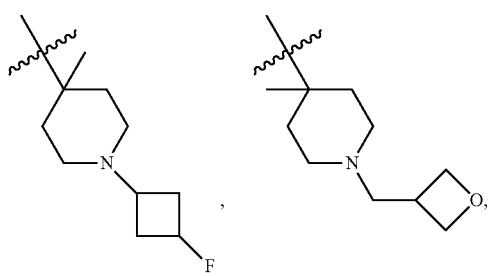
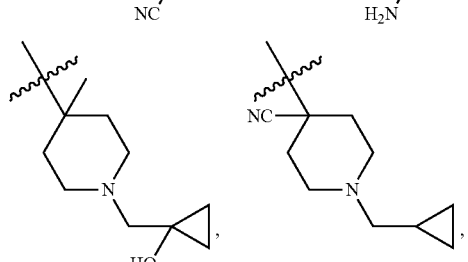
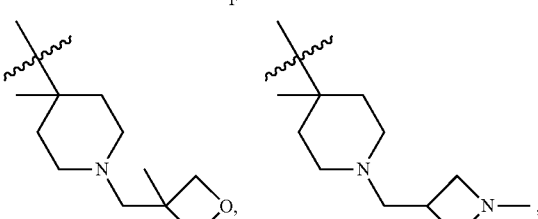
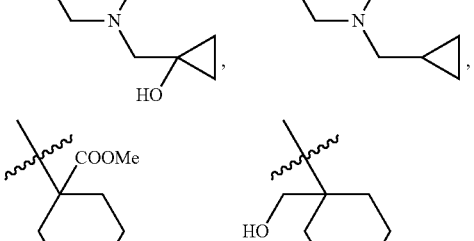
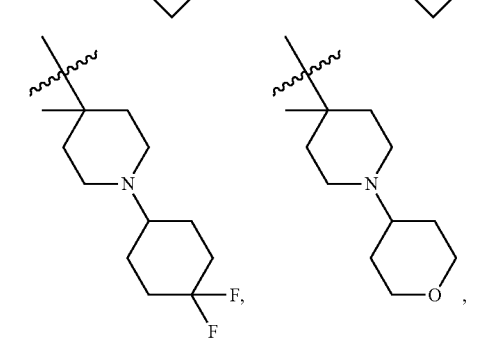

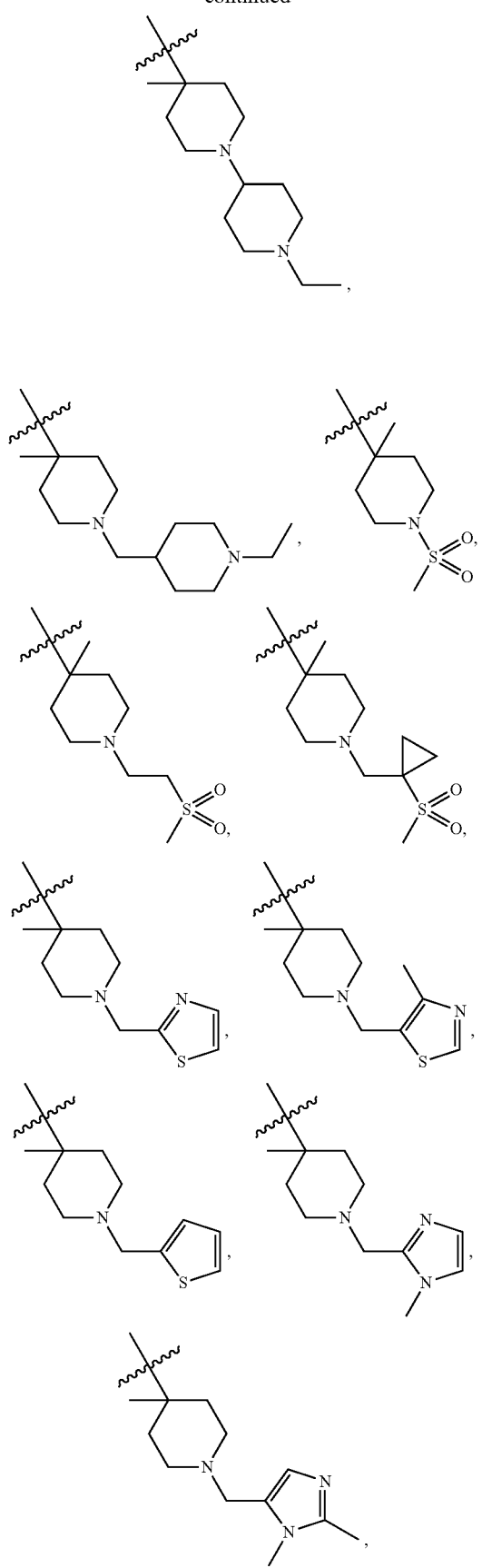
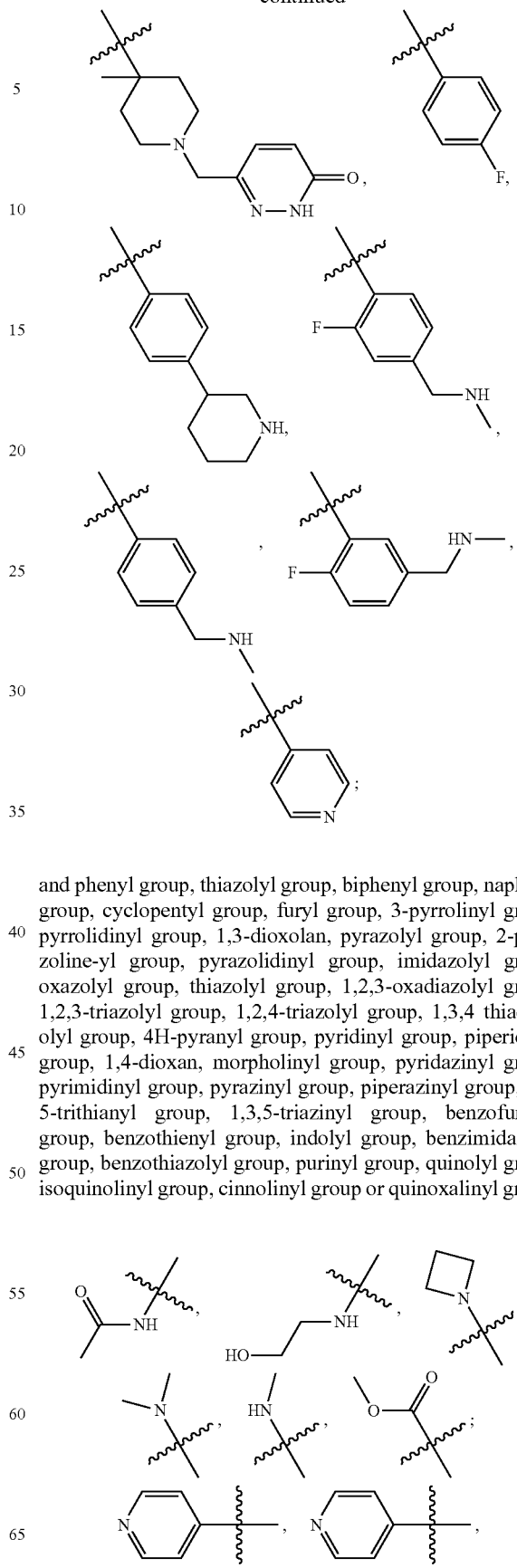

and phenyl group, thiazolyl group, biphenyl group, naphthyl group, cyclopentyl group, furyl group, 3-pyrrolinyl group, pyrrolidinyl group, 1,3-dioxolan, pyrazolyl group, 2-pyrazoline-yl group, pyrazolidinyl group, imidazolyl group, oxazolyl group, thiazolyl group, 1,2,3-oxadiazolyl group, 1,2,3-triazolyl group, 1,2,4-triazolyl group, 1,3,4 thiadiazolyl group, 4H-pyranyl group, pyridinyl group, piperidinyl group, 1,4-dioxan, morpholinyl group, pyridazinyl group, pyrimidinyl group, pyrazinyl group, piperazinyl group, 1,3,5-trithianyl group, 1,3,5-triazinyl group, benzofuranyl group, benzothienyl group, indolyl group, benzimidazolyl group, benzothiazolyl group, purinyl group, quinolyl group, isoquinolinyl group, cinnolinyl group or quinoxalinyl group;

The term "pharmaceutically-acceptable" used here refers to the compound(s), material(s), composition(s) and/or dosage form(s) that is suitable within the scope of reliable medical judgments to be used in contact with the human and animal tissues, without posing excessive toxicity, irritation, allergic reactions or other issues or complications and with reasonable benefit/risk ratio.

The term "pharmaceutically-acceptable salt(s)" refers to the salt(s) of the compound(s) according to the present invention that is prepared from the compound(s) with specific substituting group developed according to the present invention and relatively-nontoxic acid or base. If any compound according to the present invention contains a relatively-acidic functional group, an adequate amount of base can be added in its pure solution or appropriate inert solvent to contact with such compound in neutral form to yield a salt of base addition. The pharmaceutically-acceptable base(s) includes the salts of sodium, potassium, calcium, ammonia, organic ammonium or magnesium or similar salts. If any compound according to the present invention contains a relatively-basic functional group, an adequate amount of acid can be added in its pure solution or appropriate inert solvent to contact with such compound in neutral form to yield a salt of acid addition. The examples of the pharmaceutically-acceptable salt(s) include the inorganic acid salt(s) that includes hydrochloric acid, hydrobromic acid, nitric acid, carbonate, bicarbonate, phosphate, hydrogen phosphate, phosphate, dihydrogen phosphate, sulfate, bisulfate, hydroiodic, phosphorous, etc, and the organic acid salt(s) that includes acetic acid, propionic acid, isobutyric acid, maleic acid, propionic acid, benzoic acid, succinic acid, suberic acid, fumaric acid, lactic acid, mandelic acid, phthalic acid, benzenesulfonic acid, p-toluene sulfonic acid, citric acid, tartaric acid, methanesulfonic acid, etc, and also the salt(s) of amino acid(s) (such as arginine) as well as the salt(s) of organic acid(s) such as glucuronic acid (see Berge et al., "Pharmaceutical Salts", Journal of Pharmaceutical Science 66:1-19 (1977)). Some specific compounds according to the present invention contain basic and acidic functional group(s) and hence can be transformed into any salt of basic or acid addition.

Preferentially, the salt contacts with base or acid in a conventional way before the parent compounds are separated to regenerate the neutral form of compounds. The differences between the compounds in parent form and in the form of various salts lie in some physical properties, e.g. the different solubility in polar solvent.

The "pharmaceutically-acceptable salt(s)" used here is the derivative(s) of the compound according to the present invention, wherein said parent compound(s) is modified by the means of salification with acid or salification with base. The examples of pharmaceutically-acceptable salt(s) include but are not limited to inorganic acid salt(s) or organic acid salt of basic group such as amine and the alkali metal or organic slat(s) of acid group such as carboxylic acid, etc. The pharmaceutically-acceptable salt(s) includes the conventional non-toxic salt(s) or the quaternary ammonium salts of parent compound, e.g. the salt(s) produced from non-toxic inorganic acid organic acid. The conventional non-toxic salt(s) includes but is not limited to those salts derived from inorganic acid and organic acid that is selected from 2-acetoxybenzoic acid, 2-hydroxyethane sulfonic, acetic, ascorbic, benzenesulfonic, benzoic, bicarbonate radical, carbonate, citric acid, edetic acid, ethane disulfonic acid, ethanesulfonic acid, fumaric acid, glucoheptonic acid, gluconic acid, glutamic acid, glycolic acid, hydrobromic acid, hydrochloric acid, hydroiodide acid, hydroxyl, hydroxynaphthoic acid, isethionic acid, lactic acid, lactobionic acid, dodecyl sulfonic acid, maleic acid, malic acid, mandelic acid, methane sulfonic acid, nitric acid, oxalic acid, pamoic acid, pantothenic acid, phenylacetic acid, phosphoric acid, poly-galacturonic acid, propionic acid, salicylic acid, stearic acid, sub-acetic acid, succinic acid, sulfamic acid, sulfanilic acid, sulfuric acid, tannin, tartaric acid and p-toluenesulfonic acid.

The pharmaceutically-acceptable salt according to the present invention can be synthesized with the conventional chemical method(s) from the parent compounds containing acidic or basic group(s). Generally, the methods of preparing such salt are as follows: in water or organic solvent or in a mixture of them, these compounds in the form of free acid or base react with appropriate base or acid in stoichiometry. Usually, it is preferable to select a non-aqueous media such as ether, ethyl acetate, ethanol, isopropanol, or acetonitrile.

In addition to the form of salt, the compound(s) provided according to the present invention also include the form of prodrug. The prodrug of a compound(s) described here can easily undergo chemical change under physiological conditions so as to transform to the compound(s) according to the present invention. In addition, the prodrug can be transformed into the compound(s) according to the present invention via a chemical or biochemical method in an in-vivo environment.

Some compounds according to the present invention can exist in the form of non-solvation or solvation, including the form of hydrate. In general, the form of solvation and the form of non-solvation are equivalent to each other and both covered within the scope of the present invention. Some compounds according to the present invention can exist in the form of polycrystal or amorphism.

Some compounds according to the present invention can contain asymmetric carbon atoms (optical center) or double bond. The raceme, diastereoisomer, geometric isomer and single isomer are all covered within the scope of the present invention.

The graphic method for the pure compounds of racemate, ambiscalemic and scalemic or antipode is sourced from Maehr, J. Chem. Ed. 1985, 62:114-120. 1985, 62: 114-120. Unless indicated otherwise, the wedge key and the dotted-line key are used to indicate the absolute configuration of a stereocenter. If said compounds here contain olefinic double bond or other asymmetric geometry center, they should include the geometric isomers of E and Z. Similarly, all the tautomeric forms shall be covered within the scope of the present invention.

The compound(s) according to the present invention can present in the form of specific geometric isomer or stereoisomer. All these compounds proposed by the present invention, including the cis- and trans-isomers, (−)- and (+)-enantiomer, (R)- and (S)-enantiomer, diastereoisomer, (D)-isomer, (L)-isomer and their racemic mixtures and other mixtures, e.g. the mixture enriched in enantiomer or non-enantiomer, are all covered within the scope of the present invention. The substituting group such as alkyl may contain other asymmetric atoms. All these isomers and their mixtures are covered within the scope of the present invention.

The chiral synthesis or chiral reagent or other routine techniques can be used to prepare the (R)- and (S)-isomers as well as D and L isomers with optical activity. If an enantiomer of some compound according to the present invention is desired, it can be prepared through asymmetric synthesis or the derivatization effect of chiral auxiliary reagent, where the prepared non-enantiomer mixture is separated and the auxiliary group is split to provide the necessary enantiomer. Or, if a molecule contains basic function group (e.g. amino) or acid functional group (e.g. carboxyl), it can form the salt of non-enantiomer with appropriate acid or base with optical activity before the non-enantiomer is separated via the fractional crystallization process or chromatography generally known by those skilled in the art and then recovered to obtain the pure enantiomer. In addition, the separation between enantiomer and non-enantiomer is usually finished via chromatography, which utilizes chiral stationary phase and necessarily combines with chemical derivatization method (e.g. an amine is used to produce carbamate).

The compound(s) according to the present invention may contain a non-natural ratio of isotope of one or more atoms constituting the compound, e.g., the radioactive isotope labeled compound such as tritium ($^3$H), I-125 ($^{125}$I) or C-14 ($^{14}$C) can be used. All the transformations of the isotope composition of a compound according to the present invention shall, regardless of being radioactive or not, be covered within the scope of the present invention.

The term "pharmaceutically-acceptable carrier" refers to any preparation or carrier medium that can deliver an effective dose of active substance according to the present invention, not interfere with the biological activity of the active substance and pose no toxic and side effect to host or patient. The representative carriers include water, oil, vegetable and mineral, paste, lotion base and ointment base, etc. These bases include suspending agent, tackifier and transdermal enhancer, etc. Their preparations are known by the technicians in cosmetics and toiletries or in the partial pharmaceutical field. As for other information of the carriers, the following reference is available "Remington: The Science and Practice of Pharmacy, 21st Ed., Lippincott, Williams & Wilkins (2005)", whose content are incorporated into this patent by means of referring.

The term "excipient" usually refers to the carriers, diluents, and/or medium necessary to prepare effective pharmaceutical composition.

With regard to a drug or a pharmacological active agent, the term "effective dose" or "therapeutically effective dose" refers to the level of a drug or agent that is non-toxic but adequate to achieve expected effect. As for the oral dosage form in the present invention, the "effective dose" of an active substance in the composition refers to the level necessary to achieve the expected effect in the case of combination with other active substance. The determination of such effective dose varies from person to person, depending on the age of receptor and the general conditions as well as the specific active substance. The individual appropriate effective dose can be determined according to the routine experiments by those skilled in the art.

The terms "active ingredient", "therapeutic agent", "active substance" or "active agent" refer to a chemical entity that can effectively cure a targeted disorder, disease or symptom.

The term "substituted" refers to that any one or several hydrogen atoms bonding to specific atom are replaced by substituting groups including deuterium or the variants of hydrogen as long as the valence state of the specific atom is normal and the compound after substitution is stable. If the substituting group is a ketone group (i.e., =O), it means that two hydrogen atoms are substituted. The ketone substitution will not occur to an aryl group. The term "optionally substituted" refers to that it can optionally be substituted or not substituted. Unless specified otherwise, the type and number of the substituting group are random on a chemically-achievable basis.

In the event that any variable (e.g. R) appears more than once in the composition or structure of a compound, its definition is independent on a case by case basis. For example, if one group is substituted by 0-2 R, said group can be optionally substituted by up to two R and each of them can be selected independently in each case. Moreover, any combination of substituting groups and/or their variants can only be acceptable if such combination can give a stable compound.

If one variable of them is selected from those with single bond, it means that the two groups it bonds to are connected directly, e.g. the single bond of "L" in "A-L-Z" denotes an actual structure of A-Z.

If the bond of a substituting group can be cross-linked to two atoms of one ring, such substituting group can bond with any atom on the ring. If the enumerated substituting group is not specified as for the atom to bond a compound covered by the general formula of a chemical structure but not mentioned specifically, such substituting group can bond with any atom of it. Any combination of the substituting groups and/or their variants can only be acceptable if such combination can give a stable compound. e.g., the structural unit

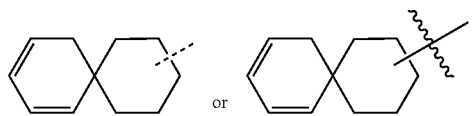

indicates that it can substitute any position of the cyclohexyl group or cyclo-diene.

The substituting groups of alkyl and heteroalkyl radical are usually referred to as "alkayl substituents." They can be selected from but not limited to one or more from the following groups: —R', —OR', =O, =NR', =N—OR', —NR'R", —SR', halogen, —SiR'R"R'", OC(O)R', —C(O)R', —CO₂R', —CONR'R", —OC(O)NR'R", —NR"C(O)R', NR'C(O)NR"R'", —NR"C(O)₂R', —NR"", —C(NR'R"R'")= NR"", NR""C(NR'R")=NR'", —S(O)R', —S(O)₂R', —S(O)₂NR'R", NR"SO₂R', —CN, —NO₂, —N₃, —CH(Ph)₂ and fluoro(C₁-C₄) alkayl groups. The number of substituting groups is 0~(2m'+1), where m' is the total number of carbon atoms in these atom radicals. The R', R", R'", R"" and R""' are independently selected preferentially from hydrogen, the substituted or unsubstituted heteroalkyl groups, substituted or unsubstituted aryl groups (e.g., those substituted by 1~3 halogen atoms), the substituted or unsubstituted alkyl groups, alkoxy groups, thio-alkoxy radicals or aralkyl groups. If a compound according to the present invention contains more than one R group, e.g., each R group is independently selected as if it is any from more than one R', R", R'", R"" and R""'. If R' and R" bond with the same N atom, they can from a 5-, 6- or 7-membered ring with this N atom, e.g., —NR'R" refers to include but not limited to 1-pyrrolidinyl and 4-morpholinyl. As per the aforementioned discussion of substituting group, those skilled in the art can understand the term "alkyl group" refers to include the groups formed by the carbon atoms bonding with non-hydrogen groups, for example halogenated alkyls (e.g. —CF₃, —CH₂CF₃) and acyl groups (e.g. —C(O)CH₃, —C(O)CF₃, —C(O)CH₂OCH₃, etc).

Similar to said substituting groups of alkyl groups, the substituting groups of aryl groups and heteroaryl groups are generally referred to as "aryl substituents" and are selected from, e.g. —R', —OR', —NR'R", —SR', -halogen, —SiR'R"R'", OC(O)R', —C(O)R, —CO2R', —CONR'R", —OC(O)NR'R", —NR"C(O)R', NR'C(O)NR"R'", —NR"C(O)2R', —NR"""—C(NR'R"R'")=NR"", NR""C(NR'R")=NR'", —S(O)R', —S(O)₂R', —S(O)₂NR'R", NR"SO₂R', —CN, —NO₂, —N₃, —CH(Ph)₂, fluoro(C₁-C₄) alkoxy and fluoro-(C₁-C₄) alkyl groups. The number of substituting groups is in the range of 0 to the total number of open valence of the aromatic ring, where R', R", R'", R"" and R""' are independently selected respectively from hydrogen, the substituted or unsubstituted alkly groups, the substituted or unsubstituted hetero alkyl groups, the substituted or unsubstituted aryl groups and the substituted or unsubstituted hetero aryl groups. If a compound according to the present invention contains more than one R group, e.g., each R group is independently selected as if it is any from more than one R', R", R'", R"" and R""'.

The two substituting groups on two adjacent atoms of aryl group or hetero aryl group can be substituted by a group with the general formula as -T-C(O)—(CRR')q-U—, where T and U are independently selected respectively from —NR—, —O—, CRR' or single bond and q is an integer of 0 and 3. As an alternative, the two substituting groups on two adjacent atoms of aryl group or hetero aryl group can be replaced by a substituting group with a general formula of -A(CH2)rB—, where A and B are independently selected respectively from —CRR'—, —O—, —NR—, —S—, —S(O)—, S(O)₂—, —S(O)₂NR'— or single bond and r is an integer of 1~4. Optionally, one single bond on the new ring formed thereby can be replaced by double bond. As an alternative, the two substituting groups on two adjacent atoms of aryl group or hetero aryl group can be replaced by a substituting group with a general formula of -A(CH2)rB—, where s and d are integers of 0~3 respectively selected independently, X is —O—, —NR', —S—, —S(O)—, —S(O)₂— or —S(O)₂NR'—. The substituting group R, R', R" and R'" are respectively selected independently from the preferential hydrogen and the substituted or unsubstituted (C₁-C₆) alkyl groups.

Unless specified otherwise, the term "halogenating element" or "halogen" denotes fluorine, chlorine, bromine or iodine atom by itself or as a part of other substituting group. In addition, the term "halogenated alkyl group" refers to the monohalogenated and polyhalogenated alkyl groups. For example, the term "halo(C₁-C₄)alkyl group" means to include but be not limited to trifluoromethyl, 2,2,2-trifluoroethyl, 4-chlorobutyl and 3-bromopropyl, etc.

The examples of halogenated alkyl groups include but are not limited to trifluoromethyl group, trichloromethyl group, pentafluoroethyl group and pentachlorophenol ethyl group. The "alkoxy group" denotes the aforementioned alkyl groups with specific number of carbon atoms linked by oxygen bridge. The C₁₋₆ alkoxy groups include those of C₁, C₂, C₃, C₄, C₅ and C₆. The examples of alkoxy groups include but are not limited to methoxy, ethoxy, n-butoxy, isobutoxy, n-butoxy, sec-butoxy, tert-butoxy, n-pentyloxy and 5-pentyloxy group. The "cycloalkyl group" includes saturated ring group, e.g., cyclopropyl, cyclobutyl or cyclopentyl group. The 3-7 cycloalkyl group includes those of C₃, C₄, C₅, C₆ and C₇. The "alkenyl group" includes the linear or branched hydrocarbon chains, where any stable point on the chain has one or more carbon-carbon double bond, e.g. vinyl and allyl groups.

The term "halogen" or "halogen element" refers to flouorine, chlorine, bromine, and iodine.

Unless specified otherwise, the term "hetero" refers to a hetero atom or hetero atom radical (i.e., atom radical containing hetero atom), including the atoms except carbon (C) and hydrogen (H) and their atom radicals, e.g. O, N, S, Si, Ge, Al, B, —O—, —S—, =O, =S, —C(=O)O—, —C(=O)—, —C(=S)—, —S(=O), —S(=O)$_2$— and any one selected from the substituted —C(=O)N(H)—, —N(H)—, —C(=NH)—, —S(=O)$_2$N(H)— or —S(=O)N(H)—.

Unless specified otherwise, the "ring" denotes a substituted or unsubstituted cycloalkyl group, heterocycloalkyl group, cycloalkenyl group, heterocycloalkenyl group, cycloalkynyl group, heterocyclyl alkynyl group, aryl, or heteroaryl group. The so-called ring includes monocycle, linked ring, spiro ring, bi-ring or bridged ring. The number of atoms in the ring is generally defined as the member number of ring, e.g., the "5~7 membered ring" means that 5~7 atoms are contained to form a ring. Unless specified otherwise, this ring optionally contains 1~3 hetero atoms. Thus, the "5~7 membered ring" includes, e.g. phenyl pyridine and piperidinyl group, on the other hand, the term "5~7 membered heterocycloalkyl ring" includes pyridyl group and piperidinyl group rather than phenyl group. The term "ring" includes the ring system containing at least one ring, where each "ring" independently conforms to the aforementioned definition.

Unless specified otherwise, the term "heterocycle" or "heterocyclic group" refers to a monocycle, bi-cycle and tricycle containing hetero atoms or hetero atom radical. They can be saturated, partially saturated or unsaturated (aromatic) and consist of carbon atoms and 1, 2, 3 or 4 hetero atoms independently selected from N, O, and S, where any of the aforementioned heterocycles can be condensed together with benzene ring to form a bi-cycle. The N and S hetero atoms can be optionally oxidized (i.e., NO and S(O)p). The N atom can be substituted or unsubstituted (i.e., N or NR where R is H or other substituting group already defined in the patent). The hetero ring can bond to the side group of any hetero atom or carbon atom to form stable structure. If the generated compound is stable, said heterocycle according to the present invention can undergo substitution on C atom or N atom and N atom in the heterocycle can be optionally quaternized. One preferential scheme is that the atoms will not be adjacent if the total number of S and O atoms in the heterocycle is over 1. Another preferential scheme is that the total number of S and O in the heterocycle will not exceed 1. As employed in the present invention, the term "aromatic heterocyclic group" or "heteroaryl group" refers to the aromatic rings with stable 5,6 or 7-membered monocycles or bi-cycles or 7, 8, 9 or 10-membered bicyclic heterocyclic group. It can contain carbons atoms and 1, 2, 3, or 4 hetero atoms of N, O and S independently selected from N, O and S. N atom can be substituted or unsubstituted (i.e., N or NR, where R is H or other substituting group already defined in the patent). N and S hetero atoms can be optionally oxidized (i.e., NO and S(O)p). It is noteworthy that the total number of S and O atoms in the aromatic heterocycle will not exceed 1. The bridged rings are also covered by the definition of heterocycle. One or more atoms (i.e., C, O, N or S) will form a bridged ring when two non-adjacent C atoms or N atoms are linked. The preferential bridged rings include but are not limited to: one C atom, two C atoms, one N atom, two N atoms and one C—N group. It is noteworthy that one bridge always converts a monocycle ring into a tricycle. The substituting group in the ring can also be located on the bridge.

The examples of heterocyclic compounds include but are not limited to acridinyl group, azocine group, benzimidazolyl group, benzofuranyl group, mercaptobenzofuranyl group, mercaptobenzophenyl group, benzoxazolyl group, benzoxazolyl group, benzothiazolyl group, benzotriazolyl group, benzotetrazolyl group, benzoisoxazolyl group, benzisothiazol group, benzimidazolyl group, carbazolyl group, 4aH-carbazolyl group, carboline group, chromanyl group, chromene, cinnolinyl decahydroquinolyl group, 2H, 6H-1,5,2-dithiazine group, dihydro-furo [2,3-b] tetrahydrofuran, furyl group, furazanyl group, imidazolidinyl group, imidazolinyl group, imidazolyl group, 1H-indazolyl group, indolenyl group, indolinyl group, indolizinyl group, indolyl group, 3H-indolyl group, isatino group, isobenzofuran group, pyranyl, isoindolyl group, isoindoline group, isoindolyl group, indolyl group, isoquinolinyl group, isothiazolyl group, isoxazolyl group, methylenedioxy phenyl group, morpholino group, naphthyridinyl group, octahydro-isoquinolinyl group, oxadiazolyl group, 1,2,3-oxadiazolyl group, 1,2,4-oxadiazolyl group, 1,2,5-oxadiazolyl group, 1,3,4-oxadiazolyl group, oxazolidinyl group, oxazolyl group, isoxazolyl group, oxindole group, pyrimidinyl group, phenanthridine group, phenanthroline group, phenazine, phenothiazine, xanthine benzo group, phenoxazine group, phthalazinyl group, piperazinyl group, piperidinyl group, piperidonyl group, 4-piperidonyl group, piperonyl group, pteridinyl group, purinyl group, pyranyl group, pyrazolyl group, pyrazolidinyl group, pyrazolinyl group, pyrazolyl group, pyridazinyl group, pyridine-oxazole, pyridine-imidazole, pyridine-thiazole, pyridinyl group, pyrimidinyl group, pyrrolidinyl group, pyrrolinyl group, 2H-pyrrolyl group, pyrrolyl group, pyrazolyl group, quinazolinyl group, quinolinyl group, 4H-quinolizinyl group, quinoxalinyl group, quinuclidinyl group, tetrahydrofuranyl group, tetrahydroisoquinolinyl group, tetrahydroquinolinyl group, tetrazolyl group, 6H-1,2,5-thiadiazolyl group, 1,2,3-thiadiazolyl group, 1,2,4-thiadiazolyl group, 1,2,5-thiadiazolyl group, 1,3,4-thiadiazolyl group, thianthrenyl group, thiazolyl group, isothiazolyl thienyl group, thienyl group, thieno oxazolyl group, thienyl-thiazolyl group, thienyl-imidazolyl group, thienyl group, triazinyl group, 1,2,3-triazolyl group, 1,2,4-triazolyl group, 1,2,5-triazolyl group, 1,3,4-triazolyl group and xanthenyl group. The condensed ring compounds and spiro-compounds are also included.

Unless specified otherwise, the term "hydrocarbyl group" or its inferior concept (e.g., alkyl, alkenyl, alkynyl and phenyl, etc) denotes a linear, branched, or cyclic hydrocarbon radical or its combination by itself or as part of other substituting group. It can be fully saturated, mono-unsaturated or poly-unsaturated, can be mono-substituted, di-substituted or poly-substituted, can be univalent (e.g. methyl group), divalent (e.g. methylene group) or multivalent (e.g. methine), can be divalent or multivalent atom radical with specified number of carbon atoms (for example $C_1$-$C_{10}$ indicating 1 to 10 carbon atoms). The "hydrocarbyl group" includes but is not limited to aliphatic group and aromatic group. Said aliphatic group includes chains and rings, specifically including but not limited to alkyl group, alkenyl group and alkynyl group. Said aromatic group includes but is not limited to 6-12 membered aromatic group, e.g. benzene and naphthalene, etc.

In some embodiments, the term "alkyl group" denotes a linear or branched atom radical or their combination. It can be fully saturated, mono-unsaturated or poly-unsaturated and can be divalent and multivalent atom radical. The examples of saturated atom radical include but are not limited to the homologs or isomers of radicals such as methyl group, ethyl group, n-propyl group, isopropyl group, n-butyl group, tert-butyl group, isobutyl group, sec-butyl group, isobutyl group, cyclohexyl group, (cyclohexyl)methyl group, cyclopropylmethyl group and n-pentyl group, n-hexyl group, n-heptyl group and n-octyl, etc. The unsaturated alkyl group comprises one or more double bonds or triple bonds and its examples include but are not limited to ethenyl group, 2-propenyl group, butenyl group, crotyl group, 2-isopentenyl group, 2-(butadienyl) group, 2,4-pentadienyl group, 3-(1,4-pentadienyl) group, ethynyl group, 1- and 3-propynyl group, 3-butyny group and their higher homologs and isomers.

Unless specified otherwise, the term "heterohydrocarbyl group" or its inferior concept (e.g. heteroalkyl group, heteroalkenyl group, heteroalkynyl group and heteroaryl group, etc.) denotes a stable linear, branched or cyclic hydrocarbon radical or its combination by itself or in combination with other term and it consists of a number of carbon atoms and at least one hetero atom. In some embodiments, the term "heteroalkyl group" denotes a stable linear, branched hydrocarbon radical or its combination by itself or in combination with other term and it consists of a number of carbon atoms and at least one hetero atom. In a typical embodiment, the hetero atom is selected from B, O, N and S, where the N and S atoms are optionally oxidized and the N hetero atom is optionally quaternized. The hetero atoms B, O, N and S can be located at any internal position of heterohydrocarbyl group (including the positions except that where the hydrocarbon group is bonded). The examples include but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. No more than two hetero atoms are consecutive, e.g. $CH_2$—NH—$OCH_3$.

The term "alkoxy group", "alkylamino group" and "alkylthio group" (thioalkoxy group) is idiomatic expression and refers to those alkyl groups bonded to other parts of the molecule via O atom, amino group or S atom.

Unless specified otherwise, the term "cyclic hydrocarbon group", "heterocyclic hydrocarbon group" or their inferior concepts (e.g. aryl group, heteroaryl group, cycloalkyl group, heterocycloalkyl group, cycloalkenyl group, heterocycloalkenyl group, cycloalkynyl group and heterocyclyl alkynyl group, etc) denote respectively the cyclic "hydrocarbon group" and "hetero hydrocarbon group" by itself or in combination with other term. In addition, as for the hetero hydrocarbon groups or heterocyclic hydrocarbon groups (e.g. hetero alkyl group and heterocyclic alkyl group), the hetero atom can occupy other positions except that the hetero ring bonds to the molecule. The examples of cycloalkyl group include but are not limited to cyclopentyl group, cyclohexyl group, 1-cyclohexenyl group, 3-cyclohexenyl group and cycloheptyl group, etc. The non-restrictive examples of heterocyclic group include 1-(1,2,5,6-tetrahydropyridyl) group, 1-piperidinyl group, 2-piperidinyl group, 3-piperidinyl group, 4-morpholinyl group, 3-morpholinyl group, tetrahydrofuran-2-yl group, tetrahydrofuran-3-yl group, tetrahydro-thiophen-2-yl group, tetrahydro-thiophen-3-yl group, 1-piperazinyl group and 2-piperazinyl group.

Unless specified otherwise, the term "aryl group" denotes poly-unsaturated aromatic substituent and can be monosubstituted, disubstituted or polysubstituted. It can be monocyclic or polycyclic (preferably 1 to 3 rings) and can be condensed together or linked covalently. The term "heteroaryl group" refers to aryl group (or ring) containing one to four hetero atoms. In a demonstrative embodiment, the hetero atom is selected from B, O, N and S, where the N and S atoms are optionally oxidized and the N hetero atom is optionally quaternized. The heteroaryl group can bond to other part of the molecule via hetero atom. The non-restrictive embodiments of aryl group or heteroaryl group include phenyl group, 1-naphthyl group, 2-naphthyl group, 4-biphenyl group, 1-pyrrolyl group, 2-pyrrolyl group, 3-pyrrolyl group, 3-pyrazolyl group, 2-imidazolyl group, 4-imidazolyl group, pyrazinyl group, 2-oxazolyl group, 4-oxazolyl group, 2-phenyl-4-oxazolyl group, 5-oxazolyl group, 3-isoxazolyl group, 4-isoxazolyl group, 5-isobutyl oxazolyl group, 2-thiazolyl group, 4-thiazolyl group, 5-thiazolyl group, 2-furyl group, 3-furyl group, 2-thienyl group, 3-thienyl group, 2-pyridyl group, 3-pyridyl group, 4-pyridyl group, 2-pyrimidinyl group, 4-pyrimidinyl group, 5-benzothiazolyl group, purinyl group, 2-benzimidazolyl group, 5-indolyl group, 1-isoquinolyl group, 5-isoquinolinyl group, 2-quinoxalinyl group, 5-quinoxalinyl group, 3-quinolyl group and 6-quinolyl group. Any aforementioned substituting group of aryl and heteroaryl ring is selected from the acceptable substituting group described as follows.

For simplicity, the aryl group to be used in combination with other term (e.g. aryloxy group, arylthio group and aralkyl group) includes the aryl group and heteroaryl ring as defined above. Thus, the term "aralkyl group" means to include those radicals via which the aryl group bonds to the alkyl group (e.g. benzyl, phenethyl, pyridylmethyl etc), including those alkyl groups that any C atom (e.g. methylene) is replaced by O atom, e.g., phenoxymethyl group, 2-pyridyloxy methyl-3-(1-naphthyloxy) propyl group, etc.

The term "leaving group" refers to a functional group or atom that can be replaced by another functional group or atom via substitution reaction (e.g., nucleophilic substitution reaction). For example, the representative leaving groups include triflate; chloro, bromo, iodo; sulfonate group such as mesylate, tosylate, brosylate, p-toluenesulfonate, etc; acyloxy group such as acetoxy group and trifluoroacetyl group, etc.

The term "protecting group" includes but is not limited to "amino protecting group", "hydroxy protecting group" or "mercapto-protecting group". The term "amino protecting group" refers to the protecting groups suitable to prevent secondary reaction on the position of amino nitrogen. The representative amino protecting groups include but are not limited to: formyl group; acyl groups such as alkanoyl group (e.g. acetyl group, trichloroacetyl group or trifluoroacetyl group); alkoxycarbonyl group such as tert-butoxycarbonyl (Boc); arylmethoxycarbonyl groups such as benzyloxycarbonyl (Cbz) and 9-fluorenyl methoxycarbonyl (Fmoc); arylmethyl group such as benzyl group (Bn), trityl group (Tr), 1,1-di-(4'-methoxwhenyl) methyl group; silyl groups such as trimethylsilyl group (TMS) and tert-butyldimethylsilyl (TBS), etc. The term "hydroxy protecting group" refers to the protecting groups suitable to prevent secondary reaction of hydroxy group. The representative hydroxy groups includes but are not limited to: alkyl groups such as methyl group, ethyl group and t-butyl group; acyl groups such as alkanoyl groups (e.g. acetyl group); arylmethyl groups such as benzyl (Bn), p-methoxybenzyl group (PMB), 9-fluorenyl methyl (Fm) and diphenylmethyl group (benzhydryl, DPM); silyl groups such as trimethylsilyl group (TMS) and tert-butyldimethylsilyl (TBS), etc.

The compound(s) according to the present invention can be prepared via many synthesis methods known by those skilled in the art, which include the following embodiments, the implementation ways formed by them with other chemical synthesis methods and the equivalent replacements known by those skilled in the art. The preferred embodiments include but are not limited to the examples according to the present invention.

All the solvents used in the present invention are commercially available and can be used directly without further purification. The present invention employs the following abbreviations: aq denoting water; HATU denoting O-(7-azabenzotriazol-1-yl)-N,N,N',N'-tetramethyluronium hexafluorophosphate; EDC denoting N-(3-dimethylaminopropyl)-N'-ethylcarbodiimide hydrochloride; m-CPBA denoting 3-chloroperoxybenzoic acid; eq denoting equivalent and equal amount; CDI denoting carbonyl diimidazole; DCM denoting dichloromethane; PE denoting petroleum ether; DIAD denoting diisopropyl azodicarboxylate; DMF denoting N,N-dimethylformamide; DMSO denoting dimethylsulfoxide; EtOAc denoting ethyl acetate; EtOH denoting ethanol; MeOH denoting methanol; CBz denoting benzyloxycarbonyl that is an amine-protecing group; BOC denoting tert-carbonyl that is an amine-protecing group; HOAc denoting acetic acid; NaCNBH$_3$ denoting sodium cyanoborohydride; r.t. denoting room temperature; O/N denoting over night; THF denoting etrahydrofuran; Boc$_2$O denoting di-tert-butyl dicarbonate; TFA denoting trifluoroacetate; DIPEA denoting diisopropylethyl amine; SOCl$_2$ denoting thionyl chloride; CS$_2$ denoting carbon disulfide; TsOH denoting p-toluene sulfonic acid; NFSI denoting N-fluoro-N-(phenylsulfonyl) benzenesulfonamide; NCS denoting 1-chlorine pyrrolidine-2,5-diketone; n-Bu$_4$NF denoting tetrabutylammonium fluoride; iPrOH denoting 2-propanol; mp denoting meling point; LDA denoting lithium diisopropylamide; Xantphos denoting 4,5-bisdiphenylphosphino-methyl-9,9-xanthene; Pd$_2$(dba)$_3$ denoting tris(dibenzylideneacetone) dipalladium; DAST denoting diethylaminosulphur trifluoride; Pd(dppf)Cl2 denoting 1,1'-bis(diphenylphosphino) ferrocene; PCC denoting pyridinium chlorochromate; TsCl denoting toluenesulfonyl chloride; Et$_3$N denoting triethylamine.

The compound(s) are named manually or via ChemDraw® software. The commercially-available compounds are used with the names from supplier directory.

Compared with the existing technologies, the compound(s) according to the present invention is efficient with low toxicity and realizes obvious or even unexpected progress in the factors such as activity, half time, solubility and pharmacokinetics and hence more suitable to prepare pharmaceuticals.

DESCRIPTION OF THE EMBODIMENTS

In order to describe the present invention in more detail, the following examples are provided although the scope of the present invention is not limited to them.

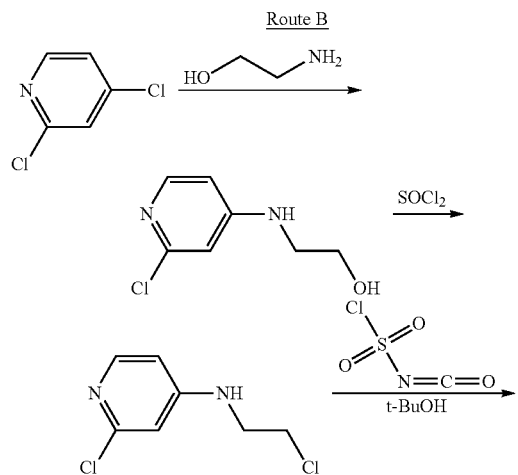

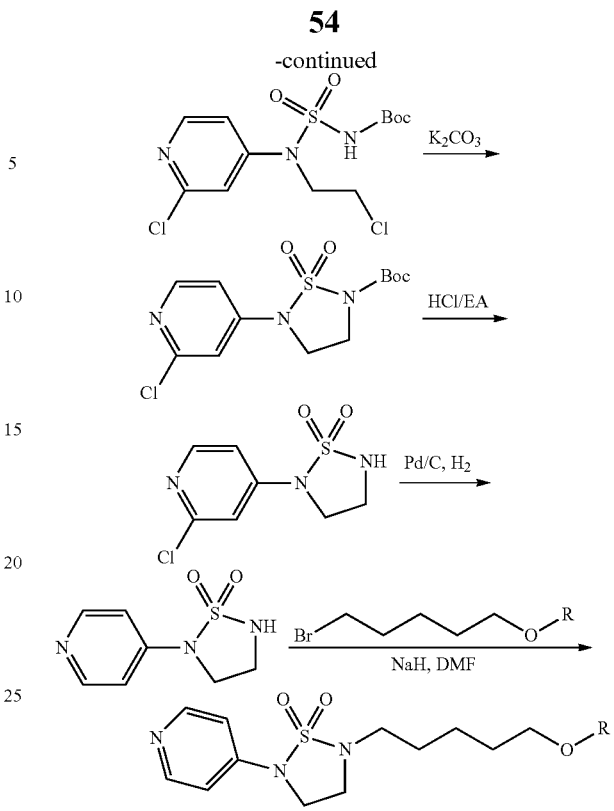

Embodiment 4

2-(5-((4-fluorophenoxy) pentyl)-5-(pyridin-4-yl)-1,2,5-thiadiazole-1,1-dioxide

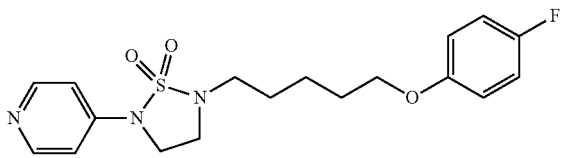 [SMILES: O=S1(=O)N(CCCCCOc2ccc(F)cc2)CCN1c1ccncc1]

Embodiment 4A 2-((2-chloropyridine-4-yl) amino) ethanol

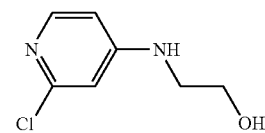

Agitate the solution of 2,4-dichloropyridine (100 g, 675.7 mmol), triethylamine (136.7 g, 1.35 mol) and 2-aminoethanol (41.3 g, 675.7 mmol)) in ethanol (500 ml) 72 hours at 100° C. and then allow it to undergo rotary evaporation to remove the solvents. Then purify the residue through the chromatograpy column and yield the title compound (yellow oil, 46 g, yield of 40%). $^1$H-NMR(CDCl$_3$, 400 MHz) δ7.90 (d, J=5.8 Hz, 1H), 6.49 (d, J=2.0 Hz, 1H), 6.41 (dd, J=5.8, 2.0 Hz, 1H), 5.17 (brs, 1H), 3.87 (t, J=5.1 Hz, 2H), 3.31 (q, J=5.0 Hz, 2H); LCMS(ESI) m/z: 173 (M+1).

Embodiment 4B 2-chloro-N-(2-chloroethyl) pyridin-4-amine

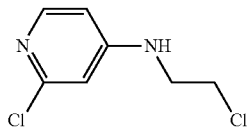

Dissolve Embodiment 4A (5 g, 28.9 mmol) in the mixture solvent of dichloromethane and N,N-dimethylformamide (50 ml/5 ml) and then drop the thionyl chloride (60 ml) into this mixture solution at 15° C. before heat to 40° C. to react for 16 hours. Then cool the system to room temperature and pour ice water (200 ml) into it. Then add 1 mol/L aqueous NaOH solution to adjust pH value to 10. Extract the aqueous layer with ethyl acetate (100 ml×6) and wash the combined organic layers with saline (50 ml) before dry with $Na_2SO_4$. Then filter and evaporate to get the crude product. Then purify the crude product via the chromatography column to obtain the title compound (white solid, 1.7 g, yield of 45%) and recycle the raw materials (white solid, 2.0 g). LCMS (ESI) m/z: 191 (M+1). $^1$H-NMR (CDCl$_3$, 400 MHz) δ 7.99 (d, J=6.0 Hz, 1H), 6.38-6.55 (m, 2H), 4.75 (brs, 1H), 3.67-3.78 (m, 2H), 3.55 (q, J=5.5 Hz, 2H).

Embodiment 4C

N-(2-chloroethyl)-N-(2-chloropyridin-4-yl) aminosulfonyl tert-Butyl carbamate

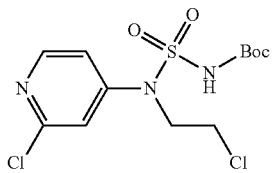 [SMILES: CC(C)(C)OC(=O)NS(=O)(=O)N(CCCl)c1ccnc(Cl)c1]

Under the protection of N$_2$ gas at 0° C., drop the chlorosulfonyl isocyanate (2.7 ml) into the solution of tert-butanol (3.4 ml) in dichloromethane (27 ml). After the dropping is completed, heat the solution gradually to room temperature and then continue to agitate 30 minutes to clear up. Transfer the solution at vacuum into a constant pressure funnel to mix with triethylamine (11.6 ml). Then under the protection at 0° C., drop the aforementioned mixture solution into the solution of Embodiment 4B (1.7 g, 8.9 mmol) in dichloromethane (20 ml). After the dropping is completed, agitate the solution 48 hours at 12° C. before quench with ice water. Then extract the aqueous phase with dichloromethane (50 ml×4). Dry the combined organic layers with Na$_2$SO$_4$ before filtering and evaporation to obtain the crude product (7 g) of the title compound that can be directly used without necessity to purify any more. $^1$H-NMR (CDCl$_3$, 400 MHz) δ 8.45 (d, J=5.5 Hz, 1H), 7.42 (d, J=1.5 Hz, 1H), 7.34 (dd, J=5.3, 1.8 Hz, 1H), 4.32 (t, J=6.4 Hz, 2H), 3.67 (t, J=6.3 Hz, 2H), 1.49 (s, 9H); LCMS (ESI) m/z: 370 (M+1).

Embodiment 4D 5-(2-chloropyridine-4-yl)-1,2,5-thiadiazolidine-2-tert-Butyl carboxylate-1,1-dioxide

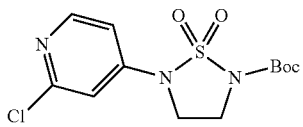 [SMILES: CC(C)(C)OC(=O)N1CCN(c2ccnc(Cl)c2)S1(=O)=O]

At 15° C., add K$_2$CO$_3$ powder (3.4 g) into the solution of Embodiment 4C (7 g, crude product) in dimethylsulfoxide (30 ml) and agitate 3 hours. Then pour it into 1 L water and filter to obtain the white solid. Dissolve the solid in dichloromethane and then dry with Na$_2$SO$_4$ before filter and evaporate to obtain the title compound (2 g, yield of 69%). $^1$H-NMR(CDCl$_3$, 400 MHz) δ 8.32 (d, J=6.0 Hz, 1H), 7.06-7.21 (m, 2H), 3.98-4.12 (m, 2H), 3.79-3.92 (m, 2H), 1.59 (s, 10H). LCMS(ESI) m/z: 334 (M+1).

Embodiment 4E 2-(2-chloropyridine-4-yl)-1,2,5-thiadiazolidine-1,1-dioxide

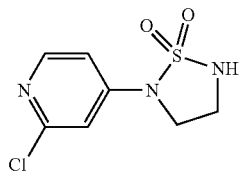 [SMILES: O=S1(=O)NCCN1c1ccnc(Cl)c1]

Add ethyl acetate hydrochloride (4 mol/L, 40 ml) into the mixture solution of Embodiment 4D (1.9 g, 5.69 mmol) in ethyl acetate/methanol (40 ml/4 ml) and agitate it 5 hours at 60° C. After removing the solution at vacuum, adjust the pH value of the residue with saturated sodium bicarbonate solution to 8. Extract the aqueous layer with ethyl acetate (250 ml×3) and dry the combined organic layers with Na$_2$SO$_4$ before filter and evaporate to obtain the title compound (white solid, 1.2 g, 92%). $^1$H-NMR (CDCl$_3$, 400 MHz) δ 8.29 (d, J=5.8 Hz, 1H), 7.05-7.09 (m, 1H), 7.00 (d, J=2.0 Hz, 1H), 3.95-3.99 (m, 2H), 3.78-3.85 (m, 2H); LCMS (ESI) m/z: 234 (M+1).

Embodiment 4F 2-(pyridin-4-yl)-1,2,5-thiadiazolidine-1,1-dioxide

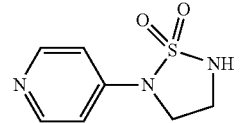 [SMILES: O=S1(=O)NCCN1c1ccncc1]

Mix Embodiment 4E (1.3 g, 5.5 mmol), Pd/C (100 mg) and triethylamine (2 ml) into methanol (30 ml). Agitate this mixture 12 hours at 25° C. before filter. Then remove the solvent at vacuum to obtain the title compound (3.8 g, yeild of 100%) that can be directly used without necessity to purify any more. $^1$H-NMR (DMSO-D$_6$, 400 MHz) 8.75 (s, br, 1H), 8.68 (d, J=7.0 Hz, 2H), 7.45 (d, J=7.0 Hz, 2H), 4.08 (t, J=6.3 Hz, 2H), 3.64 (d, J=6.3 Hz, 2H); LCMS (ESI) m/z: 200 (M+1).

Embodiment 4G 1-(5-bromopentyl) oxy-4-fluorobenzene

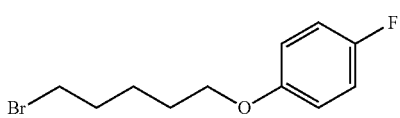 [SMILES: Fc1ccc(OCCCCCBr)cc1]

Add K$_2$CO$_3$ (14.79 g, 107 mmol), KI (0.59 g, 3.6 mmol) and 1,5-dibromopentane (24.61 g, 107 mmol) into the solution of p-fluorophenol (4 g, 35.68 mmol) in acetone (40 ml). Agitate the mixture solution 12 hours at 80° C. Then extract it with ethyl acetate. Dry the organic phase with anhydrous Na$_2$SO$_4$ before filter and evaporate. Then purify the residue with chromatography column (petroleum ether:ethyl acetate=10:1) to obtain the title compound (white solid, 6.6 g, yield of 70.8%). $^1$H-NMR (CDCl$_3$, 400 MHz) δ 6.93-7.01 (m, 2H) 6.79-6.86 (m, 2H) 3.90-3.97 (m, 2H) 3.45 (t, J=6.8 Hz, 2H) 1.94 (q, J=7.2 Hz, 2H) 1.76-1.86 (m, 2H) 1.60-1.68 (m, 2H). LCMS (ESI) m/z: 262 (M+1).

Embodiment 4H 2-(5-((4-fluorophenoxy) pentyl)-5-(pyridin-4-yl)-1,2,5-thiadiazolidine-1,1-dioxide

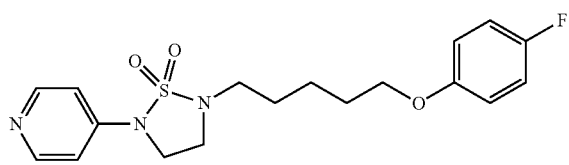 [SMILES: O=S1(=O)N(CCCCCOc2ccc(F)cc2)CCN1c1ccncc1]

At 0° C., add sodium hydride (6 mg, 0.16 mmol, 60% content) into the solution of Embodiment 4F (30 mg, 0.15 mmol) in N,N-dimethylformamide (2 ml). Keep it still 30 minutes at 0° C. Then add the solution of Embodiment 4G (39.3 mg, 0.15 mmol) in N,N-dimethylformamide (1 ml) into the aforementioned mixture solution. Agitate it 6 hours at 15° C. Then add water to quench the reaction and extract the aqueous phase with ethyl acetate. Dry the combined organic phases with anhydrous Na$_2$SO$_4$ before filter and evaporate. Then separate it with HPLC to obtain the title compound (white solid, 28 mg, yield of 49%). $^1$H-NMR (400 MHz, CDCl$_3$) δ 8.51 (d, J=6.0 Hz, 2H), 7.05 (d, J=5.5 Hz, 2H), 6.91-7.01 (m, 2H), 6.82 (dd, J=9.0, 4.0 Hz, 2H), 3.93 (t, J=6.3 Hz, 2H), 3.84 (t, J=6.5 Hz, 2H), 3.54 (t, J=6.3 Hz, 2H), 3.18 (t, J=7.0 Hz, 2H), 1.72-1.87 (m, 5H), 1.56-1.61 (m, 1H). LCMS (ESI), m/z: 380 (M+1).

Embodiment 5

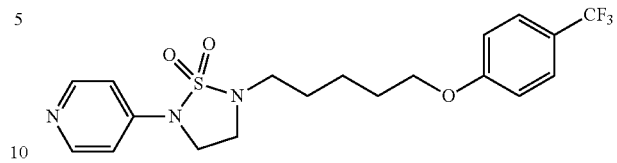

Embodiment 5A 1-(5-bromo-pentyl) oxy-4-trifluoromethyl benzene

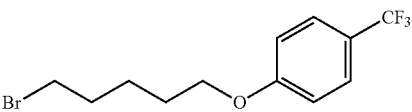 [SMILES: FC(F)(F)c1ccc(OCCCCCBr)cc1]

Please refer to the preparation method of Embodiment 4G for this embodiment. $^1$H-NMR (400 MHz, CDCl$_3$) δ 7.54 (d, J=8.53 Hz, 2H), 6.95 (d, J=8.53 Hz, 2H), 4.01 (t, J=6.27 Hz, 2H), 3.42-3.51 (m, 2H), 1.95 (quin, J=7.15 Hz, 2H), 1.76-1.89 (m, 2H), 1.61-1.68 (m, 2H).

Embodiment 5B 2-(pyridin-4-yl)-5-(5-(4-trifluoromethyl-phenoxy) pentyl)-1,2,5-thiadiazolidine-1,1-dioxide

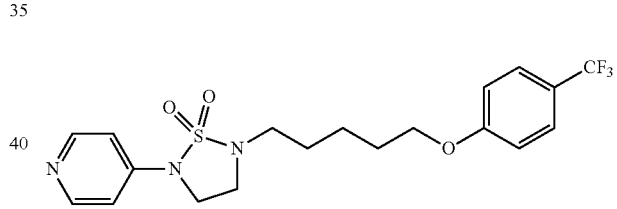

Please refer to the preparation method of Embodiment 4H for this embodiment. $^1$H-NMR (400 MHz, CDCl$_3$) δ 8.53 (d, J=6.27 Hz, 2H), 7.50-7.60 (m, 2H), 7.07 (d, J=6.27 Hz, 2H), 6.96 (d, J=8.78 Hz, 2H), 4.04 (t, J=6.27 Hz, 2H), 3.87 (t, J=6.40 Hz, 2H), 3.57 (t, J=6.40 Hz, 2H), 3.21 (t, J=7.15 Hz, 2H), 1.86-1.94 (m, 2H), 1.77-1.85 (m, 2H), 1.60-1.68 (m, 2H).

Embodiment 6

2-(5-((4'-chloro-[1,1'-biphenyl]-4-yl)oxy) pentyl)-5-(pyridin-4-yl)-1,2,5-thiadiazolidine-1,1-dioxide

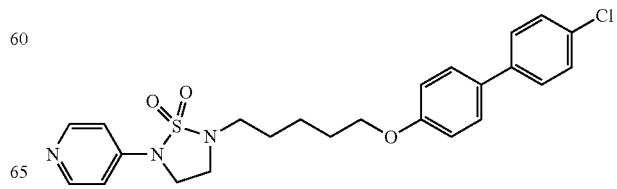

Embodiment 6A

4'-chloro-[1,1'-biphenyl]-4-ol

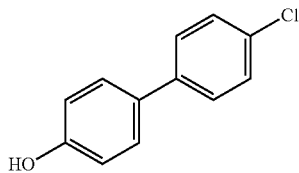 [SMILES: Oc1ccc(-c2ccc(Cl)cc2)cc1]

Mix 4-bromophenol (62 g, 360 mmol), 4-chlorophenyl boronic acid (56 g, 360 mmol), Pd(dppf)Cl$_2$ (10 g, 10 mmol) and Na$_2$CO$_3$ (76 g, 720 mmol) into THF/H$_2$O (600 ml/100 ml) and heat this mixture 6 hours at 70° C. under the protection of N$_2$. Pour the reaction mixture into water and extract with ethyl acetate. Dry the combined organic phases with anhydrous Na$_2$SO$_4$ before filter and evaporate. Then purify the residue with chromatography column (petroleum ether:ethyl acetate=20:1) to obtain the title compound (60 g, yield of 80%). LCMS(ESI) m/z: 205 (M+1).

Embodiment 6B 4-((5-bromopentyl)oxy)-4'-chloro-1,1'-biphenyl

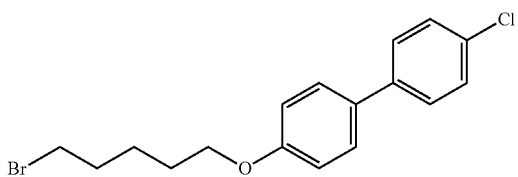 [SMILES: Clc1ccc(-c2ccc(OCCCCCBr)cc2)cc1]

Add 1,5-dibromopentane (67 g, 293.2 mmol), K$_2$CO$_3$ (27 g, 195.4 mmol) and KI (1.62 g, 9.77 mmol) into the solution of Embodiment 6A (20 g, 97.72 mmol) in acetone (200 ml). After the substances are added, heat the mixture solution 12 hours at 80° C. After the reaction is completed, filter the reaction solution and then concentrate the filtrate. Then add petroleum ether (200 ml) into the residue and agitate the system 2 hours at 0° C. before filter to obtain the solid as the title compound (white solid, 25 g, yield of 75%). $^1$H-NMR (400 MHz, CDCl$_3$) 7.48 (dd, J=2.01, 8.53 Hz, 4H), 7.35-7.41 (m, 2H), 6.91-7.00 (m, 2H), 3.96-4.06 (m, 2H), 3.41-3.50 (m, 2H), 1.96 (q, J=7.15 Hz, 2H), 1.80-1.90 (m, 2H), 1.60-1.71 (m, 2H).

Embodiment 6C 2-(5-((4'-chloro-[1,1'-biphenyl]-4-yl)oxy)pentyl)-5-(pyridin-4-yl)-1,2,5-thiadiazolidine-1,1-dioxide

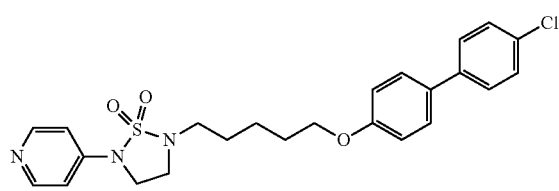 [SMILES: O=S1(=O)N(CCCCCOc2ccc(-c3ccc(Cl)cc3)cc2)CCN1c1ccncc1]

At 0° C., add sodium hydride (10 mg, 0.4 mmol, 60% content) into the solution of Embodiment 4F (40 mg, 0.2 mmol) in N,N-dimethylformamide (10 ml). Then agitate it 0.5 hour at 0° C. before add the solution of Embodiment 6B (71 mg, 0.2 mmol) in N,N-dimethylformamide (2 ml). Continue to agitate it to react 2 hours at 15° C. Then add water to quench the reaction and extract the aqueous phase with ethyl acetate. Dry the combined organic phases with anhydrous Na$_2$SO$_4$ before evaporate. Then purify the residue with HPLC to obtain the title compound (white solid, 10 mg, yield of 11%). $^1$H-NMR (CDCl$_3$, 400 MHz) δ 8.51 (d, J=6.3 Hz, 2H), 7.50-7.44 (m, 4H), 7.41-7.34 (m, 2H), 7.10-7.04 (m, 2H), 6.95 (d, J=8.8 Hz, 2H), 4.02 (t, J=6.3 Hz, 2H), 3.89-3.81 (m, 2H), 3.55 (t, J=6.4 Hz, 2H), 3.19 (t, J=7.2 Hz, 2H), 1.90-1.84 (m, 2H), 1.82-1.78 (m, 2H), 1.67-1.58 (m, 2H), LCMS (ESI) m/z: 472 (M+1).

Embodiment 7

(E)-4-((5-(1,1-dioxo-5-(pyridin-4-yl)-1,2,5-thiadiazol-2-yl)pentyl)oxy)benzaldehyde-O-ethyl oxime

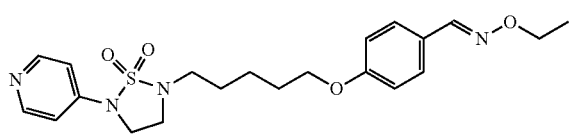 [SMILES: CCO/N=C/c1ccc(OCCCCCN2CCN(c3ccncc3)S2(=O)=O)cc1]

Embodiment 7A (E)-4-hydroxybenzaldehyde-oxo-ethyl oxime

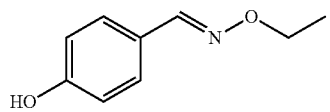

Add sodium acetate (3.36 g, 40.94 mmol) into the solution of p-hydroxy benzaldehyde (2.5 g, 20.47 mmol) and ethoxycarbonyl amino hydrochloride (3.91 g, 40.94 mmol) in water (50 ml) and agitate the mixture 4 hours at 80° C. Add ethyl acetate (50 ml) into the reaction system. Extract the aqueous layer with ethyl acetate (50 ml×3) and then dry the combined organic layers with Na$_2$SO$_4$ before filter and evaporate to obtain the title compound (brown solid, 3 g, yield of 89%). $^1$H-NMR (CDCl$_3$, 400 MHz) 8.03 (s, 1H), 7.46 (d, J=8.5 Hz, 2H), 6.78-6.85 (m, 2H), 4.20 (q, J=7.0 Hz, 2H), 1.31 (t, J=7.0 Hz, 3H).

Embodiment 7B (E)-4-((5-bromo-pentyl)-oxy) benzaldehyde-oxo-ethyloxime

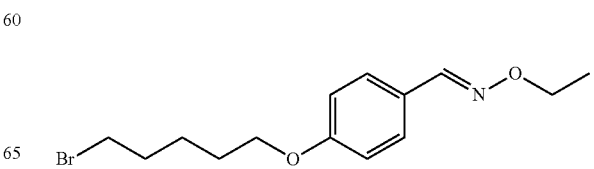

Mix Embodiment 7A (1.0 g, 6.05 mmol), 1,5-dibromopentane (1.39 g, 6.05 mmol), K$_2$CO$_3$ (1.67 g, 12.11 mmol) and KI (0.1 g, 0.605 mmol) into acetone (100 ml). Then heat to reflux 10 hours. Filter and then dry the filtrate through rotation before purify with chromatography column to obtain the title compound (white crystal, 1.2 g, 63%).
$^1$H-NMR(CDCl$_3$, 400 MHz) δ8.01-8.05 (m, 1H), 7.49-7.55 (m, 2H), 6.86-6.91 (m, 2H), 4.17-4.24 (m, 2H), 3.96-4.01 (m, 2H), 3.41-3.47 (m, 2H), 1.89-1.99 (m, 2H), 1.78-1.86 (m, 2H), 1.60-1.68 (m, 2H), 1.29-1.34 (m, 3H).

Embodiment 7C (E)-4-((5-(1,1-dioxo-5-(pyridin-4-yl)-1,2,5-thiadiazolidine-2-yl)-pentyl)-oxy)-benzaldehyde-O-ethyloxime

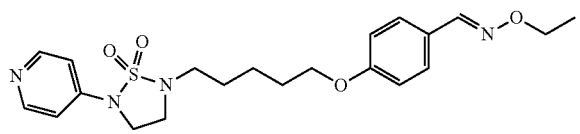 [SMILES: CCO/N=C/c1ccc(OCCCCCN2CCN(c3ccncc3)S2(=O)=O)cc1]

At 0° C., add sodium hydroxide (10 mg, 250 mmol, 60% content) in batch into the solution of Embodiment 4F (60 ml, 301.2 mmol) in N,N-dimethylformamide (1 ml) and then agitate 1.5 hours. Then drop the solution of Embodiment 7B (114 mg, 361.4 mmol) in N,N-dimethylformamide (0.5 ml) and heat it to room temperature before agitating for 2 hours. Then pour it into water (10 ml) and extract with ethyl acetate (3 ml×3). Then dry the combined organic phases with anhydrous Na$_2$SO$_4$ and dry through rotation. Then purify with preparative HPLC to obtain the title compound (white solid, 40 mg, yield of 30.7%).

$^1$H-NMR(CDCl$_3$, 400 MHz) δ8.53 (d, J=6.02 Hz, 1H), 8.04 (s, 1H), 7.53 (d, J=8.78 Hz, 2H), 7.07 (d, J=6.27 Hz, 2H), 6.89 (d, J=8.78 Hz, 2H), 4.22 (q, J=7.03 Hz, 2H), 4.02 (t, J=6.27 Hz, 2H), 3.87 (t, J=6.40 Hz, 2H), 3.56 (t, J=6.40 Hz, 2H), 3.20 (t, J=7.15 Hz, 2H), 1.85-1.93 (m, 2H), 1.76-1.84 (m, 2H), 1.67 (br.s., 2H), 1.34 (t, J=7.03 Hz, 3H). LCMS(ESI) m/z: 433 (M+1).

Embodiment 8

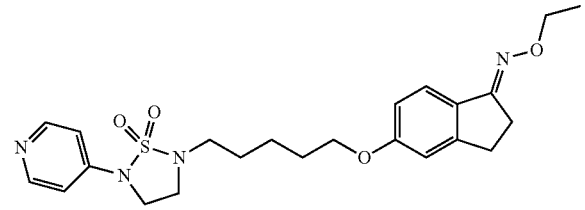 [SMILES: CCO/N=C1\CCc2cc(OCCCCCN3CCN(c4ccncc4)S3(=O)=O)ccc21]

Embodiment 8A 5-hydroxy-2,3-dihydro-1H-inden-1-one

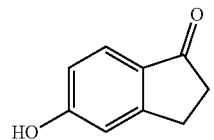

Under the protection of N$_2$ gas, mix 5-bromo-1-indanone (1.0 g, 4.7 mmol), N,N,N',N'-tetramethylethylenediamine (210 mg, 2.37 mmol), K$_3$PO$_4$ (1.0 mg, 4.74 mmol) and CuI (90 mg, 0.47 mmol) into water (5.0 ml). Heat it with microwave for 2 hours at 120° C. After the reactions ends, extract the solution mixture with ethyl acetate (10 ml×3). Dry the combined organic phases with anhydrous Na$_2$SO$_4$ before filter and concentrate. Then purify it with TLC to obtain the title compound (white solid, 120 mg, yield of 17%).
$^1$H-NMR(CDCl$_3$, 400 MHz) δ7.71-7.69 (m, 1H), 6.92-6.87 (m, 2H), 3.11-3.09 (m, 2H), 2.72-2.70 (m, 2H).

Embodiment 8B (E)-5-hydroxy-2,3-dihydro-1H-inden-1-one-O-ethyloxime

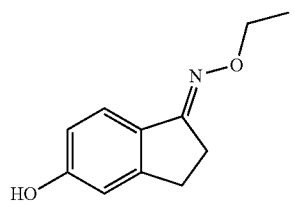

Add ethoxyamino hydrochloride (65 mg, 0.67 mmol) and sodium acetate (55 mg, 0.67 mmol) into the mixture solution of Embodiment 8A (50 mg, 0.3 mmol) and water (5 ml). Heat this mixture solution 1 hour at 80° C. Then extract the aqueous phase with ethyl acetate (5.0 ml×3). Dry the combined organic phases with anhydrous Na$_2$SO$_4$ before filter and concentrate to obtain the crude product that will be used directly in the following reaction.
$^1$H-NMR(CDCl$_3$, 400 MHz) δ7.52-7.66 (m, 1H), 6.68-6.87 (m, 2H), 4.12-4.30 (m, 2H), 2.78-3.07 (m, 4H), 1.27-1.41 (m, 3H).

Embodiment 8C (E)-5-((5-bromo-pentyl)-oxy-)-2,3-dihydro-1H-inden-1-one-O-ethyloxime

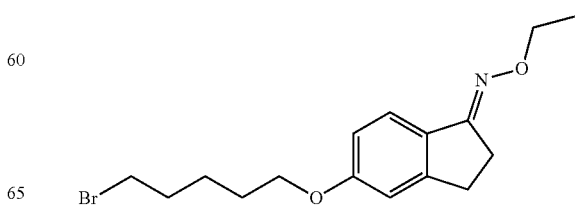

Add 1,5-dibromopentane (288 mg, 1.26 mmol, 3.0 equivalent), K₂CO₃ (578 mg, 4.18 mmol, 10 equivalent) and KI (7 mg, 0.04 mmol, 0.1 equivalent) into the mixture solution of Embodiment 8B (80 mg, 0.4 mmol) and acetone (5.0 ml). Then heat this mixture solution 5 hours at 80° C. Filter the reaction solution before concentrate the filtrate. Then purify the residue obtained from concentrating with TLC to obtain the title compound (yellow solid, 140 mg, yield of 98%). LCMS(ESI) m/z: 340 (M+1).

Embodiment 8D (E)-2-(5-((1-(ethoxy-imino)-2,3-dihydro-1H-inden-5-yl)-oxy)-pentyl)-5-(pyridin-4-yl)-1,2,5-thiadiazole-1,1-dioxide

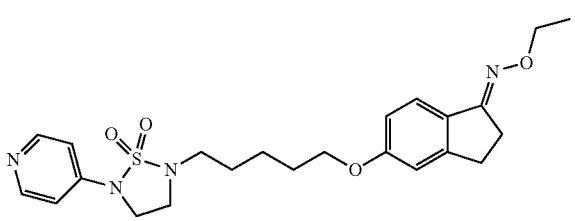 [SMILES: CCO/N=C1\CCc2cc(OCCCCCN3CCN(c4ccncc4)S3(=O)=O)ccc21]

Under the protection of N₂ gas, add sodium hydride (8 mg, 0.2 mmol) into the solution of Embodiment 4F (20 mg, 0.10 mmol) in N,N-dimethylformamide (1.0 ml). Agitate it 0.5 hour at 0° C., then add slowly the solution of Embodiment 8C (34 mg, 0.1 mmol) in N,N-dimethylformamide (1.0 ml) into the solution above. Agitate it at 15° C. to react over night. Then add water (0.5 ml) to quench the reaction and then extract the aqueous phase with dichloromethane. Then dry the combined organic phases with anhydrous Na₂SO₄ before filter and evaporate. Then purify the residue with the preparative HPLC to obtain the title compound (17 mg, yield of 37%).

¹H-NMR(CDCl₃, 400 MHz) δ8.50 (d, J=5.0 Hz, 2H), 7.59 (d, J=9.5 Hz, 1H), 7.05 (d, J=5.5 Hz, 2H), 6.74-6.82 (m, 2H), 4.19 (q, J=7.0 Hz, 2H), 3.96-4.08 (m, 2H), 3.84 (t, J=5.8 Hz, 2H), 3.50-3.58 (m, 2H), 3.17 (t, J=7.0 Hz, 2H), 2.94-3.11 (m, 2H), 2.81-2.9 (m, 2H), 1.72-1.94 (m, 4H), 1.56-1.68 (m, 2H), 1.22-1.40 (m, 3H). LCMS(ESI) m/z: 459 (M+1).

Embodiment 9

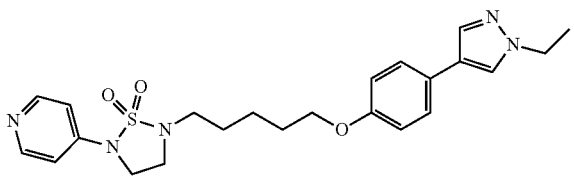 [SMILES: CCn1cc(-c2ccc(OCCCCCN3CCN(c4ccncc4)S3(=O)=O)cc2)cn1]

Embodiment 9A 1-bromo-4-((5-bromo-pentyl)-oxy)-benzene

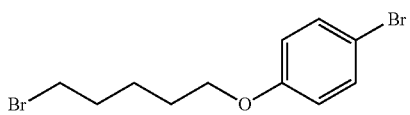 [SMILES: BrCCCCCOc1ccc(Br)cc1]

Add 1,5-dibromopentane (19.95 g, 86.7 mmol), K₂CO₃ (8 g, 57.8 mmol) and KI (0.4 g, 2.89 mmol) into the solution of 4-bromophenol (5 g, 28.9 mmol) in acetone (50 ml). After the substances are added, agitate the mixture solution 12 hours at 80° C. Filter before concentrate the filtrate. Then add the petroleum ether (100 ml) into the concentrated residue and then agitate 1 hour at 0° C. before filter to obtain the title compound (yellow solid, 4 g, yield of 43%).

¹H-NMR(CDCl₃, 400 MHz) δ7.37-7.39 (m, 1H), 7.34-7.36 (m, 1H), 6.77-6.79 (m, 1H), 6.75-6.77 (m, 1H), 3.93 (t, J=6.27 Hz, 2H), 3.44 (t, J=6.78 Hz, 2H), 1.90-1.99 (m, 2H), 1.75-1.84 (m, 2H), 1.58-1.67 (m, 2H). LCMS(ESI) m/z: 323 (M+1).

Embodiment 9B 4-(4-((5-bromo-pentyl)-oxy)-phenyl)-1-ethyl-1H-pyrazole

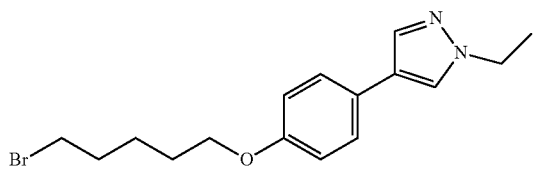 [SMILES: CCn1cc(-c2ccc(OCCCCCBr)cc2)cn1]

Under the protection of N₂ gas at 25° C., add the catalyst Pd(dppf)Cl₂ (9 mg, 12.4 mmol) into the mixture solution of Embodiment 9A (80 mg, 0.25 mmol), 1-ethyl-4-boronic acid pinacol ester (55 mg, 0.25 mmol) and Na₂CO₃ (53 mg, 0.5 mmol) in 1,4-dioxane (3 ml) and water (0.5 ml). Then agitate it 16 hours at 80° C. and add water (10 ml). Extract the aqueous layer with dichloromethane (10 ml×3). Then dry the combined organic layer with Na₂SO₄ before filter and evaporate. Then purify the residue with the preparative TLC to obtain the title compound (white solid, 26 mg, yield of 31%).

¹H-NMR(CDCl₃, 400 MHz) δ7.70 (s, 1H), 7.52-7.60 (m, 1H), 7.38 (d, J=8.8 Hz, 2H), 6.89 (d, J=8.8 Hz, 2H), 4.20 (q, J=7.3 Hz, 2H), 3.98 (t, J=6.4 Hz, 2H), 3.45 (t, J=6.8 Hz, 2H), 1.95 (q, J=7.2 Hz, 2H), 1.77-1.86 (m, 2H), 1.60-1.71 (m, 2H), 1.49-1.54 (m, 3H).

Embodiment 9C 2-(5-(4-(1-ethyl-1H-pyrazol-4-yl) phenoxy) pentyl)-5-(pyridin-4-yl)-1,2,5-thiadiazolidine-1,1-dioxide

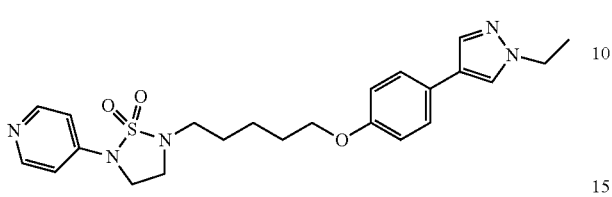

Please refer to the preparation method of Embodiment 8D for this embodiment.

$^1$H-NMR(CDCl$_3$, 400 MHz) δ8.51 (d, J=6.5 Hz, 2H), 7.70 (s, 1H), 7.56 (s, 1H), 7.38 (d, J=8.5 Hz, 2H), 7.05 (d, J=6.3 Hz, 2H), 6.89 (d, J=8.8 Hz, 2H), 4.17-4.23 (m, 2H), 3.99 (t, J=6.1 Hz, 2H), 3.83-3.86 (m, 2H), 3.53-3.56 (m, 2H), 3.18 (t, J=7.2 Hz, 2H), 1.70-1.99 (m, 4H), 1.64 (s, br., 2H), 1.57-1.58 (m, 3H). LCMS(ESI) m/z: 456 (M+1).

Embodiment 10

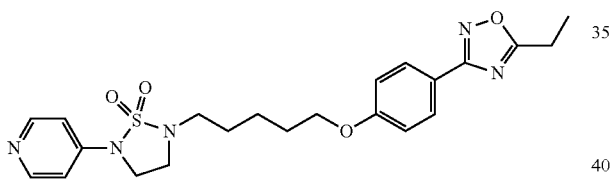

Embodiment 10A

N', 4-dihydroxyphenyl formamidine

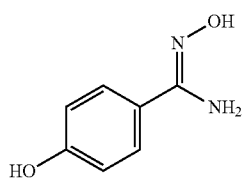 [SMILES: N/C(=N\O)c1ccc(O)cc1]

Add DIPEA (42 g, 419 mmol) and NH$_2$OH.HCl (29.1 mg, 1.15 mmol) into the 4-hydroxy-nitrile (5 g, 42 mmol) in isopropanol (90 ml). Heat this mixture solution 4 hours at 80° C. After cool it to room temperature, filter the solution to obtain the solid as the title compound (4 g, yield of 62.6%).

$^1$H-NMR(CDCl$_3$, 400 MHz) δ7.50 (d, J=8.5 Hz, 2H), 6.82 (d, J=8.5 Hz, 2H). LCMS(ESI) m/z: 153 (M+1).

Embodiment 10B 4-(5-ethyl-1,2,4-oxadiazol-3-yl)-phenol

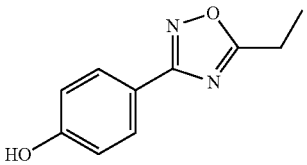

At 0° C., add propionic anhydride (2.57 g, 19.57 mmol) into the solution of Embodiment 10A (3 g, 19.57 mmol) in pyridine (10 ml). After the substances are added, heat the mixture solution 1 hour at 60° C. Cool the reaction solution to room temperature and then concentrate it under vacuum before purity with column chromatography (petroleum ether:ethyl acetate=10:1) to obtain the title compound (3 g, yield of 80%).

$^1$H-NMR(CDCl$_3$, 400 MHz) δ7.97 (d, J=8.5 Hz, 2H), 6.94 (d, J=8.5 Hz, 2H), 2.99 (q, J=7.6 Hz, 2H), 1.46 (t, J=7.5 Hz, 3H). LCMS(ESI) m/z: 191 (M+1).

Embodiment 10C 3-(4-((5-bromo-pentyl)oxy) phenyl)-5-ethyl-1,2,4-oxadiazole

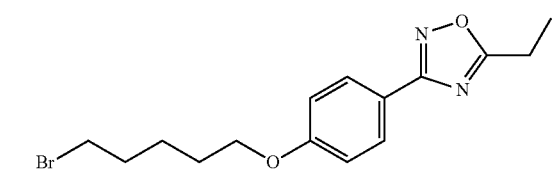 [SMILES: CCc1nc(-c2ccc(OCCCCCBr)cc2)no1]

Add cesium carbonate (34.26 g, 105.15 mmol) and 1,5-dibromopentane (36.27 g, 157.73 mmol) into the solution of Embodiment 10B (10 g, 52.58 mmol) in N,N-dimethylformamide (100 ml). Agitate the mixture solution 12 hours at 10° C. Then extract it with ethyl acetate. Dry the organic phase with anhydrous Na$_2$SO$_4$ before filter and evaporate. Then purify the residue with column chromatography (petroleum ether:ethyl acetate=10:1) to obtain the title compound (white solid, 10 g, yield of 56%).

$^1$H-NMR(CDCl$_3$, 400 MHz) δ8.02 (d, J=8.5 Hz, 2H), 6.95-7.03 (m, 2H), 4.00-4.08 (m, 2H), 3.41-3.51 (m, 2H), 2.97 (q, J=7.6 Hz, 2H), 1.92-2.01 (m, 2H), 1.82-1.91 (m, 2H), 1.64-1.71 (m, 2H), 1.46 (t, J=7.5 Hz, 3H). LCMS(ESI) m/z: 339 (M+1).

Embodiment 10D 2-(5-(4-(5-ethyl-1,2,4-oxadiazol-3-yl)-phenoxy)-pentyl)-5-(pyridin-4-yl)-1,2,5-thiadiazolidine-1,1-dioxide

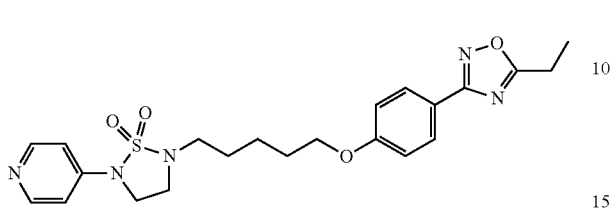

At 0° C., add sodium hydride (3.6 mg, 0.15 mmol) into the solution of Embodiment 4F (20 mg, 0.1 mmol) in N,N-dimethylformamide (5 ml). Keep it still 30 minutes at 0° C. Then add the solution of Embodiment 10C (34 mg, 0.1 mmol) in N,N-dimethylformamide (1 ml) into the aforementioned mixture solution. Agitate it 4 hours at 15° C. Then add water to quench the reaction and extract the aqueous phase with ethyl acetate. Dry the combined organic phases with anhydrous $Na_2SO_4$ before filter and evaporate to obtain the title compound (white solid, 3 mg, yield of 7%).

$^1$H-NMR (400 MHz, $CDCl_3$) δ8.51 (d, J=5.0 Hz, 2H), 8.00 (d, J=9.0 Hz, 2H), 7.05 (d, J=6.3 Hz, 2H), 6.96 (d, J=8.8 Hz, 2H), 4.04 (t, J=6.1 Hz, 2H), 3.85 (t, J=6.4 Hz, 2H), 3.54 (t, J=6.4 Hz, 2H), 3.19 (t, J=7.3 Hz, 2H), 2.96 (q, J=7.5 Hz, 2H), 1.91-1.76 (m, 4H), 1.68-1.62 (m, 2H), 1.44 (t, J=7.7 Hz, 3H). LCMS(ESI) m/z: 458 (M+1).

Embodiment 11

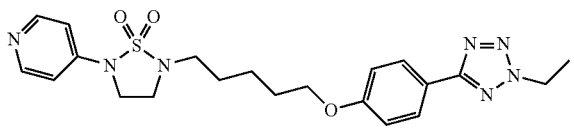 [SMILES: CCn1nnc(-c2ccc(OCCCCCN3CCN(c4ccncc4)S3(=O)=O)cc2)n1]

Embodiment 11A 5-(4-methoxyphenyl)-1H-tetrazole

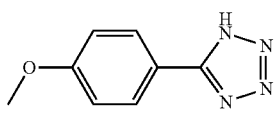

Add sodium azide (3.2 g, 496 mmol) and $NH_4Cl$ (600 mg, 11.2 mmol) into the solution of 4-methoxybenzonitrile (6 g, 450 mmol) in N,N-dimethylformamide (60 ml). Heat the mixture solution 24 hours at 110° C. Cool it to room temperature before add water and then extract with dichloromethane. Then add 1 mol/L HCl into the aqueous phase to adjust the pH value to 8 and filter the aqueous phase to obtain the solid as the title compound (white solid, 7 g, yield of 88%). $^1$H-NMR($CDCl_3$, 400 MHz) δ7.96 (d, J=8.8 Hz, 2H) 7.13 (d, J=8.8 Hz, 2H) 3.90 (s, 3H). LCMS(ESI) m/z: 177 (M+1).

Embodiment 11B 2-ethyl-5-(4-methoxyphenyl)-2H-tetrazolium

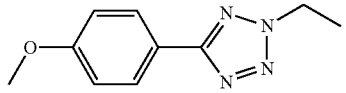

At 0° C., add $K_2CO_3$ (4.71 g, 34.06 mmol) and iodoethane (2.92 g, 18.73 mmol) into the solution of Embodiment 11A (3 g, 17.07 mmol) in acetonitrile (30 ml). After the substances are added, heat the mixture solution 5 hours at 100° C. Cool the reaction solution to room temperature and then concentrate under vacuum before purity with column chromatography (petroleum ether:ethyl acetate=10:1) to obtain the title compound (white solid, 2.1 g, yield of 60%).

$^1$H-NMR($CDCl_3$, 400 MHz) δ8.08 (d, J=8.5 Hz, 2H) 7.00 (d, J=8.5 Hz, 2H) 4.68 (q, J=7.2 Hz, 2H) 3.87 (s, 3H) 1.68 (t, J=7.5 Hz, 3H). LCMS(ESI) m/z: 205 (M+1).

Embodiment 11C 4-(2-ethyl-2H-tetrazol-5-yl)-phenol

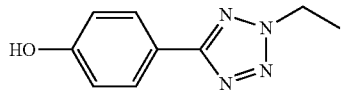

Add 10 ml hydrogen bromide in acetic acid into Embodiment 11B (1 g, 450 mmol). Heat this mixture solution 24 hours at 110° C. Then cool the reaction solution to room temperature and add it into ice water. Filter the aqueous phase to obtain the solid as the title compound (white solid, 0.7 g, yield of 75.2%).

$^1$H-NMR($CDCl_3$, 400 MHz) δ8.08 (d, J=8.5 Hz, 2H), 7.00 (d, J=8.5 Hz, 2H), 4.68 (q, J=7.2 Hz, 2H), 3.87 (s, 2H), 1.68 (t, J=7.5 Hz, 3H). LCMS(ESI) m/z: 191 (M+1).

Embodiment 11D 5-(4-((5-bromo-pentyl)-oxy)-phenyl)-2-ethyl-2H-tetrazolium

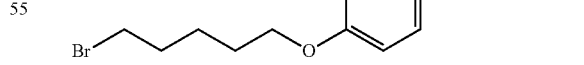

Add $K_2CO_3$ (0.653 g, 4.73 mmol) and 1,5-dibromopentane (1.09 g, 4.73 mmol) into the solution of Embodiment 11C (0.3 g, 1.58 mmol) in acetone (5 ml). Agitate the mixture solution 12 hours at 80° C. Then extract it with ethyl acetate. Dry the organic phase with anhydrous $Na_2SO_4$ before filter and evaporate. Then purify the residue with column chromatography (petroleum ether:ethyl acetate=10:1) to obtain the title compound (white solid, 0.3 g, yield of 56%).

¹H-NMR(CDCl₃, 400 MHz) δ8.08 (d, J=8.8 Hz, 2H), 7.01 (d, J=8.8 Hz, 2H), 4.70 (q, J=7.4 Hz, 2H), 4.05 (t, J=6.4 Hz, 2H), 3.44-3.52 (m, 2H), 1.93-2.03 (m, 2H), 1.83-1.91 (m, 2H), 1.64-1.73 (m, 5H). LCMS(ESI) m/z: 340 (M+1).

Embodiment 11E 2-(5-(4-(2-ethyl-2H-tetrazol-5-yl)-phenoxy) pentyl)-5-(pyridin-4-yl)-1,2,5-thiadiazolidine-1,1-dioxide

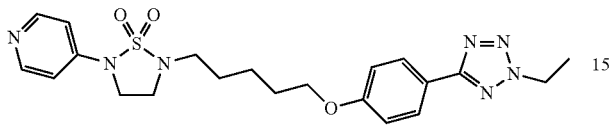

At 0° C., add sodium hydride (7 mg, 0.17 mmol, 60% content) into the solution of Embodiment 4F (30 mg, 0.15 mmol) in N,N-dimethylformamide (2 ml). Keep it still 30 minutes at 0° C. Then add the solution of Embodiment 11D (51 mg, 0.15 mmol) in N,N-dimethylformamide (1 ml) into the mixture solution above. Agitate it 6 hours at 15° C. Then add water to quench the reaction and extract the aqueous phase with ethyl acetate. Dry the combined organic phases with anhydrous Na₂SO₄ before filter and evaporate to obtain the title compound (white solid, 5 mg, yield of 7.26%).

¹H-NMR (400 MHz, CDCl₃): δ8.51 (d, J=6.5 Hz, 2H), 8.06 (d, J=8.5 Hz, 2H), 7.05 (d, J=6.0 Hz, 2H), 6.99 (d, J=9.0 Hz, 2H), 4.68 (q, J=7.5 Hz, 2H), 4.04 (t, J=6.0 Hz, 2H), 3.85 (t, J=6.3 Hz, 2H), 3.55 (t, J=6.3 Hz, 2H), 3.19 (t, J=7.3 Hz, 2H), 1.85-1.93 (m, 2H), 1.75-1.82 (m, 2H), 1.68 (t, J=7.5 Hz, 5H). LCMS(ESI) m/z: 458 (M+1).

Embodiment 12

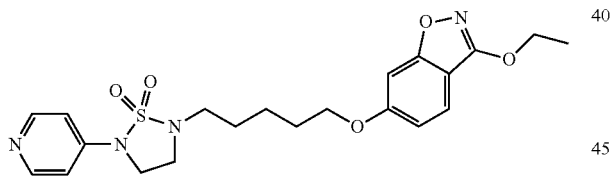

Embodiment 12A

N, 2-dihydroxy-4-methoxybenzamide

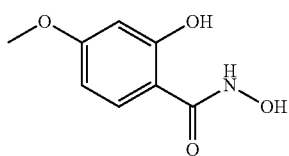

With magnetic stirring, drop slowly the solution of NaOH (71 g, 1.78 mol) in water (250 ml) into the solution of hydroxylamine hydrochloride (53 g, 766 mmol) in water (500 ml). Under the protection of N₂ gas, immediately drop slowly the solution of 4-methoxy salicylate (93 g, 510 mmol) in dioxane (250 ml) into the solution above to react 12 hours. After the reaction ends, add slowly the reaction solution into ice water before drop the concentrated hydrochloric acid until the pH value becomes 2. Then filter to obtain the title compound (84 g, yield of 90%).

¹H-NMR (400 MHz, MeOD) δ7.57 (d, J=9.04 Hz, 1H), 6.41-6.54 (m, 2H), 3.75-3.87 (m, 3H). LCMS(ESI) m/z: 184 (M+1).

Embodiment 12B 6-methoxy-benzo[d]isoxazol-3 (2H)-one

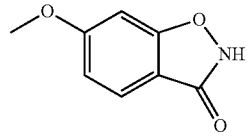

Drop Embodiment 12A (40 g, 0.22 mol) into the solution of carbonyl diimidazole (50 g, 0.31 mol) in anhydrous THF (600 ml). After the dropping is completed, heat to reflux 8 hours. After the reaction ends, dry the reaction solution through rotation. Then add 400 ml water and adjust it with citric acid to pH=6. Then filter to obtain the title compound (23 g, yield of 63%).

¹H-NMR (400 MHz, MeOD) δ7.57 (d, J=8.53 Hz, 1H), 6.97 (d, J=1.51 Hz, 1H), 6.91 (dd, J=1.76, 8.78 Hz, 1H), 3.84-3.93 (m, 3H). LCMS(ESI) m/z: 166 (M+1).

Embodiment 12C 3-ethoxy-6-methoxy-benzo[d]isoxazole

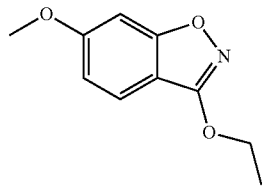

In ice bath, add sequentially anhydrous ethanol (3.5 g, 76 mmol) and triphenylphosphine (24 g, 90 mmol) into the solution of Embodiment 12B (10 g, 60 mmol) in anhydrous THF (200 ml). Then add slowly DIAD (18 ml, 90 mmol) into the solution above and agitate it to react 15 minutes at 0° C. Heat slowly it to room temperature and agitate over night. After the reaction ends, add water (200 ml) to quench the reaction. Then extract the aqueous layer with ethyl acetate (200 ml×2). Then wash the combined organic layers with water and saline water sequentially. Then dry it with anhydrous Na₂SO₄ before filter and evaporate. Then purify the residue with the silica gel column chromatography to obtain the title compound (5.6 g, yield of 48%). LCMS(ESI) m/z: 194 (M+1).

Embodiment 12D 3-ethoxy-benzo[d]isoxazole-6-ol

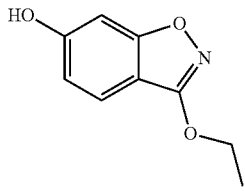

Under the protection of N$_2$ gas at −78° C., drop slowly boron tribromide (4.2 g, 16.8 mmol) into the solution of Embodiment 12C (810 mg, 4.2 mmol) in dichloromethane (10 ml). After the dropping is completed, heat the reaction solution slowly to room temperature and agitate over night. After the reaction is completed, drop slowly the reaction solution into ice water (100 ml) to quench the reaction. Then extract the aqueous layer with ethyl acetate (100 ml×2). Then wash the combined organic layers with water and saline water. Then dry it with anhydrous Na$_2$SO$_4$ before filter and evaporate to obtain the title compound (650 mg, yield of 86.7%).

$^1$H-NMR(CDCl$_3$, 400 MHz) δ7.48 (d, J=8.53 Hz, 1H), 6.90-7.08 (m, 2H), 6.85 (d, J=8.03 Hz, 1H), 4.47 (q, J=7.03 Hz, 2H), 1.51 (t, J=7.03 Hz, 3H).

Embodiment 12E 6-((5-bromo-pentyl)oxy)-3-ethoxypropionate[d]isoxazole

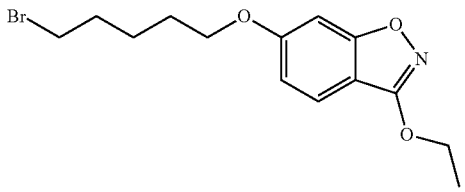 [SMILES: CCOc1noc2cc(OCCCCCBr)ccc12]

Under the protection of N$_2$ gas at 0° C., add sodium hydride (54 mg, 1.34 mmol, 60% content) in batch into the solution of Embodiment 12D (0.2 g, 1.12 mmol) in N,N-dimethylformamide (20 ml). After the substances are added, agitate the mixture solution 1 hour at room temperature, then add the solution of 1,5-dibromopentane (770 ml, 2.33 mmol) in N,N-dimethylformamide (10 ml) into the solution above. Then agitate it to react 10 hours at room temperature. Pour the reaction solution into water (100 ml) and then extract the aqueous phase with ethyl acetate (50 ml×3). Then dry the combined organic phases with anhydrous Na$_2$SO$_4$ before filter and concentrate to obtain the title compound (yellow liquid, 0.2 g, yield of 54.6%). LCMS(ESI) m/z: 328 (M+1).

Embodiment 12F 2-(5-((3-ethoxy-benzo[d]isoxazole-6-yl)-oxy) pentyl)-5-(pyridin-4-yl)-1,2,5-thiadiazolidine-1,1-dioxide

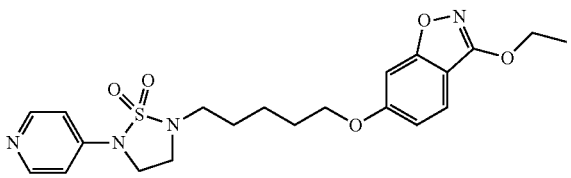 [SMILES: CCOc1noc2cc(OCCCCCN3CCN(c4ccncc4)S3(=O)=O)ccc12]

Under the protection of N$_2$ gas at 0° C., add sodium hydride (24 mg, 0.6 mmol, 60% content) into the solution of Embodiment 4F (60 mg, 0.3 mmol) in N,N-dimethylformamide (3 ml). Agitate it 0.5 hour at 0° C. Then drop the solution of Embodiment 12E (100 mg, 0.3 mmol) in N,N-dimethylformamide (1 ml) dropwise into it. Agitate the reaction mixture 1.5 hours at 0° C. Quench the reaction mixture with the saturated NH$_4$Cl aqueous solution (5 ml). Then dilute it with water (50 ml) and extract with ethyl acetate (15 ml×4). Dry the combined organic phases with the saturated salt water. Then dry with anhydrous Na$_2$SO$_4$ before filter and dry through rotation. Then purify the residue with preparative chromatography to obtain the title compound (white solid, 60 mg, yield of 45%). $^1$H-NMR (400 MHz, CDCl$_3$) δ 8.53 (br.s., 1H), 7.47 (d, J=8.5 Hz, 1H), 7.27 (s, 1H), 7.07 (br.s., 2H), 6.78-6.89 (m, 2H), 4.46 (q, J=7.0 Hz, 2H), 4.03 (t, J=6.2 Hz, 2H), 3.85 (t, J=6.2 Hz, 2H), 3.55 (t, J=6.27 Hz, 2H), 3.19 (t, J=7.28 Hz, 2H), 1.85-1.94 (m, 2H), 1.80 (q, J=7.4 Hz, 2H), 1.64-1.68 (m, 2H), 1.50 (t, J=7.0 Hz, 3H). LCMS (ESI) m/z: 447 (M+1).

Routine C

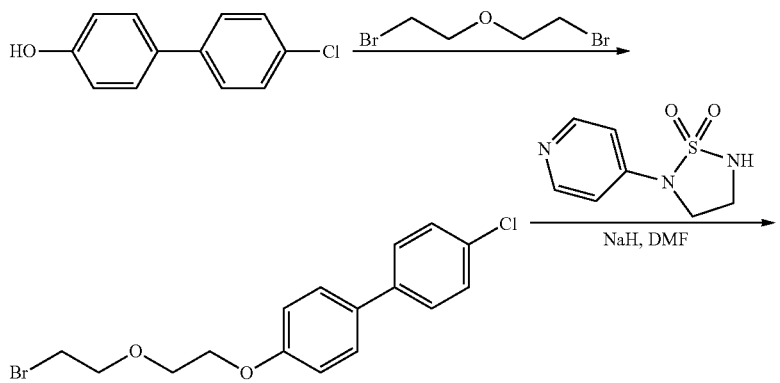

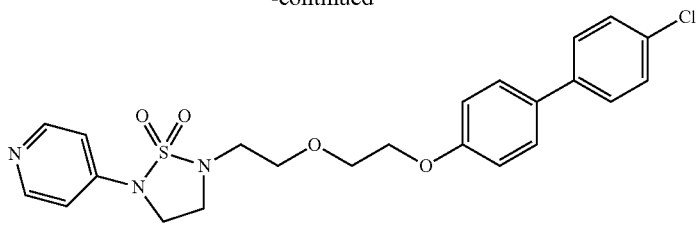

Embodiment 13

2-(2-(2-((4'-chloro-[1,1'-biphenyl]-4-yl)oxy)ethoxy)ethyl)-5-(pyridin-4-yl)-1,2,5-thiadiazolidine-1,1-dioxide

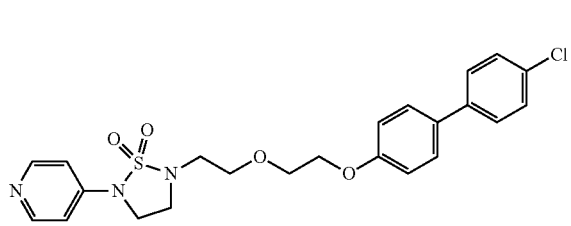 [SMILES: O=S1(=O)N(CCOCCOc2ccc(-c3ccc(Cl)cc3)cc2)CCN1c1ccncc1]

Embodiment 13A 4-(2-(2-bromoethoxy) ethoxy)-4'-chloro-1,1'-biphenyl

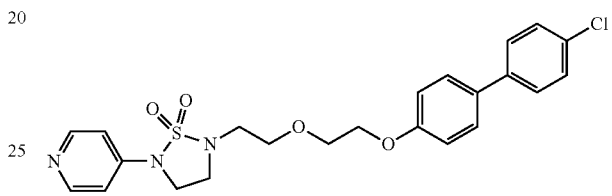

Add 1-bromo-2-(2-bromoethoxy)-ethane (3.4 g, 14.66 mmol) into the mixture of Embodiment 6A (1 g, 4.89 mmol), K₂CO₃ (1.35 g, 9.77 mmol) and KI (810 mg, 4.89 mmol) in acetone (15 ml). Agitate the mixture 3 hours at 70° C. before dry through rotation. Then add 20 ml petroleum ether into the system and filter it to obtain the title compound (1.5 g, yield of 86%).

¹H-NMR(CDCl₃, 400 MHz) 7.47 (dd, J=8.5, 4.0 Hz, 4H), 7.34-7.41 (m, 2H), 6.99 (d, J=8.5 Hz, 2H), 4.16-4.22 (m, 2H), 3.85-3.96 (m, 4H), 3.51 (t, J=6.3 Hz, 2H).

Embodiment 13B 2-(2-(2-((4'-chloro-[1,1'-biphenyl]-4-yl)-oxy)-ethoxy)-ethyl)-5-(pyridin-4-yl)-1,2,5-thiadiazolidine-1,1-dioxide

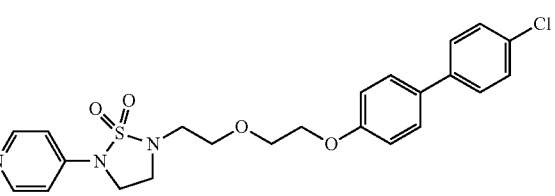

Please refer to the preparation method of Embodiment 12F for this embodiment.

¹H-NMR(CDCl₃, 400 MHz) 8.48 (d, J=6.0 Hz, 2H), 7.45-7.51 (m, 4H), 7.36-7.41 (m, 2H), 7.02 (d, J=6.3 Hz, 2H), 6.98 (d, J=8.8 Hz, 2H), 4.16-4.20 (m, 2H), 3.88 (q, J=4.9 Hz, 4H), 3.76 (dd, J=11.9, 5.1 Hz, 4H), 3.40 (t, J=4.9 Hz, 2H). LCMS(ESI) m/z: 474 (M+1).

Routine D

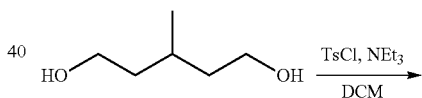

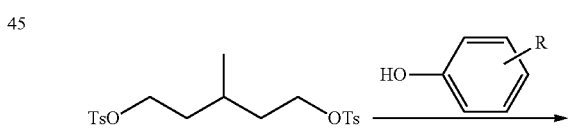

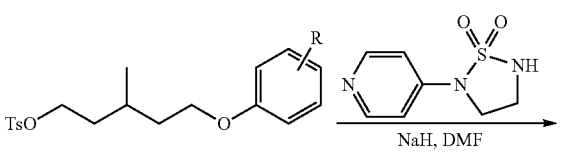

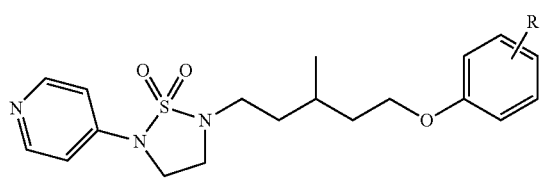

Embodiment 14

(E)-4-((5-(1,1-dioxo-5-(pyridin-4-yl)-1,2,5-thiadi-azolidine-2-yl)-3-methyl-pentyl)-oxy)-benzaldehyde-O-ethyloxime

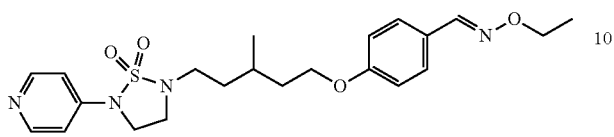

Embodiment 14A 3-methylpentane-1,5-bis (4-methyl-benzenesulfonyl)

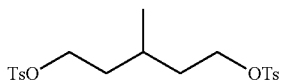 [SMILES: Cc1ccc(S(=O)(=O)OCCC(C)CCOS(=O)(=O)c2ccc(C)cc2)cc1]

Add triethylamine (160 ml) and p-toluensulfonyl chloride (258.1 g, 1.35 mol) into the solution of 3-methyl-1,5-pentanediol (40 g, 338.5 mmol) in dichloromethane (400 ml). Agitate the mixture solution 12 hours at 20° C. Then extract it with ethyl acetate. Dry the combined organic phases with anhydrous $Na_2SO_4$ before filter and evaporate. Then purify the residue with column chromatography (petroleum ether:ethyl acetate=20:1) to obtain the title compound (colorless liquid, 80 g, yield of 55%).

$^1$H-NMR(CDCl$_3$, 400 MHz) δ7.78 (d, J=8.0 Hz, 4H), 7.37 (d, J=8.0 Hz, 4H), 4.01 (q, J=6.0 Hz, 4H), 2.46 (s, 6H) 1.57-1.69 (m, 3H) 1.43 (dq, J=13.4, 6.7 Hz, 2H), 0.78 (d, J=6.3 Hz, 3H). LCMS(ESI) m/z: 299 (M+1).

Embodiment 14B (E)-5-(4-((ethoxyimino)methyl)-phenoxy)-3-methyl-pentyl-4-methylbenzenesulfonyl

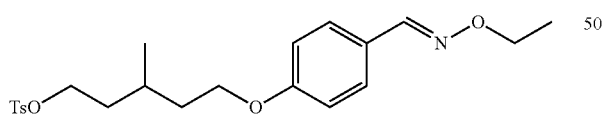

Allow the mixture of Embodiment 7A (4.98 g, 30.17 mmol), Embodiment 14A(11.7 g, 27.43 mmol), $K_2CO_3$ (7.58 g, 54.86 mmol) and acetonitrile (110 ml) to react 16 hours at 80° C. Add ethyl acetate (50 ml) and water (50 ml) into the reaction system. Extract the aqueous layer with ethyl acetate (100 ml×3) and then dry the combined organic layers with $Na_2SO_4$ before filter and evaporate. Then purify the residue with column chromatography to obtain the title compound (colorless solid, 3.7 g, yield of 32%).

$^1$H-NMR(CDCl$_3$, 400 MHz) 8.03 (s, 1H), 7.46 (d, J=8.5 Hz, 2H), 6.78-6.85 (m, 2H), 4.20 (q, J=7.0 Hz, 2H), 1.31 (t, J=7.0 Hz, 3H).

Embodiment 14C (E)-4-((5-(1,1-dioxo-5-(pyridin-4-yl)-1,2,5-thiadi-azolidine-2-yl)-3-methyl-pentyl)-oxy)-benzaldehyde-O-ethyloxime Please refer to the preparation method of Embodiment 12F for this embodiment.

$^1$H-NMR(CDCl$_3$, 400 MHz) δ8.51 (d, J=5.5 Hz, 2H), 8.02 (s, 1H), 7.50 (d, J=8.5 Hz, 2H), 7.04 (d, J=6.0 Hz, 2H), 6.87 (d, J=8.5 Hz, 2H), 4.17-4.24 (m, 2H), 3.98-4.07 (m, 2H), 3.82 (t, J=6.5 Hz, 2H), 3.48-3.55 (m, 2H), 3.20 (t, J=7.5 Hz, 2H), 1.79-1.93 (m, 3H), 1.66-1.73 (m, 1H), 1.56-1.61 (m, 1H), 1.31 (t, J=7.0 Hz, 3H), 1.03 (d, J=6.5 Hz, 3H). LCMS(ESI) m/z: 447 (M+1).

Embodiment 15

2-(5-((3-ethoxy-benzo[d]isoxazole-6-yl)-oxy)-3-methyl-pentyl)-5-(pyridin-4-yl)-1,2,5-thiadiazolidine-1,1-dioxide

Embodiment 15A 5-((3-ethoxy-benzo[d]isoxazole-6-yl)-oxy)-3-methyl-pentyl-4-methylbenzenesulfonate Add $K_2CO_3$ (0.69 g, 5.0 mmol) and Embodiment 14A (2.14 g, 5.0 mmol) into the solution of Embodiment 12D (0.3 g, 1.67 mmol) in N,N-dimethylformamide (5 ml). Agitate the mixture solution 12 hours at 80° C. Then extract it with ethyl acetate. Dry the organic phase with anhydrous $Na_2SO_4$ before filter and evaporate. Then purify the residue with column chromatography (petroleum ether:ethyl acetate=10:1) to obtain the title compound (white solid, 0.3 g, yield of 41.3%).

$^1$H-NMR(CDCl$_3$, 400 MHz) δ7.79 (d, J=8.0 Hz, 2H) 7.46 (d, J=8.5 Hz, 1H) 7.33 (d, J=8.0 Hz, 2H) 6.78-6.84 (m, 2H) 4.47 (q, J=7.0 Hz, 2H) 4.07-4.15 (m, 2H) 3.93-4.01 (m, 2H)

2.43 (s, 3H) 1.74-1.89 (m, 3H) 1.60-1.66 (m, 1H) 1.54-1.58 (m, 1H) 1.51 (t, J=7.0 Hz, 3H) 0.92 (d, J=6.5 Hz, 3H). LCMS(ESI) m/z: 434 (M+1).

Embodiment 15B 2-(5-((3-ethoxy-benzo[d]isoxazole-6-yl)oxy)-3-methyl-pentyl)-5-(pyridin-4-yl)-1,2,5-thiadiazolidine-1,1-dioxide

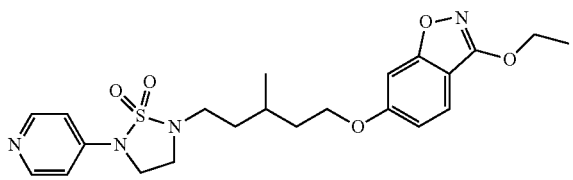 [SMILES: CCOc1noc2cc(OCCC(C)CCN3CCN(c4ccncc4)S3(=O)=O)ccc12]

At 0° C., add sodium hydride (6.62 mg, 0.165 mmol) into the solution of Embodiment 4F (30 mg, 0.15 mmol) in N,N-dimethylformamide (2 ml). Agitate 30 minutes at 0° C. Then add the solution of Embodiment 15A (65 mg, 0.15 mmol) in N,N-dimethylformamide (1 ml) into the mixture solution above. Agitate it 6 hours at 15° C. Then add water to quench the reaction and extract the aqueous phase with ethyl acetate. Dry the combined organic phases with anhydrous $Na_2SO_4$ before filter and evaporate to obtain the title compound (white solid, 18 mg, yield of 25.8%).

$^1$H-NMR (400 MHz, $CDCl_3$) δ8.53 (d, J=6.0 Hz, 2H) 7.46-7.51 (m, 1H) 7.06 (d, J=6.3 Hz, 2H) 6.86 (dd, J=4.3, 2.5 Hz, 2H) 4.48 (q, J=7.0 Hz, 2H) 4.08 (q, J=5.7 Hz, 2H) 3.86 (t, J=6.4 Hz, 2H) 3.50-3.60 (m, 2H) 3.24 (t, J=7.4 Hz, 2H) 1.88-1.99 (m, 2H) 1.77-1.87 (m, 1H) 1.61-1.75 (m, 3H) 1.52 (t, J=7.2 Hz, 3H) 1.07 (d, J=6.3 Hz, 3H). LCMS(ESI) m/z: 461 (M+1).

Routine E

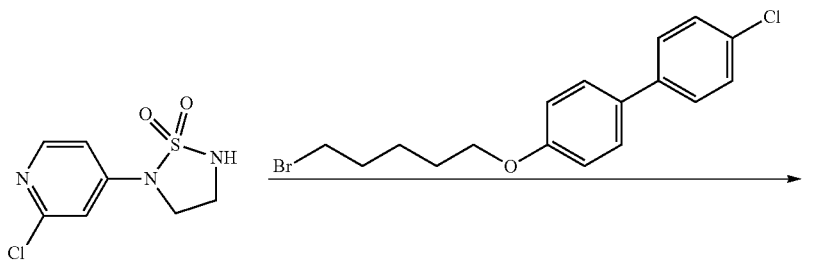

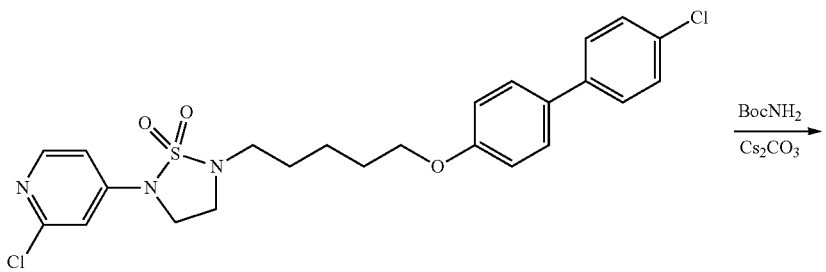

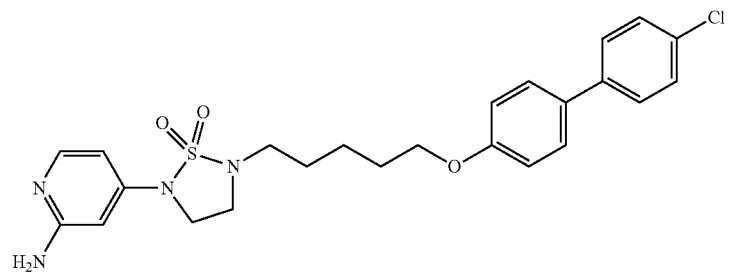

Embodiment 16

2-(2-aminopyridine-4-yl)-5-(5-((4'-chloro-[1,1'-biphenyl]-4-yl)-oxy)-pentyl)-1,2,5-thiadiazolidine-1,1-dioxide

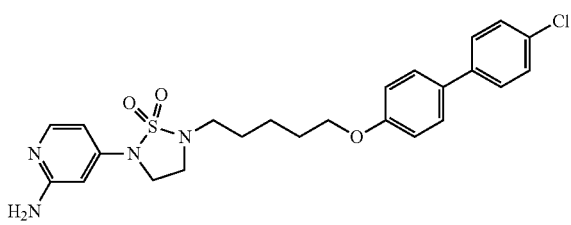 [SMILES: Nc1cc(N2CCN(CCCCCOc3ccc(-c4ccc(Cl)cc4)cc3)S2(=O)=O)ccn1]

Embodiment 16A 2-(5-((4'-chloro-[1,1'-biphenyl]-4-yl)-oxy)-pentyl)-5-(2-chloro-pyridin-4-yl)-1,2,5-thiadiazolidine-1,1-dioxane

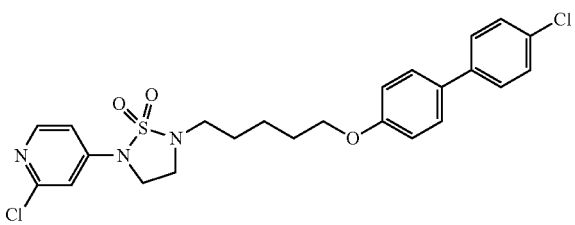 [SMILES: O=S1(=O)N(CCCCCOc2ccc(-c3ccc(Cl)cc3)cc2)CCN1c1ccnc(Cl)c1]

Under the protection of $N_2$ gas at 0° C., add sodium hydride (68 mg, 1.72 mmol, 60% content) in batch into the solution of Embodiment 4E (200 mg, 0.86 mmol) in N,N-dimethylformamide (3 ml). Agitate the reaction solution 0.5 hour at room temperature. Then add the solution of Embodiment 6B (303 mg, 0.86 mmol) in N,N-dimethylformamide (5 ml). Then agitate it 8 hours at room temperature. Add water to quench the reaction. Then, extract it with ethyl acetate (50 ml×3) and dry the combined organic layer with $Na_2SO_4$ before filter and evaporate. Then separate and purify the residue with TLC plate to obtain the title compound (80 mg, yield of 22%).

$^1$H-NMR(CDCl$_3$, 400 MHz) 8.29 (d, J=5.8 Hz, 1H), 7.48-7.52 (m, 4H), 7.38-7.42 (m, 2H), 7.09 (dd, J=5.8, 2.3 Hz, 1H), 7.01 (d, J=2.0 Hz, 1H), 6.98 (d, J=8.8 Hz, 2H), 4.05 (t, J=6.3 Hz, 2H), 3.86 (t, J=6.4 Hz, 2H), 3.58 (t, J=6.4 Hz, 2H), 3.21 (t, J=7.2 Hz, 2H), 1.76-1.95 (m, 4H), 1.63-1.70 (m, 2H). LCMS(ESI) m/z: 506 (M+1).

Embodiment 16B 2-(2-aminopyridine-4-yl)-5-(5-((4'-chloro-[1,1'-biphenyl]-4-yl)-oxy)-pentyl)-1,2,5-thiadiazolidine-1,1-dioxide

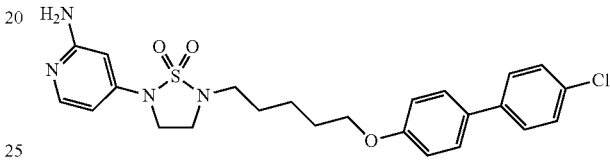

Under the protection of $N_2$ gas, add Pd$_2$(dba)$_3$ (20 mg, 0.03 mmol) and Xant-Phos (10 mg, 0.03 mmol) into the mixture solution of Embodiment 16A (80 mg, 0.16 mmol), tert-butyl carbamate (74 mg, 0.63 mmol) and cesium carbonate (103 mg, 0.32 mmol) in dioxane/N,N-dimethylformamide (1.5 ml/0.5 ml). After the substances are added, agitate the mixture solution 16 hours at 110° C. After remove the solvent under vacuum, extract the residue with ethyl acetate (250 ml×3) and then dry the combined organic layers with Na$_2$SO$_4$ before filter and evaporate. Then purify the residue with the preparative HPLC to obtain the title compound (30 mg, yield of 31%).

$^1$H-NMR(CDCl$_3$, 400 MHz): 7.80 (sbr, 1H), 7.48 (dd, J=8.8, 3.3 Hz, 4H), 7.35-7.41 (m, 2H), 6.96 (d, J=8.5 Hz, 2H), 6.58 (s, br, 1H), 6.33 (s, br, 1H), 4.02 (t, J=6.0 Hz, 2H), 3.87 (s, br, 2H), 3.55 (t, J=6.3 Hz, 2H), 3.19 (t, J=7.3 Hz, 2H), 1.85-1.90 (m, 2H), 1.76-1.82 (m, 2H), 1.63 (d, J=6.5 Hz, 2H). LCMS(ESI) m/z: 487 (M+1).

Routine F

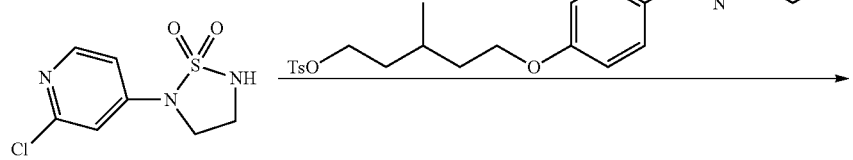

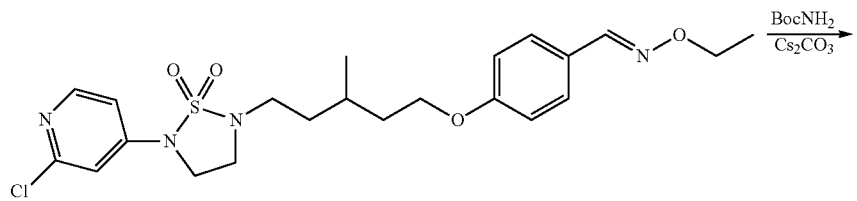

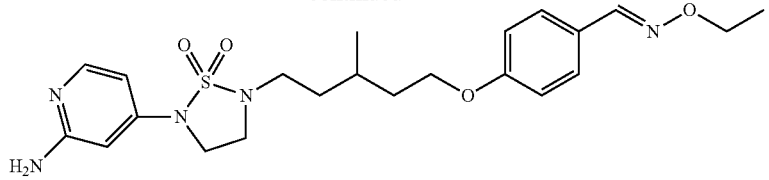

Embodiment 17

(E)-4-((5-(5-(2-amino-pyridin-4-yl)-1,1-dioxo-1,2,5-thiadiazolidine-2-yl)-3-methyl-pentyl)-oxy)-benzaldehyde-O-ethylketoxime

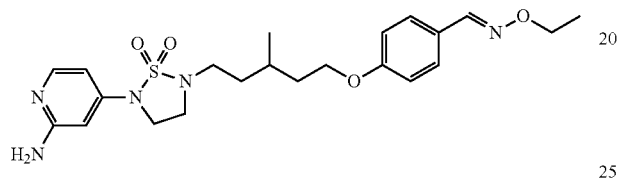

Embodiment 17A (E)-4-((5-(5-(2-chloropyridin-4-yl)-1,1-dioxo-1,2,5-thiadiazolidine-2-yl)-3-methyl-pentyl)-oxy)-benzaldehyde-O-ethylketoxime

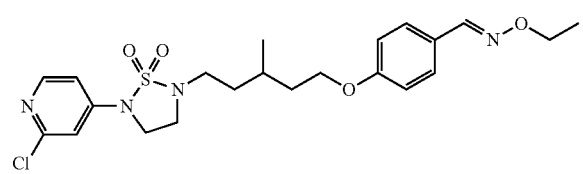

This embodiment is prepared with the method as described in Embodiment 16A.

$^1$H-NMR(CDCl$_3$, 400 MHz): 8.29 (d, J=5.5 Hz, 1H), 8.04 (s, 1H), 7.53 (d, J=8.8 Hz, 2H), 7.08 (dd, J=5.8, 2.0 Hz, 1H), 7.01 (s, 1H), 6.90 (d, J=8.5 Hz, 2H), 4.22 (q, J=7.0 Hz, 2H), 4.01-4.12 (m, 2H), 3.80-3.88 (m, 2H), 3.50-3.61 (m, 2H), 3.23 (t, J=7.5 Hz, 2H), 1.60-1.98 (m, 5H), 1.34 (t, J=7.0 Hz, 3H), 1.06 (d, J=6.5 Hz, 3H). LCMS(ESI) m/z: 481 (M+1).

Embodiment 17B (E)-4-((5-(5-(2-amino-pyridin-4-yl)-1,1-dioxo-1,2,5-thiadiazolidine2-yl)-3-methyl-pentyl)-oxy)-benzaldehyde-O-ethylketoxime

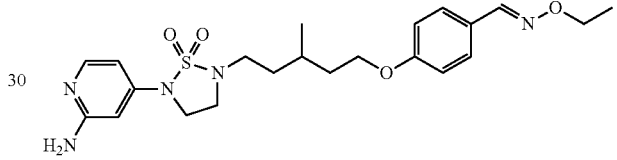

Please refer to the preparation method of Embodiment 16 for this embodiment.

$^1$H-NMR(CDCl$_3$, 400 MHz) 8.03 (s, 1H), 7.98 (d, J=5.5 Hz, 1H), 7.51 (d, J=8.5 Hz, 2H), 6.88 (d, J=8.5 Hz, 2H), 6.41 (d, J=6.0 Hz, 1H), 6.29 (s, 1H), 4.20 (q, J=7.2 Hz, 2H), 4.01-4.09 (m, 2H), 3.77 (t, J=6.3 Hz, 2H), 3.43-3.55 (m, 2H), 3.19 (t, J=7.5 Hz, 2H), 1.63-1.95 (m, 5H), 1.32 (t, J=7.0 Hz, 3H), 1.03 (d, J=6.5 Hz, 3H). LCMS(ESI) m/z: 462 (M+1).

Routine G

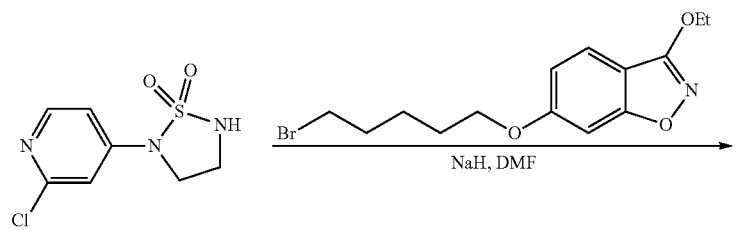

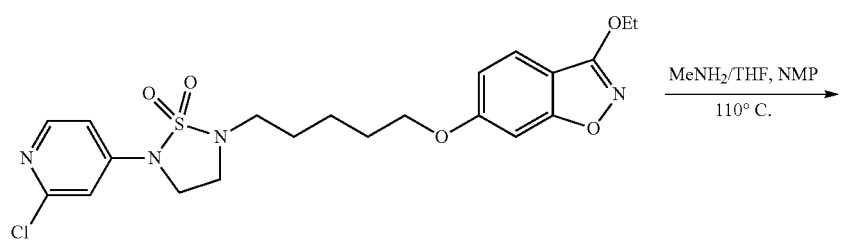

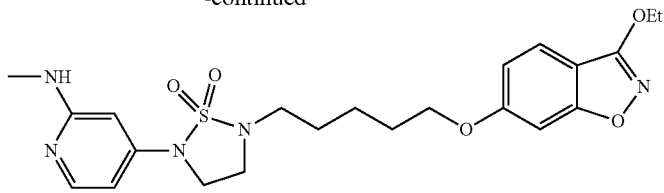

Embodiment 18

2-(5-((3-ethoxy-benzo[d]isoxazol-6)-oxo)-pentyl)-5-(2-(methylamino)-pyridine-4)-1,2,5-thiadiazoline-1,1-dioxide

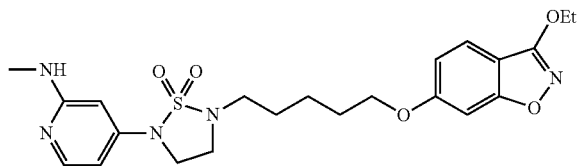 [SMILES: CCOc1noc2cc(OCCCCCN3CCN(c4ccnc(NC)c4)S3(=O)=O)ccc12]

Embodiment 18A 2-(2-chloro-pyridine-4-)-5-(5-((3-ethoxy-benzo[d]isoxazol-6-)oxo)-pentyl)-1,2,5-thiadiazoline-1,1-dioxide

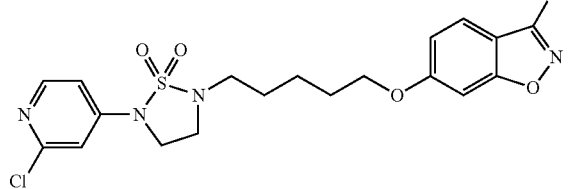

Under the protection of N₂ gas at 0° C., add sodium hydride (93 mg, 2.32 mmol) into the solution of Embodiment 4E (271 mg, 1.16 mmol) in N,N-dimethylformamide. Agitate it 0.5 hour at 0° C. Then add the solution of Embodiment 12E (400 mg, 1.22 mmol) in N,N-dimethylformamide (5 ml). Agitate the reaction mixture 1 hour at 0° C. and then agitate 12 hours at room temperature. Quench the reaction mixture with the saturated NH₄Cl aqueous solution (5 ml). Then dilute it with a large amount of water (120 ml) before extract with ethyl acetate (30 ml×3). Then wash the combined organic phases with the saturated salt water. Then dry with anhydrous Na₂SO₄ before filter and dry through rotation. Then purify the residue with column chromatography (dichloromethane:methanol=20:1) to obtain the title compound (white solid, 210 mg, yield of 38%).

$^1$H-NMR (400 MHz, CDCl₃) δ8.27 (d, J=6.0 Hz, 1H), 7.47 (d, J=9.0 Hz, 1H), 7.06 (dd, J=6.0, 2.0 Hz, 1H), 6.99 (d, J=2.0 Hz, 1H), 6.81-6.87 (m, 2H), 4.46 (q, J=7.0 Hz, 2H), 4.02 (t, J=6.2 Hz, 2H), 3.84 (t, J=6.2 Hz, 2H), 3.56 (t, J=6.2 Hz, 2H), 3.19 (t, J=7.0 Hz, 2H), 1.85-1.93 (m, 2H), 1.80 (q, J=7.4 Hz, 2H), 1.50 (t, J=7.0 Hz, 3H), 0.80-0.92 (m, 2H). LCMS(ESI) m/z: 481 (M+1).

Embodiment 18B 2-(5-((3-ethoxy-benzo[d]isoxazol-6)-oxo)-pentane)5-(2-(methylamino)-pyridine-4)-1,2,5-thiadiazoline-1,1-dioxide

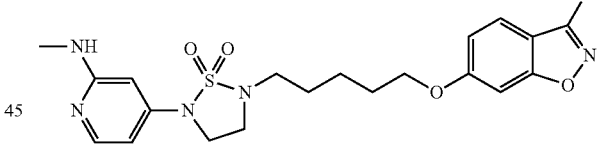

Add the solution of methylamine in THF (5 ml, 2 mol/L, 12.5 mmol) into the solution of Embodiment 18A (100 mg, 0.2 mmol) in N-methylpyrrolidone (8 ml). Place the mixture into a sealed pot and agitate it to react 72 hours at 110° C. Then remove the solvent of the reaction solution at vacuum. Then separate and purify the residue with the preparative chromatography to obtain the title compound (yellow powder, 10 mg, yield of 10%).

$^1$H-NMR (400 MHz, CDCl₃) δ8.02 (br s, 1H), 7.48 (br s, 1H), 6.85 (br s, 2H), 6.38 (br s, 1H), 6.16 (br s, 1H), 4.49 (br s, 2H), 4.04 (br s, 2H), 3.84 (br s, 2H), 3.52 (br s, 2H), 3.19 (br s, 2H), 2.94 (br s, 3H), 1.91 (br s, 2H), 1.81 (br s, 2H), 1.69-1.75 (m, 2H), 1.52 (br s, 3H). LCMS(ESI) m/z: 476 (M+1).

Routine H

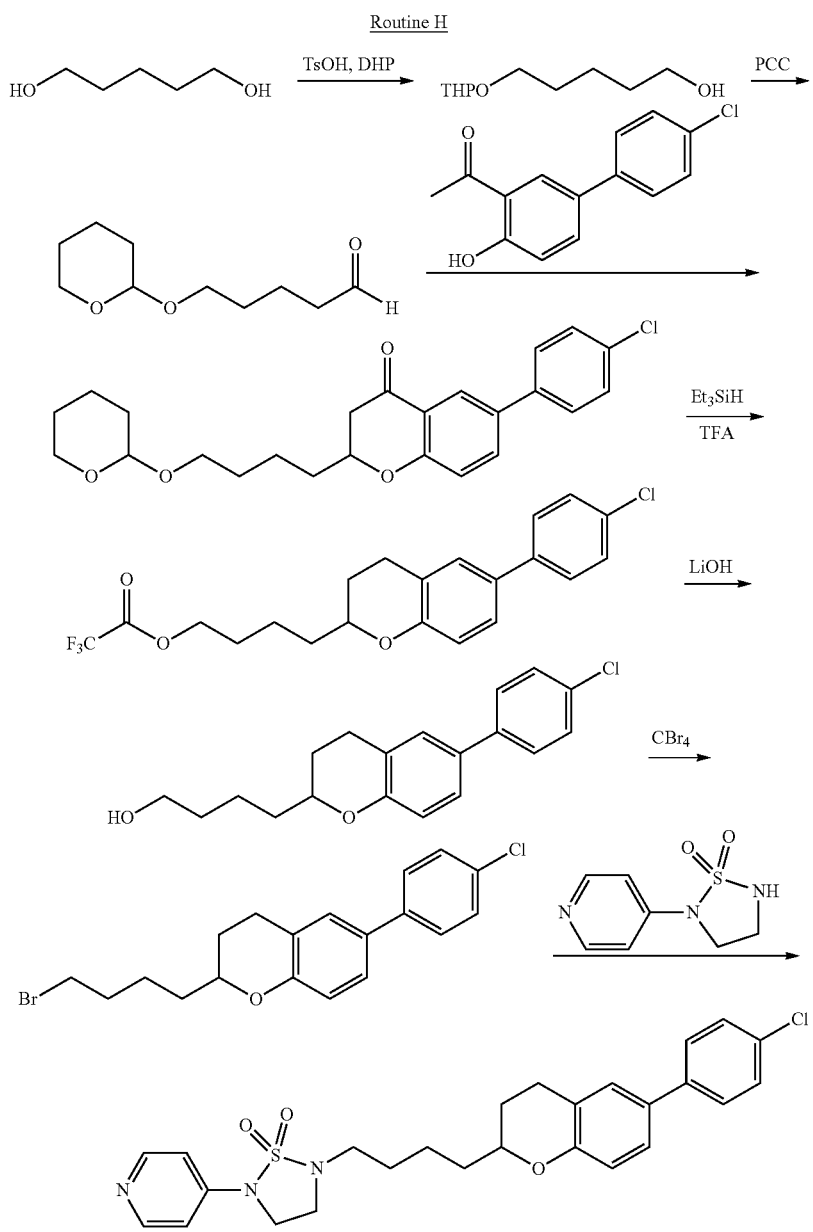

Embodiment 19

2-(4-(6-(4-chlorophenyl)-chroman-2-yl)-butyl)-5-(pyridin-4-yl)-1,2,5-thiadiazolidine-1,1-dioxide Embodiment 19A 5-((tetrahydro-2H-pyran-2-yl)-oxy)-pentan-1-ol

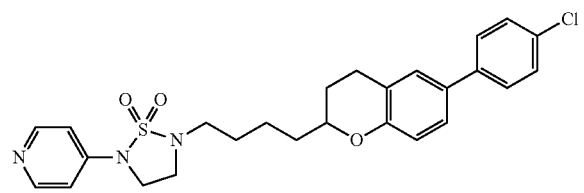 [SMILES: O=S1(=O)N(CCCCC2CCc3cc(-c4ccc(Cl)cc4)ccc3O2)CCN1c1ccncc1]

Agitate 1,5-pentanediol (60 g, 0.57 mol), 3,4-dihydropyran (48.5 g, 0.57 mol) and p-toluenesulfonic acid (50 mg) 3 hours at 40° C. After the reaction ends, add $K_2CO_3$ solution (200 ml) before extract the aqueous phase with ethyl acetate (150 ml×3). Dry the combined organic phases with anhydrous $Na_2SO_4$. Then filter and dry through evaporation to obtain the residue to directly use further.

$^1$H-NMR(CDCl$_3$, 400 MHz) δ4.54 (d, J=3.5 Hz, 1H), 3.78-3.89 (m, 1H), 3.68-3.77 (m, 1H), 3.60 (br.s., 2H), 3.43-3.52 (m, 1H), 3.32-3.41 (m, 1H), 2.02 (br.s., 1H), 1.80 (m, 1H), 1.65-1.68 (m, 1H), 1.39-1.70 (m, 10H).

Embodiment 19B 5-((tetrahydro-2H-pyran-2-yl)-oxy)-pentanal

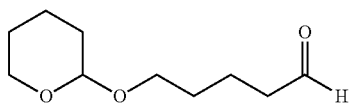 [SMILES: O=CCCCCOC1CCCCO1]

Add PCC (90 g) in batch into the solution of Embodiment 19A (60 g, 0.30 mol) in dichloromethane (400 ml) and agitate the reaction mixture 5 hours at room temperature. Filter and then concentrate the filtrate. Then purify it with column chromatography to obtain the title compound.

$^1$H-NMR (400 MHz, CDCl$_3$) δ9.62-9.79 (m, 1H), 4.50 (br.s., 1H), 3.58-3.91 (m, 2H), 3.25-3.53 (m, 2H), 2.50-2.68 (m, 2H), 2.42 (dd, J=1.25, 3.51 Hz, 2H), 1.48-1.79 (m, 8H).

Embodiment 19C 6-(4-chlorophenyl)-2-(4-((tetrahydro-2H-pyran-2-yl)-oxy)-butyl)-chroman-4-one

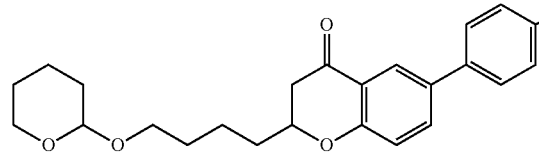

Agitate the mixture of Embodiment 19B (7.5 g, 40.27 mmol), Embodiment 1F (9.93 g, 40.27 mmol) and piperidine (3.43 g, 40.27 mmol) in ethanol (100 ml) 3 hours at 85° C. Add ethyl acetate (50 ml) and water (50 ml) into the reaction system. Then adjust the pH value of the reaction system with dilute aqueous hydrochloric acid to 6. Extract the aqueous layer with dichloromethane (100 ml×3) and then dry the combined organic layers with Na$_2$SO$_4$ before filter and evaporate. Then purify the residue with column chromatography to obtain the title compound (yellow liquid, 7 g, yield of 42%).

$^1$H-NMR (400 MHz, CDCl$_3$) δ8.05 (d, J=2.3 Hz, 1H), 7.67 (dd, J=8.7, 2.4 Hz, 1H), 7.48 (d, J=8.5 Hz, 2H), 7.38 (d, J=8.5 Hz, 2H), 7.04 (d, J=8.5 Hz, 1H), 4.58 (d, J=4.3 Hz, 1H), 4.43-4.52 (m, 1H), 3.86 (td, J=7.3, 3.9 Hz, 1H), 3.74-3.82 (m, 1H), 3.47-3.54 (m, 1H), 3.39-3.45 (m, 1H), 2.67-2.76 (m, 2H), 1.89-1.99 (m, 1H), 1.76-1.86 (m, 2H), 1.63-1.71 (m, 4H), 1.49-1.59 (m, 5H).

Embodiment 19D 4-(6-(4-chlorophenyl)-chroman-2-yl)-butyl-2,2,2-trifluoroacetate

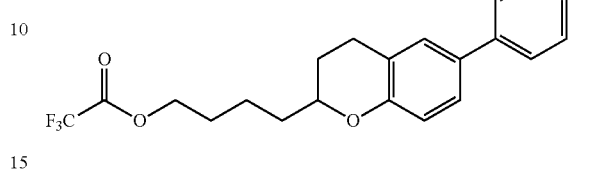

Add the triethylsilyl hydride (10 ml) into the solution of Embodiment 19C (2.5 g, 6.03 mmol) in trifluoroacetic acid (20 ml). Allow the mixture to react 3 hours at 50° C. Evaporate it to dry the solvent. Then add ethyl acetate (20 ml) and water (20 ml) into the reaction system. Extract the aqueous layer with ethyl acetate (20 ml×3) and then dry the combined organic layers with Na$_2$SO$_4$ before filter and evaporate to obtain the title compound (yellow liquid, 2 g, yield of 80%).

Embodiment 19E 4-(6-(4-chlorophenyl)-chroman-2-yl)-butan-1-ol

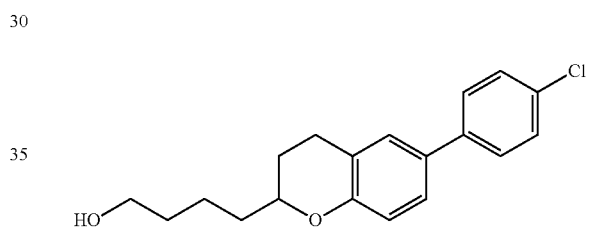

Add LiOH (29 mg, 1.21 mmol) into the mixture of Embodiment 19D (500 mg, 1.21 mmol) in 1,4-dioxane (5 ml) and water (2 ml). Then allow the mixture to react 3 hours at 25° C. Add ethyl acetate (10 ml) and water (10 ml) into the reaction system. Extract the aqueous layer with ethyl acetate (10 ml×3) and then dry the combined organic layers with Na$_2$SO$_4$ before filter and evaporate. Then purify the residue with column chromatography to obtain the title compound (colorless solid, 300 mg, yield of 78%).

$^1$H-NMR (400 MHz, CDCl$_3$) δ7.43-7.47 (m, 2H), 7.33-7.38 (m, 2H), 7.26-7.30 (m, 2H), 6.86 (d, J=8.3 Hz, 1H), 4.03 (br.s., 1H), 3.70 (t, J=5.9 Hz, 2H), 2.76-2.95 (m, 2H), 1.98-2.08 (m, 1H), 1.71-1.85 (m, 2H), 1.58-1.70 (m, 5H).

Embodiment 19F 2-(4-bromobutyl)-6-(4-chlorophenyl)-chroman

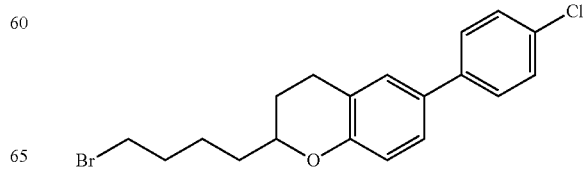

At 0° C., add slowly the triphenylphosphine (420 mg, 1.6 mmol) into the mixture of Embodiment 19E (500 mg, 1.6 mmol), CBr₄ (3.4 g, 10.3 mmol) in THF (5 ml). Allow the mixture to react 1 hour at 60° C. Concentrate the reaction solution under reduced pressure. Purify the residue with column chromatography to obtain the title compound (yellow solid, 658 mg, yield of 83%).

¹H-NMR (400 MHz, CDCl₃) δ7.43-7.48 (m, 2H), 7.34-7.38 (m, 2H), 7.24-7.29 (m, 2H), 6.86 (d, J=8.5 Hz, 1H), 4.00-4.07 (m, 1H), 3.45-3.49 (m, 2H), 2.77-2.96 (m, 2H), 1.90-2.02 (m, 3H), 1.62-1.80 (m, 5H).

Embodiment 19G 2-(4-(6-(4-chlorophenyl)-chroman-2-yl)-butyl)-5-(pyridin-4-yl)-1,2,5-thiadiazolidine-1,1-dioxide

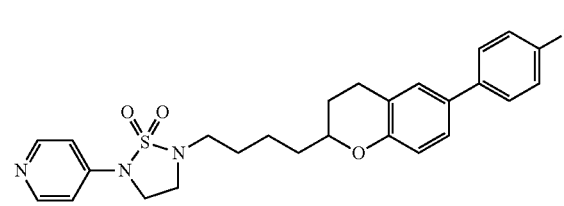

This embodiment is prepared with the method as described in Embodiment 18A.

¹H-NMR (400 MHz, CDCl₃) δ8.51 (d, J=6.0 Hz, 2H), 7.42-7.48 (m, 2H), 7.33-7.40 (m, 2H), 7.29 (s, 3H), 7.05 (d, J=6.0 Hz, 2H), 6.85 (d, J=8.5 Hz, 1H), 4.03 (br.s., 1H), 3.86 (t, J=6.5 Hz, 2H), 3.52-3.59 (m, 2H), 3.20 (t, J=7.0 Hz, 2H), 2.77-2.95 (m, 2H), 2.03 (d, J=13.1 Hz, 1H), 1.64-1.85 (m, 7H). LCMS(ESI) m/z: 498 (M+1).

Routine I

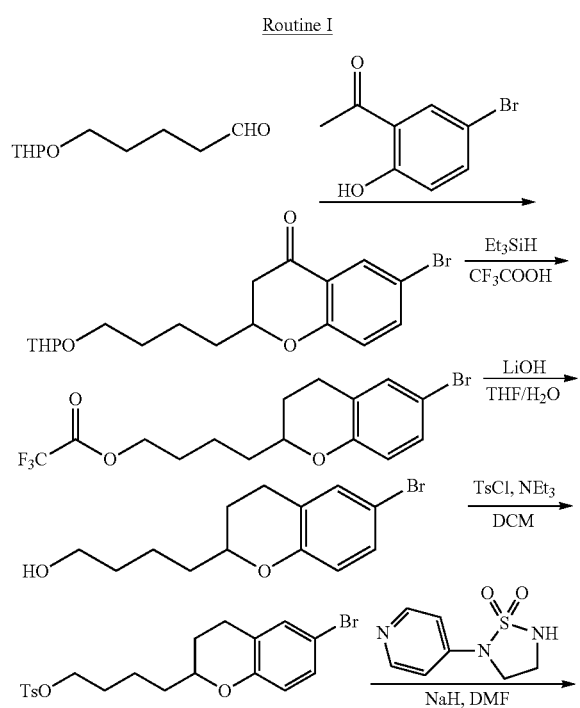

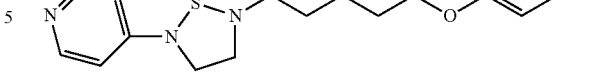

Embodiment 20

2-(4-(6-bromo-chroman-2-yl)-butyl)-5-(pyridin-4-yl)-1,2,5-thiadiazolidine-1,1-dioxide

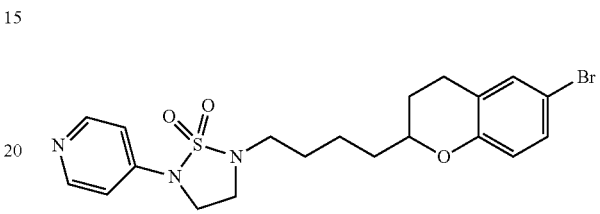

Embodiment 20A 6-bromo-2-(4-((tetrahydro-2H-pyran-2-yl)-oxy)-butyl)-chroman-4-one

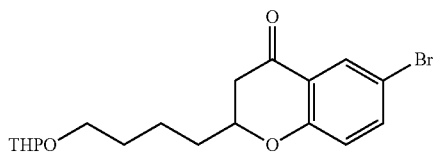

Mix Embodiment 19B (5.0 g, 29 mmol), 5'-bromo-2'-hydroxyacetophenone (6.37 g, 29 mmol) and piperidine (2.0 ml) into ethanol (150 ml) and reflux 4 hours. Then dry it under reduced pressure and purify the yielded residue with column chromatography to obtain the title compound (yellow solid, 6.5 g, yield of 57%).

¹H-NMR(CDCl₃, 400 MHz) δ8.00 (d, J=2.3 Hz, 1H), 7.56 (dd, J=8.8, 2.3 Hz, 1H), 6.90 (d, J=8.8 Hz, 1H), 4.60 (br.s., 1H), 4.40-4.52 (m, 1H), 3.72-3.95 (m, 2H), 3.37-3.59 (m, 2H), 2.66-2.80 (m, 2H), 1.48-2.01 (m, 12H).

Embodiment 20B 4-(6-bromo-chroman-2-yl)-2,2,2-trifluoroacetate

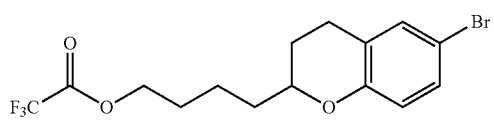 [SMILES: O=C(OCCCCC1CCc2cc(Br)ccc2O1)C(F)(F)F]

Mix Embodiment 20A (1.0 g, 2.57 mmol) and triethylsilane hydrogen (7.3 g, 62.8 mmol) into trifluoroacetate (20 ml). Then heat it 5 hours at 60° C. After concentrate it under reduced pressure, use directly the crude product (5.8 g, yield of crude product is 97%).

¹H-NMR(CDCl₃, 400 MHz) δ7.17 (d, J=2.0 Hz, 2H), 6.60-6.70 (m, 1H), 4.30-4.47 (m, 2H), 3.96 (td, J=7.8, 2.0 Hz, 1H), 2.67-2.90 (m, 2H), 1.97 (ddt, J=13.5, 5.6, 2.8 Hz, 1H), 1.48-1.89 (m, 8H).

Embodiment 20C 4-(6-bromo-chroman-2-yl)-butan-1-ol

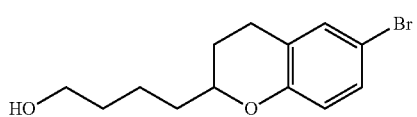 [SMILES: OCCCCC1CCc2cc(Br)ccc2O1]

Please refer to the preparation method of Embodiment 19E for this embodiment.

¹H-NMR(CDCl₃, 400 MHz) δ7.11-7.24 (m, 1H), 6.64-6.75 (m, 1H), 3.99 (d, J=5.0 Hz, 1H), 3.61-3.80 (m, 2H), 2.66-2.91 (m, 2H), 1.93-2.06 (m, 1H), 1.47-1.84 (m, 10H).

Embodiment 20D 4-(6-bromo-chroman-2-yl)-butyl-4-methyl-benzene-sulfonate

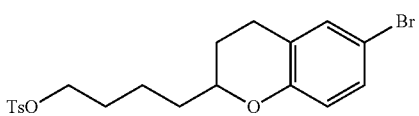 [SMILES: Cc1ccc(S(=O)(=O)OCCCCC2CCc3cc(Br)ccc3O2)cc1]

Add triethylamine (76 mg, 0.75 mmol) and p-toluensulfonyl chloride (95 mg, 0.5 mmol) into the solution of Embodiment 20C (71 mg, 0.25 mmol) in dichloromethane (5.0 ml). Agitate the reaction mixture 4 hours at 12° C. After concentrate it under reduced pressure, purify the crude product with TLC to obtain the title compound (colorless liquid, 60 mg, yield of 55%).

¹H-NMR(CDCl₃, 400 MHz) δ7.73-7.85 (m, 2H), 7.36 (d, J=8.0 Hz, 2H), 7.17 (d, J=4.8 Hz, 2H), 6.61-6.69 (m, 1H), 4.03-4.11 (m, 2H), 3.84-3.97 (m, 1H), 2.66-2.89 (m, 2H), 2.45 (s, 3H), 1.88-2.01 (m, 1H), 1.42-1.83 (m, 7H).

Embodiment 20E 2-(4-(6-bromo-chroman-2-yl)-butyl)-5-(pyridin-4-yl)-1,2,5-thiadiazolidine-1,1-dioxide

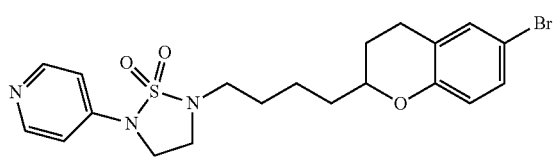 [SMILES: O=S1(=O)N(CCCCC2CCc3cc(Br)ccc3O2)CCN1c1ccncc1]

Please refer to the preparation method of Embodiment 18A for this embodiment.

¹H-NMR(CDCl₃, 400 MHz) δ8.52 (d, J=6.0 Hz, 2H), 7.14-7.19 (m, 2H), 7.06 (d, J=6.0 Hz, 2H), 6.65-6.69 (m, 1H), 3.97 (s., 1H), 3.86 (t, J=6.3 Hz, 2H), 3.56 (t, J=6.5 Hz, 2H), 3.19 (t, J=7.0 Hz, 2H), 2.67-2.89 (m, 2H), 1.94-2.04 (m, 1H), 1.53-1.84 (m, 7H). LCMS(ESI) m/z: 466 (M+1).

Routine J

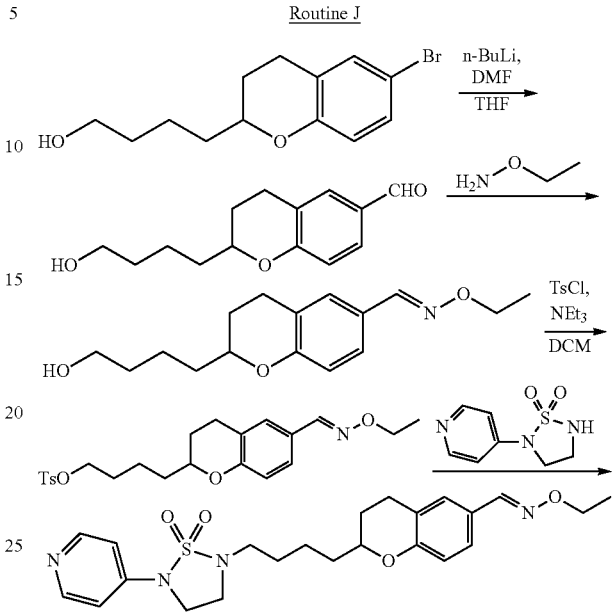

Embodiment 21

(E)-2-(4-(1,1-dioxo-5-(pyridin-4-yl)-1,2,5-thiadiazolidine-2-yl)-butyl)-chroman-6-formaldehyde-O-ethyloxime

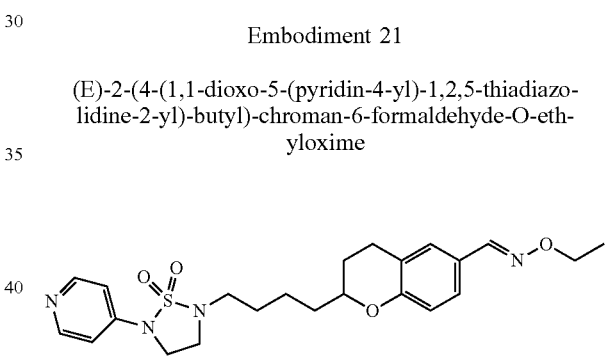

Embodiment 21A 2-(4-hydroxybutyl)-chroman-6-carbaldehyde

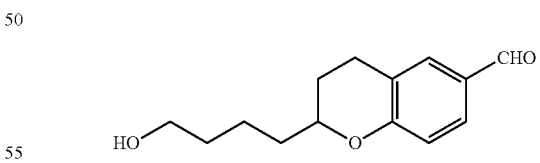

Under the protection of N₂ gas at −78° C., add slowly N-butyllithium (2.5 mol/L, 1.8 ml, 4.6 mmol) into the solution of Embodiment 20C (600 mg, 2.1 mmol) in anhydrous THF (10.0 ml). After the substances are added, continue to agitate 2 hours. Then lower down the temperature of the reaction solution again to −78° C. and then drop slowly N,N-dimethylformamide (380 mg, 5.2 mmol). After the dropping is completed, heat the reaction solution slowly to room temperature and agitate over night. Add water (5 ml) to quench the reaction. Then extract the aqueous phase with ethyl acetate (10.0 ml×2). Dry the combined organic phases with anhydrous Na₂SO₄ before filter and evaporate. Then purify the residue with TLC to obtain the title compound (colorless liquid, 70.0 mg, yield of 15%).

¹H-NMR(CDCl₃, 400 MHz) δ9.83 (s, 1H), 7.55-7.68 (m, 2H), 6.83-6.92 (m, 1H), 4.03-4.20 (m, 1H), 3.71 (t, J=6.0 Hz, 2H), 2.72-2.92 (m, 2H), 2.00-2.13 (m, 1H), 1.46-1.87 (m, 7H).

Embodiment 21B (E)-2-(4-hydroxybutyl)-chroman-6-carbaldehyde-O-ethyloxime

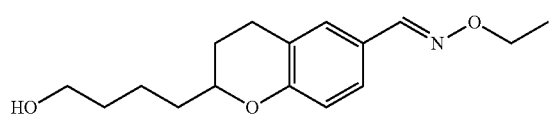 [SMILES: CCO/N=C/c1ccc2c(c1)CCC(CCCCO)O2]

Add ethoxyamino hydrochloride (97 mg, 1.6 mmol) and sodium acetate (130 mg, 1.59 mmol) into the solution of Embodiment 21A (70 mg, 0.32 mmol) in water (2.0 ml). Then heat it 3 hours at 60° C. before stop the reaction. Extract the aqueous phase with ethyl acetate (5.0 ml×3). Dry the combined organic phases with anhydrous Na₂SO₄. Then filter and concentrate to obtain the crude product that can be directly used further (70 mg, yield of 79%).

Embodiment 21C (E)-4-(6-((ethoxyiminomethyl)-methyl)-chroman-2-yl)-butyl-4-methylbenzenesulfonate

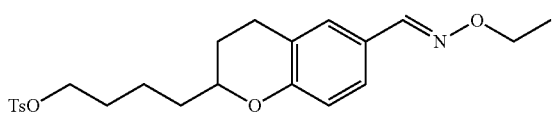 [SMILES: CCO/N=C/c1ccc2c(c1)CCC(CCCCOS(=O)(=O)c1ccc(C)cc1)O2]

Add triethylamine (76 ml, 0.75 mmol) and p-toluensulfonyl chloride (95 mg, 0.5 mmol) into the solution of Embodiment 21B (70 mg, 0.25 mmol) in dichloromethane (5.0 ml). Agitate the reaction mixture 4 hours at 12° C. After concentrate it under reduced pressure, purify the crude product with TLC to obtain the title compound (colorless liquid, 60 mg, yield of 55%).

¹H-NMR(CDCl₃, 400 MHz) δ7.98 (s, 1H), 7.79 (d, J=8.0 Hz, 2H), 7.24-7.39 (m, 2H), 6.69-6.77 (m, 1H), 4.12-4.23 (m, 2H), 4.06 (t, J=6.3 Hz, 2H), 3.92 (br s, 1H), 2.68-2.87 (m, 2H), 2.43 (s, 3H), 1.89-1.99 (m, 1H), 1.43-1.78 (m, 7H), 1.26-1.37 (m, 3H).

Embodiment 21D (E)-2-(4-(1,1-dioxo-5-(pyridin-4-yl)-1,2,5-thiadiazolidine-2-yl)-butyl)-chroman-6-carbaldehyde-O-ethyloxime

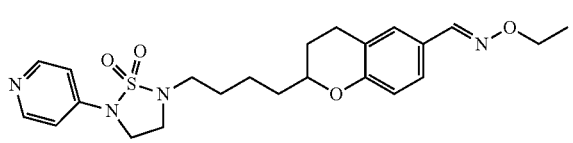 [SMILES: CCO/N=C/c1ccc2c(c1)CCC(CCCCN1CCN(c3ccncc3)S1(=O)=O)O2]

Please refer to the preparation method of Embodiment 18A for this embodiment.

1H-NMR(CDCl3,400 MHz) 8.52 (brs, 2H), 7.98 (s, 1H), 7.21-7.35 (m, 2H), 7.07 (d, J=5.0 Hz, 2H), 6.77 (d, J=9.0 Hz, 1H), 4.15-4.28 (m, 2H), 4.02 (brs, 1H), 3.86 (t, J=6.5 Hz, 2H), 3.52-3.61 (m, 2H), 3.19 (t, J=7.0 Hz, 2H), 2.72-2.90 (m, 2H), 1.95-2.04 (m, 1H), 1.57-1.84 (m, 8H), 1.31 (t, J=7.0 Hz, 3H). LCMS(ESI) m/z: 459 (M+1).

Embodiment 22

(R)-1-(4-(6-(4-chlorophenyl)-chroman-2-yl)-butyl)-3-(pyridin-4-yl)-imidazolidinone

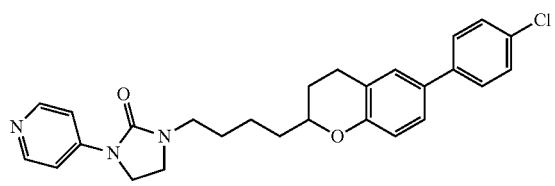 [SMILES: O=C1N(CCCCC2CCc3cc(-c4ccc(Cl)cc4)ccc3O2)CCN1c1ccncc1]

(S)-1-(4-(6-(4-chlorophenyl)-chroman-2-yl)-butyl)-3-(pyridin-4-yl)-imidazolidinone

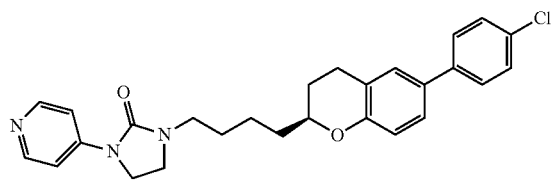 [SMILES: O=C1N(CCCC[C@H]2CCc3cc(-c4ccc(Cl)cc4)ccc3O2)CCN1c1ccncc1]

Use SFC to split the products of Embodiment 2 to obtain two chiral isomers. The conditions used to split are as follows:

Method: AS-H_S_5_40_3 ML_8 MIN_15 CM

Chromatographic column: Chiralpak AS-H 150*4.6 mm I.D., 5 um

Mobile phase: 40% ethanol (0.05% DEA)-CO2

Flow rate: 3 mL/min

Wavelength: 220 nm;

Embodiment 22a as the first isomer has a retention time of 2.80 minutes; Embodiment 22b as the second isomer has a retention time of 4.04 minutes.

Procedure K

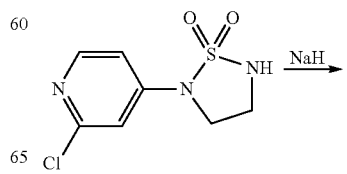

95

-continued

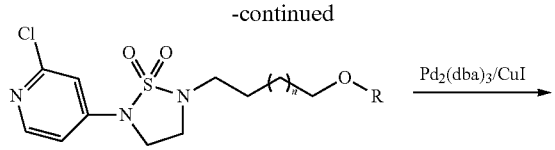

n = 1, 2, 3

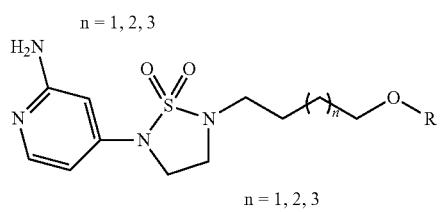

n = 1, 2, 3

Embodiment 23

(E)-4-((5 (5 (2-amino-pyridin-4-yl)-1,1-dioxide-1,2,
5-thiadiazolidine-2-yl)-pentyl)-oxy)-benzaldehyde-
O-ethyl ketoxime

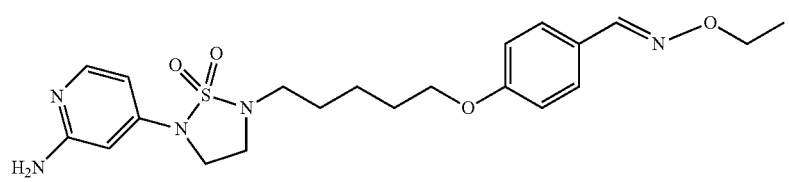 [SMILES: CCO/N=C/c1ccc(OCCCCCN2CCN(c3ccnc(N)c3)S2(=O)=O)cc1]

Embodiment 23A (E)-4-hydroxybenzaldehyde-O-ethyloxime

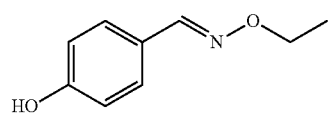

Add sodium acetate (3.4 g, 40.9 mmol) into the solution of p-hydroxy benzaldehyde (2.5 g, 20.5 mmol) and ethoxyamino hydrochloride (3.9 g, 40.9 mmol) in water (50 ml) and then agitate the mixture 4 hours at 80° C. Add ethyl acetate (50 ml) into the reaction system. Extract the aqueous layer with ethyl acetate (50 ml×3) and then dry the combined organic layer with Na$_2$SO$_4$ before filter and evaporate to obtain the title compound (brown solid, 3 g, yield of 89%). $^1$H NMR(CDCl$_3$, 400 MHz) 8.03 (s, 1H), 7.46 (d, J=8.5 Hz, 2H), 6.78-6.85 (m, 2H), 4.20 (q, J=7.0 Hz, 2H), 1.31 (t, J=7.0 Hz, 3H).

96

Embodiment 23B (E)-4-((6-bromohexyl)-oxy)-benzaldehyde-O-ethyl-ketoxime

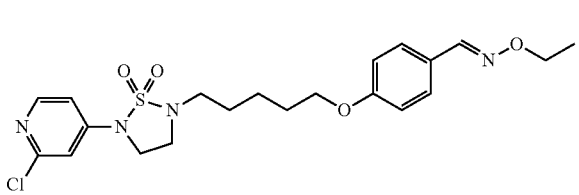

Heat and reflux the solution of Embodiment 23A (1.0 g, 6.1 mmol), 1,5-dibromopentane (1.4 g, 6.1 mmol), K$_2$CO$_3$ (1.67 g, 12.1 mmol) and KI (0.1 g, 0.61 mmol) in acetone (100 ml) for 10 hours. After the reaction solution cools to room temperature, filter and then dry the filtrate through rotation. Then purify it with column chromatography to obtain the title compound (white crystal, 1.2 g, 63%). $^1$H NMR(CDCl$_3$, 400 MHz) δ8.01-8.05 (m, 1H), 7.49-7.55 (m, 2H), 6.86-6.91 (m, 2H), 4.17-4.24 (m, 2H), 3.96-4.01 (m, 2H), 3.41-3.47 (m, 2H), 1.89-1.99 (m, 2H), 1.78-1.86 (m, 2H), 1.60-1.68 (m, 2H), 1.29-1.34 (m, 3H).

Embodiment 23C (E)-4-((5-(5-(2-chloropyridin-4-yl)-1,1-dioxide-1,2,
5-thiadiazolidine-2-yl)-pentyl)-oxy)-benzaldehyde-
O-ethyl ketoxime Under the protection of N$_2$ gas at 10° C., add the sodium hydroxide (51.4 mg, 1.3 mmol) into the solution of Embodiment 4E (100 mg, 428 μmol) in N,N-dimethylformamide (3 ml). After agitate the reaction solution 2 hours, add the solution of Embodiment 23B (134.5 mg, 428 μmol) in N,N-dimethylformamide (1 ml) into it. Then agitate the system to react 8 hours at 40° C. After the TLC verifies that reaction is completed, add water (10 ml) to quench the reaction. Then extract the aqueous layer with ethyl acetate (20 ml×3). Then combine the organic layers and dry anhydrous Na₂SO₄ before filter and evaporate. Then separate the crude product with TLC plate (petroleum ether/ethyl acetate=1:1) to obtain the title compound (white solid, 140 mg, yield of 70%). ¹H NMR (400 MHz, CHLOROFORM-d) 8.29 (d, J=5.77 Hz, 1H), 8.05 (s, 1H), 7.53 (d, J=9.03 Hz, 2H), 7.09 (dd, J=2.01, 5.77 Hz, 1H), 7.01 (d, J=2.01 Hz, 1H), 6.89 (d, J=8.78 Hz, 2H), 4.22 (q, J=7.03 Hz, 2H), 4.02 (t, J=6.15 Hz, 2H), 3.86 (t, J=6.40 Hz, 2H), 3.54-3.60 (m, 2H), 3.20 (t, J=7.28 Hz, 2H), 1.60-1.91 (m, 6H), 1.34 (t, J=7.15 Hz, 3H). LCMS (M+1): 467.

Embodiment 23D (E)-4-((5-(5-(2-aminopyridin-4-yl)-1,1-dioxide-1,2,5-thiadiazolidine-2-yl)-pentyl)-oxy)-benzaldehyde-O-ethyl ketoxime

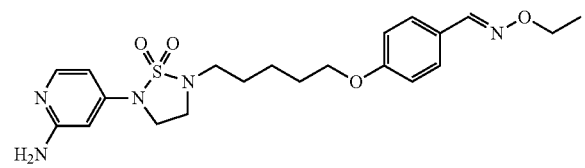 [SMILES: CCO/N=C/c1ccc(OCCCCCN2CCN(c3ccnc(N)c3)S2(=O)=O)cc1]

Under the protection of N₂ gas, add Pd₂(dba)₃ (30 mg, 343 µmol) and Xant-Phos (15 mg, 38 µmol) into the mixture solution of Embodiment 23C (80 mg, 171.3 µmol), tert-butyl carbamate (120 mg, 1.0 mmol) and Cs₂CO₃ (112 mg, 343 µmol) in dioxane/N,N-dimethylformamide (3 ml)/(1 ml). After agitate the mixture solution evenly, heat it to 110° C. to react 10 hours. After the TLC (petroleum ether/ethyl acetate=2:1 dichloromethane:methanol=20:1), verify that the reaction is complete, add water (10 ml) to quench. Then extract it with ethyl acetate (30 ml×3). Then combine the organic layers and dry with Na₂SO₄ before filter and evaporate. Separate the crude product with the preparative HPLC (trifluoroacetate) to obtain the title compound (white solid, 20 mg, yield of 26%). ¹H NMR (400 MHz, CHLOROFORM-d) 7.95-8.07 (m, 2H), 7.51 (d, J=8.53 Hz, 2H), 6.88 (d, J=8.53 Hz, 2H), 6.42 (dd, J=2.01, 5.52 Hz, 1H), 6.29 (d, J=2.01 Hz, 1H), 4.52 (br.s., 1H), 4.20 (q, J=7.19 Hz, 2H), 4.00 (t, J=6.27 Hz, 2H), 3.80 (t, J=6.53 Hz, 2H), 3.50 (t, J=6.27 Hz, 2H), 3.16 (t, J=7.28 Hz, 2H), 1.73-1.90 (m, 4H), 1.62-1.65 (m, 2H), 1.32 (t, J=7.03 Hz, 3H). LCMS (M+1): 448.

Embodiment 24

4-((5-(5-(2-aminopyridin-4-yl)-1,1-dioxide-1,2,5-thiadiazolidine-2-yl)-pentyl)-oxy)-benzaldehyde

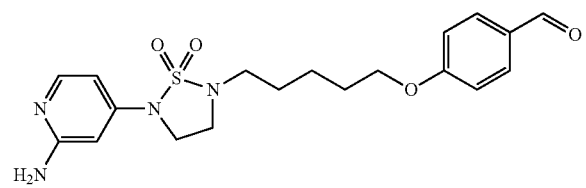 [SMILES: Nc1cc(N2CCN(CCCCCOc3ccc(C=O)cc3)S2(=O)=O)ccn1]

Agitate the reaction solution of Embodiment 23 (30 mg, 67 µmol) and trifluoroacetate (0.5 ml) in water (0.5 ml) and methanol (0.5 ml) 16 hours at 40° C. Dry it through rotation and then separate the residue with the preparative HPLC to obtain the title compound (2 mg, yield of 7%). ¹H NMR (CDCl₃, 400 MHz): 7.75 (d, J=8.5 Hz, 2H), 7.68 (s, 1H), 6.96 (d, J=8.8 Hz, 2H), 4.45 (q, J=7.4 Hz, 2H), 3.84 (s, 3H), 1.59 (d, J=3.8 Hz, 3H). LCMS(ESI) m/z: 405 (M+1).

Embodiment 25

(E)-4-((6-(5-(2-aminopyridin-4-yl)-1,1-dioxide-1,2,5-thiadiazolidine-2-yl)-hexyl)-oxy)-benzaldehyde-O-ethyl ketoxime

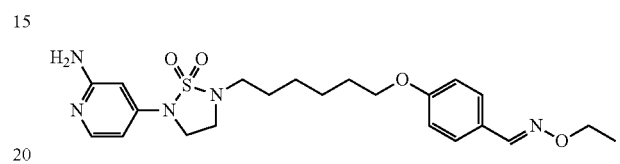

Embodiment 25A

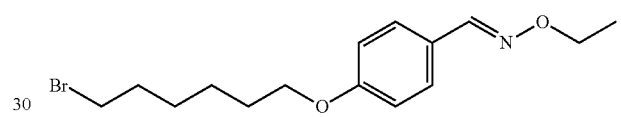

(E)-4-((6-bromohexyl)-oxy)-benzaldehyde-O-ethyl ketoxime

Please refer to the preparation method of Embodiment 23B for this embodiment. ¹H NMR (400 MHz, CHLOROFORM-d) 8.04 (d, J=4.52 Hz, 1H), 7.51 (d, J=4.52 Hz, 2H), 6.88 (d, J=5.77 Hz, 2H), 4.15-4.29 (m, 2H), 3.99 (d, J=5.77 Hz, 2H), 3.37-3.50 (m, 2H), 1.74-2.00 (m, 4H), 1.52 (br.s., 4H), 1.23-1.37 (m, 3H).

Embodiment 25B 4-((6-(5-(2-chloropyridin-4-yl)-1,1-dioxide-1,2,5-thiadiazolidine-2-yl)-hexyl)-oxy)-benzaldehyde-O-ethyl ketoxime

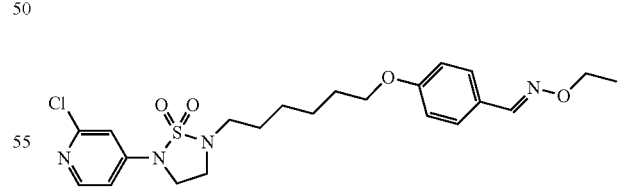

Please refer to the preparation method of Embodiment 23C for this embodiment. ¹H NMR (400 MHz, CHLOROFORM-d) 8.28 (d, J=6.02 Hz, 1H), 8.04 (s, 1H), 7.52 (d, J=8.78 Hz, 2H), 7.07 (dd, J=2.13, 5.90 Hz, 1H), 7.01 (d, J=2.01 Hz, 1H), 6.89 (d, J=8.78 Hz, 2H), 4.21 (q, J=7.03 Hz, 2H), 4.00 (t, J=6.27 Hz, 2H), 3.84 (t, J=6.40 Hz, 2H), 3.55 (t, J=6.27 Hz, 2H), 3.17 (t, J=7.28 Hz, 2H), 1.79-1.87 (m, 2H), 1.70-1.78 (m, 2H), 1.49-1.58 (m, 4H), 1.33 (t, J=7.03 Hz, 4H). LCMS(ESI) m/z: 480 (M+1).

Embodiment 25C (E)-4-((6-(5-(2-aminopyridin-4-yl)-1,1-dioxide-1,2,5-thiadiazolidine-2-yl)-hexyl)-oxy)-benzaldehyde-O-ethyl ketoxime

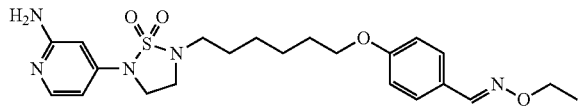 [SMILES: CCO/N=C/c1ccc(OCCCCCCN2CCN(c3ccnc(N)c3)S2(=O)=O)cc1]

Please refer to the preparation method of Embodiment 23 for this embodiment. ¹H NMR (400 MHz, CHLOROFORM-d) 8.00-8.06 (m, 1H), 7.93 (d, J=6.02 Hz, 1H), 7.51 (d, J=9.03 Hz, 3H), 6.87 (d, J=8.53 Hz, 3H), 6.46 (d, J=4.52 Hz, 1H), 6.28 (s, 1H), 4.12-4.24 (m, 3H), 3.98 (t, J=6.27 Hz, 3H), 3.79 (t, J=6.27 Hz, 2H), 3.49 (t, J=6.27 Hz, 2H), 3.13 (t, J=7.03 Hz, 3H), 1.77-1.85 (m, 2H), 1.67-1.76 (m, 3H), 1.51 (t, J=10.54 Hz, 5H), 1.32 (t, J=7.03 Hz, 4H). LCMS (ESI) m/z: 462 (M+1).

Embodiment 26

(E)-4-(4-(5-(2-aminopyridin-4-yl)-1,1-dioxide-1,2,5-thiadiazolidine-2-yl)-butyl)-oxy)-benzaldehyde-O-ethyl ketoxime

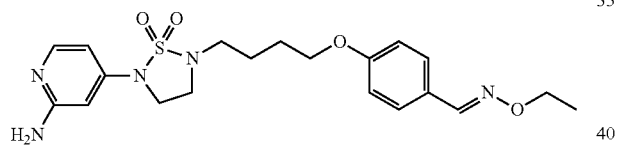

Please refer to the preparation method of Embodiment 25 for this embodiment. ¹H NMR (400 MHz, CHLOROFORM-d) 8.05 (s, 1H), 7.99 (d, J=5.77 Hz, 1H), 7.53 (d, J=8.78 Hz, 2H), 6.90 (d, J=8.78 Hz, 2H), 6.43 (d, J=4.52 Hz, 1H), 6.30 (s, 1H), 4.56 (br.s., 1H), 4.22 (q, J=7.03 Hz, 2H), 4.06 (t, J=5.14 Hz, 2H), 3.77 (t, J=6.27 Hz, 2H), 3.51 (t, J=6.27 Hz, 2H), 3.22 (t, J=6.40 Hz, 2H), 1.93 (br.s., 5H), 1.34 (t, J=7.15 Hz, 4H). LCMS(ESI) m/z: 434 (M+1).

Embodiment 27

4-(5-(5-(4-(2-ethyl-tetrazol-5-yl)-phenoxy)-pentyl)-1,1-dioxide-1,2,5-thiadiazolidine-2-yl)-pyridin-2-amine

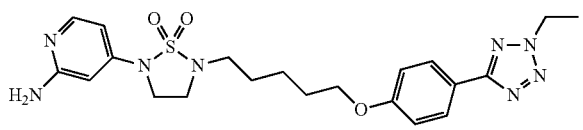 [SMILES: CCn1nnc(-c2ccc(OCCCCCN3CCN(c4ccnc(N)c4)S3(=O)=O)cc2)n1]

Embodiment 27A 2-(5-(4-(2-ethyl-tetrazol-5-yl)-phenoxy)-pentyl)-5-(pyridin-4-yl)-1,2,5-thiadiazolidine-1,1-dioxide

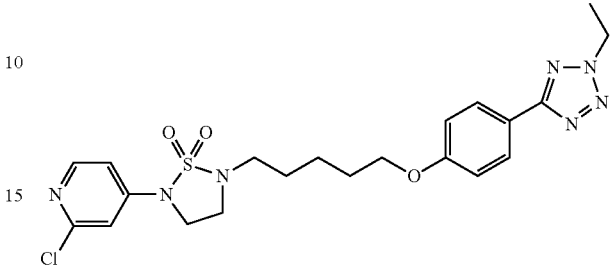

At 0° C., add sodium hydride (20 mg, 0.85 mmol) into the solution of Embodiment 4E (100 mg, 0.43 mmol) in N,N-dimethylformamide (3 ml). Keep it still 30 minutes at 0° C. Then add the solution of Embodiment 11D (51 mg, 0.15 mmol) in N,N-dimethylformamide (1 ml) into the mixture solution above. Agitate it 6 hours at 15° C. Then add water to quench the reaction and extract the aqueous phase with ethyl acetate. Dry the combined organic phases with anhydrous Na₂SO₄. Then filter and evaporate it before separate it with column (petroleum ether:ethyl acetate=1:1) to obtain the title compound (white solid, 120 mg, yield of 57%). ¹H NMR(CDCl₃ 400 MHz) δ8.27 (d, J=6.0 Hz, 1H), 8.07 (d, J=8.5 Hz, 2H), 7.07 (dd, J=5.8, 2.3 Hz, 1H), 6.99-7.00 (m, 2H), 4.69 (q, J=7.2 Hz, 2H), 4.05 (t, J=6.3 Hz, 2H), 3.84 (t, J=6.3 Hz, 2H), 3.56 (t, J=6.3 Hz, 2H), 3.19 (t, J=7.0 Hz, 2H), 1.86-1.93 (m, 2H), 1.76-1.83 (m, 2H), 1.64-1.71 (m, 5H). LCMS(ESI) m/z: 492 (M+1).

Embodiment 27B 4-(5-(5-(4-(2-tetrazol-5-yl)-phenoxy)-pentyl)-1,1-oxide-1,2,5-thiadiazolidine-2-yl)-pyridin-2-amine

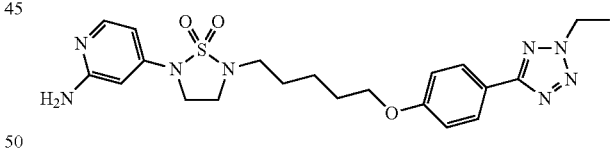

At 0° C., add cesium carbonate (159 mg, 0.49 mmol) and tert-butyl carbamate (171 mg, 1.5 mmol) into the solution of Embodiment 27A (120 mg, 0.24 mmol) in N,N-dimethylformamide (1 ml). Under the protection of N₂ gas, add Pd₂(dba)₃ (8.6 mg, 20 mmol) and Xantphos (11.7 mg, 20 mmol). Agitate it 15 hours at 110° C. Then add water to quench the reaction and extract the aqueous phase with ethyl acetate. Dry the combined organic phases with anhydrous Na₂SO₄ before filter and evaporate to obtain the title compound (white solid, 15 mg, yield of 12%). ¹H NMR(CDCl₃ 400 MHz) δ8.51 (d, J=6.5 Hz, 2H) 8.06 (d, J=8.5 Hz, 2H) 7.05 (d, J=6.0 Hz, 2H) 6.99 (d, J=9.0 Hz, 2H) 4.68 (q, J=7.5 Hz, 2H) 4.04 (t, J=6.0 Hz, 2H) 3.85 (t, J=6.3 Hz, 2H) 3.55 (t, J=6.3 Hz, 2H) 3.19 (t, J=7.3 Hz, 2H) 1.85-1.93 (m, 2H) 1.76-1.83 (m, 2H) 1.68 (t, J=7.5 Hz, 5H). LCMS(ESI) m/z: 473 (M+1).

Embodiment 28

4-(5-(5-((3-ethoxy-1,2-benzoxazol-6-yl)-oxy)-pentyl)-1,1-dioxide-1,2,5-thiadiazolidine-2-yl)-pyridin-2-amine

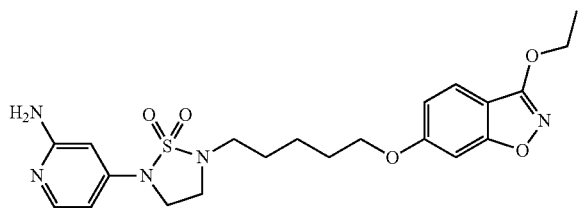 [SMILES: CCOc1noc2cc(OCCCCCN3CCN(c4ccnc(N)c4)S3(=O)=O)ccc12]

Embodiment 28A 2-(2-chloro-4-pyridyl)-5-(5-((3-ethoxy-1,2-benzoxazol-6-yl)-oxy)-pentyl)-1,2,5-thiadiazolidine-1,1-dioxide

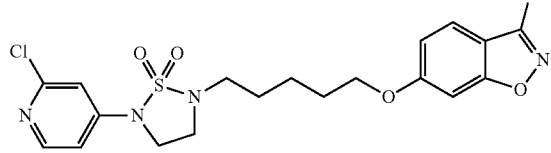

Under the protection of N₂ gas at 0° C., add the sodium hydroxide (53.3 mg, 2.2 mmol) in batch into the solution of Embodiment 4E (500 mg, 1.8 mmol) in N,N-dimethylformamide (1 ml). After allow it to react 1 hour at 0° C., drop the solution of Embodiment 12E (911 mg, 2.8 mmol) in N,N-dimethylformamide (1 ml) into the system above. Then heat it to room temperature to react 2 hours. Then pour the reaction solution into water (10 ml). Then extract with ethyl acetate (10 ml×3). Then dry the combined organic phases with anhydrous Na₂SO₄ before filter. Then remove the solvent with rotary evaporator to obtain the title compound (white solid, 50.00 mg, yield of 5.6%). LCMS(ESI) m/z: 481 (M+1).

Embodiment 28B 4-(5-(5-((3-ethoxy-1,2-benzoxazol-6-yl)-oxy)-pentyl)-1,1-dioxide-1,2,5-thiadiazolidine-2-yl)-pyridin-2-amine

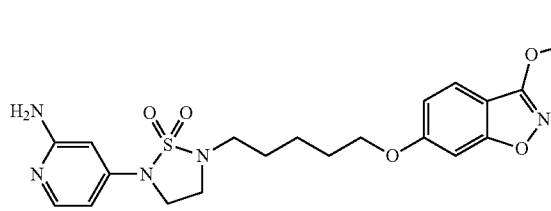

Under the protection of N₂ gas, add cesium carbonate (339 mg, 1.0 mmol), Pd₂(dba)₃ (47.6 mg, 52 μmol) and Xantphos (60.2 mg, 0.1 mmol) into the solution of Embodiment 28A (250 mg, 0.5 mmol) and tert-butyl carbamate (61 mg, 0.5 mmol) in dioxane (2 ml) and N,N-dimethylformamide (1 ml). Then heat the reaction solution to 110° C. to react 10 hours. Then pour the reaction solution into water (150 ml) and extract with ethyl acetate (100 ml×3). Combine the organic phases and wash it with the saturated salt water (100 ml×2). Then dry it with anhydrous Na₂SO₄ before filter and evaporate. Then purify the residue with the preparative HPLC to obtain the title compound (white solid, 25 mg, yield of 10.4%). ¹H NMR(CDCl₃, 400 MHz) δ7.98 (d, J=6.02 Hz, 1H), 7.47 (d, J=9.54 Hz, 1H), 6.81-6.87 (m, 2H), 6.42 (dd, J=1.76, 5.77 Hz, 1H), 6.30 (d, J=1.51 Hz, 1H), 4.53 (br.s., 1H), 4.47 (q, J=7.03 Hz, 2H), 4.03 (t, J=6.02 Hz, 2H), 3.81 (t, J=6.53 Hz, 2H), 3.51 (t, J=6.53 Hz, 2H), 3.17 (t, J=7.28 Hz, 2H), 1.85-1.95 (m, 2H), 1.79 (quin, J=7.40 Hz, 2H), 1.65-1.68 (m, 2H), 1.51 (t, J=7.28 Hz, 3H). LCMS (ESI) m/z: 462 (M+1).

Procedure L

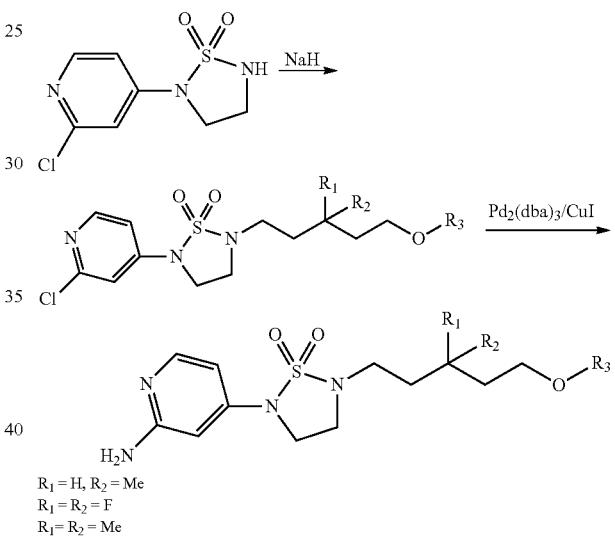

R₁ = H, R₂ = Me
R₁ = R₂ = F
R₁ = R₂ = Me

Embodiment 29

(S,E)-2-(2-aminopyridin-4-yl)-5-(5-((1-(ethoxyimino)-2,3-dihydro-1H-inden-5-yl)-oxy)-3-methylpentyl)-1,2,5-thiadiazolidine-1,1-dioxide and (R,E)-2-(2-aminopyridin-4-yl)-5-(5-((1-(ethoxyimino)-2,3-dihydro-1H-inden-5-yl)-oxy)-3-methylpentyl)-1,2,5-thiadiazolidine-1,1-dioxide

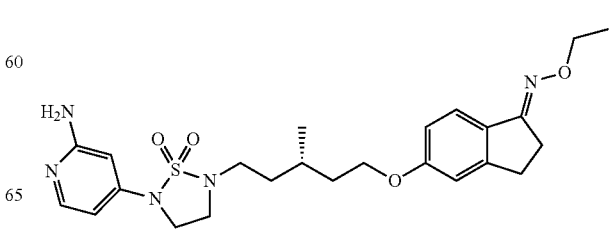

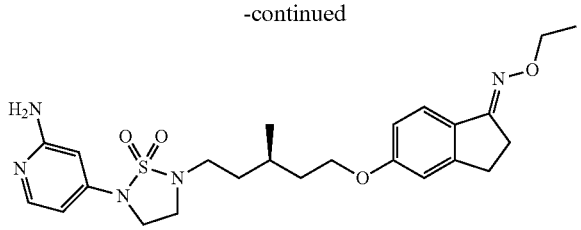

Embodiment 29A (E)-5-hydroxy-2,3-dihydro-1H-inden-1-O-ethyl ketoxime

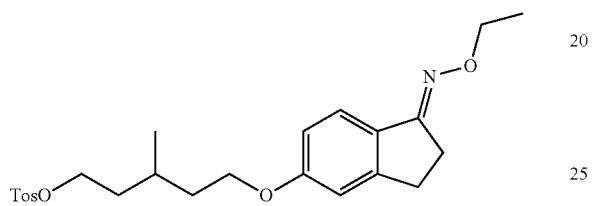

Allow the mixture solution of Embodiment 8B (2.5 g, 13.1 mmol), 14A (6.1 g, 14.4 mmol) and K$_2$CO$_3$ (3.6 g, 26.1 mmol) in acetonitrile (50 ml) to react 16 hours at 80° C. Add ethyl acetate (50 ml) and water (50 ml) into the reaction system. Extract the aqueous layer with ethyl acetate (50 ml×3) and then dry the combined organic layers with Na$_2$SO$_4$ before filter and evaporate. Then purify the residue with column chromatography (petroleum ether:ethyl acetate=20:1-5:1) to obtain the title compound (colorless solid, 2.5 g, yield of 39%).

$^1$H-NMR(CDCl$_3$, 400 MHz) 7.79 (d, J=8.0 Hz, 2H), 7.60 (d, J=9.0 Hz, 1H), 7.34 (d, J=8.0 Hz, 2H), 6.74-6.80 (m, 2H), 4.20 (q, J=7.0 Hz, 2H), 4.08-4.13 (m, 2H), 3.91-4.01 (m, 2H), 2.95-3.03 (m, 2H), 2.85-2.93 (m, 2H), 2.44 (s, 3H), 1.72-1.87 (m, 3H), 1.50-1.61 (m, 2H), 1.33 (t, J=7.0 Hz, 3H), 0.91 (d, J=6.5 Hz, 3H).

Embodiment 29B (E)-2-(2-chloropyridin-4-yl)-5-(5-((1-(ethoxy-imino)-2,3-dihydro-1H-inden-5-yl)-oxy)-3-methyl-pentyl)-1,2,5-thiadiazolidine-1,1-dioxide

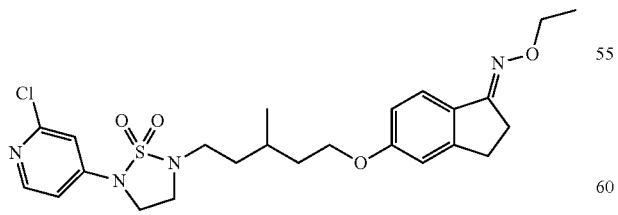

At 0° C., add slowly sodium hydroxide (673 mg, 16.8 mmol) into the mixture solution of Embodiment 4E (1.3 g, 4.8 mmol) in N,N-dimethylformamide (40 ml). Thirty minutes later, drop the mixture solution of Embodiment 29A (2.5 g, 5.6 mmol) in N,N-dimethylformamide (40 ml). Then allow the mixture to react 12 hours at 25° C. Add water (30 ml) into the reaction system. Extract the aqueous layer with dichloromethane (40 ml×3) and then dry the combined organic layers with Na$_2$SO$_4$ before filter and evaporate. Then purify the residue with column chromatography (petroleum ether:ethyl acetate=5:1-1:1) to obtain the title compound (yellow liquid, 2.1 g, yield of 66%).

$^1$H-NMR(CDCl$_3$, 400 MHz) 8.25 (d, J=6.0 Hz, 1H), 7.55-7.61 (m, 1H), 7.04 (dd, J=5.5, 2.0 Hz, 1H), 6.98 (d, J=2.0 Hz, 1H), 6.75-6.80 (m, 2H), 4.18 (q, J=7.0 Hz, 2H), 4.11 (q, J=7.4 Hz, 1H), 3.97-4.05 (m, 2H), 3.80 (t, J=6.5 Hz, 2H), 3.47-3.55 (m, 2H), 3.19 (t, J=7.3 Hz, 2H), 2.94-2.98 (m, 2H), 2.86-2.90 (m, 2H), 1.78-1.87 (m, 2H), 1.53-1.71 (m, 2H), 1.31 (t, J=7.0 Hz, 3H), 1.02 (d, J=6.5 Hz, 3H). LCMS(ESI) m/z: 507 (M+1).

Embodiment 29C (E)-2-(2-amino-pyridin-4-yl)-5-(5-((1-(ethoxy-imino)-2,3-dihydro-1H-inden-5-yl)-oxy)-3-methyl-pentyl)-1,2,5-thiadiazolidine-1,1-dioxide

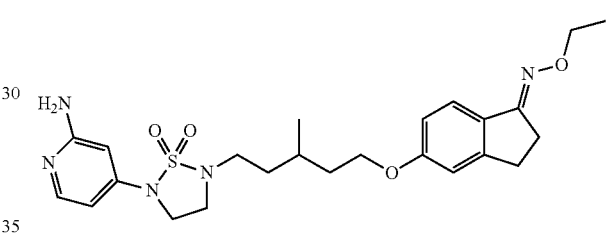

Please refer to the preparation method of Embodiment 28 for this embodiment.

$^1$H-NMR(CDCl$_3$, 400 MHz) 7.97 (d, J=5.8 Hz, 1H), 7.53-7.68 (m, 1H), 6.76-6.80 (m, 2H), 6.41 (dd, J=5.8, 2.0 Hz, 1H), 6.27 (d, J=2.0 Hz, 1H), 4.49 (br.s., 2H), 4.19 (q, J=7.0 Hz, 2H), 4.03 (q, J=6.0 Hz, 2H), 3.76 (t, J=6.4 Hz, 2H), 3.44-3.50 (m, 2H), 3.18 (t, J=7.5 Hz, 2H), 2.95-3.00 (m, 2H), 2.86-2.91 (m, 2H), 1.68-1.92 (m, 5H), 1.32 (t, J=7.0 Hz, 3H), 1.03 (d, J=6.3 Hz, 3H). LCMS(ESI) m/z: 488 (M+1).

Embodiment 29D (S,E)-2-(2-amino-pyridin-4-yl)-5-(5-((1-(ethoxy-imino)-2,3-dihydro-1H-inden-5-yl)-oxy)-3-methyl-pentyl)-1,2,5-thiadiazolidine-1,1-dioxide

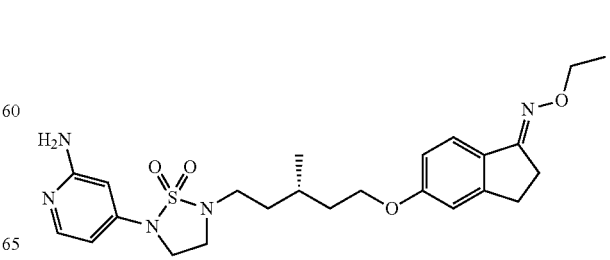

(R,E)-2-(2-amino-pyridin-4-yl)-5-(5-((1-(ethoxy-imino)-2,3-dihydro-1H-inden-5-yl)oxy)-3-methyl-pentyl)-1,2,5-thiadiazolidine-1,1-dioxide

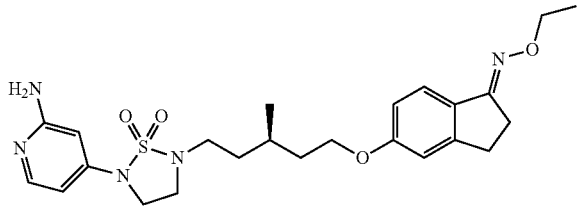 [SMILES: CCO/N=C1\CCc2cc(OCC[C@H](C)CCN3CCN(c4ccnc(N)c4)S3(=O)=O)ccc21]

Embodiment 29C undergoes chiral separation (AD-H_3 UM_3_60_3 ml_5 MIN, Column: Chiralpak AD-350*4.6 mm I.D., 3 um mobile phase: 60% methanol (0.05% DEA)-$CO_2$ flow rate: 3 ml/M; wavelength: 220 nm; peak appearance time: 1.334 min, 1.823 min) to obtain the title compound.

$^1$H-NMR(CDCl$_3$, 400 MHz) 7.97 (d, J=6.0 Hz, 1H), 7.56-7.63 (m, 1H), 6.79 (br.s., 2H), 6.41 (dd, J=6.0, 2.0 Hz, 1H), 6.27 (d, J=1.8 Hz, 1H), 4.51 (br.s., 2H), 4.17-4.23 (m, 2H), 3.99-4.08 (m, 2H), 3.76 (t, J=6.4 Hz, 2H), 3.45-3.51 (m, 2H), 3.18 (t, J=7.5 Hz, 2H), 2.95-3.00 (m, 2H), 2.86-2.91 (m, 2H), 1.69-1.93 (m, 5H), 1.32 (t, J=7.0 Hz, 3H), 1.03 (d, J=6.5 Hz, 3H). LCMS(ESI) m/z: 488 (M+1).

$^1$H-NMR(CDCl$_3$, 400 MHz) 7.97 (d, J=5.8 Hz, 1H), 7.53-7.68 (m, 1H), 6.76-6.80 (m, 2H), 6.41 (dd, J=5.8, 2.0 Hz, 1H), 6.27 (d, J=2.0 Hz, 1H), 4.49 (br.s., 2H), 4.19 (q, J=7.0 Hz, 2H), 4.03 (q, J=6.0 Hz, 2H), 3.76 (t, J=6.4 Hz, 2H), 3.44-3.50 (m, 2H), 3.18 (t, J=7.5 Hz, 2H), 2.95-3.00 (m, 2H), 2.86-2.91 (m, 2H), 1.68-1.92 (m, 5H), 1.32 (t, J=7.0 Hz, 3H), 1.03 (d, J=6.3 Hz, 3H). LCMS(ESI) m/z: 488 (M+1).

Embodiment 30

(E)-2-(2-amino-pyridin-4-yl)-5-(5-((1-(ethoxy-imino)-2,3-dihydro-1H-inden-5-yl)oxy)-3,3-dimethylpentyl)-1,2,5-thiadiazolidine-1,1-dioxide

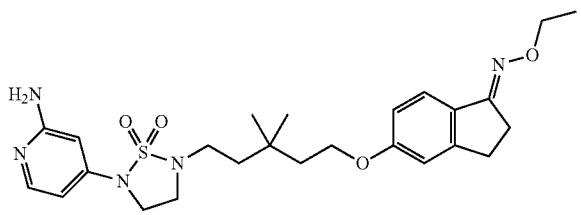 [SMILES: CCO/N=C1\CCc2cc(OCCC(C)(C)CCN3CCN(c4ccnc(N)c4)S3(=O)=O)ccc21]

Embodiment 30A 3,3-dimethyl pentane-1,5-diol

Under the protection of N$_2$ gas at 0° C., add LiAlH$_4$ (534 mg, 14.1 mmol) into the solution of 4,4-dimethyl glutaric anhydride (500 mg, 3.5 mmol) in THF (20 ml). After the substances are added, agitate the reaction mixture 12 hours at 80° C. Cool the reaction solution to room temperature and then pour it into ice water (50 ml) and agitate 10 minutes. Extract the aqueous phase with ethyl acetate (30 ml×3). Then dry the combined organic phases with anhydrous Na$_2$SO$_4$ before filter and concentrate to obtain the title compound (yellow liquid, 300 mg, yield of 64%).

1H NMR (400 MHz, CHLOROFORM-d) 3.69 (t, J=7.15 Hz, 4H), 3.25 (br.s., 2H), 1.49-1.63 (m, 4H), 0.89-0.95 (m, 6H).

Embodiment 30B 3,3-dimethylpentane-1,5-bis(4-methylbenzenesulfonate)

At 0° C., add p-toluensulfonyl chloride (43 g, 227 mmol) and triethylamine (23 g, 227 mmol) into the solution of Embodiment 30A (10 g, 75.6 mmol) in dichloromethane (200 ml). After the substances are added, agitate the mixture solution above 12 hours at 25° C. After the raw materials disappear, pour the reaction solution into ice water (300 ml) and then agitate 20 minutes. Extract the aqueous phase with dichloromethane (50 ml×4). Wash the combined organic phases with the saturated salt water (50 ml) and then dry with anhydrous Na$_2$SO$_4$ before filter and concentrate. Then purify the crude product with column chromatography (petroleum ether:ethyl acetate=3:1) to obtain the title compound (yellow liquid, 20 g, yield of 60%). 1H NMR (400 MHz, CHLOROFORM-d) 7.77 (d, J=8.53 Hz, 2H), 7.35 (d, J=8.03 Hz, 2H), 4.02 (t, J=7.03 Hz, 2H), 2.45 (s, 3H), 1.55 (t, J=7.03 Hz, 2H), 0.84 (s, 3H).

Embodiment 30C (E)-5-((1-(ethoxy-imino)-2,3-dihydro-1H-inden-5-yl)-oxy)-3,3-dimethylpentyl-4-methly-benzenesulfonic acid

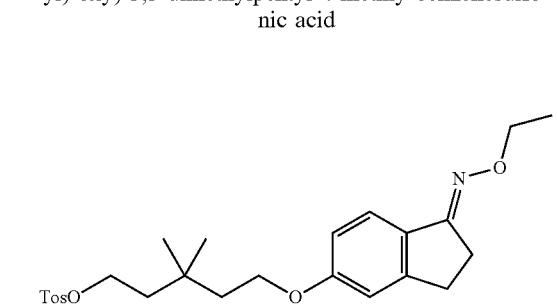

Add K$_2$CO$_3$ (627 mg, 4.54 mmol) into the solution of Embodiment 30C (1.0 g, 2.3 mmol) and Embodiment 8B (173.6 mg, 908 μmol) in acetone (20 ml). Agitate the reaction solution 12 hours at 70° C. and cool it to room temperature before concentrate under reduced pressure. Add water (50 ml) into the residue and then extract with ethyl acetate (30 ml×3). Dry the combined organic phases with anhydrous Na$_2$SO$_4$. Then filter and concentrate it before purifying it with column (petroleum ether:ethyl acetate=3:1) to obtain the title compound (yellow solid, 300 mg, yield of 72%). 1H NMR (400 MHz, CHLOROFORM-d) 7.77-7.82 (m, 2H), 7.59 (d, J=8.53 Hz, 1H), 7.33 (d, J=8.53 Hz, 2H), 6.75 (br.s., 2H), 4.11-4.24 (m, 4H), 3.97 (t, J=6.78 Hz, 2H), 2.81-3.02 (m, 4H), 2.38-2.46 (m, 4H), 1.70 (dt, J=2.51, 7.03 Hz, 4H), 1.32 (t, J=7.03 Hz, 3H), 0.96 (s, 6H).

Embodiment 30D (E)-2-(2-chloropyridin-4-yl)-5-(5-((1-(ethoxy-imino)-2,3-dihydro-1H-inden-5-yl)-oxy)-3,3-dimethylpentyl)-1,2-thiadiazolidine-1,1-dioxide

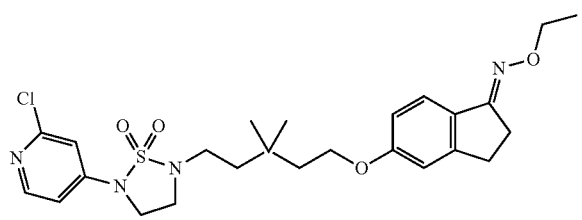

Under the protection of N₂ gas at 0° C., add sodium hydride (52 mg, 1.3 mmol) into the solution of Embodiment 4E (153 mg, 653 μmol) in N,N-dimethylformamide (5 ml). After the substances are added, agitate the solution at room temperature to react 30 minutes. Add Embodiment 30C (300 mg, 653 μmol) into the solution above. Then continue to agitate 11 hours at room temperature. Pour the reaction solution into ice water (30 ml) and extract the aqueous phase with ethyl acetate (20 ml×3). Dry the combined organic phases with anhydrous Na₂SO₄. Then filter and concentrate it before purify the crude product with column (petroleum ether:ethyl acetate=3:1) to obtain the title compound (yellow solid, 150 mg, yield of 44%). 1H NMR (400 MHz, CHLOROFORM-d) 8.27 (d, J=6.02 Hz, 1H), 8.02 (s, 2H), 7.60 (d, J=9.03 Hz, 1H), 7.06 (dd, J=2.26, 5.77 Hz, 1H), 6.99 (d, J=2.01 Hz, 1H), 6.77-6.82 (m, 2H), 4.20 (q, J=7.03 Hz, 2H), 4.05 (t, J=6.78 Hz, 2H), 3.82 (t, J=6.27 Hz, 2H), 3.54 (t, J=6.27 Hz, 2H), 3.18-3.26 (m, 2H), 2.97-3.03 (m, 2H), 1.79 (t, J=6.53 Hz, 2H), 1.68-1.76 (m, 2H), 1.32 (t, J=7.03 Hz, 4H), 1.06 (s, 6H). LCMS(ESI) m/z: 521 (M+1).

Embodiment 30E (E)-2-(2-amino-pyridin-4-yl)-5-(5-((1-(ethoxy-imino)-2,3-dihydro-1H-inden-5-yl)-oxy)-3,3-dimethylpentyl)-1,2-thiadiazolidine-1,1-dioxide

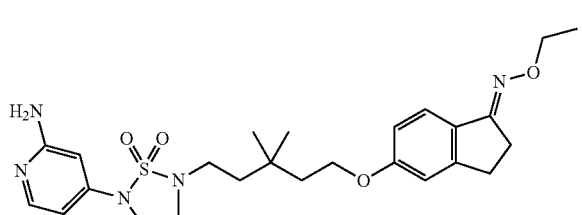

Please refer to the preparation method of Embodiment 29 for this embodiment. ¹H NMR (400 MHz, CHLOROFORM-d) 7.82 (br.s., 1H), 7.61 (d, J=8.53 Hz, 1H), 6.81 (br.s., 2H), 6.58 (d, J=4.02 Hz, 1H), 6.36 (br.s., 1H), 4.21 (d, J=6.78 Hz, 2H), 4.06 (br.s., 2H), 3.84 (br.s., 2H), 3.53 (br.s., 2H), 3.21 (br.s., 2H), 2.74-3.07 (m, 4H), 1.58-1.85 (m, 4H), 1.33 (t, J=6.53 Hz, 4H), 1.06 (br.s., 6H). LCMS(ESI) m/z: 502 (M+1).

Embodiment 31

(E)-2-(2-amino-pyridin-4-yl)-5-(5-((1-(ethoxy-imino)-2,3-dihydro-1H-inden-5-yl)-oxy)-3,3-difluoropentyl)-1,2,5-thiadiazolidine-1,1-dioxide

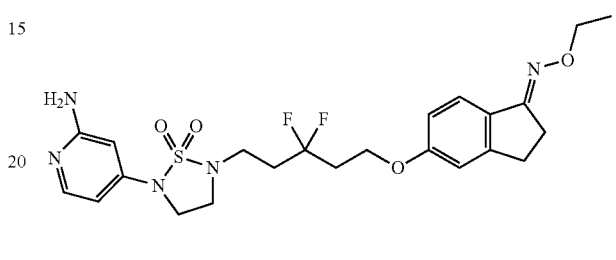

Embodiment 31A

Diethyl-3,3-difluoro-glutarate

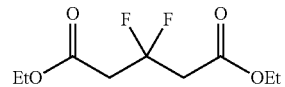 [SMILES: CCOC(=O)CC(F)(F)CC(=O)OCC]

At −65° C., add slowly the solution of diethyl-2,2'-(1,3-dithiolane-2,2-diyl)diacetate (501 mg, 1.8 mmol) in dichloromethane into the solution of dibromohydantoin (2.16 g, 7.5 mmol) and pyridine hydrofluoride solution (2.2 ml, 1.8 mmol) in dichloromethane (15 ml). Continue to agitate the mixture solution 5 hours at −65° C. before heat to 25° C. to agitate 3 hours. Add water (10 ml) into the reaction system. Adjust the pH value of the system with Na₂CO₃ aqueous solution to 3-4. Then extract the aqueous layer with dichloromethane (20 ml×3) before filter and dry through rotation. Then purify the residue with column chromatography (petroleum ether:ethyl acetate=10:1) to obtain the title compound (white solid, 210 mg, yield of 38%) and the title compound (yellow liquid, 300 mg, yield of 74%). ¹H NMR(CDCl₃, 400 MHz) δ4.18 (q, J=7.0 Hz, 4H), 3.24 (t, J=15.1 Hz, 4H), 1.26-1.30 (m, 6H).

Embodiment 31B 3,3-difluoro pentane-1,5-diol

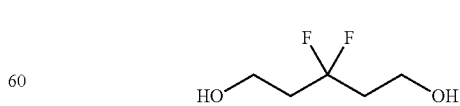

At 0° C., drop Embodiment 31A (300 mg, 1.34 mmol) into the solution of LiAlH₄ (102 mg, 2.68 mmol) in THF (3 ml). After it is added, agitate the mixture solution 3 hours at 25° C. Add water (0.5 ml) and 10% NaOH solution (0.5 ml) into the reaction system. Dry the system with Na₂SO₄ before filter and evaporate to obtain the title compound (160 mg, yield of 72%). $^1$H NMR(CDCl$_3$, 400 MHz): 3.77-3.90 (m, 4H), 2.21 (tt, J=16.8, 5.8 Hz, 4H).

Embodiment 31C 1,5-dibromo-3,3-difluoro-pentane

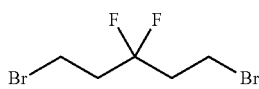

At 0° C., drop CBr4 (1.5 g, 4.6 mmol) into the solution of Embodiment 31B (160 mg, 1.1 mmol), triphenyl phosphine (1.79 g, 6.8 mmol) in THF (5 ml). After the substances are added, agitate the mixture solution 3 hours at 60° C. Filter the solution before wash the filter cake with ethyl acetate (300 ml×3). Then dry the filter through rotation and purify the residue with column chromatography (petroleum ether: ethyl estate=10:1) to obtain the title compound (200 mg, yield of 53%). $^1$H NMR(CDCl$_3$, 400 MHz): 3.45-3.51 (m, 4H), 2.48 (tt, J=16.2, 7.9 Hz, 4H).

Embodiment 31D (E)-5-((5-bromo-3,3-difluoro-pentyl)-oxy)-2,3-dihydro-1H-inden-1-one-O-ethyl ketoxime

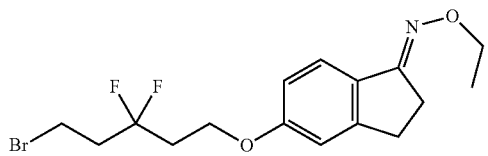 [SMILES: CCO/N=C1\CCc2cc(OCCC(F)(F)CCBr)ccc21]

Please refer to the preparation method of Embodiment 30C for this embodiment. $^1$H NMR(CDCl$_3$), 400 MHz): 7.56-7.62 (m, 1H), 6.76-6.83 (m, 2H), 4.19 (g, J=6.9 Hz, 2H), 4.01 (t, J=6.0 Hz, 2H), 3.43-3.52 (m, 2H), 2.95-3.02 (m, 2H), 2.84-2.92 (m, 2H), 2.03-2.12 (m, 2H), 1.91-2.00 (m, 2H), 1.32 (t, J=7.0 Hz, 3H).

Embodiment 31E (E)-2-(2-chloropyridin-4-yl)-5-(5-((1-(ethoxy-imino)-2,3-dihydro-1H-inden-5-yl)-oxy)-3,3-difluoro-pentyl)-1,2-thiadiazolidine-1,1-dioxide

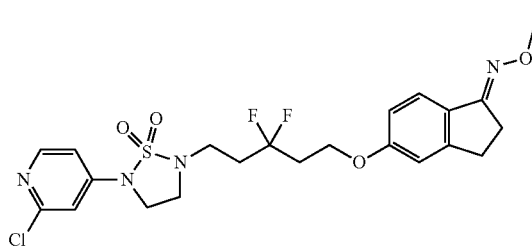

Please refer to the preparation method of Embodiment 30D for this embodiment. $^1$H NMR(CDCl$_3$, 400 MHz): 8.26 (d, J=5.8 Hz, 1H), 7.60 (d, J=9.3 Hz, 1H), 7.04 (dd, J=5.8, 2.3 Hz, 1H), 6.98 (d, J=2.0 Hz, 1H), 6.73-6.86 (m, 3H), 4.19 (d, J=7.0 Hz, 2H), 4.00-4.05 (m, 2H), 3.76-3.84 (m, 2H), 3.55 (t, J=6.4 Hz, 2H), 3.23 (t, J=6.1 Hz, 2H), 2.96 (d, J=7.3 Hz, 2H), 2.86-2.90 (m, 2H), 1.86-1.96 (m, 4H), 1.32 (s, 3H). LCMS(ESI) m/z: 529 (M+1).

Embodiment 31F (E)-2-(2-amino-pyridin-4-yl)-5-(5-((1-(ethoxy-imino)-2,3-dihydro-1H-inden-5-yl)-oxy)-3,3-difluoropentyl)-1,2,5-thiadiazolidine-1,1-dioxide

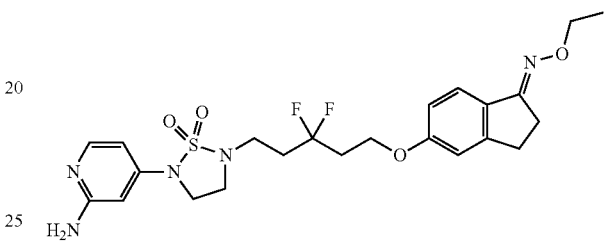

Please refer to the preparation method of Embodiment 29 for this embodiment. $^1$H NMR(CDCl$_3$, 400 MHz): 7.96 (d, J=5.8 Hz, 1H), 7.51-7.64 (m, 1H), 6.71-6.84 (m, 2H), 6.40 (dd, J=5.8, 1.8 Hz, 1H), 6.24 (d, J=1.5 Hz, 1H), 4.55 (br.s., 2H), 4.19 (g, J=7.0 Hz, 2H), 4.04 (t, J=5.4 Hz, 2H), 3.72 (t, J=6.4 Hz, 2H), 3.42-3.55 (m, 2H), 3.20 (t, J=6.5 Hz, 2H), 2.92-3.00 (m, 2H), 2.83-2.92 (m, 2H), 1.86-1.95 (m, 4H), 1.32 (t, J=7.0 Hz, 3H). LCMS(ESI) m/z: 510 (M+1).

Procedure M

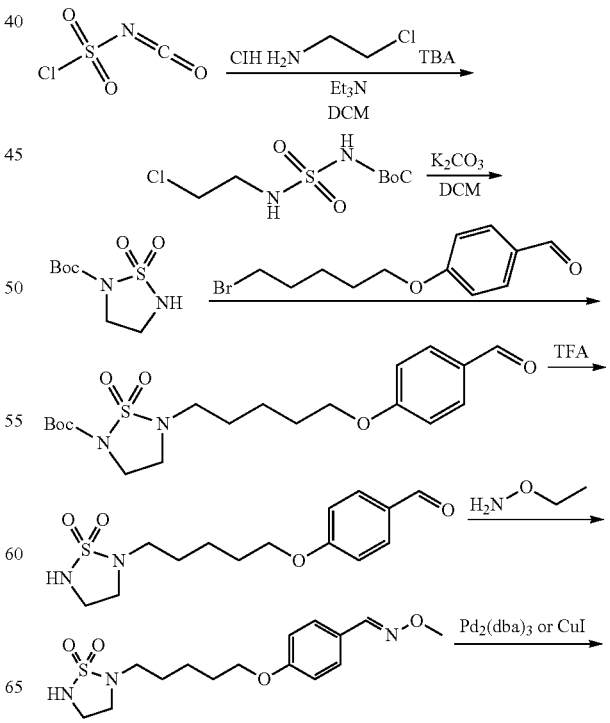

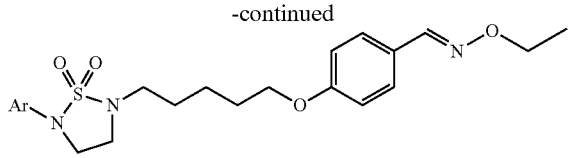

Embodiment 32

(E)-4-((5-(5-(2-methylpyridin-4-yl)-1,1-dioxide-1,2,5-thiadiazol-2-yl)-pentyl)-oxy)-benzaldehyde-O-ethyl ketoxime

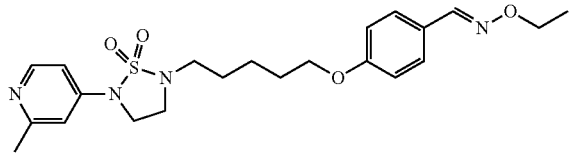 [SMILES: CCO/N=C/c1ccc(OCCCCCN2CCN(c3ccnc(C)c3)S2(=O)=O)cc1]

Embodiment 32A

N-t-butyl-N-(2-chloroethyl)-sulfonylurea

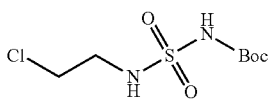 [SMILES: CC(C)(C)OC(=O)NS(=O)(=O)NCCCl]

Under the protection of $N_2$ gas at 0° C., drop the solution of N-(oxymethylene)-sulfamoyl chloride (244 g, 1.73 mol) in dichloromethane (1.0 L) into t-butanol (453 g, 2.1 mol) in 1 hour. After the substances are added, agitate the mixture solution 1 hour at 25° C. Add the mixture of this mixture solution and triethylamine (872 g, 8.6 mol) into the solution of 2-chloro-ethylamine (200 g, 1.73 mol) in chloromethane (2 L) in 2 hours. Agitate the mixture solution 10 hours at 25° C. before filter. Then concentrate the filtrate before dissolve it in 2 L water. Then adjust it with 4N salt to pH=5-6. A large amount of solids will precipitate out. Then filter the solids and wash them with petroleum ether (1 L) to obtain the title compound (white solid, 350 g, yield of 78.5%) that can be directly used without necessity to purify further.

Embodiment 32B t-butyl-1,2,5-thiadiazolidine-2-carboxylate-1,1-dioxide

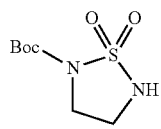

At room temperature, add the mixture solution of $K_2CO_3$ (280 g, 2.03 mol) into the solution of Embodiment 32A (350 g, 1.35 mol) in dimethylsulfoxide (3 L) and agitate 10 hours at room temperature before filter. Pour the filtrate into 5 L water and adjust it with 4N hydrochloric acid to pH=5-6. Then filter the solid and wash the solids with petroleum ether (1 L). Then recrystallize the solids with (petroleum ether/ethyl acetate=1/1) (1 L) to obtain the title compound (white solid, 250 g, yield of 84%).

Embodiment 32C 4-((5-bromophenyl)-pentyl)-benzaldehyde

Please refer to the preparation method of Embodiment 4G for this embodiment. $^1$H NMR (400 MHz, CHLOROFORM-d) 9.81-9.89 (m, 1H), 7.81 (d, J=8.80 Hz, 2H), 6.97-7.02 (m, 2H), 4.04 (t, J=6.40 Hz, 2H), 3.39-3.46 (m, 2H), 1.94 (t, J=7.60 Hz, 2H), 1.84 (t, J=7.20 Hz, 2H), 1.61-1.65 (m, 2H).

Embodiment 32D tert-butyl-5-(5-(4-formyl-phenoxy)-pentyl)-1,2,5-thiadiazolidine-2-carboxylate-1,1-dioxide

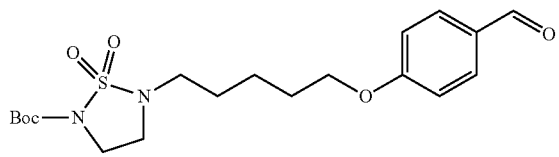 [SMILES: CC(C)(C)OC(=O)N1CCN(CCCCCOc2ccc(C=O)cc2)S1(=O)=O]

Under the protection of $N_2$ gas at 0° C., add sodium hydroxide (81 mg, 2.0 mmol) into the solution of Embodiment 32C (550 mg, 2.5 mmol) in N,N-dimethylformamide (8 ml). After agitate it 0.5 hour at 0° C., drop the solution of 4-((5-bromophenyl)-pentyl)-benzaldehydein (671 mg, 2.5 mmol) in N,N-dimethylformamide (19 ml) into it. Agitate it 0.5 hour at 0° C. and then the TLC verifies the reaction ends. Add water (10 ml) to quench the reaction. Then extract the aqueous layer with ethyl acetate (10 ml×3). Then combine the organic layers and dry with anhydrous $Na_2SO_4$ before filter and evaporate. Then separate the crude product with TLC plate (petroleum ether/ethyl acetate=3:1) to obtain the title compound (white solid, 400 mg, yield of 60%). $^1$H NMR (400 MHz, CHLOROFORM-d) 9.88 (s, 1H), 7.82 (d, J=8.53 Hz, 2H), 6.98 (d, J=8.53 Hz, 2H), 4.05 (t, J=6.27 Hz, 2H), 3.79 (t, J=6.53 Hz, 2H), 3.32 (t, J=6.27 Hz, 2H), 3.08 (t, J=7.28 Hz, 2H), 1.82-1.91 (m, 2H), 1.72-1.79 (m, 2H), 1.57-1.64 (m, 2H), 1.54 (s, 10H).

Embodiment 32E 4-((5-(1,1-dioxide-1,2,5-thiadiazolidine-2-yl)-pentyl)-oxy)-benzaldehyde

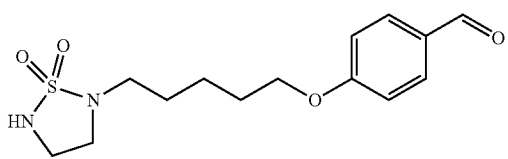 [SMILES: O=Cc1ccc(OCCCCCN2CCNS2(=O)=O)cc1]

At 0° C., add trifluoroacetate (5 ml) into the solution of Embodiment 32D (4 g, 9.7 mmol) in dichloromethane (40 ml) and agitate it 4 hours at 15° C. After TLC verifies the reaction ends, adjust it with the saturated NaHCO$_3$ solution to pH=7 at 0° C. and extract it with dichloromethane (30 ml×2). Then combine the organic layers with Na$_2$SO$_4$ before filter and evaporate to obtain the crude product of the title compound (colorless oily form, 2.66 g, yield of 88%) that can be used directly further.

Embodiment 32F (E)-4-((5-(1,1-dioxide-1,2,5-thiadiazolidine-2-yl)-pentyl)-oxy)-benzaldehyde-O-ethyl ketoxime

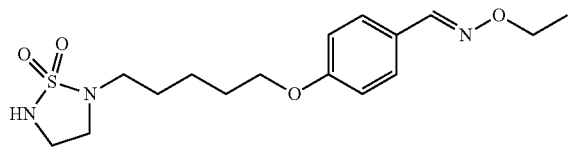 [SMILES: CCO/N=C/c1ccc(OCCCCCN2CCNS2(=O)=O)cc1]

Under the protection of N$_2$ gas, add ethoxyamino hydrochloride (1.56 g, 16 mmol) and sodium acetate (1.31 g, 16 mmol) into the solution of Embodiment 32E (1.0 g, 3.2 mmol) in ethanol (50 ml) and heat it to 60° C. to react 1 hour. After TLC verifies that the reaction ends, concentrate and evaporate the solvent before add water (20 ml). Then extract it with ethyl acetate (20 ml×3). Then combine the organic layers and dry it with Na$_2$SO$_4$ before filter and evaporate. Purify the crude product with column chromatogratphy (petroleum ether:ethyl acetate=2:1) to obtain the title compound (colorless oily form, 1.1 g, yield of 97%) that can be directly used further.

Embodiment 32G (E)-4-((5-(5-2-methylpyridin-4-yl)-1,1-dioxide-1,2,5-thiadiazolidine-2-yl)-pentyl)-oxy)-benzaldehyde-O-ethyl ketoxime

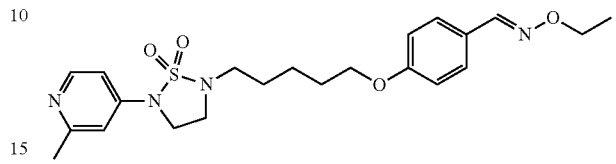

Under the protection of N$_2$ gas, heat the solution of Embodiment 32F (130 mg, 366 μmol), 4-bromo-2-methyl-pyridine (189 mg, 1.1 mmol), Cs$_2$CO$_3$ (179 mg, 549 μmol), Pd$_2$(dba)$_3$ (34 mg, 37 μmol) and Xant-phos (21 mg, 37 μmol) in dioxane (2 ml) to 100° C. for 6 hours. TLC indicates that the raw materials are consumed completely. Cool the reaction solution to room temperature. Then add ethyl acetate (20 ml). Then wash the organic phase with saturated salt water (30 ml) and dry the organic phase with Na$_2$SO$_4$. Then filter and concentrate before purify it with the preparative TLC (dichloromethane:methanol=30:1) to obtain the title compound (white solid, 100 mg, yield of 61%). $^1$H NMR (400 MHz, CHLOROFORM-d) 8.39 (d, J=5.52 Hz, 1H), 8.02 (s, 1H), 7.51 (d, J=8.53 Hz, 2H), 6.95 (s, 1H), 6.87 (d, J=8.53 Hz, 3H), 4.20 (q, J=7.36 Hz, 2H), 4.00 (t, J=6.27 Hz, 2H), 3.84 (t, J=6.27 Hz, 2H), 3.53 (t, J=6.27 Hz, 2H), 3.18 (t, J=7.28 Hz, 2H), 2.56 (s, 3H), 1.82-1.90 (m, 2H), 1.74-1.81 (m, 2H), 1.62 (br.s., 2H), 1.25-1.36 (m, 3H). LCMS(ESI) m/z: 447 (M+1).

Embodiment 33

(E)-4-((5-(5-(6-methyl-pyridazin-3-yl)-1,1-dioxide-1,2,5-thiadiazolidine-2-yl)-pentyl)-oxy)-benzaldehyde-O-ethyl ketoxime

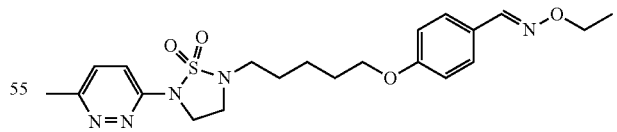

Please refer to the preparation method of Embodiment 32 for this embodiment. $^1$H NMR (400 MHz, CHLOROFORM-d) 8.02 (s, 1H), 7.61 (d, J=9.03 Hz, 1H), 7.51 (d, J=8.53 Hz, 2H), 7.32 (d, J=9.54 Hz, 1H), 6.87 (d, J=8.53 Hz, 2H), 4.16-4.30 (m, 4H), 4.00 (t, J=6.27 Hz, 2H), 3.56 (t, J=6.27 Hz, 2H), 3.19 (t, J=7.28 Hz, 2H), 2.66 (s, 3H), 1.75-1.91 (m, 4H), 1.60-1.66 (m, 2H), 1.32 (t, J=7.03 Hz, 3H). LCMS(ESI) m/z: 447 (M+1).

Embodiment 34

(E)-4-((5-(5-(6-chloro-pyridazin-3-yl)-1,1-dioxide-1,2,5-thiadiazolidine-2-yl)-pentyl)-oxy)-benzaldehyde-O-ethyl ketoxime

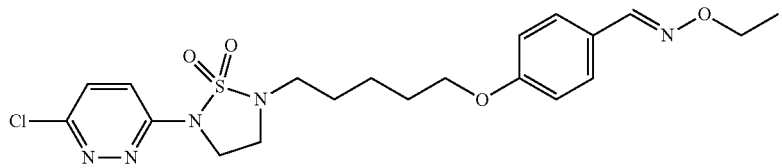 [SMILES: CCO/N=C/c1ccc(OCCCCCN2CCN(c3ccc(Cl)nn3)S2(=O)=O)cc1]

Please refer to the preparation method of Embodiment 32 for this embodiment. 1H NMR (400 MHz, CHLOROFORM-d) d 8.02 (s, 1H), 7.68 (d, J=9.03 Hz, 1H), 7.45-7.54 (m, 1H), 6.87 (d, J=8.53 Hz, 1H), 4.15-4.29 (m, 5H), 4.00 (t, J=6.02 Hz, 2H), 3.57 (t, J=6.53 Hz, 2H), 3.20 (t, J=7.28 Hz, 2H), 1.75-1.91 (m, 4H), 1.60-1.67 (m, 2H), 1.32 (t, J=7.03 Hz, 3H). LCMS(ESI) m/z: 468 (M+1).

Embodiment 35

(E)-4-((5-(1,1-dioxide-5-(thiazol-2-yl)-1,2,5-thiadiazolidine-2-yl)-pentyl)-oxy)-benzaldehyde-O-ethyl ketoxime

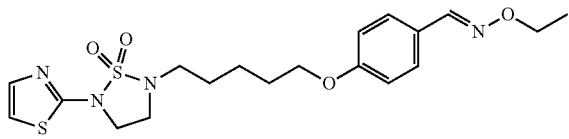 [SMILES: CCO/N=C/c1ccc(OCCCCCN2CCN(c3nccs3)S2(=O)=O)cc1]

Please refer to the preparation method of Embodiment 32 for this embodiment. 1H NMR (400 MHz, CHLOROFORM-d) d 8.02 (s, 1H), 7.51 (d, J=8.53 Hz, 2H), 7.43 (d, J=3.51 Hz, 1H), 6.98 (d, J=3.51 Hz, 1H), 6.87 (d, J=9.03 Hz, 2H), 4.20 (q, J=7.03 Hz, 2H), 4.12 (t, J=6.53 Hz, 2H), 4.00 (t, J=6.27 Hz, 2H), 3.56 (t, J=6.53 Hz, 2H), 3.19 (t, J=7.28 Hz, 2H), 1.82-1.89 (m, 2H), 1.74-1.80 (m, 2H), 1.58-1.65 (m, 2H), 1.32 (t, J=7.03 Hz, 3H). LCMS(ESI) m/z: 439 (M+1).

Embodiment 36

(E)-N-(4-(5-(5-(4-((ethoxy-imino)-methyl)-phenoxy)-pentyl)-1,1-dioxide-1,2,5-thiadiazolidine-2-yl)-pyridin-2-yl)-acetamide

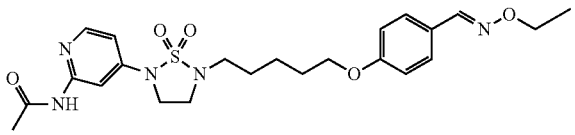 [SMILES: CCO/N=C/c1ccc(OCCCCCN2CCN(c3ccnc(NC(C)=O)c3)S2(=O)=O)cc1]

Embodiment 36A

N-(4-bromo-2-yl)-acetamide

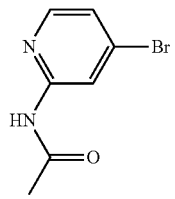

Under the protection of $N_2$ gas at 0° C., add acetyl chloride (454 mg, 5.8 mmol) into the solution of 4-bromo-2-aminopyridine (1.0 g, 5.8 mmol) and triethylamine (1.75 g, 17 mmol) in dichloromethane (50 ml). Allow the solution to react 1 hour at room temperature. Then pour it into ice water (50 ml) to quench before extract with dichloromethane (20 ml). Combine the organic layers and dry it with anhydrous $Na_2SO_4$ before filter and evaporate. Separate and purify the crude product with column chromatography (petroleum ether:ethyl acetate=5:1) to obtain the title compound (white solid, 400 mg, 33%). $^1$H NMR (400 MHz, CHLOROFORM-d) 8.38-8.53 (m, 1H), 8.08 (d, J=5.02 Hz, 1H), 7.93 (br.s., 1H), 7.21 (d, J=4.52 Hz, 1H), 2.22 (s, 3H).

Embodiment 36B (E)-N-(4-(5-(5-(4-((ethoxy-imino)-methyl)-phenoxy)-pentyl)-1,1-dioxide-1,2,5-thiadiazolidine-2-yl)-pyridin-2-yl)-acetamide

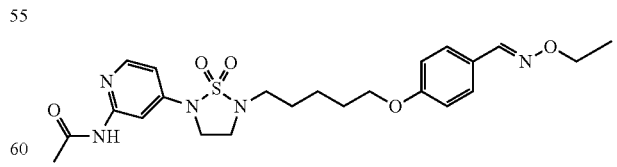

Please refer to the preparation method of Embodiment 32 for this embodiment. $^1$H NMR (400 MHz, CHLOROFORM-d) 8.13 (d, J=5.52 Hz, 1H), 8.02 (s, 1H), 7.92 (br.s., 1H), 7.79 (s, 1H), 7.51 (d, J=8.53 Hz, 2H), 7.17 (dd, J=2.01, 6.02 Hz, 1H), 6.87 (d, J=8.53 Hz, 2H), 4.13-4.28 (m, 2H), 4.00 (t, J=6.27 Hz, 2H), 3.90 (t, J=6.53 Hz, 2H), 3.53 (t, J=6.53 Hz, 2H), 3.18 (t, J=7.28 Hz, 2H), 2.21 (s, 3H), 1.73-1.92 (m, 4H), 1.60-1.65 (m, 2H), 1.28-1.40 (m, 3H). LCMS(ESI) m/z: 490 (M+1).

Embodiment 37

(E)-ethyl-4-(5-(5-(4-((ethoxycarbonyl)-methyl)-phenoxy)-pentyl)-dioxide-1,2,5-thiadiazolidine-2-yl)-pyridin-2-carboxylate

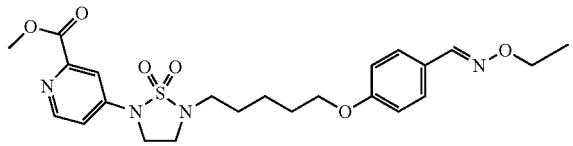 [SMILES: CCO/N=C/c1ccc(OCCCCCN2CCN(c3ccnc(C(=O)OC)c3)S2(=O)=O)cc1]

Please refer to the preparation method of Embodiment 32 for this embodiment. $^1$H NMR (400 MHz, CHLOROFORM-d) 8.63 (d, J=5.77 Hz, 1H), 8.04 (s, 1H), 7.75 (d, J=2.26 Hz, 1H), 7.53 (d, J=8.78 Hz, 2H), 7.40 (dd, J=2.38, 5.65 Hz, 1H), 6.89 (d, J=8.78 Hz, 2H), 4.22 (q, J=7.03 Hz, 2H), 4.00-4.06 (m, 5H), 3.93 (t, J=6.40 Hz, 2H), 3.59 (t, J=6.40 Hz, 2H), 3.21 (t, J=7.28 Hz, 2H), 1.77-1.93 (m, 4H), 1.61-1.70 (m, 5H), 1.33 (t, J=7.03 Hz, 3H). LCMS(ESI) m/z: 491 (M+1).

Embodiment 38

(E)-4-((5-(5-(6-amino-pyrimidin-4-yl)-1,1-dioxide-1,2,5-thiadiazolidine-2-yl)-pentyl)-oxy)-benzaldehyde-O-ethyl ketoxime

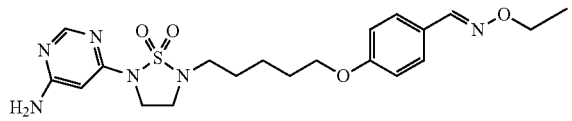 [SMILES: CCO/N=C/c1ccc(OCCCCCN2CCN(c3cc(N)ncn3)S2(=O)=O)cc1]

Embodiment 38A (E)-4-(5-(5-(6-chloro-pyrimidin-4-yl)-1,1-dioxide-1,2,5-thiadiazolidine-2-yl)-pentyl)-oxy)-benzaldehyde-O-ethyl ketoxime

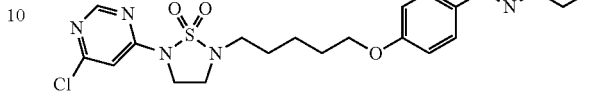

Please refer to the preparation method of Embodiment 32 for this embodiment. LCMS(ESI) m/z: 468 (M+1).

Embodiment 38B (E)-4-((5-(5-(6-amino-pyrimidin-4-yl)-1,1-dioxide-1,2,5-thiadiazolidine-2-yl)-pentyl)-oxy)-benzaldehyde-O-ethyl ketoxime

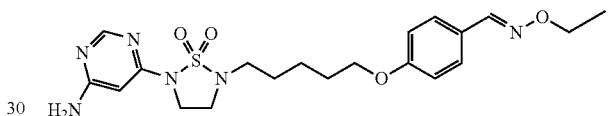

Please refer to the preparation method of Embodiment 28 for this embodiment. $^1$H NMR(CHLOROFORM-d, 400 MHz): 8.33 (s, 1H), 8.02 (s, 1H), 7.51 (d, J=8.5 Hz, 2H), 6.87 (d, J=8.5 Hz, 2H), 6.34 (s, 1H), 4.93 (br.s., 2H), 4.16-4.25 (m, 2H), 4.05 (t, J=6.5 Hz, 2H), 4.00 (t, J=6.3 Hz, 2H), 3.44-3.50 (m, 2H), 3.16 (t, J=7.3 Hz, 2H), 1.82-1.90 (m, 2H), 1.74-1.79 (m, 2H), 1.55-1.60 (m, 2H), 1.32 (t, J=7.0 Hz, 3H). LCMS(ESI) m/z: 449 (M+1).

Precedure N

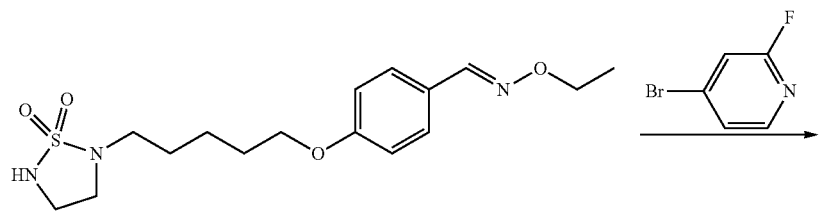

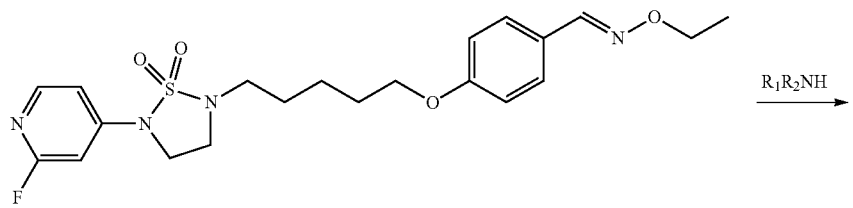

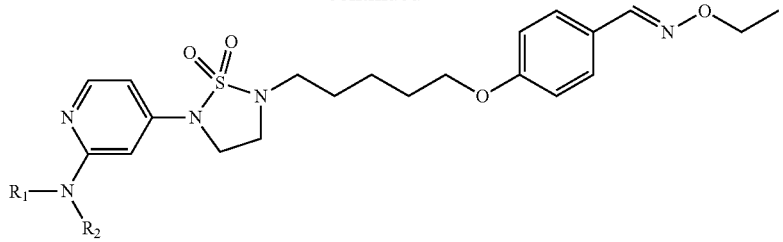

Embodiment 39

(E)-4-((5-(5-(2-Fluoro-4-yl)-1,1-dioxide-1,2,5-thia-diazolidine-2-yl)-pentyl)-oxy)-benzaldehyde-O-ethyl ketoxime

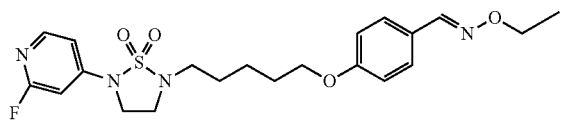 [SMILES: CCO/N=C/c1ccc(OCCCCCN2CCN(c3ccnc(F)c3)S2(=O)=O)cc1]

Under the protection of N₂ gas, add Pd₂(dba)₃ (15 mg, 17 μmol) and Xant-Phos (10 mg, 17 μmol) into the solution of Embodiment 32F (60 mg, 169 μmol), 4-bromo-2-fluoro-pyridine (30 mg, 169 μmol) and Cs₂CO₃ (83 mg, 253 μmol) in dioxane (2 ml). Then agitate it evenly and heat it to 100° C. to react for 4 hours. After TLC verifies that the reaction ends, concentrate and evaporate the solvent. Add water (20 ml) and then extract with ethyl acetate (20 ml×3). Then combine the organic layers and dry with anhydrous Na₂SO₄ before filter and evaporate. Then separate and purify the crude product with TLC plate (petroleum ether/ethyl acetate=2:1) to obtain the title compound (white solid, 70 mg, yield of 92%). ¹H NMR (400 MHz, CHLOROFORM-d) 8.12 (d, J=6.02 Hz, 1H), 8.03 (s, 1H), 7.51 (d, J=8.53 Hz, 2H), 7.02 (d, J=5.52 Hz, 1H), 6.82-6.93 (m, 2H), 6.58 (d, J=2.01 Hz, 1H), 4.20 (q, J=7.03 Hz, 2H), 4.00 (t, J=6.02 Hz, 2H), 3.85 (t, J=6.53 Hz, 2H), 3.52-3.59 (m, 2H), 3.19 (t, J=7.28 Hz, 2H), 1.74-1.91 (m, 4H), 1.59-1.67 (m, 2H), 1.29-1.39 (m, 3H). LCMS (M+1): 451.

Embodiment 40

(E)-4-((5-(5-(2-((2-hydroxyethyl)-amino)-pyridin-4-yl)-1,1-dioxide-1,2,5-thiadiazolidine-2-yl)-pentyl)-oxy)-benzaldehyde-O-ethyl ketoxime

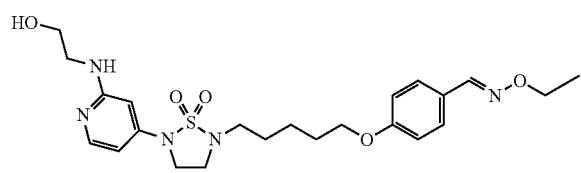 [SMILES: CCO/N=C/c1ccc(OCCCCCN2CCN(c3ccnc(NCCO)c3)S2(=O)=O)cc1]

Under the protection of N₂ gas, add triethylamine (27 mg, 266 μmol) into the solution of Embodiment 39 (20 mg, 44 μmol) and 2-aminoethanol (27 mg, 444 μmol) in dimethyl-sulfoxide (0.5 ml). Allow the mixture solution to react for 2 hours at 100° C. After TLC verifies that the reaction ends, add water (5 ml) to quench and extract with ethyl acetate (10 ml). Combine the organic layers and dry it with anhydrous Na₂SO₄ before filter and evaporate. Separate and purify the crude product with TLC (dichloromethane:methnol=20:1) to obtain the title compound (colorless oily liquid, 12 mg, 55%). ¹H NMR (400 MHz, CHLOROFORM-d) 8.02 (s, 1H), 7.84-7.95 (m, 1H), 7.51 (d, J=8.53 Hz, 2H), 6.85-6.93 (m, 2H), 6.41 (dd, J=1.76, 6.27 Hz, 1H), 6.25 (d, J=1.51 Hz, 1H), 5.47 (br.s., 1H), 4.15-4.29 (m, 2H), 4.00 (t, J=6.27 Hz, 2H), 3.81 (t, J=4.77 Hz, 4H), 3.45-3.56 (m, 4H), 3.16 (t, J=7.03 Hz, 2H), 1.81-1.90 (m, 2H), 1.72-1.81 (m, 2H), 1.56-1.67 (m, 2H), 1.27-1.40 (m, 3H). LCMS (ESI) m/z: 492 (M+1).

Embodiment 41

(E)-4-((5-(5-(2-(methylamino)-pyridin-4-yl)-1,1-dioxide-1,2,5-thiadiazolidine-2-yl)-pentyl)-oxy)-benzaldehyde-O-ethyl ketoxime

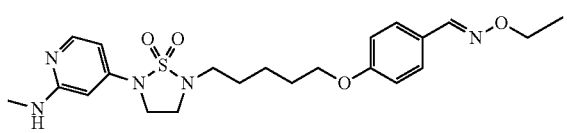 [SMILES: CCO/N=C/c1ccc(OCCCCCN2CCN(c3ccnc(NC)c3)S2(=O)=O)cc1]

Please refer to the preparation method of Embodiment 40 for this embodiment. ¹H NMR (400 MHz, CHLOROFORM-d) 7.97-8.05 (m, 2H), 7.51 (d, J=8.53 Hz, 2H), 6.87 (d, J=8.53 Hz, 2H), 6.36 (dd, J=2.01, 6.02 Hz, 1H), 6.14 (d, J=2.01 Hz, 1H), 4.64 (br.s., 1H), 4.20 (q, J=7.03 Hz, 2H), 4.00 (t, J=6.27 Hz, 2H), 3.82 (t, J=6.27 Hz, 2H), 3.49 (t, J=6.27 Hz, 2H), 3.16 (t, J=7.28 Hz, 2H), 2.92 (d, J=5.02 Hz, 3H), 1.73-1.91 (m, 4H), 1.62-1.66 (m, 2H), 1.28-1.39 (m, 3H). LCMS(ESI) m/z: 462 (M+1).

Embodiment 42

(E)-4-((5-(5-(2-(azetidin-1-yl)-pyridin-4-yl)-1,1-dioxide-1,2,5-thiadiazolidine-2-yl)-pentyl)-oxy)-benzaldehyde-O-ethyl ketoxime

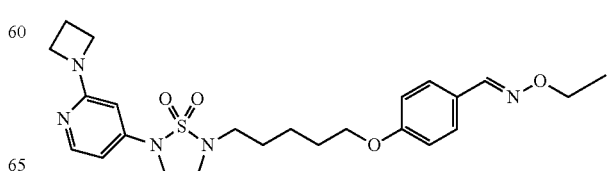

Please refer to the preparation method of Embodiment 40 for this embodiment. ¹H NMR (400 MHz, CHLOROFORM-d) 8.00-8.06 (m, 1H), 7.50 (d, J=8.78 Hz, 1H), 6.87 (d, J=8.78 Hz, 1H), 6.40 (dd, J=2.01, 5.77 Hz, 1H), 5.92 (d, J=1.76 Hz, 1H), 4.19 (q, J=7.03 Hz, 2H), 4.05 (t, J=7.40 Hz, 4H), 3.99 (t, J=6.27 Hz, 2H), 3.80 (t, J=6.40 Hz, 2H), 3.43-3.51 (m, 3H), 3.15 (t, J=7.15 Hz, 2H), 2.38 (quin, J=7.34 Hz, 2H), 1.81-1.89 (m, 2H), 1.72-1.79 (m, 2H), 1.57-1.65 (m, 2H), 1.31 (t, J=7.03 Hz, 3H). LCMS(ESI) m/z: 488 (M+1).

Embodiment 43

(E)-4-((5-(5-(2-(dimethylamino)-pyridin-4-yl)-1,1-dioxide-1,2,5-thiadiazolidine-2-yl)-pentyl)-oxy)-benzaldehyde-O-ethyl ketoxime

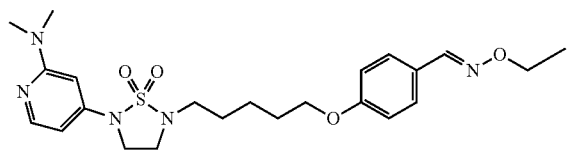 [SMILES: CCO/N=C/c1ccc(OCCCCCN2CCN(c3ccnc(N(C)C)c3)S2(=O)=O)cc1]

Please refer to the preparation method of Embodiment 40 for this embodiment. 1H NMR (400 MHz, CHLOROFORM-d) 8.09 (d, J=5.77 Hz, 1H), 8.03 (s, 1H), 7.52 (d, J=8.53 Hz, 2H), 6.88 (d, J=8.78 Hz, 2H), 6.38 (dd, J=1.88, 5.90 Hz, 1H), 6.26 (d, J=1.76 Hz, 1H), 4.21 (q, J=7.03 Hz, 2H), 3.97-4.04 (m, 2H), 3.85 (t, J=6.27 Hz, 2H), 3.51 (t, J=6.27 Hz, 2H), 3.17 (t, J=7.15 Hz, 2H), 3.12 (s, 5H), 1.73-1.92 (m, 4H), 1.58-1.67 (m, 2H), 1.33 (t, J=7.03 Hz, 3H). LCMS(ESI) m/z: 476 (M+1).

Embodiment 44

(E)-4-(5-(5-(4-((ethoxy)-methyl)-phenoxy)-pentyl)-1,1-dioxide-1,2,5-thiadiazolidine-2-yl)-benzonitrile

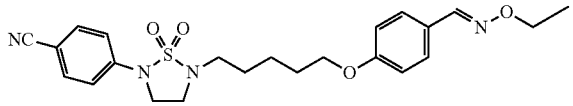 [SMILES: CCO/N=C/c1ccc(OCCCCCN2CCN(c3ccc(C#N)cc3)S2(=O)=O)cc1]

Under the protection of N₂ gas at 0° C., add K₂CO₃ (39 mg, 281 μmol) into the solution of Embodiment 32F (50 mg, 141 μmol) and 4-fluorobenzonitrile (17 mg, 141 μmol) in N,N-dicarboximide (1 ml). Allow the mixture solution to react for 3 hours at 80° C. After the reaction ends, pour the solution into water (40 ml) and extract with ethyl acetate (20 ml). Combine the organic layers and dry it with anhydrous Na₂SO₄ before filter and evaporate. Separate and purify the crude product with TLC (petroleum ether:ethyl acetate=2:1) to obtain the title compound (white solid, 30 mg, 66%). ¹H NMR (400 MHz, CHLOROFORM-d) 8.02 (s, 1H), 7.66 (d, J=8.53 Hz, 2H), 7.51 (d, J=8.53 Hz, 2H), 7.25 (s, 2H), 6.82-6.93 (m, 2H), 4.16-4.29 (m, 2H), 4.00 (t, J=6.53 Hz, 2H), 3.86 (t, J=6.53 Hz, 2H), 3.54 (t, J=6.27 Hz, 2H), 3.18 (t, J=7.28 Hz, 2H), 1.74-1.90 (m, 4H), 1.60-1.67 (m, 2H), 1.29-1.40 (m, 3H). LCMS(ESI) m/z: 457 (M+1).

Procedure O

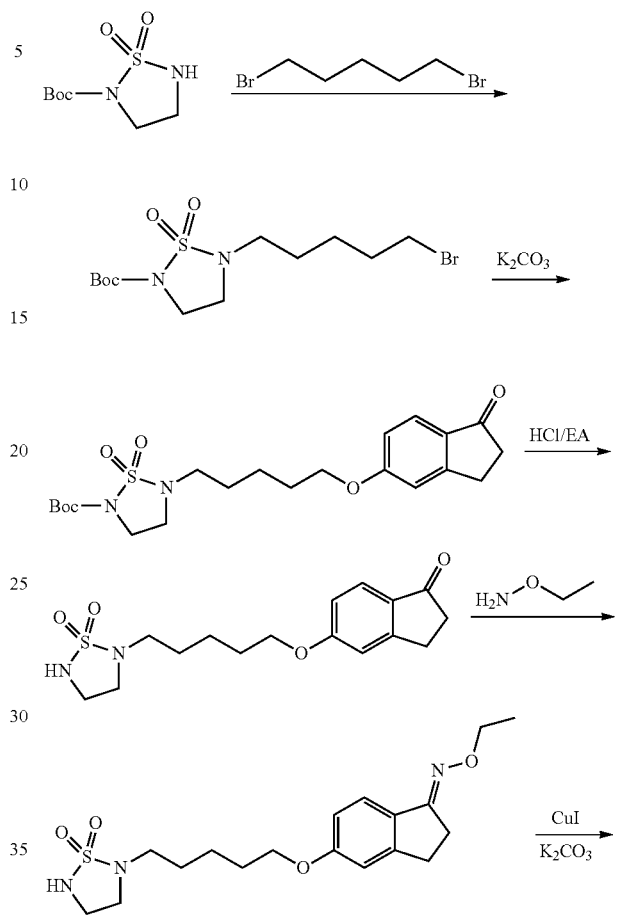

Embodiment 45

(E)-2-(2-amino-pyridin-4-yl)-5-(5-((1-(ethoxy-imino)-2,3-dihydro-1H-inden-5-yl)-oxy)-pentyl)-1,2,5-thiadiazolidine-1,1-dioxide

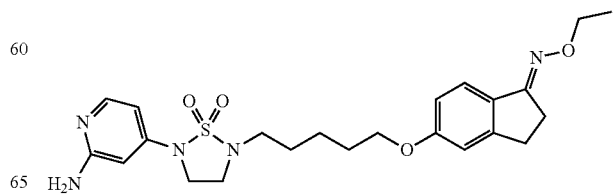

Embodiment 45A tert-butyl-5-(5-bromo-pentyl)-1,2,5-thiadiazolidine-2-t-butyl formate-1,1-dioxide

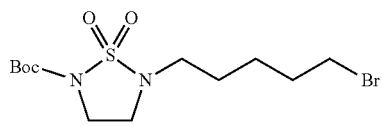

Under the protection of N₂ gas at 10° C., add sodium hydride (17 mg, 428 μmol) into the solution of Embodiment 32B (100 mg, 428 μmol) in DMF (8 ml). One hour later, add this mixture solution into the solution of 1,5-dibromopentane (98 mg, 428 μmol) in DMF (4 ml). Then agitate it react 10 hours at 10° C. before add water to quench the reaction. Then extract the aqueous phase with ethyl acetate (20 ml×3) and wash the combined organic phase with saturated salt water (10 ml×2). Then dry with anhydrous Na₂SO₄ before filter and concentrate. Then purify the crude product with the preparative TLC (dichloromethane:methanol=20:1) to obtain the title compound (yellow liquid, 50 mg, yield of 38%). ¹H NMR (400 MHz, CHLOROFORM-d) 3.82 (t, J=6.53 Hz, 2H), 3.44 (t, J=6.65 Hz, 2H), 3.34 (t, J=6.53 Hz, 2H), 3.08 (t, J=7.15 Hz, 2H), 1.92 (quin, J=7.09 Hz, 2H), 1.66-1.79 (m, 2H), 1.56-1.62 (m, 12H).

Embodiment 45B (E)-tert-butyl-5-(5-((1-(ethoxy-imino)-2,3-dihydro-1H-inden-5-yl)-oxy)-pentyl)-1,2,5-thiadiazolidine-2-tert-butyl formate-1,1-dioxide

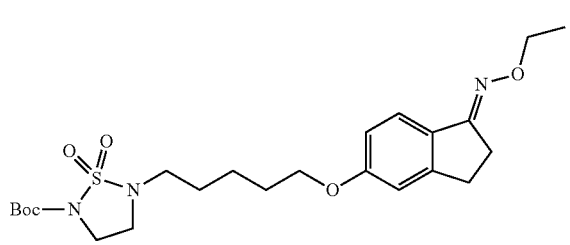 [SMILES: CCO/N=C1\CCc2cc(OCCCCCN3CCN(C(=O)OC(C)(C)C)S3(=O)=O)ccc21]

Under the protection of N₂ gas, add K₂CO₃ (112 mg, 808 μmol) into the solution of Embodiment 45A (100 mg, 269 μmol) and Embodiment 8B (52 mg, 269 μmol) in N,N-dimethylformamide (1 ml). Allow the reaction solution to react for 10 hours at 80° C. After TLC shows the reaction ends, add water (50 ml) to quench the reaction and extract the aqueous phase with ethyl acetate (20 ml). Dry the organic layer with anhydrous Na₂SO₄ before filter and evaporate. Separate and purify the crude product with TLC (petroleum ether:ethyl acetate=2:1) to obtain the title compound (white solid, 70 mg, 54%). ¹H NMR (400 MHz, CHLOROFORM-d) 7.54-7.64 (m, 1H), 6.74-6.83 (m, 2H), 4.20 (q, J=7.03 Hz, 2H), 3.98 (t, J=6.27 Hz, 2H), 3.80 (t, J=6.53 Hz, 2H), 3.32 (t, J=6.53 Hz, 2H), 3.08 (t, J=7.28 Hz, 2H), 2.95-3.02 (m, 2H), 2.85-2.93 (m, 2H), 1.67-1.87 (m, 4H), 1.51-1.59 (m, 11H), 1.32 (t, J=7.03 Hz, 3H).

Embodiment 45C (E)-2-(5-((1-(ethoxy-imino)-2,3-dihydro-1H-inden-5-yl)-oxy)-pentyl)-1,2,5-thiadiazolidine-1,1-dioxide

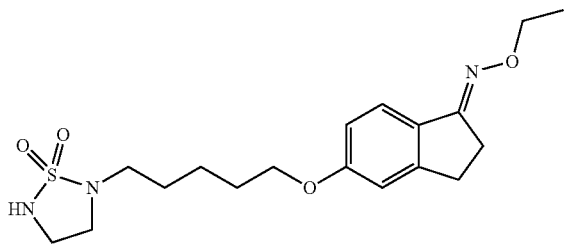 [SMILES: CCO/N=C1\CCc2cc(OCCCCCN3CCNS3(=O)=O)ccc21]

Under the protection of N₂ gas, add K₂CO₃ (57 mg, 415 μmol) into the solution of Embodiment 45B (100 mg, 208 μmol) in methanol (1 ml). Allow the reaction solution to react for 72 hours at 50° C. After TLC shows the reaction ends, concentrate, and evaporate the solvent out. Then add water (10 ml) before extract with ethyl acetate (20 ml). Combine the organic layers and dry it with anhydrous Na₂SO₄ before filter and evaporate. Separate and purify the crude product with TLC (petroleum ether:ethyl acetate=2:1) to obtain the title compound (white solid, 50 mg, 63%). ¹H NMR (400 MHz, CHLOROFORM-d) 8.09 (d, J=8.78 Hz, 2H), 7.03 (d, J=8.78 Hz, 2H), 4.40 (s, 3H), 3.89 (s, 3H).

Embodiment 45D (E)-2-(2-amino-pyridin-4-yl)-5-(5-((1-(ethoxy-imino)-2,3-dihydro-1H-inden-5-yl)-oxy)-pentyl)-1,2,5-thiadiazolidine-1,1-dioxide

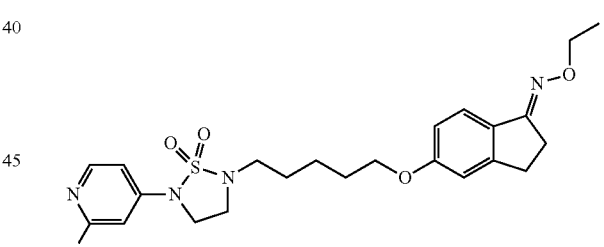

Under the protection of N₂ gas, heat the solution of Embodiment 45C (550 mg, 1.4 mmol), 4-bromo-2-aminopyridine (499 mg, 2.9 mmol), K₂CO₃ (498 mg, 3.6 mmol), 8-hydroxyquinoline (209 mg, 1.4 mmol), (1R,2R)-cyclohexanediamine (165 mg, 1.4 mmol) and CuI (275 mg, 1.4 mmol) in DMF (10 ml) to 120° C. to react for 10 hours. After the reaction ends, add water to quench and extract the aqueous phase with ethyl acetate (10 ml×3). Wash the organic phase with saturated salt water (5 ml). Then dry and concentrate with anhydrous Na₂SO₄. Then purify the crude product with the preparative TLC (dichloromethane:methanol=30:1) to obtain the title compound (white solid, 350 mg, yield of 51%). ¹H NMR (400 MHz, DMSO-d6) 8.09 (d, J=8.78 Hz, 1H), 7.44 (d, J=8.53 Hz, 1H), 6.92 (s, 1H), 6.82 (d, J=8.53 Hz, 1H), 6.34 (br.s., 1H), 6.15 (br.s., 1H), 4.09 (q, J=7.03 Hz, 2H), 3.99 (t, J=6.40 Hz, 2H), 3.79 (t, J=6.40 Hz, 2H), 3.49 (t, J=6.40 Hz, 2H), 3.04 (t, J=7.03 Hz, 2H), 2.89-2.98 (m, 2H), 2.69-2.82 (m, 2H), 1.59-1.81 (m, 5H), 1.40-1.54 (m, 2H), 1.22 (t, J=7.03 Hz, 3H). LCMS(ESI) m/z: 474 (M+1).

Embodiment 46

(E)-2-(5-((1-(ethoxy-imino)-2,3-dihydro-1H-inden-5-yl)-oxy)-pentyl)-5-(thiophen-3-yl)-1,2,5-thiadiazolidine-1,1-dioxide

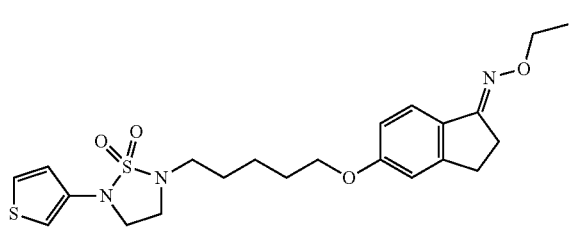 [SMILES: CCO/N=C1\CCc2cc(OCCCCCN3CCN(c4ccsc4)S3(=O)=O)ccc21]

Please refer to the preparation method of Embodiment 44 for this embodiment. ¹H NMR(CDCl3 400 MHz) δ7.60 (d, J=9.5 Hz, 1H) 7.35 (dd, J=5.0, 3.0 Hz, 1H) 7.18 (dd, J=5.5, 1.0 Hz, 1H) 6.76-6.85 (m, 3H) 4.20 (q, J=7.0 Hz, 2H) 3.99 (t, J=6.3 Hz, 2H) 3.79 (t, J=6.3 Hz, 2H) 3.49 (t, J=6.5 Hz, 2H) 3.16 (t, J=7.3 Hz, 2H) 2.95-3.02 (m, 2H) 2.86-2.92 (m, 2H) 1.81-1.89 (m, 2H) 1.70-1.79 (m, 2H) 1.64 (br.s., 2H) 1.32 (t, J=7.0 Hz, 3H). LCMS(ESI) m/z: 464 (M+1).

Embodiment 47

(E)-2-(6-amino-pyridin-3-yl)-5-(54 1-(ethoxy-imino)-2,3-dihydro-1H-inden-5-yl)-oxy)-pentyl)-1,2,5-thiadiazolidine-1,1-dioxide

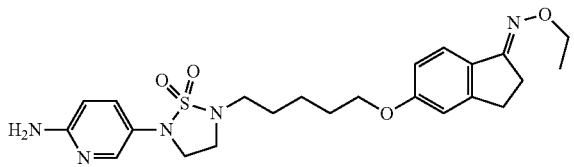 [SMILES: CCO/N=C1\CCc2cc(OCCCCCN3CCN(c4ccc(N)nc4)S3(=O)=O)ccc21]

Please refer to the preparation method of Embodiment 44 for this embodiment. ¹H NMR (400 MHz, CHLOROFORM-d) 8.01 (br.s., 1H), 7.59 (dt, J=3.26, 6.02 Hz, 2H), 6.76-6.85 (m, 2H), 6.56 (d, J=9.03 Hz, 1H), 4.20 (q, J=7.19 Hz, 2H), 3.99 (t, J=6.27 Hz, 2H), 3.74 (t, J=6.27 Hz, 2H), 3.46 (t, J=6.40 Hz, 2H), 3.15 (t, J=7.28 Hz, 2H), 2.95-3.01 (m, 2H), 2.86-2.92 (m, 2H), 1.72-1.89 (m, 4H), 1.56-1.60 (m, 2H), 1.28-1.38 (m, 3H).

Embodiment 48

(E)-2-(2-amino-3-fluoropyridin-4-yl)-5-(5-((1-(ethoxy-imino)-2,3-dihydro-1H-indene-5-yl)-oxy)-pentyl)-1,2,5-thiadiazolidine-1,1-dioxide

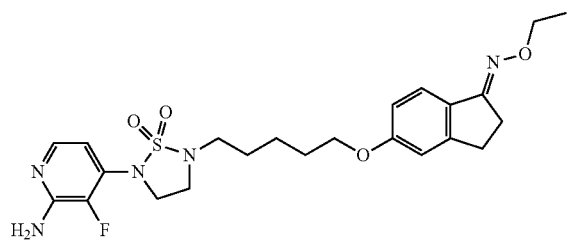

Embodiment 48A (E)-2-(2-chloro-3-fluoropyridin-4-yl)-5-(5-((1-(ethoxy-imino)-2,3-dihydro-1H-indene-5-yl)-oxy)-pentyl)-1,2,5-thiadiazolidine-1,1-dioxide

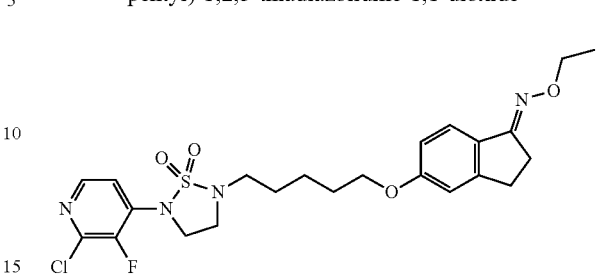

Under the protection of N₂ gas, add 2-chloro-5-fluoro-4-iodopyridine (101 mg, 393 μmol), K₂CO₃ (54 mg, 393 μmol), 8-hydroxyquinoline (38 mg, 262 μmol) and CuI (25 mg, 131 μmol) into the solution of Embodiment 45C (100 mg, 262 μmol) in N,N-dimethylformamide (3 ml). Allow the mixture solution to react for 10 hours at 120° C. After TLC verifies that the reaction ends, add water (10 ml) to quench and extract with ethyl acetate (10 ml×2). Combine the organic layers and dry it with anhydrous Na₂SO₄ before filter and evaporate. Separate and purify the crude product with TLC plate (petroleum ether:ethyl acetate=2:1) to obtain the title compound (white solid, 50 mg, 37%). ¹H NMR (400 MHz, CHLOROFORM-d) 8.21 (d, J=3.51 Hz, 1H), 7.60 (d, J=9.03 Hz, 1H), 7.46 (d, J=6.02 Hz, 1H), 6.74-6.84 (m, 2H), 4.20 (q, J=7.03 Hz, 2H), 4.07 (dt, J=3.01, 6.27 Hz, 2H), 4.00 (t, J=6.27 Hz, 2H), 3.54 (t, J=6.27 Hz, 2H), 3.18 (t, J=7.28 Hz, 2H), 2.95-3.02 (m, 2H), 2.86-2.93 (m, 2H), 1.73-1.91 (m, 4H), 1.61-1.66 (m, 2H), 1.32 (t, J=7.03 Hz, 3H).

Embodiment 48B (E)-2-(2-amino-3-fluoropyridin-4-yl)-5-(5-((1-(ethoxy-imino)-2,3-dihydro-1H-indene-5-yl)-oxy)-pentyl)-1,2,5-thiadiazolidine-1,1-dioxide

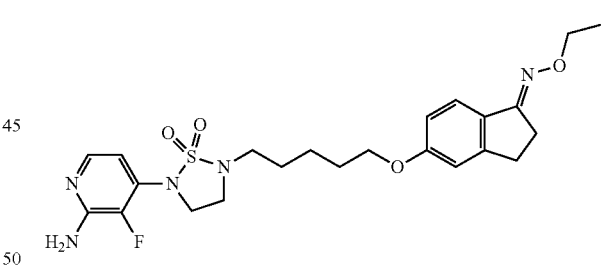

Under the protection of N₂ gas, add tert-butyl carbamate (69 mg, 587 μmol), Cs₂CO₃ (64 mg, 196 μmol), Pd₂(dba)₃ (9 mg, 9.8 μmol) and Xant-phos (6 mg, 10 μmol) into the solution of Embodiment 48A (50 mg, 98 μmol) in dioxane (1 ml). Allow the mixture solution to react for 10 hours at 110° C. After TLC verifies that the reaction ends, add water (10 ml) to quench and extract with ethyl acetate (10 ml×3). Combine the organic layers and dry it with anhydrous Na₂SO₄ before filter and evaporate. Separate and purify the crude product with TLC plate (dichloromethane:methnol=20:1) to obtain the title compound as white solid (5 mg, 10%). ¹H NMR (400 MHz, METHANOL-d4) 7.97 (d, J=6.53 Hz, 1H), 7.56 (d, J=8.53 Hz, 1H), 6.91 (s, 1H), 6.79-6.88 (m, 2H), 4.05 (t, J=6.27 Hz, 2H), 3.65 (t, J=6.27 Hz, 2H), 3.22 (t, J=7.03 Hz, 2H), 2.99-3.05 (m, 2H), 2.86-2.92 (m, 2H), 1.73-1.93 (m, 5H), 1.58-1.70 (m, 2H), 1.31 (t, J=7.03 Hz, 4H). LCMS(ESI) m/z: 492 (M+1).

Embodiment 49

(E)-2-(2-amino-5-fluoro-pyridin-4-yl)-5-(5-((1-(ethoxy-imino)-2,3-dihydro-1H-indene-5-yl)-oxy)-pentyl)-1,2,5-thiadiazolidine-1,1-dioxide

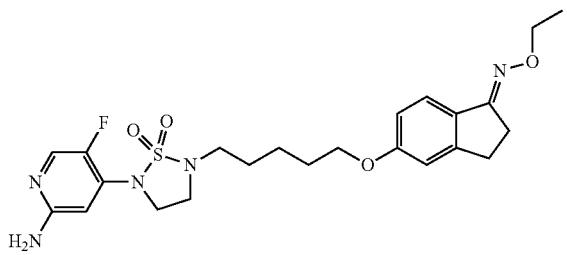 [SMILES: CCO/N=C1\CCc2cc(OCCCCCN3CCN(c4cc(N)ncc4F)S3(=O)=O)ccc21]

Embodiment 49A (E)-2-(2-chloro-5-fluoro-pyridin-4-yl)-5-(5-((1-(ethoxy-imino)-2,3-dihydro-1H-indene-5-yl)-oxy)-pentyl)-1,2,5-thiadiazolidine-1,1-dioxide

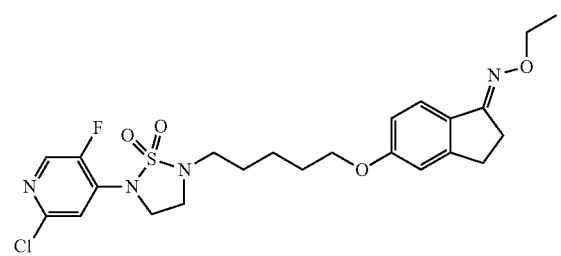 [SMILES: CCO/N=C1\CCc2cc(OCCCCCN3CCN(c4cc(Cl)ncc4F)S3(=O)=O)ccc21]

Under the protection of $N_2$ gas, add 2-chloro-5-fluoro-4-iodopyridine (101 mg, 393 μmol), $K_2CO_3$ (54 mg, 393 μmol), 8-hydroxyquinoline (38 mg, 262 μmol) and CuI (25 mg, 131 μmol) into the solution of Embodiment 45C (100 mg, 262 μmol) in N,N-dimethylformamide (3 ml). Allow the mixture solution to react for 10 hours at 120° C. After TLC verifies that the reaction ends, add water (10 ml) to quench and extract with ethyl acetate (10 ml×2). Combine the organic layers and dry it with anhydrous $Na_2SO_4$ before filter and evaporate. Separate and purify the crude product with TLC plate (petroleum ether:ethyl acetate=2:1) to obtain the title compound (white solid, 50 mg, 37%). $^1$H NMR (400 MHz, CHLOROFORM-d) 8.21 (d, J=3.51 Hz, 1H), 7.60 (d, J=9.03 Hz, 1H), 7.46 (d, J=6.02 Hz, 1H), 6.74-6.84 (m, 2H), 4.20 (q, J=7.03 Hz, 2H), 4.07 (dt, J=3.01, 6.27 Hz, 2H), 4.00 (t, J=6.27 Hz, 2H), 3.54 (t, J=6.27 Hz, 2H), 3.18 (t, J=7.28 Hz, 2H), 2.95-3.02 (m, 2H), 2.86-2.93 (m, 2H), 1.73-1.91 (m, 4H), 1.61-1.66 (m, 2H), 1.32 (t, J=7.03 Hz, 3H).

Embodiment 49B (E)-2-(2-amino-5-fluoro-pyridin-4-yl)-5-(5-((1-(ethoxy-imino)-2,3-dihydro-1H-indene-5-yl)-oxy)-pentyl)-1,2,5-thiadiazolidine-1,1-dioxide

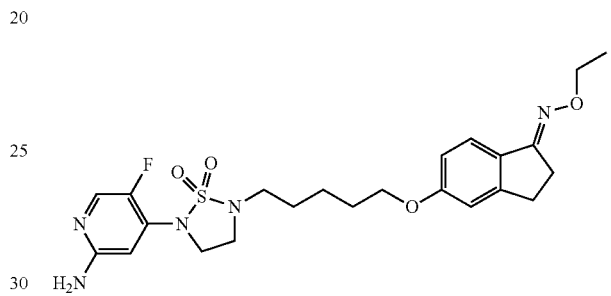

Under the protection of $N_2$ gas, add tert-butyl carbamate (69 mg, 587 μmol), $Cs_2CO_3$ (64 mg, 196 μmol), $Pd_2$(dba)$_3$ (9 mg, 9.8 μmol) and Xant-phos (5.6 mg, 9.8 μmol) into the solution of Embodiment 49A (50 mg, 98 μmol) in dioxane (1 ml). Allow the mixture solution to react for 10 hours at 110° C. After TLC verifies that the reaction ends, add water (10 ml) to quench and extract with ethyl acetate (10 ml×3). Combine the organic layers and dry it with anhydrous $Na_2SO_4$ before filter and evaporate. Separate and purify the crude product with TLC (dichloromethane:methnol=20:1) to obtain the title compound as white solid (5 mg, 10%). $^1$H NMR (400 MHz, METHANOL-d4) 7.97 (d, J=6.53 Hz, 1H), 7.56 (d, J=8.53 Hz, 1H), 6.91 (s, 1H), 6.79-6.88 (m, 2H), 4.05 (t, J=6.27 Hz, 2H), 3.65 (t, J=6.27 Hz, 2H), 3.22 (t, J=7.03 Hz, 2H), 2.99-3.05 (m, 2H), 2.86-2.92 (m, 2H), 1.73-1.93 (m, 5H), 1.58-1.70 (m, 2H), 1.31 (t, J=7.03 Hz, 4H). LCMS(ESI) m/z: 492 (M+1).

Procedure P

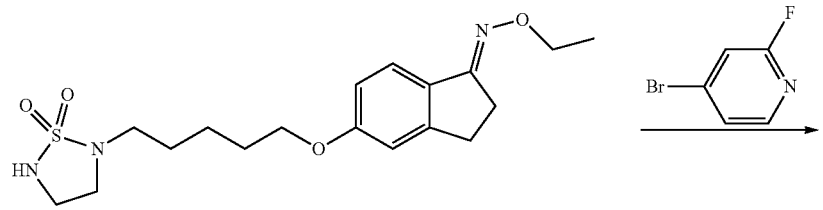

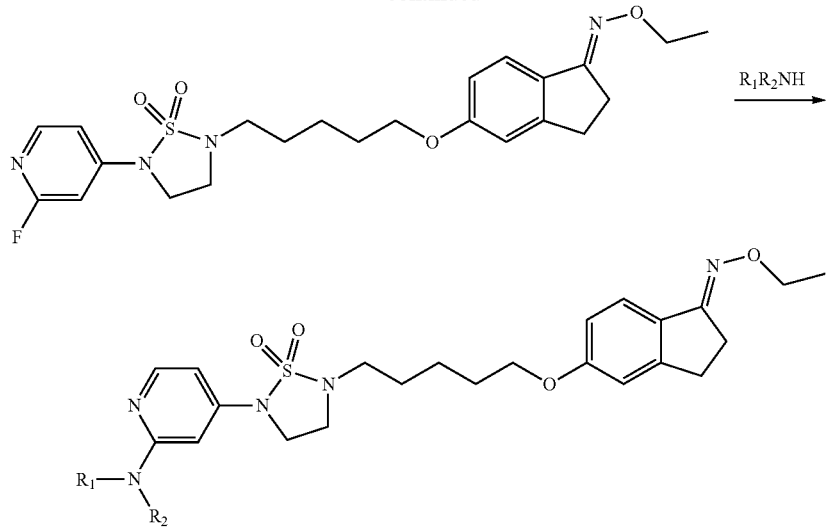

Embodiment 50

(E)-2-(5-((1-(ethoxy-imino)-2,3-dihydro-1H-inden-5-yl)-oxy)-pentyl)-5-(2-(methylamino)-pyridin-4-yl)-1,2-thiadiazolidine-1,1-dioxide

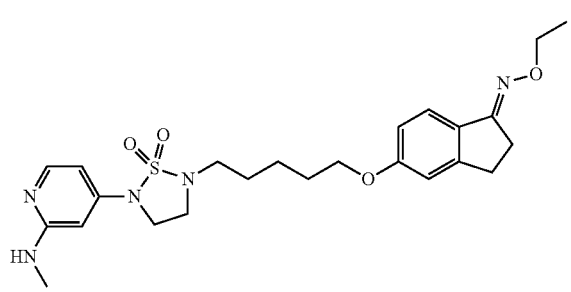 [SMILES: CCO/N=C1\CCc2cc(OCCCCCN3CCN(c4ccnc(NC)c4)S3(=O)=O)ccc21]

Embodiment 50A (E)-2-(5-((1-(ethoxy-imino)-2,3-hydrogen-1H-inden-5-yl)-oxy)-pentyl)-5-(2-fluoro-pyridin-4-yl)-1,2,5-thiadiazolidine-1,1-dioxide

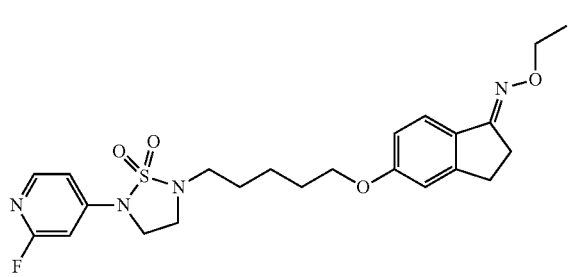 [SMILES: CCO/N=C1\CCc2cc(OCCCCCN3CCN(c4ccnc(F)c4)S3(=O)=O)ccc21]

This embodiment is prepared with the method as described in Embodiment 50A. $^1$H NMR (400 MHz, CHLOROFORM-d) 7.80 (d, J=5.5 Hz, 1H) 7.62 (d, J=9.3 Hz, 1H) 6.77-6.85 (m, 3H) 4.65 (br.s., 2H) 4.22 (q, J=7.0 Hz, 2H) 3.99-4.05 (m, 4H) 3.52 (t, J=6.4 Hz, 2H) 3.18 (t, J=7.2 Hz, 2H) 2.97-3.04 (m, 2H) 2.87-2.94 (m, 2H) 1.75-1.91 (m, 4H) 1.63-1.68 (m, 2H) 1.34 (t, J=7.0 Hz, 3H). LCMS(ESI) m/z: 474 (M+1).

Embodiment 50B (E)-2-(5-((1-(ethoxy-imino)-2,3-dihydro-1H-inden-5-yl)-oxy)-pentyl)-5-(2-methylamino)-pyridin-4-yl)-1,2-thiadiazolidine-1,1-dioxide Please refer to the preparation method of Embodiment 40 for this embodiment. $^1$H NMR (400 MHz, METHANOL-d4) 7.80 (d, J=7.53 Hz, 1H), 7.56 (d, J=8.53 Hz, 1H), 6.81-6.93 (m, 3H), 6.39 (d, J=2.01 Hz, 1H), 4.17 (g, J=7.03 Hz, 2H), 4.05 (t, J=6.15 Hz, 2H), 3.99 (t, J=6.53 Hz, 2H), 3.66 (t, J=6.53 Hz, 2H), 3.22 (t, J=7.03 Hz, 2H), 2.96-3.05 (m, 5H), 2.84-2.92 (m, 2H), 1.76-1.91 (m, 4H), 1.58-1.71 (m, 2H), 1.31 (t, J=7.03 Hz, 3H. LCMS(ESI) m/z: 488 (M+1).

Embodiment 51

(E)-2-(5-((1-(ethoxy-imino)-2,3-dihydro-1H-inden-5-yl)-oxy)-pentyl)-5-(2-((2-hydroxyethyl)-amino)-pyridin-4-yl)-1,2,5-thiadiazolidine-1,1-dioxide

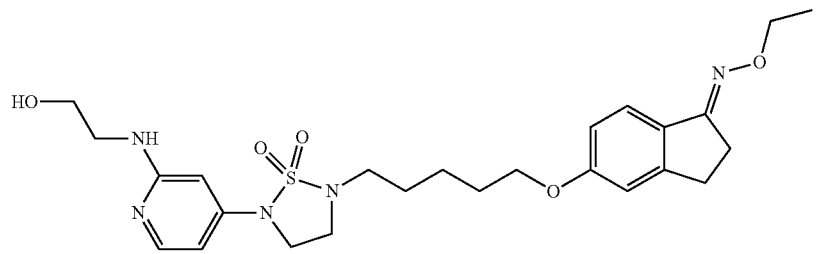 [SMILES: CCO/N=C1\CCc2cc(OCCCCCN3CCN(c4ccnc(NCCO)c4)S3(=O)=O)ccc21]

Please refer to the preparation method of Embodiment 40 for this embodiment. $^1$H NMR (400 MHz, CHLOROFORM-d) 7.84 (d, J=6.3 Hz, 1H), 7.61 (d, J=9.0 Hz, 1H), 6.74-6.85 (m, 2H), 6.52 (d, J=5.3 Hz, 1H), 6.27 (s, 1H), 4.22 (q, J=7.0 Hz, 2H), 4.01 (t, J=6.1 Hz, 2H), 3.87 (d, J=4.8 Hz, 4H), 2.86-3.62 (m, 10H), 1.85-1.89 (m, 2H), 1.76-1.82 (m, 2H), 1.63 (d, J=7.0 Hz, 2H), 1.34 (t, J=7.0 Hz, 3H). LCMS(ESI) m/z: 518 (M+1).

Procedure Q

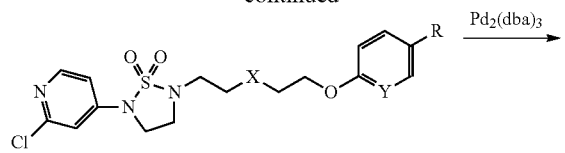

X = C, O
Y = C, N

Embodiment 52

4-(5-(2-(2-(4-((E)-ethoxy-imino-methyl)-phenoxy)-ethoxy)-ethyl)-1,1-dioxide-1,2,5-thiadiazolidine-2-yl)-pyridin-2-amine

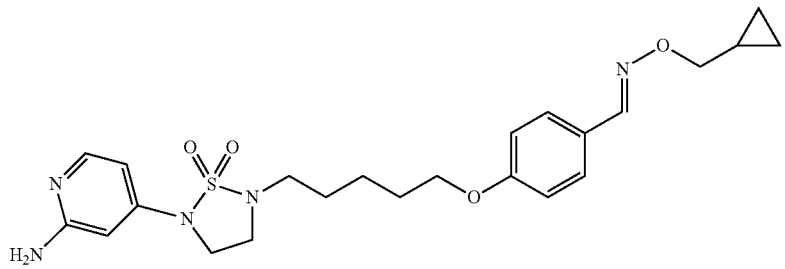 [SMILES: Nc1cc(N2CCN(CCCCCOc3ccc(/C=N/OCC4CC4)cc3)S2(=O)=O)ccn1]

Embodiment 52A 2-(5-bromo-pentyl)-5-(2-chloro-4-yl)-1,2,5-thiadiazolidine-1,1-dioxide

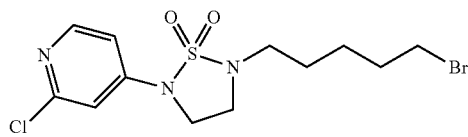 [SMILES: O=S1(=O)N(CCCCCBr)CCN1c1ccnc(Cl)c1]

At 10° C., add sodium hydroxide (1.0 g, 27 mmol) into the solution of Embodiment 4E (4.0 g, 17 mmol) in N,N-dimethylformamide (140 ml). After the substance is added, agitate at 10° C. to react 1 hour. Keep this temperature and drop the solution of 1,5-dibromopentane (3.9 g, 17 mmol) in N,N-dimethylformamide (40 ml) into the reaction solution. Then continue to react 1 hour.

After TLC verifies the reaction ends, pour the reaction solution into ice water (100 ml) and extract with ethyl acetate (100 ml×2). Take and dry the supernatant liquid. Concentrate it and purify with column chromatography (petroleum ether:ethyl acetate=2:1) to obtain the title compound (white solid, 2.7 g, yield of 41%). $^1$H NMR (400 MHz, CHLOROFORM-d) 8.27 (d, J=5.5 Hz, 1H), 7.07 (dd, J=6.0, 2.0 Hz, 1H), 7.00 (d, J=1.5 Hz, 1H), 3.85 (t, J=6.5 Hz, 2H), 3.56 (t, J=6.3 Hz, 2H), 3.44 (t, J=6.5 Hz, 2H), 3.17 (t, J=7.0 Hz, 2H), 1.88-1.98 (m, 2H), 1.74 (q, J=7.4 Hz, 2H), 1.58-1.64 (m, 2H).

Embodiment 52B (E)-1-(4-(2-(2-(5-(2-chloro-4-pyridyl)-1,1-dioxo-1,2,5-thiadiazolidine-2-yl)-ethoxy)-ethoxy)-phenyl)-N-ethoxy formimidate

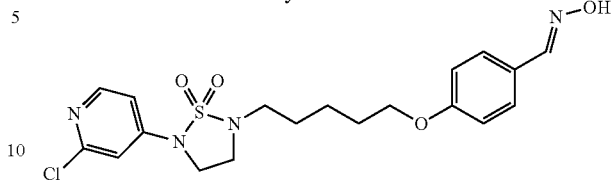

Add K$_2$CO$_3$ (36 mg, 0.26 mmol), KI (43 mg, 0.26 mmol) and 4-ammonia hydroxy phenol (43 mg, 0.26 mmol) into the solution of Embodiment 52A (0.1 g, 0.26 mmol) in N,N-dimethylformamide (5 ml). Agitate the mixture solution for 15 hours at 80° C. Then extract it with ethyl acetate. Dry the organic phase with anhydrous Na$_2$SO$_4$ before filter and evaporate. Then purify the residue with column chromatography (petroleum ether:ethyl acetate=2:1) to obtain the title compound (white solid, 60 mg, yield of 49%). LCMS(ESI) m/z: 439 (M+1).

Embodiment 52C (E)-1-(4-(5-(5-(2-chloro-4-pyridyl)-1,1-dioxide-1,2,5-thiadiazolidine-2-yl)-pentyloxy)-phenyl)-N-(cyclopropyl)-methylamine

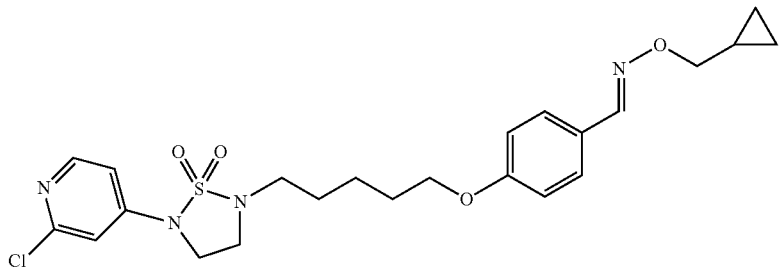 [SMILES: O=S1(=O)N(CCCCCOc2ccc(/C=N/OCC3CC3)cc2)CCN1c1ccnc(Cl)c1]

At 0° C., add cyclopropyl bromide (34 mg, 0.25 mmol) and K$_2$CO$_3$ (35 mg, 0.15 mmol) into the solution of Embodiment 52B (110 mg, 0.25 mmol) in N,N-dimethylformamide (2 ml). Agitate it to react for 15 hours at 50° C. Then add water to quench the reaction and extract the aqueous phase with ethyl acetate. Dry the combined organic phases with anhydrous Na$_2$SO$_4$. Then filter and evaporate it before separate it with column chromatography (petroleum ether:ethyl acetate=1:1) to obtain the title compound (yellow solid, 50 mg, yield of 40%). LCMS(ESI) m/z: 450 (M+1). $^1$H NMR (400 MHz, CDCl$_3$) 8.04 (s, 1H), 7.63 (d, J=7.0 Hz, 1H), 7.53 (d, J=8.5 Hz, 2H), 6.90 (d, J=8.5 Hz, 2H), 6.62 (d, J=7.5 Hz, 1H), 6.10 (s, 1H), 4.16-4.25 (m, 4H), 3.82-3.88 (m, 4H), 3.72 (dd, J=11.5, 5.0 Hz, 4H), 3.40 (t, J=4.8 Hz, 2H), 1.32 (t, J=7.0 Hz, 3H).

Embodiment 52D 4-(5-(2-(2-(4-((E)-ethoxy-imino-methyl)-phenoxy)-ethoxy)-ethyl)-1,1-dioxide-1,2,5-thiadiazolidine-2-yl)-pyridin-2-amine

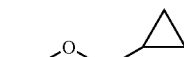
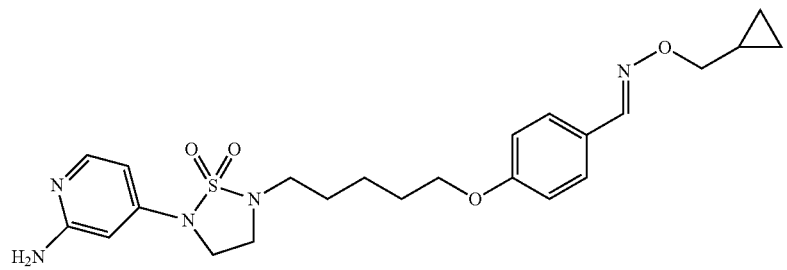

At 0° C., add cesium carbonate (66 mg, 0.2 mmol) and tert-butyl carbamate (23 mg, 0.2 mmol) into the solution of Embodiment 52C (50 mg, 0.1 mmol) in N,N-dimethylformamide (1.5 ml). After replace with $N_2$ gas, under the protection of $N_2$ gas, add $Pd_2(dba)_3$ (19 mg, 20 μmol) and Xantphos (12 mg, 20 μmol). Agitate it to react for 15 hours at 110° C. Then add water to quench the reaction and extract the aqueous phase with ethyl acetate. Dry the combined organic phase with anhydrous $Na_2SO_4$ before filter and evaporate. Then purify it with HPLC to obtain the title compound (white solid, 5 mg, yield of 10%). $^1$H NMR (400 MHz, CDCl$_3$) 8.08 (s, 1H), 7.65 (d, J=7.0 Hz, 1H), 7.53 (d, J=8.8 Hz, 2H), 6.89 (d, J=8.5 Hz, 2H), 6.70 (d, J=6.8 Hz, 1H), 6.21 (br.s., 1H), 3.95-4.06 (m, 4H), 3.83-3.90 (m, 2H), 3.59 (t, J=6.1 Hz, 2H), 3.21 (t, J=7.2 Hz, 2H), 1.75-1.92 (m, 3H), 1.57-1.69 (m, 3H), 1.16-1.28 (m, 1H), 0.57-0.64 (m, 2H), 0.34 (q, J=4.9 Hz, 2H). LCMS(ESI) m/z: 474 (M+1).

Embodiment 53

(E)-4-((5-(5-(2-amino-pyridin-4-yl)-1,1-dioxide-1,2,5-thiadiazolidine-2-yl)-pentyl)-oxy)-benzaldehyde-O-isopropyl oxime

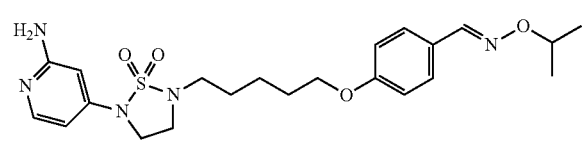 [SMILES: CC(C)O/N=C/c1ccc(OCCCCCN2CCN(c3ccnc(N)c3)S2(=O)=O)cc1]

Please refer to the preparation method of Embodiment 52 for this embodiment. $^1$H NMR (400 MHz, CHLOROFORM-d) 8.00 (s, 1H), 7.95 (d, J=6.0 Hz, 1H), 7.50 (d, J=8.5 Hz, 2H), 6.86 (d, J=9.0 Hz, 2H), 6.43 (d, J=5.0 Hz, 1H), 6.28 (br.s., 1H), 4.42 (dt, J=12.3, 6.4 Hz, 1H), 3.99 (t, J=6.3 Hz, 2H), 3.80 (t, J=6.3 Hz, 2H), 3.47-3.53 (m, 2H), 3.15 (t, J=7.3 Hz, 2H), 1.82-1.89 (m, 2H), 1.73-1.80 (m, 4H), 1.29 (d, J=6.0 Hz, 6H). LCMS(ESI) m/z: 462 (M+1).

Embodiment 54

(E)-2-(2-amino-pyridin-4-yl)-5-(5-(4-(1-(ethoxy-imino)-propyl)-phenoxy)-pentyl)-1,2,5-thiadiazolidine-1,1-dioxide

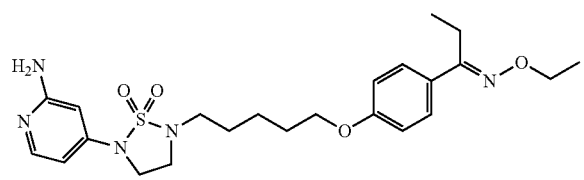 [SMILES: CCO/N=C(\CC)c1ccc(OCCCCCN2CCN(c3ccnc(N)c3)S2(=O)=O)cc1]

Embodiment 54A (E)-1-(4-hydroxyphenyl)-propan-1-one-O-ethyl ketoxime

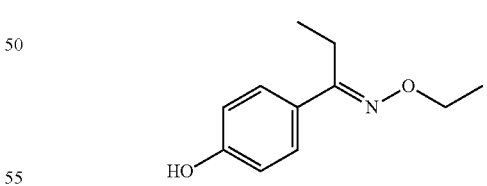

Agitate the mixture solution of 4-hydroxyphenyl acetone (1 g, 6.7 mmol), sodium acetate (1.1 g, 3.3 mmol), ethoxyamine hydrochloride (814 mg, 13.3 mmol) in ethanol (10 ml) 2 hours at 80° C. Then add water (10 ml) and ethyl acetate (20 ml) into the reaction system. Then extract the aqueous layer with ethyl acetate (20 ml×3) before filter and evaporate to obtain the title compound (brown solid, 1.28 g, yield of 99%). $^1$H NMR (400 MHz, CDCl$_3$) 7.48 (d, J=8.5 Hz, 2H), 6.74-6.79 (m, 2H), 4.20 (q, J=7.0 Hz, 2H), 2.72 (q, J=7.7 Hz, 2H), 1.30 (t, J=7.0 Hz, 3H), 1.11 (t, J=7.5 Hz, 3H).

Embodiment 54B (E)-2-(2-chloropyridin-4-yl-5-(5-(4-(1-(ethoxy-imino)-propyl)-phenoxy)-pentyl)-1,2,5-thiadiazolidine-1,1-dioxide

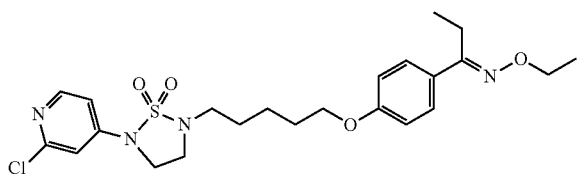 [SMILES: CCO/N=C(\CC)c1ccc(OCCCCCN2CCN(c3ccnc(Cl)c3)S2(=O)=O)cc1]

Please refer to the preparation method of Embodiment 52C for this embodiment. $^1$H NMR (400 MHz, CDCl$_3$) 8.26 (d, J=5.8 Hz, 1H), 7.57 (d, J=8.5 Hz, 2H), 7.06 (dd, J=5.8, 2.0 Hz, 1H), 6.99 (d, J=1.8 Hz, 1H), 6.86 (d, J=8.8 Hz, 2H), 4.20 (q, J=7.0 Hz, 2H), 3.99 (t, J=6.1 Hz, 2H), 3.83 (t, J=6.4 Hz, 2H), 3.54 (t, J=6.4 Hz, 2H), 3.17 (t, J=7.3 Hz, 2H), 2.72 (q, J=7.5 Hz, 2H), 1.74-1.88 (m, 4H), 1.61 (d, J=7.0 Hz, 2H), 1.31 (t, J=7.0 Hz, 3H), 1.12 (t, J=7.5 Hz, 3H). LCMS(ESI) m/z: 495 (M+1).

Embodiment 54C (E)-2-(2-amino-pyridin-4-yl)-5-(5-(4-(1-(ethoxy-imino)-propyl)-phenoxy)-pentyl)-1,2,5-thiadiazolidine-1,1-dioxide

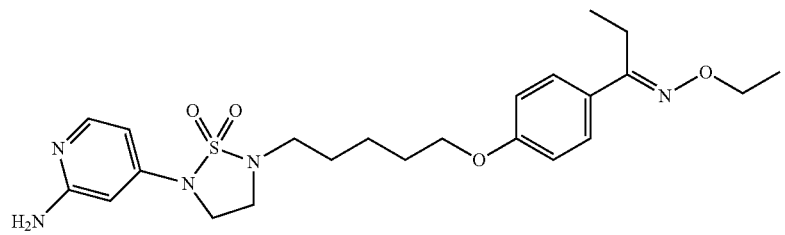 [SMILES: CCO/N=C(\CC)c1ccc(OCCCCCN2CCN(c3ccnc(N)c3)S2(=O)=O)cc1]

Please refer to the preparation method of Embodiment 52 for this embodiment. $^1$H NMR (400 MHz, CDCl$_3$) 7.85 (d, J=6.0 Hz, 1H), 7.57 (d, J=8.5 Hz, 2H), 6.86 (d, J=9.0 Hz, 2H), 6.52 (d, J=6.5 Hz, 1H), 6.29 (s, 1H), 5.58 (br.s., 2H), 4.20 (q, J=7.0 Hz, 2H), 3.99 (t, J=6.0 Hz, 2H), 3.80-3.85 (m, 2H), 3.52 (t, J=6.3 Hz, 2H), 3.17 (t, J=7.3 Hz, 2H), 2.69-2.75 (m, 2H), 1.85 (d, J=7.0 Hz, 2H), 1.75 (br.s., 2H), 1.61 (d, J=7.0 Hz, 2H), 1.31 (t, J=7.0 Hz, 3H), 1.12 (t, J=7.5 Hz, 3H). LCMS(ESI) m/z: 477 (M+1).

Embodiment 55

(E)-4-(2-2-(5-(2-amino-pyridin-4-yl)-1,1-dioxide-1,2,5-thiadiazolidine-2-yl)-ethoxy)-ethoxy)-benzaldehyde-O-ethyl ketoxime

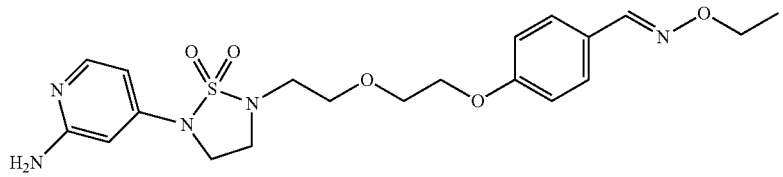 [SMILES: CCO/N=C/c1ccc(OCCOCCN2CCN(c3ccnc(N)c3)S2(=O)=O)cc1]

Embodiment 55A 2-2-2(-bromo-ethoxy)-ethyl)-5-2-chloro-pyridin-4-yl)-1,2,5-thiadiazolidine-1,1-dioxide

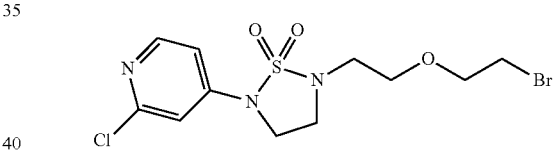

Please refer to the preparation method of Embodiment 52A for this embodiment. $^1$H NMR (400 MHz, CDCl$_3$) 8.29 (d, J=5.77 Hz, 1H), 7.08 (dd, J=2.26, 5.77 Hz, 1H), 7.02 (d, J=2.26 Hz, 1H), 3.78-3.92 (m, 8H), 3.53 (t, J=5.52 Hz, 2H), 3.42 (t, J=4.89 Hz, 2H).

Embodiment 55B (E)-1-(4-(2-(2-(5-(2-chloro-4-pyridyl)-1,1-dioxide-1,2,5-thiadiazolidine-2-yl)-ethoxy)-ethoxy)-phenyl)-N-ethoxy formimidate

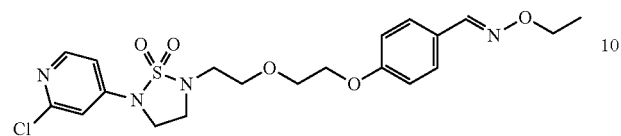

Add K$_2$CO$_3$ (72 mg, 0.52 mmol), KI (8.6 mg, 0.05 mmol) and Embodiment 7A (47 mg, 0.29 mmol) into the solution of Embodiment 55A (0.1 g, 0.26 mmol) in N,N-dimethylformamide (2 ml). Agitate the mixture solution 12 hours at 80° C. Then extract it with ethyl acetate. Dry the organic phase with anhydrous Na$_1$SO$_4$ before filter and evaporate. Then purify the residue with column chromatography (petroleum ether:ethyl acetate=1:1) to obtain the title compound (white solid, 60 mg, yield of 49%). LCMS(ESI) m/z: 469 (M+1).

Embodiment 55C 4-(5-(2-(2-(4-((E)-ethoxy-imino-methyl)-phenoxy)-ethoxy)-ethyl)-1,1-dioxo-1,2,5-thiadiazolidine-2-yl)-pyridin-2-amine

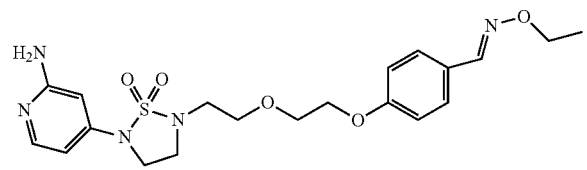 [SMILES: CCO/N=C/c1ccc(OCCOCCN2CCN(c3ccnc(N)c3)S2(=O)=O)cc1]

At 0° C., add cesium carbonate (84 mg, 0.26 mmol) and tert-butyl carbamate (18 mg, 0.15 mmol) into the solution of Embodiment 55B (60 mg, 0.13 mmol) in N,N-dimethylformamide (1 ml). After replace with N$_2$ gas, under the protection of N$_2$ gas, add Pd$_2$ (dba)$_3$ (22 mg, 24 µmol) and Xantphos (14 mg, 24 µmol). Agitate it to react for 15 hours at 110° C. Then add water to quench the reaction and extract the aqueous phase with ethyl acetate. Dry the combined organic phases with anhydrous Na$_2$SO$_4$ before filter and evaporate to obtain the title compound (white solid, 5 mg, yield of 8.7%). $^1$H NMR (400 MHz, CDCl$_3$) 8.04 (s, 1H), 7.63 (d, J=7.0 Hz, 1H), 7.53 (d, J=8.5 Hz, 2H), 6.90 (d, J=8.5 Hz, 2H), 6.62 (d, J=7.5 Hz, 1H), 6.10 (s, 1H), 4.16-4.25 (m, 4H), 3.82-3.88 (m, 4H), 3.72 (dd, J=11.5, 5.0 Hz, 4H), 3.40 (t, J=4.8 Hz, 2H), 1.32 (t, J=7.0 Hz, 3H). LCMS(ESI) m/z: 450 (M+1).

Embodiment 56

(E)-5-((5-(5-(2-amino-pyridin-4-yl)-1,1-dioxide-1,2,5-thiadiazolidine-2-yl)-pentyl)-oxy)-picolinaldehyde-O-ethyl ketoxime

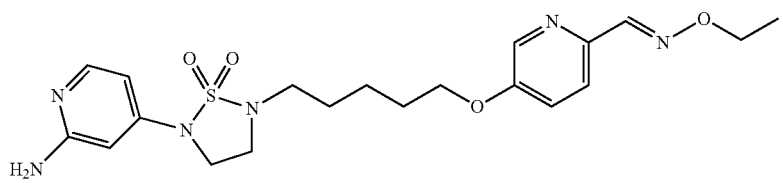

Embodiment 56A (E)-5-hydroxy-pyridinecarboxaldehyde-O-ethyl ketoxime

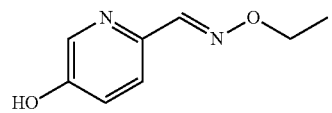

Heat the aqueous solution (5 ml) of ethoxyamino hydrochloride (244 mg, 2.5 mmol), 5-hydroxy-pyridine-2-aldehyde (308 mg, 2.5 mmol), sodium acetate (410 mg, 5.0 mmol) to 80° C. to agitate 2 hours. After TLC indicates the raw materials disappear, extract the reaction mixture with ethyl acetate (10 ml×3). Mix the organic phases and dry with anhydrous Na$_2$SO$_4$ before filter and concentrate to obtain the title compound (white solid, 410 mg, yield of 99%) that is directly used without necessity to purify further.

Embodiment 56B (E)-5-((5-(5-(2-chloropyridin-4-yl)-1,1-dioxide-1,2,5-thiadiazolidine-2-yl)-pentyl)-oxy)-picolinaldehyde-O-ethyl ketoxime

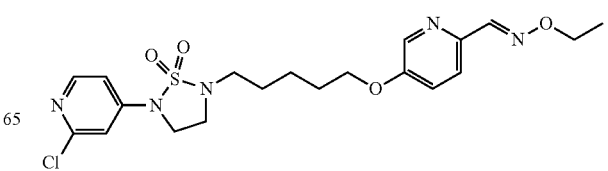

Heat the solution of Embodiment 52A (346 mg, 998 μmol), Embodiment 56A (163 mg, 978 μmol) and $K_2CO_3$ (276 mg, 2.0 mmol) and KI (17 mg, 100 μmol) in acetone solution (5 ml) to 70° C. to react for 3 hours. TLC indicates that the raw materials are consumed completely. Cool the reaction solution to room temperature before filter and concentrate to obtain the crude product. Purify the crude product with TLC plate (petroleum ether:ethyl acetate=3:1) to obtain the title compound (white solid, 150 mg, yield of 35%). $^1$H NMR (400 MHz, CHLOROFORM-d) 8.30-8.24 (m, 2H), 8.12 (s, 1H), 7.71 (d, J=9.0 Hz, 1H), 7.18 (dd, J=2.8, 8.8 Hz, 1H), 7.05 (dd, J=2.0, 5.5 Hz, 1H), 6.99 (d, J=2.0 Hz, 1H), 4.25 (q, J=7.0 Hz, 2H), 4.04 (t, J=6.3 Hz, 2H), 3.84 (t, J=6.5 Hz, 2H), 3.55 (t, J=6.5 Hz, 2H), 3.22-3.14 (m, 2H), 1.92-1.83 (m, 2H), 1.79 (quin, J=7.4 Hz, 2H), 1.70-1.56 (m, 2H), 1.33 (t, J=7.3 Hz, 3H).

Embodiment 56C (E)-5-((5-(5-(2-amino-pyridin-4-yl)-1,1-dioxide-1,2,5-thiadiazolidine-2-yl)-pentyl)-oxy)-picolinaldehyde-O-ethyl ketoxime

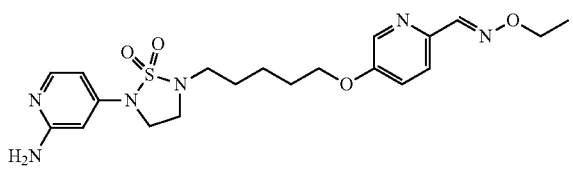 [SMILES: CCO/N=C/c1ccc(OCCCCCN2CCN(c3ccnc(N)c3)S2(=O)=O)cn1]

Under the protection of $N_2$ gas, heat the solution of tert-butyl carbamate (163 mg, 1.4 mmol) and Embodiment 56B (120 mg, 278 μml), $Pd_2$ (dba)$_3$ (25 mg, 28 μmol), Xantphos (32 mg, 56 μmol), $Cs_2CO_3$ (181 mg, 556 μmol) in dioxane (3 ml) to 100° C. to react 6 hours. Cool the reaction heat to room temperature before filter and concentrate. Then purify the obtained crude product with the preparative HPLC (neutral separation method) to obtain the title compound (white solid, 30 mg, yield of 26%). $^1$H NMR (400 MHz, CHLOROFORM-d) 8.27 (d, J=2.0 Hz, 1H), 8.11 (s, 1H), 7.97 (d, J=5.5 Hz, 1H), 7.70 (d, J=8.8 Hz, 1H), 7.18 (dd, J=2.3, 8.5 Hz, 1H), 6.41 (d, J=4.5 Hz, 1H), 6.28 (s, 1H), 4.49 (br.s., 2H), 4.25 (q, J=6.9 Hz, 2H), 4.04 (t, J=6.0 Hz, 2H), 3.79 (t, J=6.1 Hz, 2H), 3.49 (t, J=6.3 Hz, 2H), 3.15 (t, J=7.2 Hz, 2H), 1.93-1.82 (m, 2H), 1.82-1.67 (m, 2H), 1.67-1.55 (m, 2H), 1.33 (t, J=6.9 Hz, 3H). LCMS(ESI) m/z: 449 (M+1).

Embodiment 57

(E)-2-(2-amino-pyridin-4-yl)-5-(5-((1-(ethoxy-imino)-2,3-dihydro-1H-inden-5-yl)-oxy)-pentyl)-1,2,5-thiadiazolidine-1,1-dioxide

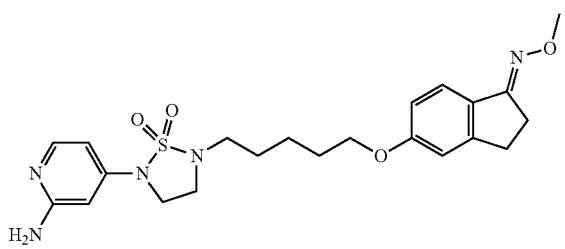 [SMILES: CO/N=C1\CCc2cc(OCCCCCN3CCN(c4ccnc(N)c4)S3(=O)=O)ccc21]

Embodiment 57A 5-((5-(5-(2-chloro-4-yl)-1,1-dioxide-1,2,5-thiadiazolidine-2-yl)-pentyl)-oxy)-2,3-dihydro-1H-inden-1-one

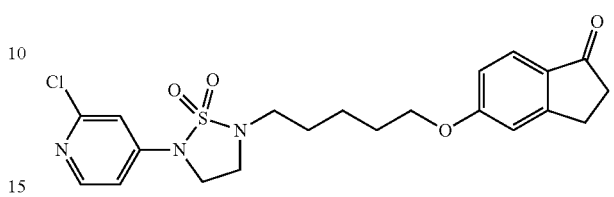

At room temperature, add $K_2CO_3$ (1.45 g, 10.5 mmol) into the solution of Embodiment 52A (2.0 g, 5.2 mmol) and 5-hydroxy-1-indanone (774 mg, 5.2 mmol) in acetone (30 ml). Then heat the reaction solution to 70° C. to react for 2 hours to consume the raw materials completely. Cool the reaction liquid to room temperature before concentrate. Then pour the residue into water (50 ml). Then extract the aqueous phase with ethyl acetate (30 ml×3) and dry the organic phase with anhydrous $Na_2SO_4$. Then filter and concentrate before purify the crude product with column chromatography (petroleum ether:ethyl acetate=2:1) to obtain the title compound (yellow solid, 1.3 g, yield of 55%). $^1$H NMR (400 MHz, CDCl$_3$) 8.28 (d, J=5.77 Hz, 1H), 7.67-7.73 (m, 1H), 7.08 (dd, J=2.01, 5.77 Hz, 1H), 7.01 (d, J=1.76 Hz, 1H), 6.88-6.93 (m, 2H), 4.07 (t, J=6.15 Hz, 2H), 3.80-3.91 (m, 2H), 3.58 (t, J=6.27 Hz, 2H), 3.21 (t, J=7.28 Hz, 2H), 3.04-3.13 (m, 3H), 2.65-2.73 (m, 3H), 1.87-1.96 (m, 2H), 1.76-1.85 (m, 2H), 1.57-1.68 (m, 2H).

Embodiment 57B (E)-2-(2-chloropyridin-4-yl)-5-(5-((1-(hydroxy-imino)-2,3-dihydro-1H-inden-5-yl)-oxy)-pentyl)-1,2,5-thiadiazolidine-1,1-dioxide

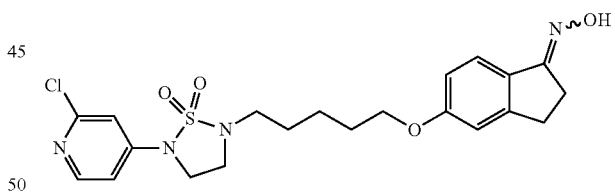

Under the protection of $N_2$ gas at room temperature, add sodium acetate (711 mg, 8.7 mmol) into the solution of Embodiment 57A (1.3 g, 2.9 mmol) and hydroxylamine hydrochloride (603 mg, 8.7 mmol) in ethanol (30 ml). Then heat the reaction solution to 70° C. to react for 2 hours to consume the raw materials completely. Concentrate the reaction solution and pour it into water (50 ml) and then extract it with ethyl acetate (30 ml×3). Then dry the organic phase with anhydrous $Na_2SO_4$ before filter and concentrate to obtain the title compound (yellow solid, 1.30 g, yield of 97%). $^1$H NMR (400 MHz, CDCl$_3$) 8.29 (d, J=5.77 Hz, 1H), 7.53-7.58 (m, 1H), 7.08 (dd, J=2.26, 5.77 Hz, 1H), 7.01 (d, J=2.01 Hz, 1H), 6.82 (d, J=5.02 Hz, 2H), 3.98-4.07 (m, 2H), 3.86 (t, J=6.40 Hz, 2H), 3.57 (t, J=6.40 Hz, 2H), 3.20 (t, J=7.15 Hz, 2H), 2.94-3.10 (m, 5H), 1.75-1.94 (m, 4H), 1.56-1.71 (m, 2H).

Embodiment 57C (E)-2-(2-amino-pyridin-4-yl)-5-(5-((1-(ethoxy-imino)-2,3-dihydro-1H-inden-5-yl)-oxy)-pentyl)-1,2,5-thiadiazolidine-1,1-dioxide

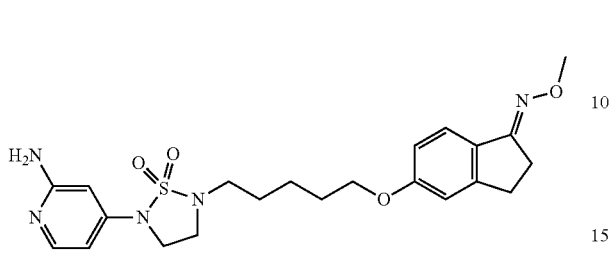

Please refer to the preparation method of Embodiment 56 for this embodiment.

$^1$H-NMR (400 MHz, CDCl$_3$) 7.97 (d, J=5.8 Hz, 1H), 7.59 (d, J=9.3 Hz, 1H), 6.77-6.81 (m, 2H), 6.42 (dd, J=5.9, 1.9 Hz, 1H), 6.29 (d, J=1.8 Hz, 1H), 4.52 (br.s., 2H), 3.99 (t, J=6.3 Hz, 2H), 3.96 (s, 3H), 3.79 (t, J=6.4 Hz, 2H), 3.47-3.52 (m, 2H), 3.16 (t, J=7.2 Hz, 2H), 2.96-3.01 (m, 2H), 2.85-2.90 (m, 2H), 1.65-1.93 (m, 4H), 1.61-1.64 (m, 2H). LCMS(ESI) m/z: 460 (M+1).

Embodiment 58

(E)-2-(2-amino-pyridin-4-yl)-5-(5-(1-(isopropoxy)-2,3-dihydro-1H-inden-5-yl)-oxy)-pentyl)-1,2,5-thiadiazolidine-1,1-dioxide

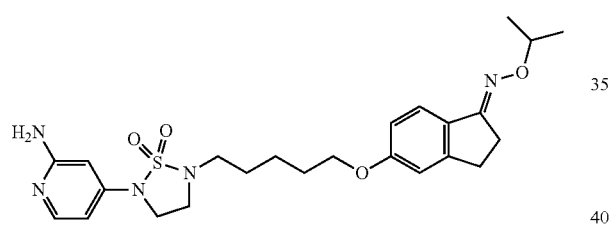

Please refer to the preparation method of Embodiment 56 for this embodiment.

$^1$H-NMR (400 MHz, CDCl$_3$) 7.80 (br.s., 1H), 7.58 (d, J=9.0 Hz, 1H), 6.77 (br.s., 2H), 6.57 (br.s., 1H), 6.36 (br.s., 1H), 4.36-4.41 (m, 1H), 3.96-4.00 (m, 2H), 3.84 (br.s., 2H), 3.51 (br.s., 2H), 3.14 (t, J=6.9 Hz, 2H), 2.93-2.98 (m, 2H), 2.83-2.88 (m, 2H), 1.80-1.85 (m, 2H), 1.71-1.77 (m, 2H), 1.59 (d, J=6.8 Hz, 2H), 1.32 (d, J=6.0 Hz, 2H), 1.24-1.28 (m, 6H). LCMS(ESI) m/z: 488 (M+1).

Embodiment 59

(E)-2-(2-amino-pyridin-4-yl)-5-(5-((1-ethoxy-imino)-7-fluoro-2,3-dihydro-1H-5-yl)-oxy)-pentyl)-1,2,5-thiadiazolidine-1,1-dioxide

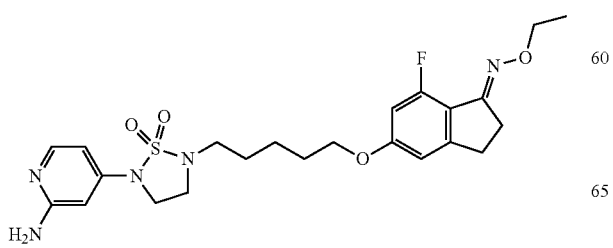

Embodiment 59A 5-bromo-7-fluoro-indan-1 keto-O-ethyl ketoxime

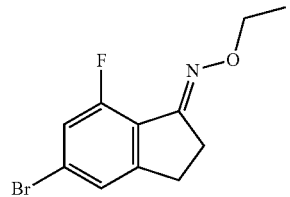

Heat the solution of 5-bromo-7-fluoro-inden-1-one (1.8 g, 7.9 mmol) and ethoxyamino hydrochloride (1.53 g, 15.7 mmol) and sodium acetate (1.29 g, 15.7 mmol) in ethanol (10 ml) to 70° C. to react for 3 hours. After the raw materials disappear, add water (20 ml). Then extract the aqueous phase with ethyl acetate (30 ml×3). Then dry the combined organic phases with anhydrous Na$_2$SO$_4$ before filter and concentrate to obtain the title compound (yellow solid, 2.0 g, yield of 94%) that is directly further.

Embodiment 59B (E)-7-fluoro-5-(4,4,5,5-tetramethyl-1,3,2-dioxaborolan-2-yl)-2,3-dihydro-1H-inden-1-one-O-ethyl ketoxime

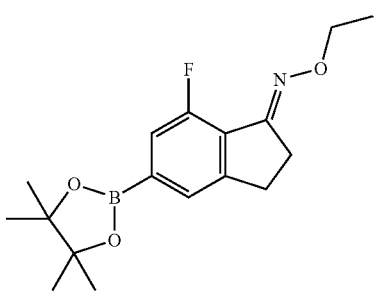 [SMILES: CCO/N=C1\CCc2cc(B3OC(C)(C)C(C)(C)O3)cc(F)c21]

Under the protection of N$_2$ gas, heat the solution of Embodiment 59A (2.00 g, 7.35 mmol), bis(pinacolato)diboron (2.24 g, 8.82 mmol), potassium acetate (2.16 g, 22.05 mmol) and Pd(dppf)Cl$_2$ (537.80 mg, 735.00 μmol) in dioxane (5 ml) to 50° C. to react for 10 hours. Cool the reaction solution to room temperature before filter out the crude product can be directly used further.

Embodiment 59C (E)-7-fluoro-5-hydroxy-2,3-dihydro-1H-inden-1-one-oxo-ethyl ketoxime

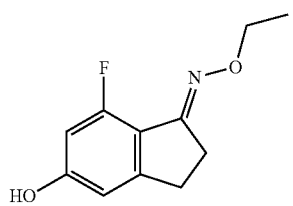

Add hydrogen peroxide (2.3 g, 65.5 mmol) into the mixture solution of Embodiment 59B (2.0 g, 6.6 mmol) in NaOH (2 ml, 2N) and THF (8 ml). Mix the mixture solution 10 minutes at 25° C. before add water (5.0 ml). Extract this mixture solution with ethyl acetate (10 ml×3). Dry the organic phase with anhydrous Na$_2$SO$_4$. Then filter and concentrate it before purify the crude product with the preparative TLC (petroleum ether:ethyl acetate=2:1) to obtain the title compound (yellow solid, 1.20 g, yield of 88%). $^1$H NMR (400 MHz, CDCl$_3$) 6.56 (m, 1H), 6.48-6.46 (m, 1H), 4.24-4.18 (m, 2H), 4.14-4.09 (m, 2H), 2.96-2.89 (m, 2H), 1.31-1.23 (m, 3H).

Embodiment 59D (E)-2-(2-chloropyridin-4-yl)-5-(5-((1-(ethoxy-imino)-7-fluoro-2,3-dihydro-1H-inden-5-yl)-oxy)-pentyl)-1,2,5-thiadiazolidine-1,1-dioxide

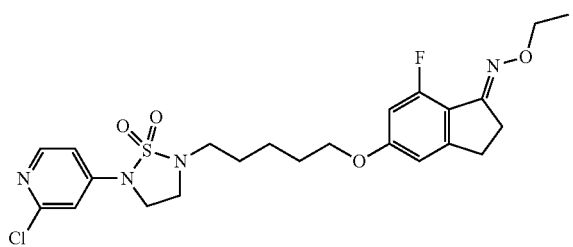 [SMILES: CCO/N=C1\CCc2cc(OCCCCCN3CCN(c4ccnc(Cl)c4)S3(=O)=O)cc(F)c21]

Add KI (8 mg, 50 μmol) and K$_2$CO$_3$ (139 mg, 1.0 mmol) into the solution of Embodiment 52A (192 mg, 502 μmol) and Embodiment 59C (105 mg, 502 μmol) in acetone solution (5 ml). Agitate the mixture solution for 15 hours at 70° C. to allow the raw materials to react completely. Add water (5.0 ml) and extrat with ethyl acetate (10 ml×3). Dry the organic phase with anhydrous Na$_2$SO$_4$ before filter and evaporate to obtain the title compound (yellow solid, 220 mg, yield of 86%). LCMS(ESI) m/z: 511 (M+1).

Embodiment 59E (E)-2-(2-amino-pyridin-4-yl)-5-(5-((1-(ethoxy-imino)-7-fluoro-2,3-dihydro-1H-inden-5-yl)-oxy)-pentyl)-1,2,5-thiadiazolidine-1,1-dioxide

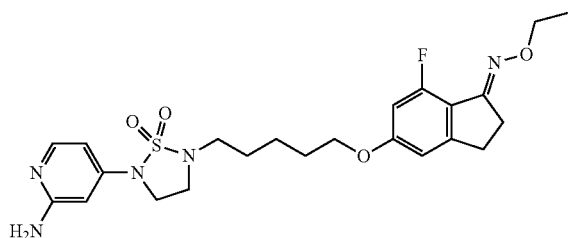

Add Xantphos (23 mg, 40 μmol) and K$_2$CO$_3$ (83 mg, 599 μmol) into the solution of Embodiment 59D (102 mg, 199 μmol), tert-butyl carbamate (222 mg, 1.9 mmol), Pd$_2$(dba)$_3$ (18 mg, 20 μmol) in dioxane (5.0 ml). Agitate the reaction solution 16 hours at 100° C. Then filter and concentrate the reaction solution to purify with the preparative HPLC (neutrual) to obtain the title compound (white solid, 52 mg, yield of 53%). $^1$H NMR (400 MHz, CHLOROFORM-d) 7.97 (d, J=6.0 Hz, 1H), 6.60 (s, 1H), 6.51 (d, J=11.5 Hz, 1H), 6.42 (d, J=4.0 Hz, 1H), 6.29 (s, 1H), 4.56 (br.s., 2H), 4.23 (q, J=7.0 Hz, 2H), 3.50 (t, J=6.5 Hz, 2H), 3.16 (t, J=7.3 Hz, 2H), 2.99 (d, J=8.0 Hz, 2H), 2.93 (d, J=8.5 Hz, 2H), 1.88-1.80 (m, 2H), 1.80-1.72 (m, 2H), 1.32 (t, J=7.0 Hz, 3H). LCMS(ESI) m/z: 492 (M+1).

Embodiment 60

2-(2-chloro-4-pyridyl)-5-(5-(4-(2-isopropyl-tetrazol-5-yl)-phenoxy)-pentyl)-1,2,5-thiadiazolidine-1,1-dioxide

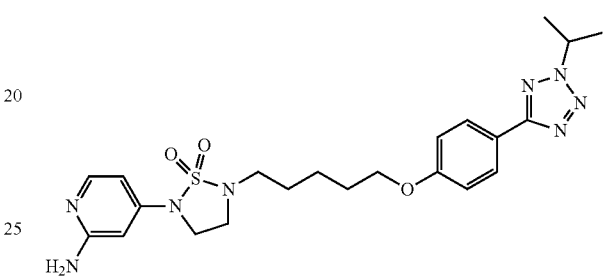

Embodiment 60A 2-isopropyl-5-(4-methoxyphenyl)-tetrazole

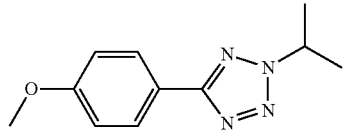 [SMILES: COc1ccc(-c2nnn(C(C)C)n2)cc1]

At 0° C., add K$_2$CO$_3$ (4.7 g, 34 mmol) and isopropyl iodide (2.92 g, 17 mmol) into the solution of Embodiment 11A (3 g, 17 mmol) in acetonitrile (30 ml). After the substances are added, heat the mixture solution for 5 hours at 100° C. Cool the reaction solution to room temperature and then concentrate under vacuum before purity with column chromatography (petroleum ether:ethyl acetate=10:1) to obtain the title compound (white solid, 2.1 g, yield of 60%). $^1$H NMR (400 MHz, CDCl$_3$) 8.08 (d, J=8.5 Hz, 2H), 7.00 (d, J=8.5 Hz, 2H), 4.68 (q, J=7.2 Hz, 2H), 3.87 (s, 3H), 1.68 (t, J=7.5 Hz, 3H). LCMS(ESI) m/z: 205 (M+1).

Embodiment 60B 4-(2-isopropyl-2H-tetrazol-5-yl)-phenol

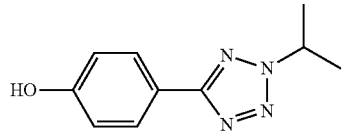

Add the solution of HBr+CH3COOH (20 ml) into Embodiment 60A (1 g, 4.6 mmol). Heat this mixture solution for 24 hours at 110° C. Then cool the reaction solution and add it into ice water. Filter the aqueous phase out to obtain the solid as the title compound (white solid, 0.7 g, yield of 75%). $^1$H NMR (400 MHz, CDCl$_3$) 8.08 (d, J=8.5 Hz, 2H), 7.00 (d, J=8.5 Hz, 2H), 4.68 (q, J=7.2 Hz, 2H), 3.87 (s, 2H), 1.68 (t, J=7.5 Hz, 3H). LCMS(ESI) m/z: 191 (M+1).

Embodiment 60C 2-(2-chloro-4-pyridyl)-5-(5-(4-(2-isopropyl-tetrazol-5-yl)-phenoxy)-pentyl)-1,2,5-thiadiazolidine-1,1-dioxide

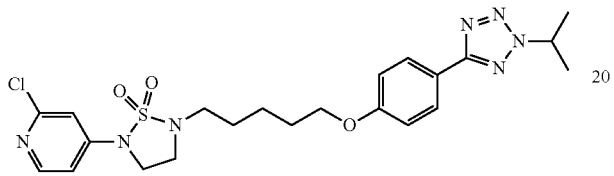

At 0° C., add K$_2$CO$_3$ (270 mg, 2 mmol) and KI (81 mg, 0.49 mmol) into the solution of Embodiment 52A (200 mg, 0.52 mmol) in acetone (3 ml). Then add Embodiment 60B (449 mg, 2.2 mmol) into the mixture solution above. Agitate it to react for 15 hours at 80° C. Then add water to quench the reaction and extract the aqueous phase with ethyl acetate. Dry the combined organic phases with anhydrous Na$_2$SO$_4$ before filter and evaporate to obtain the title compound (white solid, 200 mg, yield of 74%). $^1$H NMR (400 MHz, CDCl$_3$) 8.28 (d, J=6.0 Hz, 1H), 8.09 (d, J=8.8 Hz, 2H), 7.08 (dd, J=5.8, 2.0 Hz, 1H), 6.96-7.02 (m, 3H), 5.10 (d t, J=13.5, 6.7 Hz, 1H), 4.06 (t, J=6.1 Hz, 2H), 3.86 (t, J=6.3 Hz, 2H), 3.57 (t, J=6.3 Hz, 2H), 3.51 (s, 2H), 3.21 (t, J=7.2 Hz, 2H), 1.86-1.93 (m, 2H), 1.78-1.84 (m, 2H), 1.72 (s, 3H), 1.70 (s, 3H). LCMS(ESI) m/z: 506 (M+1).

Embodiment 60D 2-(2-chloro-4-pyridyl)-5-(5-(4-(2-isopropyl-tetrazol-5-yl)-phenoxy)-pentyl)-1,2,5-thiadiazolidine-1,1-dioxide

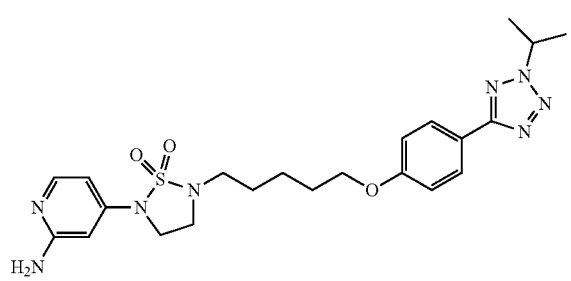 [SMILES: CC(C)n1nnc(-c2ccc(OCCCCCN3CCN(c4ccnc(N)c4)S3(=O)=O)cc2)n1]

At 0° C., add cesium carbonate (386 mg, 1.2 mmol) and tert-butyl carbamate (93 mg, 0.79 mmol) into the solution of Embodiment 60C (200 mg, 0.40 mmol) in N,N-dimethylformamide (1 ml). Under the protection of N$_2$ gas, add Pd$_2$(dba)$_3$ (19 mg, 20 µmol) and Xantphos (12 mg, 20 µmol). Agitate it to react for 15 hours at 110° C. Then add water to quench the reaction and extract the aqueous phase with ethyl acetate. Dry the combined organic phase with anhydrous Na$_2$SO$_4$ before filter and evaporate. Then purify it with the preparative HPLC to obtain the title compound (white solid, 40 mg, yield of 20%). $^1$H NMR (400 MHz, CDCl$_3$) 8.08 (d, J=8.5 Hz, 2H), 7.99 (d, J=5.3 Hz, 1H), 7.00 (d, J=8.8 Hz, 2H), 6.44 (d, J=4.0 Hz, 1H), 6.30 (s, 1H), 5.10 (dt, J=13.4, 6.7 Hz, 1H), 4.54 (br.s., 2H), 4.05 (t, J=6.1 Hz, 2H), 3.80 (t, J=6.3 Hz, 2H), 3.47-3.54 (m, 2H), 3.18 (t, J=7.2 Hz, 2H), 1.88 (d, J=7.5 Hz, 2H), 1.76-1.82 (m, 2H), 1.71 (d, J=6.8 Hz, 6H), 1.61-1.68 (m, 2H). LCMS(ESI) m/z: 487 (M+1).

Embodiment 61

2-(2-amino-pyridin-4-yl)-5-(5-(4-(2-methyl-2H-tetrazol-5-yl)-phenoxy)-pentyl)-1,2,5-thiadiazolidine-1,1-dioxide

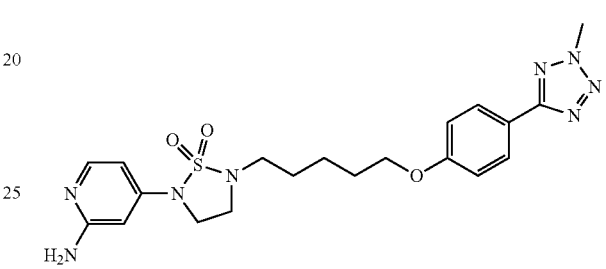

Please refer to the preparation method of Embodiment 60 for this embodiment. $^1$H NMR (400 MHz, DMSO-d$_6$) 7.95 (d, J=8.78 Hz, 2H), 7.80-7.89 (m, 1H), 7.09 (d, J=8.78 Hz, 2H), 6.59 (br.s., 2H), 6.41 (d, J=4.27 Hz, 1H), 6.25 (s, 1H), 4.38 (s, 3H), 4.04 (t, J=6.27 Hz, 2H), 3.84 (t, J=6.40 Hz, 2H), 3.52 (t, J=6.27 Hz, 2H), 3.07 (t, J=7.03 Hz, 2H), 1.62-1.83 (m, 4H), 1.44-1.56 (m, 2H). LCMS(ESI) m/z: 459 (M+1).

Embodiment 62

2-(2-amino-pyridin-4-yl)-5-(5-((3-ethyl-benzo[d]6-yl)-oxy)-pentyl)-1,2,5-thiadiazolidine-1,1-dioxide

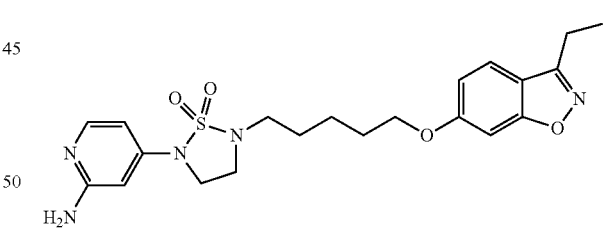

Embodiment 62A 3-ethyl-benzo[d]isoxazole-6-ol

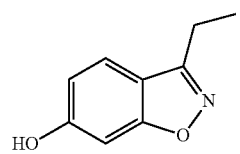

Please refer to the preparation method of Tetrahedron. Lett. 2006, 8247-8250 for this embodiment. $^1$H NMR (400 MHz, CDCl$_3$) 7.50-7.48 (m, 1H), 7.00 (m, 1H), 6.85-6.82 (m, 1H), 2.94 (m, 2H), 1.45 (t, J=8.0 Hz, 3H).

Embodiment 62B 2-(2-chloro-4-yl)-5-(5-((3-ethyl-benzo[d]6-yl)-oxy)-pentyl)-1,2,5-thiadiazolidine-1,1-dioxide

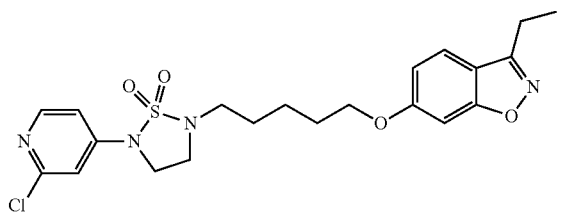 [SMILES: CCc1noc2cc(OCCCCCN3CCN(c4ccnc(Cl)c4)S3(=O)=O)ccc12]

Add K$_2$CO$_3$ (36 mg, 0.26 mmol) and KI (4.3 mg, 0.026 mmol) into the mixture solution of Embodiment 52A (100 mg, 0.26 mmol) and Embodiment 62A (42.6 mg, 0.26 mmol) in acetone (10 ml). Then allow it to react for 10 hours at 50° C. Filter and evaporate the reaction solution. Then purify the residue with HPLC to obtain the title compound (white solid, 100 mg, yield of 82%). $^1$H NMR (400 MHz, CDCl$_3$) 68.28 (d, J=5.77 Hz, 1H), 7.54 (d, J=8.53 Hz, 1H), 7.08 (dd, J=2.26, 5.77 Hz, 1H), 7.01 (d, J=2.01 Hz, 2H), 6.89 (dd, J=2.38, 8.66 Hz, 1H), 4.02 (t, J=6.15 Hz, 2H), 3.86 (t, J=6.40 Hz, 2H), 3.57 (t, J=6.40 Hz, 2H), 3.15-3.24 (m, 2H), 2.91-2.97 (m, 2H), 1.85-1.98 (m, 2H), 1.74-1.84 (m, 2H), 1.58-1.69 (m, 2H), 1.45 (t, J=7.65 Hz, 3H).

Embodiment 62C 2-(2-amino-pyridin-4-yl)-5-(5-((3-ethyl-benzo[d]isoxazol-6-yl)-oxy)-pentyl)-1,2,5-thiadiazolidine-1,1-dioxide

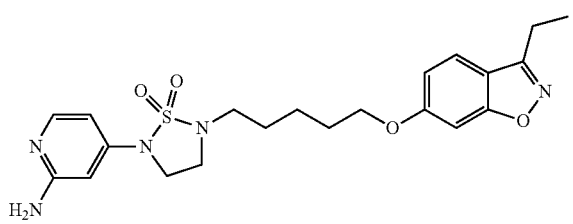 [SMILES: CCc1noc2cc(OCCCCCN3CCN(c4ccnc(N)c4)S3(=O)=O)ccc12]

Under the protection of N$_2$ gas, add Cs$_2$CO$_3$ (189 mg, 0.58 mmol), Xantphos (22 mg, 0.038 mmol) and Pd$_2$(dba)$_3$ (18 mg, 0.019 mmol) into the solution of Embodiment 62B (90 mg, 0.193 mmol) and tert-butyl carbamate (136 mg, 0.116 mmol) in dioxane (2 ml). Then allow it to react for 10 hours at 110° C. Then pour the reaction solution into water and extract with ethyl acetate (100 ml×3). Then mix the organic phases and dry with Na$_2$SO$_4$. Then filter and evaporate before purify the residue with the preparative HPLC to obtain the title compound (white solid, 20 mg, yield of 23%). $^1$H NMR (400 MHz, CDCl$_3$) 7.98 (d, J=5.52 Hz, 1H), 7.50-7.56 (m, 1H), 7.00 (d, J=2.01 Hz, 1H), 6.85-6.90 (m, 1H), 6.42 (d, J=6.02 Hz, 1H), 6.30 (s, 1H), 4.01 (t, J=6.27 Hz, 2H), 3.76-3.84 (m, 2H), 3.51 (t, J=6.27 Hz, 2H), 3.17 (t, J=7.28 Hz, 2H), 2.93 (d, J=7.53 Hz, 2H), 1.84-1.97 (m, 2H), 1.79 (t, J=7.53 Hz, 2H), 1.64 (d, J=7.03 Hz, 2H), 1.43 (t, J=7.78 Hz, 3H). LCMS(ESI) m/z: 446 (M+1).

Embodiment 63

4-(5-(5-(4-(5-ethyl-1,3,4-oxadiazol-2-yl)-phenoxy)-pentyl)-1,1-dioxo-1,2,5-thiadiazolidine-2-yl)-pyridin-2-amine

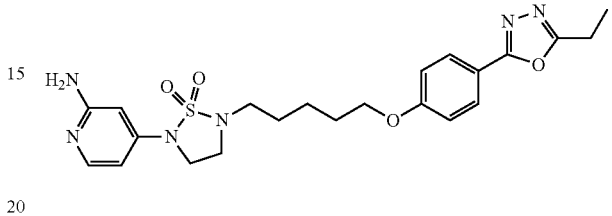

Embodiment 63A 4-(5-ethyl-1,3,4-oxadiazol-3-yl)-phenol

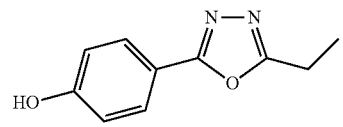

Add methanesulfonic acid (63 mg, 658 μmol) into 4-hydroxy benzoyl hydrazine (500 mg, 3.3 mmol) and triethyl orthoformate (579 mg, 3.3 mmol) in dioxane (10 ml). Then allow it to react 1 hour at 110° C. Filter the reaction system before filter and evaporate to obtain the title compound (yellow solid, 150.00 mg, yield of 24%). $^1$H NMR (400 MHz, CDCl$_3$) 7.79 (d, J=9.03 Hz, 2H), 6.87 (d, J=8.53 Hz, 2H), 2.87 (q, J=7.53 Hz, 2H), 1.36 (t, J=7.53 Hz, 3H).

Embodiment 63B 2-(2-chloro-4-pyridyl)-5-(5-(4-(5-ethyl-1,3,4-oxadiazol-2-yl)-phenoxy)-pentyl)-1,2,5-thiadiazolidine-1,1-dioxide

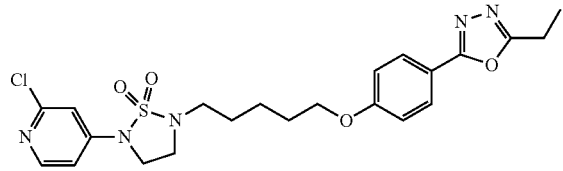 [SMILES: CCc1nnc(-c2ccc(OCCCCCN3CCN(c4ccnc(Cl)c4)S3(=O)=O)cc2)o1]

Add K$_2$CO$_3$ (29 mg, 0.02 mmol) and KI (3.5 mg, 2 μmol) into the mixture solution of Embodiment 52A (80 mg, 0.02 mmol) and Embodiment 63A (47.71 mg, 0.25 mmol) in N,N-dimethylformamide (2 ml). Allow it to react for 10 hours at 80° C. and then pour the reaction solution into water (100 ml). Extract it with ethyl acetate (100 ml×3). Mix the organic phases and dry it with anhydrous Na$_2$SO$_4$ before filter and evaporate. Then pass it through column to obtain the title compound (yellow solid, 100 mg, yield of 97%). $^1$H NMR (400 MHz, CDCl$_3$) 8.22 (d, J=5.77 Hz, 1H), 7.91 (d, J=8.78 Hz, 2H), 7.02 (dd, J=2.26, 5.77 Hz, 1H), 6.98 (d, J=1.76 Hz, 1H), 6.94 (d, J=9.03 Hz, 2H), 3.95-4.04 (m, 2H), 3.83 (t, J=6.40 Hz, 3H), 3.54 (t, J=6.40 Hz, 3H), 3.11-3.22 (m, 3H), 2.87-2.90 (m, 2H), 1.79-1.90 (m, 2H), 1.69-1.79 (m, 2H), 1.52-1.64 (m, 2H), 1.39 (t, J=7.65 Hz, 3H).

Embodiment 63C 4-(5-(5-(4-(5-ethyl-1,3,4-oxadiazol-2-yl)-phenoxy)-pentyl)-1,1-dioxo-1,2,5-thiadiazolidine-2-yl)-pyridin-2-amine

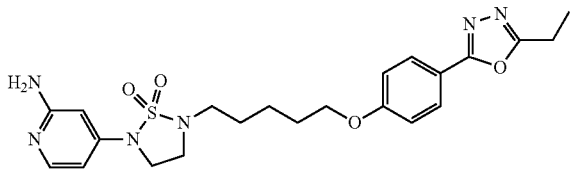 [SMILES: CCc1nnc(-c2ccc(OCCCCCN3CCN(c4ccnc(N)c4)S3(=O)=O)cc2)o1]

Under the protection of N₂ gas, add Pd₂(dba)₃ (15 mg, 0.016 mmol), cesium carbonate (106 mg, 0.032 mol), and Xantphos (19 mg, 3 μmol) into the solution of Embodiment 63B (80 mg, 0.16 mmol) and tert-butyl carbamate (114 mg, 0.40 mmol) in dioxane (1 ml). Then allow it to react for 10 hours at 110° C. After the reaction ends, pour the reaction solution into water (20 ml) and extract with ethyl acetate (10 ml×3). Then dry the organic phase with anhydrous Na₂SO₄ before filter and evaporate. Then purify the residue with the preparative HPLC to obtain the title compound (white solid, 25 mg, yield of 33%). ¹H NMR (400 MHz, CDCl₃) 7.92-8.02 (m, 3H), 6.98 (d, J=9.03 Hz, 2H), 6.43 (dd, J=1.76, 5.77 Hz, 1H), 6.30 (d, J=1.51 Hz, 1H), 4.57 (br.s., 1H), 4.05 (t, J=6.02 Hz, 2H), 3.73-3.87 (m, 2H), 3.51 (t, J=6.53 Hz, 2H), 3.18 (t, J=7.28 Hz, 2H), 2.95 (q, J=7.53 Hz, 2H), 1.84-1.94 (m, 2H), 1.75-1.83 (m, 2H), 1.65-1.69 (m, 2H), 1.44 (t, J=7.53 Hz, 3H). LCMS(ESI) m/z: 473 (M+1).

Embodiment 64

2-(2-amino-pyridin-4-yl)-5-(5-(4-(2-ethyl-2H-1,2,3-triazol-4-yl)-phenoxy)-pentyl)-1,2,5-thiadiazolidine-1,1-dioxide

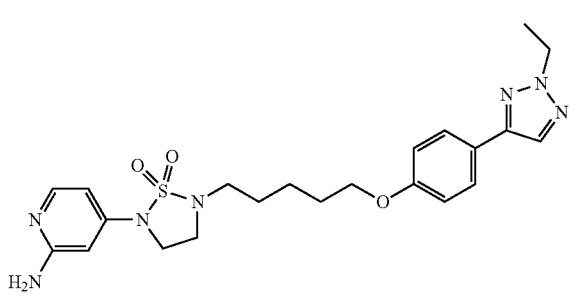 [SMILES: CCn1ncc(-c2ccc(OCCCCCN3CCN(c4ccnc(N)c4)S3(=O)=O)cc2)n1]

Embodiment 64A 4-(4-methoxyphenyl)-1,2,3-triazole

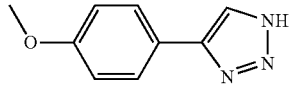

Under the protection of N₂ gas, add trimethylsilyl azide (2.62 g, 22.7 mmol) into the solution of CuI (144 g, 757 mmol), 4-methoxyphenyl acetylene (2 g, 15.1 mmol) in N,N-dimethylformamide (5.4 ml) and methanol (0.6 ml). Agitate the mixture solution 16 hours at 100° C. Then filter and evaporate before purify the residue with column chromatography (petroleum ether:ethyl acetate=10:1, petroleum ether:ethyl acetate=2:1) to obtain the title compound (yellow solid, 2 g, yield of 75%). ¹H NMR (400 MHz, CDCl₃) 7.88 (s, 1H), 7.75 (d, J=8.5 Hz, 2H), 6.98 (d, J=8.5 Hz, 2H), 3.85 (s, 3H).

Embodiment 64B 2-ethyl-4 (4-methoxyphenyl)-1,2,3-triazole

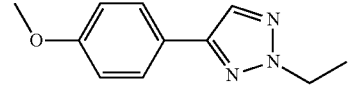

Allow the mixture of Embodiment 64A (1 g, 5.71 mmol), ethyl iodide (2.67 g, 17.13 mmol) and K₂CO₃ (1.58 g, 11.42 mmol) in acetonitrile (10 ml) to react 16 hours at 70° C. Add water (10 ml) into the reaction system. Extract the aqueous layer with ethyl acetate (10 ml×3) and then dry the combined organic layers with Na₂SO₄ before filter and evaporate. Then purify the residue with column chromatography (petroleum ether:ethyl acetate=5:1) to obtain the title compound (yellow liquid, 1 g, yield of 86%). ¹H NMR (400 MHz, CDCl₃) 7.62-7.73 (m, 3H), 6.92 (d, J=8.5 Hz, 2H), 4.45 (q, J=7.5 Hz, 2H), 3.81 (s, 3H), 1.56 (t, J=7.3 Hz, 3H).

Embodiment 64C 4-(2-ethyl-2H-1,2,3-triazol-4-yl)-phenol

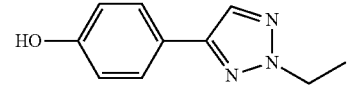

At −78° C., add BBr₃ (986 mg, 3.94 mmol) into the solution of Embodiment 64B (200 mg, 984 μmol) in dichloromethane (5 ml). Allow the mixture to react 1 hour at 25° C. Then add water (5 ml) into the reaction system and extract the aqueous layer with dichloromethane (10 ml×3). Then filter and evaporate to obtain the title compound (yellow solid, 160 mg, yield of 86%). ¹H NMR (400 MHz, CDCl₃) 67.74 (s, 1H), 7.66 (d, J=8.5 Hz, 2H), 6.89 (d, J=8.5 Hz, 2H), 4.46-4.52 (m, 2H), 1.59 (t, J=7.3 Hz, 3H).

Embodiment 64D 2-(2-chloropyridin-4-yl)-5-(5-(4-(2-ethyl-2H-1,2,3-triazol-4-yl)-phenoxy)-pentyl)-1,2,5-thiadiazolidine-1,1-dioxide

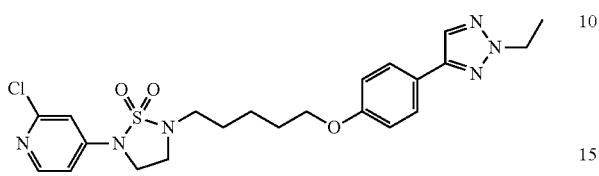

Please refer to the preparation method of Embodiment 63 for this embodiment. ¹H NMR (400 MHz, CDCl₃) 8.26 (d, J=6.0 Hz, 1H), 7.74 (s, 1H), 7.69 (d, J=9.0 Hz, 2H), 7.06 (dd, J=5.5, 2.0 Hz, 1H), 6.99 (d, J=2.0 Hz, 1H), 6.93 (d, J=8.5 Hz, 2H), 4.49 (q, J=7.4 Hz, 2H), 4.01 (t, J=6.3 Hz, 2H), 3.83 (t, J=6.5 Hz, 2H), 3.55 (t, J=6.5 Hz, 2H), 3.18 (t, J=7.0 Hz, 2H), 1.83-1.90 (m, 2H), 1.75-1.82 (m, 2H), 1.62-1.67 (m, 2H), 1.61 (d, J=4.0 Hz, 3H). LCMS(ESI) m/z: 492 (M+1).

Embodiment 64E 2-(2-amino-pyridin-4-yl)-5-(5-(4-(2-ethyl-2H-[1,2,3]triazol-4-yl)-phenoxy)-pentyl)-1,2,5-thiadiazolidine-1,1-dioxide

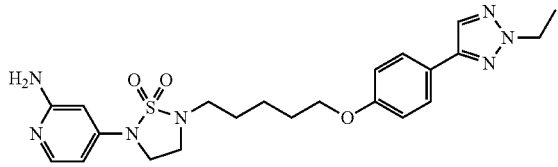 [SMILES: CCn1ncc(-c2ccc(OCCCCCN3CCN(c4ccnc(N)c4)S3(=O)=O)cc2)n1]

Under the protection of N₂ gas, add Xantphos (8 mg, 13.8 µmol) and Pd₂(dba)₃ (9 mg, 9.8 µmol) into the solution of Embodiment 64D (80 mg, 163 µmol), tert-butyl carbamate (115 mg, 978 µmol) and Cs₂CO₃ (106 mg, 326 µmol) in dioxane (3 ml) and N,N-dimethylformamide (0.5 ml). Allow the mixture to react 16 hour at 110° C. Then add water (10 ml) into the reaction system and extract the aqueous layer with dichloromethane (10 ml×3). Then filter and evaporate before obtain the title compound from the residue through preparation and separation (brown solid, 30 mg, yield of 39%). ¹H NMR (400 MHz, CDCl₃) δ7.98 (d, J=6.0 Hz, 1H), 7.74 (s, 1H), 7.69 (d, J=8.5 Hz, 2H), 6.94 (d, J=9.0 Hz, 2H), 6.38-6.44 (m, 1H), 6.29 (s, 1H), 4.49 (q, J=7.5 Hz, 4H), 4.01 (t, J=6.0 Hz, 2H), 3.80 (t, J=6.5 Hz, 2H), 3.47-3.53 (m, 2H), 3.16 (t, J=7.3 Hz, 2H), 1.84-1.91 (m, 2H), 1.74-1.80 (m, 2H), 1.64 (br.s., 3H). LCMS(ESI) m/z: 472 (M+1).

Embodiment 65

(E)-2-(2-amino-pyridin-4-yl)-5-(5-((5 (ethoxymethylene)-5,6,7,8-tetrahydronaphthalen-2-yl)-oxy)-pentyl)-1,2,5-thiadiazolidine-1,1-dioxide

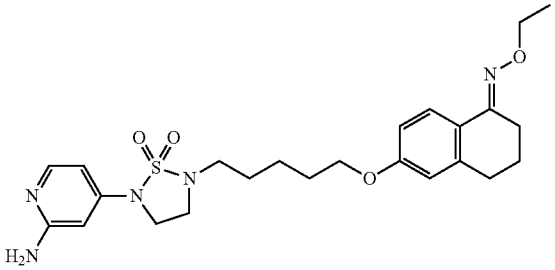 [SMILES: CCO/N=C1\CCCc2cc(OCCCCCN3CCN(c4ccnc(N)c4)S3(=O)=O)ccc21]

Embodiment 65A (E)-6-hydroxy-3,4-dihydro-naphthalene-1 (2H)-one-O-ethyl ketoxime

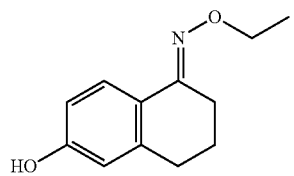

Add ethoxyamino hydrochloride (1.88 g, 30.9 mmol) and sodium acetate (2.5 g, 30.9 mmol) into the solution of 6-hydroxy-1-tetralone (1 g, 6.2 mmol) in water (10 ml). Agitate the mixture solution 2 hours at 80° C. Then extract it with ethyl acetate. Dry the organic phase with anhydrous Na₂SO₄ before filter and evaporate to obtain the title compound (yellow solid, 0.8 g, yield of 63%). LCMS(ESI) m/z: 206 (M+1).

Embodiment 65B (E)-2-(2-chloropyridin-4-yl)-5-(5-((5-(ethoxymethylene)-5,6,7,8-tetrahydronaphthalen-2-yl)-oxy)-pentyl)-1,2,5-thiadiazolidine-1,1-dioxide

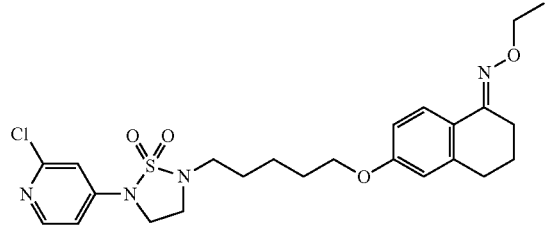 [SMILES: CCO/N=C1\CCCc2cc(OCCCCCN3CCN(c4ccnc(Cl)c4)S3(=O)=O)ccc21]

Add K₂CO₃ (72 mg, 0.52 mmol), KI (9 mg, 0.05 mmol) and Embodiment 64A (53.6 mg, 0.26 mmol) into the solution of Embodiment 52A (0.1 g, 0.26 mmol) in N,N-dimethylformamide (2 ml). Agitate the mixture solution for 15 hours at 80° C. Then extract it with ethyl acetate. Dry the organic phase with anhydrous Na₁SO₄ before filter and evaporate. Then purify the residue with column chromatography (petroleum ether:ethyl acetate=1:1) to obtain the title compound (white solid, 60 mg, yield of 45%). ¹H NMR (400 MHz, CDCl₃) 8.28 (d, J=5.8 Hz, 1H), 7.92 (d, J=8.8 Hz, 1H), 7.07 (dd, J=5.8, 2.0 Hz, 1H), 7.01 (d, J=2.0 Hz, 1H), 6.74 (dd, J=8.8, 2.5 Hz, 1H), 6.63 (d, J=2.3 Hz, 1H), 4.21 (q, J=7.0 Hz, 2H), 3.99 (t, J=6.3 Hz, 2H), 3.85 (t, J=6.3 Hz, 2H), 3.56 (t, J=6.4 Hz, 2H), 3.15-3.22 (m, 2H), 2.67-2.77 (m, 4H), 1.84 (dt, J=12.1, 6.4 Hz, 6H), 1.58-1.66 (m, 2H), 1.33 (t, J=7.0 Hz, 3H). LCMS(ESI) m/z: 507 (M+1).

Embodiment 65C (E)-2-(2-amino-pyridin-4-yl)-5-(5-((5-(ethoxymethylene)-5,6,7,8-tetrahydronaphthalen-2-yl)-oxy)-pentyl)-1,2,5-thiadiazolidine-1,1-dioxide

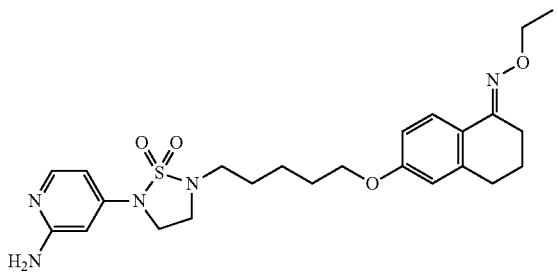 [SMILES: CCO/N=C1\CCCc2cc(OCCCCCN3CCN(c4ccnc(N)c4)S3(=O)=O)ccc21]

At 0° C., add Cs₂CO₃ (77 mg, 0.24 mmol), tert-butyl carbamate (15 mg, 0.13 mmol) into the solution of Embodiment 65B (60 mg, 0.12 mmol) in N,N-dimethylformamide (1 ml). After replace with N₂ gas, under the protection of N₂ gas, add Pd₂(dba)₃ (22 mg, 23.7 mmol) and Xantphos (14 mg, 23.7 mmol). Agitate it to react for 15 hours at 110° C. Then add water to quench the reaction and extract the aqueous phase with ethyl acetate. Dry the combined organic phase with anhydrous Na₂SO₄ before filter and evaporate. Then purify it with the preparative HPLC to obtain the title compound (white solid, 15 mg, yield of 26%). ¹H NMR (400 MHz, CDCl₃) 7.91 (d, J=8.5 Hz, 1H), 7.62 (d, J=7.0 Hz, 1H), 6.68-6.75 (m, 2H), 6.62 (d, J=2.0 Hz, 1H), 6.18 (s, 1H), 4.20 (q, J=7.0 Hz, 2H), 3.98 (t, J=6.3 Hz, 2H), 3.84 (t, J=6.3 Hz, 2H), 3.57 (t, J=6.3 Hz, 2H), 3.19 (t, J=7.0 Hz, 2H), 2.65-2.76 (m, 4H), 1.81-1.87 (m, 4H), 1.76 (d, J=7.0 Hz, 2H), 1.57-1.63 (m, 2H), 1.32 (t, J=7.0 Hz, 3H). LCMS(ESI) m/z: 488 (M+1).

Embodiment 66

2-(2-amino-pyridin-4-yl)-5-(5-((2-propyl-benzo[d]oxazole-6-yl)-oxy)-pentyl)-1,2,5-thiadiazolidine-1,1-dioxide

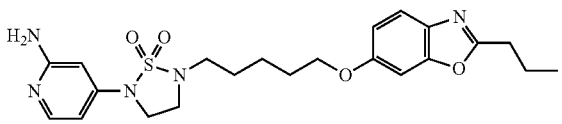 [SMILES: CCCc1nc2ccc(OCCCCCN3CCN(c4ccnc(N)c4)S3(=O)=O)cc2o1]

Embodiment 66A 2-propyl-benzo[d]oxazole-6-ol

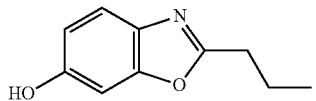

Please refer to the operation of Patent (WO 2005037814) LCMS(ESI) m/z: 178 (M+1) for this embodiment.

Embodiment 66B 2-(2-chloro-4-yl)-5-(5-((2-propyl-benzo[d]oxazole-6-yl)-oxy)-pentyl)-1,2,5-thiadiazolidine-1,1-dioxide

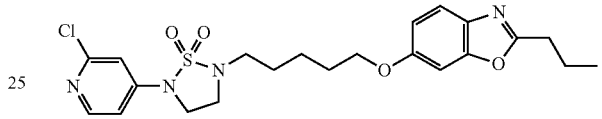

Add K₂CO₃ (72 mg, 0.52 mmol), KI (9 mg, 0.05 mmol) and 2-propyl-6-hydroxybenzoxazole (56 ml, 0.3 mmol) into the solution of Embodiment 52A (0.1 g, 0.26 mmol) in N,N-dimethylformamide (2 ml). Agitate the mixture solution for 15 hours at 80° C. Then extract it with ethyl acetate. Dry the organic phase with anhydrous Na₁SO₄ before filter and evaporate. Then purify the residue with column chromatography (petroleum ether:ethyl acetate=1:1) to obtain the title compound (white solid, 50 mg, yield of 40%). LCMS(ESI) m/z: 479 (M+1).

Embodiment 66C 2-(2-amino-pyridin-4-yl)-5-(5-((2-propyl-benzo[d]oxazole-6-yl)-oxy)-pentyl)-1,2,5-thiadiazolidine-1,1-dioxide

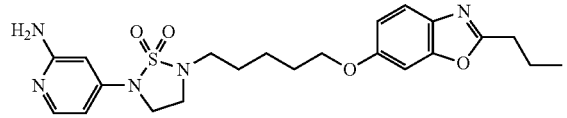 [SMILES: CCCc1nc2ccc(OCCCCCN3CCN(c4ccnc(N)c4)S3(=O)=O)cc2o1]

At 0° C., add Cs₂CO₃ (68 mg, 0.21 mmol), tert-butyl carbamate (15 mg, 0.13 mmol) into the solution of Embodiment 66B (50 mg, 0.10 mmol) in N,N-dimethylformamide (1 ml). After replace with N₂ gas, under the protection of N₂ gas, add Pd₂(dba)₃ (19 mg, 21 μmol) and Xantphos (12 mg, 20 μmol). Agitate it to react for 15 hours at 110° C. Then add water to quench the reaction and extract the aqueous phase with ethyl acetate. Dry the combined organic phases with anhydrous Na₂SO₄ before filter and evaporate. Then purify it with the preparative HPLC to obtain the title compound (white solid, 8 mg, yield of 17%). ¹H NMR (400 MHz, CDCl₃) 7.92 (d, J=6.3 Hz, 1H), 7.54 (d, J=8.5 Hz, 1H), 7.02 (d, J=2.3 Hz, 1H), 6.90 (dd, J=8.8, 2.3 Hz, 1H), 6.50 (d, J=5.8 Hz, 1H), 6.33 (s, 1H), 4.03 (t, J=6.3 Hz, 2H), 3.85 (t, J=6.4 Hz, 2H), 3.54 (t, J=6.3 Hz, 2H), 3.19 (t, J=7.2 Hz, 2H), 2.89 (t, J=7.5 Hz, 2H), 1.87-1.94 (m, 4H), 1.80 (q, J=7.3 Hz, 2H), 1.61-1.70 (m, 2H), 1.06 (t, J=7.4 Hz, 3H). LCMS(ESI) m/z: 460 (M+1).

Embodiment 67

2-(2-amino-pyridin-4-yl)-5-(5-(4-(5-ethyl isoxazole-3-yl)-phenoxy)-pentyl)-1,2,5-thiadiazolidine-1,1-dioxide

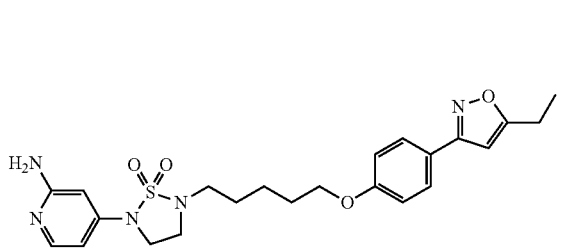 [SMILES: CCc1cc(-c2ccc(OCCCCCN3CCN(c4ccnc(N)c4)S3(=O)=O)cc2)no1]

Embodiment 67A (E)-4-hydroxybenzaldehyde oxime

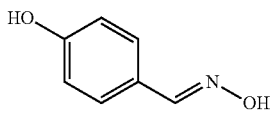

Add sodium acetate (20 g, 246 mmol) and hydroxylamine hydrochloride (17 mg, 246 mmol) into the solution of 4-hydroxybenzaldehyde (10 g, 82 mmol) in ethanol (100 ml). Heat the mixture solution for 15 hours at 70° C. Cool it to room temperature before add water and then extract with dichloromethane. Then dry the organic phase through rotation and separate through column (petroleum ether: EA=3:1) to obtain the solid as the title compound (white solid, 7 g, yield of 62%). LCMS(ESI) m/z: 138 (M+1).

Embodiment 67B 4-(5-ethyl-3-yl) phenol

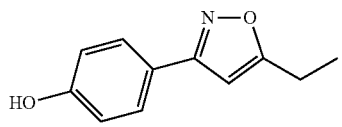

At 0° C., add chlorosuccinimide (2.9 g, 22 mmol) into the solution of Embodiment 67A (3 g, 22 mmol) in 1,2-dichloroethane (30 ml). After allow it to react 1 hour at room temperature, add 1-butyne (1.2 g, 22 mmol) in ice bath. After the substance is added, heat the mixture solution 2 hours at 20° C. Also, add triethylamine (2.2 g, 22 mmol) into the reaction solution in ice bath. After the substance is added, heat the mixture solution for 15 hours at 20° C. Cool the reaction solution to room temperature and then concentrate under vacuum before purity with column chromatography (petroleum ether:ethyl acetate=10:1) to obtain the title compound (white solid, 1 g, yield of 24%). LCMS(ESI) m/z: 190 (M+1).

Embodiment 67C 2-(2-chloropyridin-4-yl)-5-(5-(4-(5-ethyl isoxazol-3-yl)-phenoxy)-pentyl)-1,2,5-thiadiazolidine-1,1-dioxide

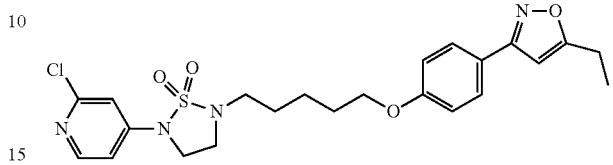

Add K$_2$CO$_3$ (72 mg, 0.5 mmol), KI (9 mg, 0.05 mmol) and Embodiment 67B (59 mg, 0.3 mmol) into the solution of Embodiment 52A (0.1 g, 0.26 mmol) in N,N-dimethylformamide (2 ml). Agitate the mixture solution for 15 hours at 80° C. Then extract it with ethyl acetate. Dry the organic phase with anhydrous Na$_2$SO$_4$ before filter and evaporate. Then purify the residue with column chromatography (petroleum ether:ethyl acetate=2:1) to obtain the title compound (white solid, 60 mg, yield of 49%). LCMS(ESI) m/z: 492 (M+1).

Embodiment 67D 2-(2-amino-pyridin-4-yl)-5-(5-(4-(5-ethyl isoxazole-3-yl)-phenoxy)-pentyl)-1,2,5-thiadiazolidine-1,1-dioxide

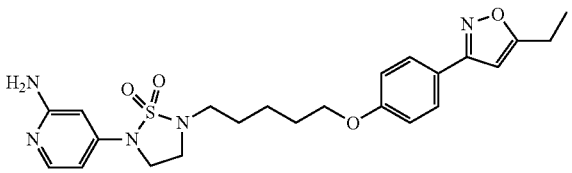 [SMILES: CCc1cc(-c2ccc(OCCCCCN3CCN(c4ccnc(N)c4)S3(=O)=O)cc2)no1]

At 0° C., add cesium carbonate (66.36 mg, 0.202 mmol) and tert-butyl carbamate (23.26 mg, 0.202 mmol) into the solution of Embodiment 67C (50 mg, 0.101 mmol) in N,N-dimethylformamide (1.5 ml). After replace with N$_2$ gas, under the protection of N$_2$ gas, add Pd$_2$ (dba)$_3$ (18.57 mg, 20.28 mmol) and Xantphos (11.74 mg, 20.28 mmol). Agitate it to react for 15 hours at 110° C. Then add water to quench the reaction and extract the aqueous phase with ethyl acetate. Dry the combined organic phases with anhydrous Na$_2$SO$_4$ before filter and evaporate to obtain the title compound (white solid, 3 mg, yield of 6.25%). $^1$H NMR (400 MHz, CDCl$_3$) 7.98 (d, J=5.5 Hz, 1H), 7.72 (d, J=8.5 Hz, 2H), 6.95 (d, J=8.5 Hz, 2H), 6.39-6.44 (m, 1H), 6.29 (s, 1H), 6.23 (s, 1H), 4.48 (br.s., 2H), 4.03 (t, J=6.0 Hz, 2H), 3.79 (t, J=6.5 Hz, 2H), 3.50 (t, J=6.3 Hz, 2H), 3.17 (t, J=7.3 Hz, 2H), 2.81 (q, J=7.5 Hz, 2H), 1.82-1.94 (m, 2H), 1.70-1.82 (m, 2H), 1.64 (br.s., 2H), 1.34 (t, J=7.8 Hz, 3H). LCMS(ESI) m/z: 472 (M+1).

Embodiment 68

2-(2-amino-pyridin-4-yl)-5-(5-(4-(5 (trifluoromethyl)-1,2,4-oxadiazol-3-yl)-phenoxy)-pentyl)-1,2,5-thiadiazolidine-1,1-dioxide

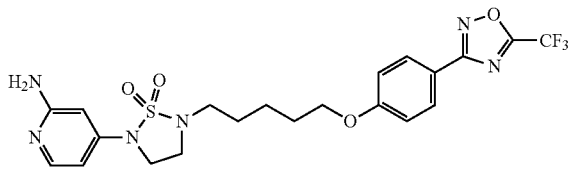 [SMILES: Nc1cc(N2CCN(CCCCCOc3ccc(-c4noc(C(F)(F)F)n4)cc3)S2(=O)=O)ccn1]

Embodiment 68A 4-(5-(5-(2-chloro-4-pyridyl)-1,1-dioxo-1,2,5-thiadiazolidine-2-yl)-pentyloxy) benzonitrile

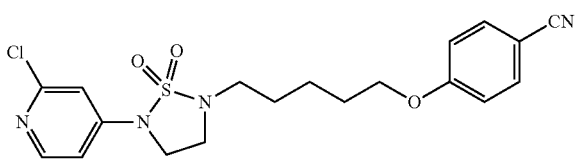 [SMILES: N#Cc1ccc(OCCCCCN2CCN(c3ccnc(Cl)c3)S2(=O)=O)cc1]

At 0° C., add 4-cyanophenol (187 mg, 1.57 mmol) into the solution of Embodiment 52A (500 mg, 1.31 mmol) in N,N-dimethylformamide (5 ml). Add $K_2CO_3$ (362 mg, 2.62 mmol) into the mixture solution above. Agitate it to react for 15 hours at 80° C. Then add water to quench the reaction and extract the aqueous phase with ethyl acetate. Dry the combined organic phases with anhydrous $Na_2SO_4$. Then filter and evaporate it before separating it with column (petroleum ether:ethyl acetate=2:1) to obtain the title compound (white solid, 350 mg, yield of 63%). LCMS(ESI) m/z: 421 (M+1).

Embodiment 68B 4-(5-(5-(2-amino-4-pyridyl)-1,1-dioxo-1,2,5-thiadiazolidine-2-yl)-pentyloxy) benzonitrile

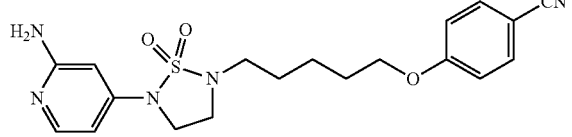

At 0° C., add cesium carbonate (154 mg, 0.48 mmol) and tert-butyl carbamate (42 mg, 0.36 mmol) into the solution of Embodiment 68A (100 mg, 0.24 mmol) in N,N-dimethylformamide (1.5 ml). Under the protection of $N_2$ gas, add $Pd_2(dba)_3$ (18.57 mg, 20.28 µmol) and Xantphos (11.7 mg, 20 µmol). Agitate it to react for 15 hours at 110° C. Then add water to quench the reaction and extract the aqueous phase with ethyl acetate. Dry the combined organic phases with anhydrous $Na_2SO_4$. Then filter and evaporate it before separating it with column (dichloromethane:methanol=10:1) to obtain the title compound (white solid, 30 mg, yield of 31%). LCMS(ESI) m/z: 402 (M+1).

Embodiment 68C

N-(4-(5-(5-(4-cyanophenoxy)-pentyl)-1,1-dioxo-1,2,5-thiadiazolidine-2-yl)-2-pyridyl) tert-butyl carbamate

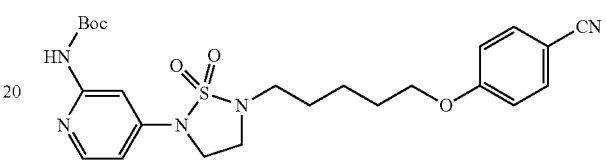

Add N,N-dimethylaminopyridine (45 mg, 0.37 mmol) and BOC anhydride (489 mg, 2.2 mmol) into the solution of Embodiment 68B (0.3 g, 0.75 mmol) in acetonitrile. Heat this mixture solution for 15 hours at 20° C. Then cool and add the reaction solution into ice water. Extract the aqueous phase with ethyl acetate. Dry the combined organic phases with anhydrous $Na_2SO_4$. Then filter and evaporate it before separating it with column (dichloromethane:methanol=10:1) to obtain the title compound (red oily form, 0.2 g, yield of 53%). LCMS(ESI) m/z: 502 (M+1).

Embodiment 68D

N-(4-(5-(5-(4-((Z)—N'-hydroxy-amidino)-phenoxy)-pentyl)-1,1-dioxo-1,2,5-thiadiazolidine-2-yl)-2-pyridinyl) tert-butyl carbamate

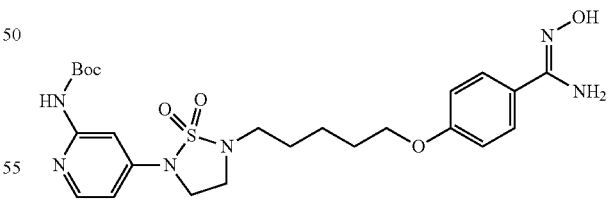

Add triethylamine (40 g, 0.4 mmol) and hydroxylamine hydrochloride (27.8 mg, 0.4 mmol) into the solution of Embodiment 68C (0.1 g, 0.2 mmol) in isopropanol (2 ml). Agitate the mixture solution for 5 hours at 80° C. Then extract it with ethyl acetate. Dry the organic phase with anhydrous $Na_2SO_4$ before filter and evaporate to obtain the title compound (white solid, 70 mg, yield of 66%). LCMS (ESI) m/z: 535 (M+1).

Embodiment 68E 2-(2-amino-pyridin-4-yl)-5-(5-(4-(5 (trifluoromethyl)-1,2,4-oxadiazol-3-yl)-phenoxy)-pentyl)-1,2,5-thiadiazolidine-1,1-dioxide

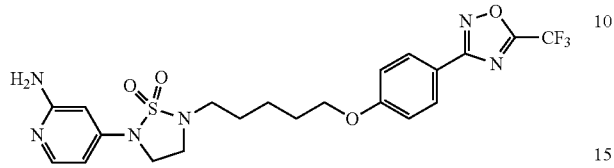

At 0° C., add TFAA (35 mg, 0.17 mmol) into the solution of Embodiment 68D (60 mg, 0.11 mmol) in pyridine (1 ml). Agitate it to react for 2 hours at 80° C. Then add water to quench the reaction and extract the aqueous phase with ethyl acetate. Dry the combined organic phases with anhydrous $Na_2SO_4$ before filter and evaporate to obtain the title compound (white solid, 5 mg, yield of 7%). $^1H$ NMR (400 MHz, $CDCl_3$) 8.06 (d, J=8.8 Hz, 2H), 8.00 (d, J=6.0 Hz, 1H), 7.02 (d, J=8.8 Hz, 2H), 6.44 (dd, J=5.8, 2.0 Hz, 1H), 6.31 (d, J=2.0 Hz, 1H), 4.50 (br.s., 2H), 4.08 (t, J=6.3 Hz, 2H), 3.83 (t, J=6.3 Hz, 2H), 3.53 (t, J=6.4 Hz, 2H), 3.19 (t, J=7.2 Hz, 2H), 1.87-1.96 (m, 2H), 1.81 (quin, J=7.4 Hz, 2H), 1.65-1.70 (m, 2H). LCMS(ESI) m/z: 513 (M+1).

Embodiment 69

2-(2-amino-pyridin-4-yl)-5-(5-(4-(5-methyl-1,2,4-oxadiazol-3-yl)-phenoxy)-pentyl-1,2,5-thiadiazolidine-1,1-dioxide

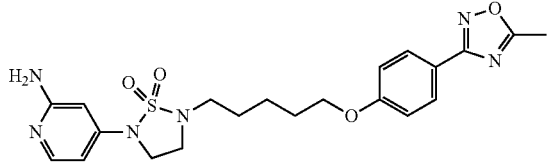 [SMILES: Cc1nc(-c2ccc(OCCCCCN3CCN(c4ccnc(N)c4)S3(=O)=O)cc2)no1]

Please refer to the preparation method of Embodiment 68 for this embodiment. $^1H$ NMR (400 MHz, $CDCl_3$) 7.96 (d, J=8.78 Hz, 1H), 7.79 (d, J=7.28 Hz, 1H), 7.06 (d, J=8.78 Hz, 2H), 6.80 (dd, J=2.51, 7.28 Hz, 1H), 6.47 (d, J=2.26 Hz, 1H), 4.10 (t, J=6.15 Hz, 2H), 3.97 (t, J=6.40 Hz, 2H), 3.60-3.71 (m, 2H), 3.22 (t, J=7.03 Hz, 2H), 2.65 (s, 3H), 1.85-1.94 (m, 2H), 1.76-1.84 (m, 2H), 1.60-1.70 (m, 2H). LCMS(ESI) m/z: 459 (M+1).

Procedure R

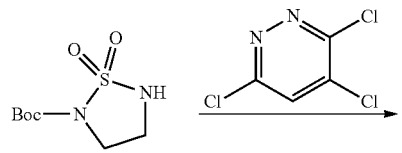

-continued

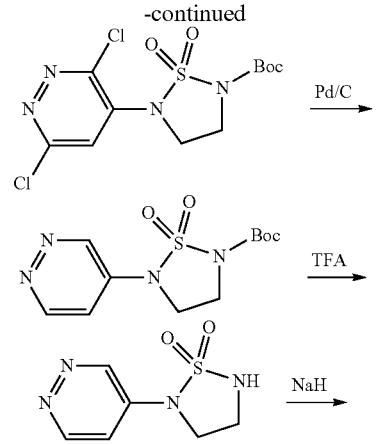

Embodiment 70

(E)-2-(5-((1-ethoxy-imino)-2,3-dihydro-1H-inden-5-yl)-oxy)-pentyl)-5-(pyridazin-4-yl)-1,2,5-thiadiazolidine-1,1-dioxide

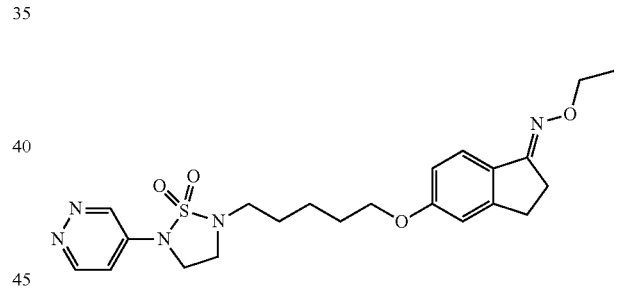

Embodiment 70A 5-(3,6-dichloro-pyridazin-4-yl)-1,2,5-thiadiazolidine-2-tert-butyl carboxylate-1,1-dioxide

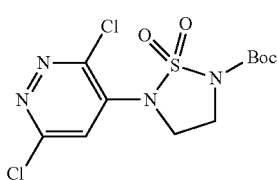 [SMILES: CC(C)(C)OC(=O)N1CCN(c2cc(Cl)nnc2Cl)S1(=O)=O]

Please refer to the preparation method of Embodiment 32G for this embodiment. $^1H$ NMR (400 MHz, $CDCl_3$) 7.87 (s, 1H), 4.02-4.12 (m, 4H), 1.58 (s, 10H). LCMS(ESI) m/z: 369 (M+1).

Embodiment 70B 5-(pyridazin-4-yl)-1,2,5-thiadiazolidine-2-tert-butyl carboxylate-1,1-dioxide

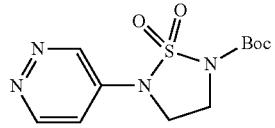 [SMILES: CC(C)(C)OC(=O)N1CCN(c2ccnnc2)S1(=O)=O]

Under the protection of N₂ gas, add sodium acetate (396 mg, 4.8 mmol) and Pd/C (1 g) into the solution of Embodiment 70A (890 mg, 2.4 mmol) in methanol (40 ml). Replace N₂ gas with H₂ gas at 15° C. and allow the mixture to react 5 hours at 15 Psi. After TLC indicates the reaction ends, filter the mixutre and concentrate the filtrate to obtain the title compound that is yellow solid (520 mg, 72%). ¹H NMR (400 MHz, CDCl₃) 9.13 (d, J=3.01 Hz, 1H), 9.08 (d, J=6.02 Hz, 1H), 7.35 (dd, J=3.01, 6.02 Hz, 1H), 4.06-4.12 (m, 2H), 3.93-3.98 (m, 2H), 1.59 (s, 9H). LCMS(ESI) m/z: 301 (M+1).

Embodiment 70C 2-(pyridazin-4-yl)-1,2,5-thiadiazolidine-1,1-dioxide

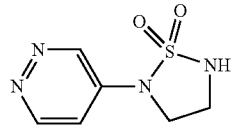

Please refer to the preparation method of Embodiment 32E for this embodiment. ¹H NMR (400 MHz, DMSO-d6) 9.07 (d, J=2.51 Hz, 1H), 9.01 (d, J=6.02 Hz, 1H), 8.26 (br.s., 1H), 7.26 (dd, J=3.01, 6.02 Hz, 1H), 3.96-4.00 (m, 2H), 3.62 (br.s., 2H).

Embodiment 70D (E)-2-(5-((1-ethoxy-imino)-2,3-dihydro-1H-inden-5-yl)-oxy)-pentyl)-5-(pyridazin-4-yl)-1,2,5-thiadiazolidine-1,1-dioxide

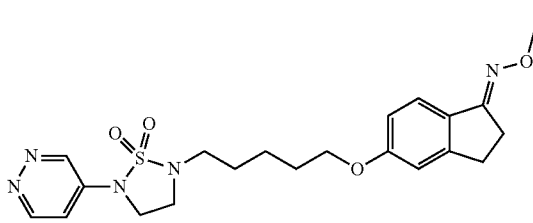

Please refer to the preparation method of Embodiment 32D for this embodiment. ¹H NMR (400 MHz, CDCl₃) 8.01 (br.s., 1H), 7.59 (dt, J=3.26, 6.02 Hz, 2H), 6.76-6.85 (m, 2H), 6.56 (d, J=9.03 Hz, 1H), 4.20 (q, J=7.19 Hz, 2H), 3.99 (t, J=6.27 Hz, 2H), 3.74 (t, J=6.27 Hz, 2H), 3.46 (t, J=6.40 Hz, 2H), 3.15 (t, J=7.28 Hz, 2H), 2.95-3.01 (m, 2H), 2.86-2.92 (m, 2H), 1.72-1.89 (m, 4H), 1.56-1.60 (m, 2H), 1.28-1.38 (m, 3H). LCMS(ESI) m/z: 474 (M+1).

Procedure S

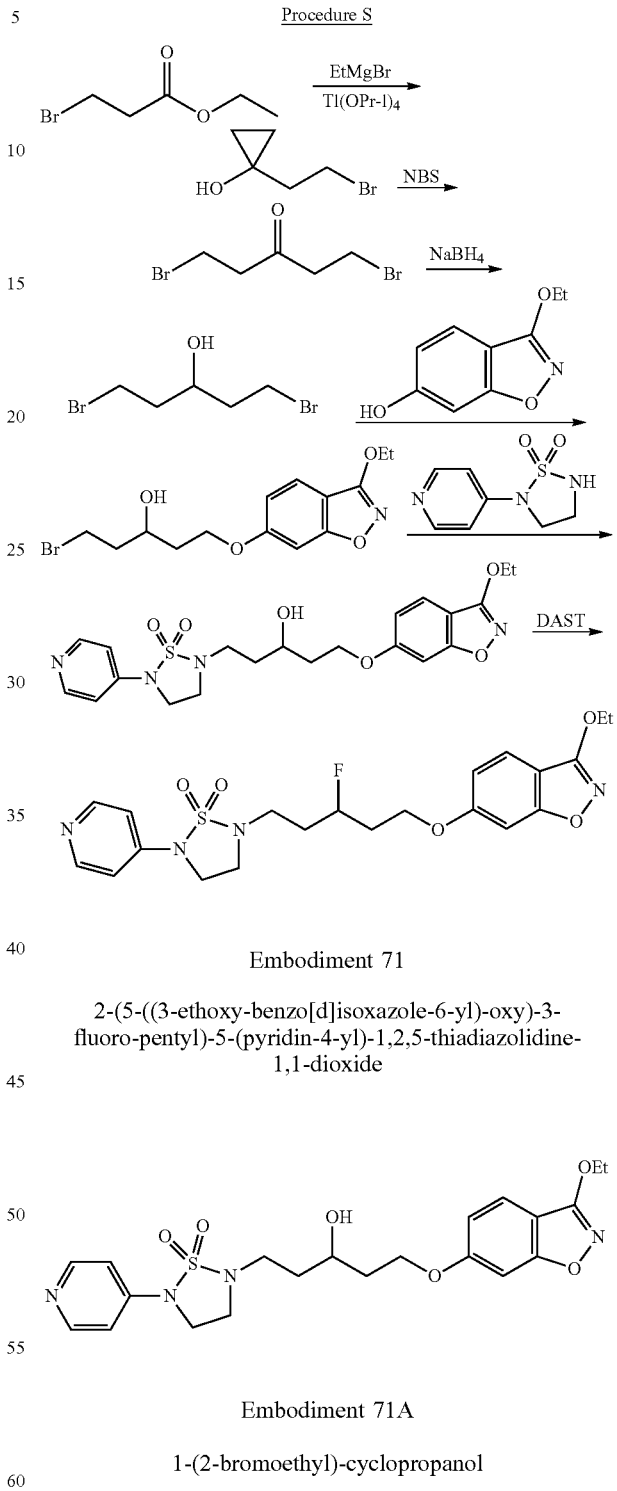

Embodiment 71

2-(5-((3-ethoxy-benzo[d]isoxazole-6-yl)-oxy)-3-fluoro-pentyl)-5-(pyridin-4-yl)-1,2,5-thiadiazolidine-1,1-dioxide

Embodiment 71A 1-(2-bromoethyl)-cyclopropanol

At 0° C., add titanium tetraisopropoxide (7.9 g, 28 mmol) into the mixture of ethyl 3-bromopropionate (10 g, 55 mmol) in THF (250 ml). Then slowly addethyl Grignard reagent (14.7 g, 110 mmol) at 0° C. into the reaction system. Agitate it 1 hour and then heat to 25° C. before agitate 2 hours. At 0° C., add saturated ammonium chloride aqueous solution into the system. Then extract with ethyl acetate. Then dry the combined organic phases with anhydrous $Na_2SO_4$. Then filter and evaporate before purify the residue with column chromatography (petroleum ether:ethyl acetate+10:1~petroleum ether:ethyl acetate=5:1) to obtain the title compound (colorless liquid, 4.9 g, yield of 54%). $^1$H NMR (400 MHz, $CDCl_3$) 3.61 (t, J=7.3 Hz, 2H), 2.26 (br. s., 1H), 2.11 (t, J=7.3 Hz, 2H), 0.78-0.82 (m, 2H), 0.50-0.56 (m, 2H).

Embodiment 71B 1,5-dibromopentane-3-one

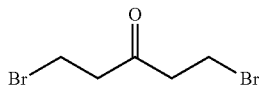

At 0° C., add N-bromosuccinimide (539 mg, 3.0 mmol) into the solution of Embodiment 71A (500 mg, 3.0 mmol) in $CCl_4$ (8 ml). Then allow the mixture to react 16 hours at 25° C. Filter and evaporate before purify the residue with column chromatography (petroleum ether:ethyl acetate=20:1 petroleum ether:ethyl acetate=10:1) to obtain the title compound (yellow liquid, 500 mg, yield of 68%). $^1$H NMR (400 MHz, $CDCl_3$) 3.56 (t, J=6.8 Hz, 2H), 3.04 (t, J=6.8 Hz, 2H).

Embodiment 71C 1,5-dibromopentane-3-ol

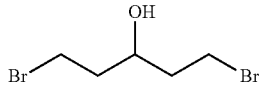

At 0° C., add $NaHB_4$ (155 mg, 4.1 mmol) into the solution of Embodiment 71B (500 mg, 2.1 mmol) in methanol (5 ml). Then allow the mixture to react for 3 hours at 25° C. Add water (5 ml) into the reaction system. Extract the aqueous layer with dichloromethane (10 ml×3) and then dry the combined organic layer with $Na_2SO_4$ before filter and evaporate to obtain the title compound (340 mg, yield of 67%). $^1$H NMR (400 MHz, $CDCl_3$) 4.07 (d, J=4.6 Hz, 1H), 3.51-3.57 (m, 4H), 1.96-2.04 (m, 4H).

Embodiment 71D 1-bromo-5-((3-ethoxy-benzo[d]isoxazole-6-yl)-oxy)-pentyl-3-ol

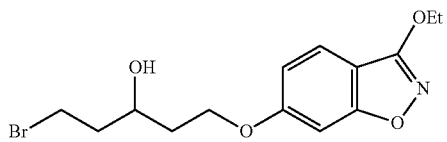 [SMILES: CCOc1noc2cc(OCCC(O)CCBr)ccc12]

Allow the mixture of Embodiment 71C (329 mg, 1.34 mmol), Embodiment 12D (150 mg, 837 µmol) and KI (14 mg, 84 µmol) in acetone (5 ml) to react 16 hours at 60° C. Add water (5 ml) and dichloromethane (10 ml) into the reaction system. Extract the aqueous layer with dichloromethane (10 ml×3) and then dry the combined organic layers with $Na_2SO_4$ before filter and evaporate. Then purify the residue with column chromatography (petroleum ether:ethyl acetate=2:1) to obtain the title compound (colorless soild, 190 mg, yield of 66%). $^1$H NMR (400 MHz, $CDCl_3$) 7.45-7.50 (m, 1H), 6.83-6.88 (m, 2H), 4.43-4.48 (m, 2H), 4.11-4.32 (m, 3H), 3.55-3.65 (m, 2H), 1.94-2.09 (m, 4H), 1.50 (t, J=7.2 Hz, 3H).

Embodiment 71E 2-(5-((3-ethoxy-benzo[d]isoxazole-6-yl)-oxy)-3-hydroxy-pentyl)-5-(pyridin-4-yl)-1,2,5-thiadiazolidine-1,1-dioxide

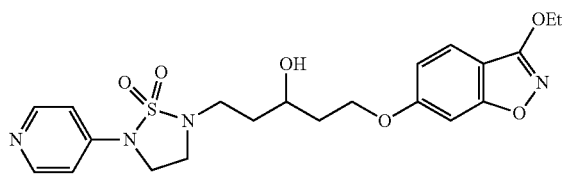 [SMILES: CCOc1noc2cc(OCCC(O)CCN3CCN(c4ccncc4)S3(=O)=O)ccc12]

Allow the mixture of Embodiment 71D (20 mg, 58 µmol), Embodiment 4F (12 mg, 58 µmol) and KI (1 mg, 5.8 µmol) in N,N-dimethylformamide (3 ml) to react for 3 hours at 60° C. Add water (5 ml) and dichloromethane (10 ml) into the reaction system. Extract the aqueous layer with dichloromethane (10 ml×3) and then dry the combined organic layers with $Na_2SO_4$ before filter and evaporate. Then separate and purify the residue with the preparative column chromatography to obtain the title compound (colorless soild, 8 mg, yield of 30%). $^1$H NMR (400 MHz, $CDCl_3$) 8.64 (d, J=6.5 Hz, 2H), 7.48 (d, J=8.5 Hz, 1H), 7.31 (d, J=6.5 Hz, 2H), 6.86 (d, J=4.5 Hz, 2H), 4.45-4.50 (m, 2H), 4.11-4.27 (m, 2H), 3.95-4.01 (m, 2H), 3.71-3.75 (m, 4H), 3.44 (dt, J=15.6, 7.8 Hz, 2H), 2.03 (br.s., 4H), 1.49-1.53 (m, 3H). LCMS(ESI) m/z: 463 (M+1).

Embodiment 72

2-(5-((3-ethoxy-benzo[d]isoxazole-6-yl)-oxy)-3-fluoro-pentyl)-5-(pyridin-4-yl)-1,2,5-thiadiazolidine-1,1-dioxide

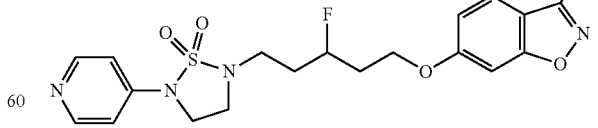

Under the protection of $N_2$ gas at −78° C., drop DAST (37 mg, 227 mmol) into the solution of Embodiment 71E (35 mg, 76 µmol) in dichloromethane (2 ml). Agitate the mixture solution 1 hour at 20° C. Then add water (5 ml) into the reaction system. Extract the aqueous layer with dichloromethane (10 ml×3) and then dry the combined organic layers with Na$_2$SO$_4$ before filter and evaporate. Then separate and purify the residue with the preparative column chromatography to obtain the title compound (colorless soild, 35 mg, yield of 95%). $^1$H NMR (400 MHz, CDCl$_3$) 8.53 (d, J=6.3 Hz, 2H), 7.47 (d, J=9.3 Hz, 1H), 7.07 (d, J=6.3 Hz, 2H), 6.84-6.87 (m, 2H), 4.83-5.12 (m, 1H), 4.42-4.49 (m, 2H), 4.06-4.19 (m, 2H), 3.83-3.89 (m, 2H), 3.57-3.62 (m, 2H), 3.31-3.42 (m, 2H), 1.98-2.29 (m, 4H), 1.48-1.50 (m, 3H). LCMS(ESI) m/z: 465 (M+1).
Procedure T
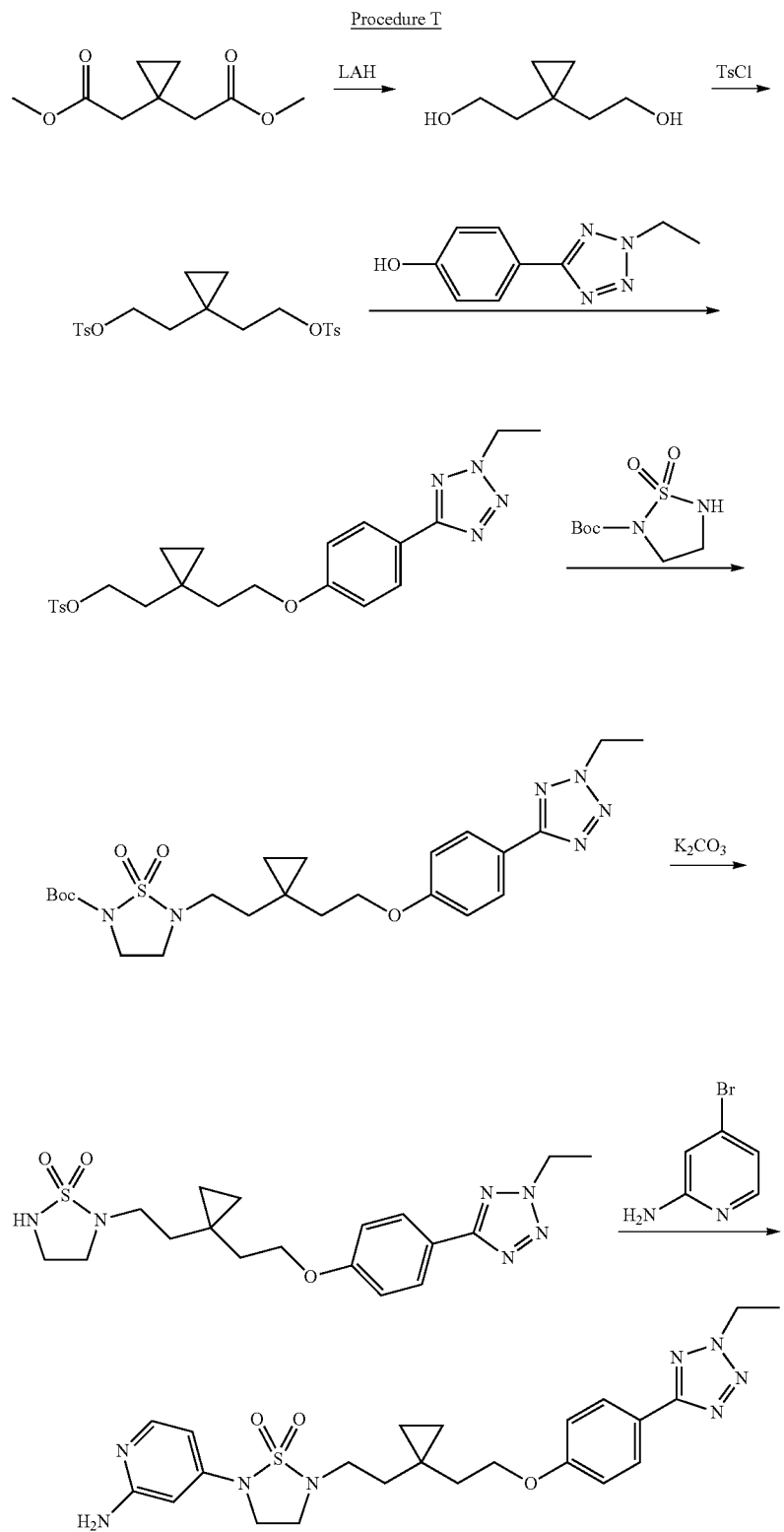

Embodiment 73

2-(2-amino-pyridin-4-yl)-5-(2-(1-(2-(4-(2-ethyl-2H-tetrazol-5-yl)-phenoxy)-ethyl)-cyclic propyl)-ethyl)-1,2,5-thiadiazolidine-1,1-dioxide

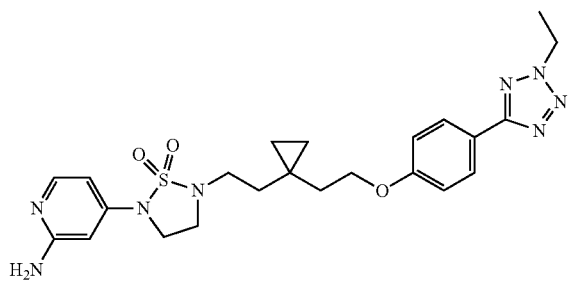 [SMILES: CCn1nnc(-c2ccc(OCCC3(CCN4CCN(c5ccnc(N)c5)S4(=O)=O)CC3)cc2)n1]

Embodiment 73A

Dimethyl 2,2'-(cyclopropane-1,1-diyl)-diacetate

Please refer to the reference (Journal of Medicinal Chemistry, 57 (2), 364-377: 2014) for the preparation method of Embodiment 8A.

Embodiment 73B 2,2'-(cyclopropane-1,1-diyl)-diethanol

At 0° C., drop Embodiment 72A (249 mg, 1.34 mmol) into the solution of LiAlH$_4$ (102 mg, 2.68 mmol) in THF (3 ml). After it is added, agitate the mixture solution 3 hours at 25° C. Add water (0.5 ml) and 10% NaOH solution (0.5 ml) into the reaction system. Dry the system with Na$_2$SO$_4$ before filter and evaporate to obtain the title compound (122 mg, yield of 72%).

Embodiment 73C 2,2'-(cyclopropane-1,1-diyl)-di-ethyl-4-methyl-benzenesulfonate

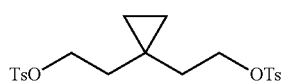 [SMILES: Cc1ccc(S(=O)(=O)OCCC2(CCOS(=O)(=O)c3ccc(C)cc3)CC2)cc1]

Agitate the mixture solution of Embodiment 73B (1 g, 7.9 mmol), p-toluensulfonyl chloride (5.9 g, 30.7 mmol), triethylamine (3.1 g, 30.7 mmol) in dichloromethane (80 ml) for 16 hours at 25° C. Then agitate it 12 hours at room temperature. Add water (40 ml) into the reaction system. Extract the aqueous layer with dichloromethane (40 ml×3) and then dry the combined organic layers with Na$_2$SO$_4$ before filter and evaporate. Then purify the residue with column chromatography (petroleum ether:ethyl acetate=10:1~petroleum ether:ethyl acetate=5:1) to obtain the title compound (yellow liquid, 730 mg, yield of 20%). $^1$H NMR (400 MHz, CDCl$_3$) 67.78 (s, 4H), 7.34 (br.s., 4H), 4.03-4.07 (m, 4H), 2.45 (s, 6H), 1.48-1.52 (m, 3H), 0.25-0.34 (m, 4H).

Embodiment 73D 2-(1-(2-(4-(2-ethyl-2H-tetrazol-5-yl)-phenoxy)-ethyl)-cyclopropyl)-ethyl-4-methylbenzenesulfonate

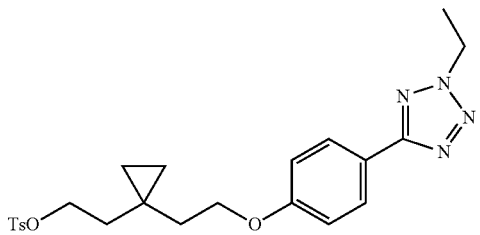 [SMILES: CCn1nnc(-c2ccc(OCCC3(CCOS(=O)(=O)c4ccc(C)cc4)CC3)cc2)n1]

This embodiment is prepared with the method as described in Embodiment 29A. $^1$H NMR (400 MHz, CDCl$_3$) 8.04-8.07 (m, 4H), 7.72-7.77 (m, 4H), 7.36 (br.s., 4H), 6.91-7.00 (m, 4H), 2.42 (s, 3H), 1.49-1.55 (m, 3H), 0.37 (d, J=9.5 Hz, 2H), 0.28 (s, 2H). LCMS(ESI) m/z: 457 (M+1).

Embodiment 73E 5 (2-(1-(2-(4-(2-ethyl-2H-tetrazol-5-yl)-phenoxy)-ethyl)-cyclopropylamino)-ethyl)-1,2-thiadiazolidine-2-tert-butyl formate-1,1-dioxide

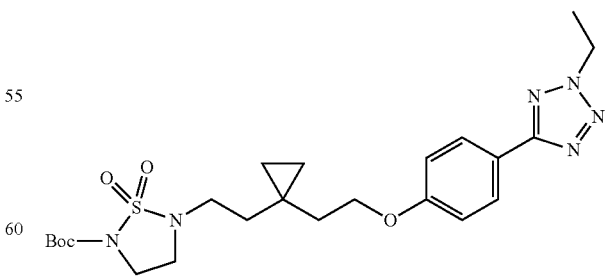

Please refer to the preparation method of Embodiment 32D for this embodiment. LCMS(ESI) m/z: 507 (M+1).

Embodiment 73F 2-(2-(1-(2-(4-(2-ethyl-2H-tetrazol-5-yl)-phenoxy)-ethyl) cyclopropyl)-ethyl)-1,2,5-thiadiazolidine-1,1-dioxide

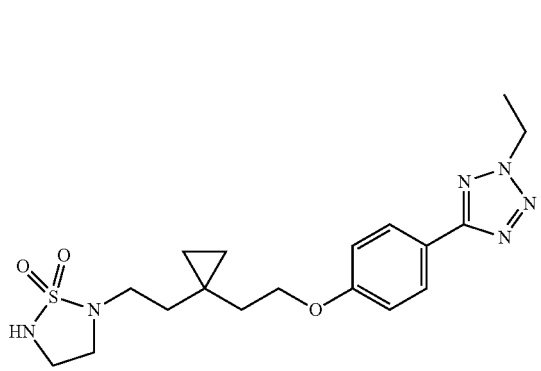 [SMILES: CCn1nnc(-c2ccc(OCCC3(CCN4CCNS4(=O)=O)CC3)cc2)n1]

Agitate the solution of Embodiment 73E (60 mg, 0.18 mmol), K$_2$CO$_3$ (82 mg, 0.6 mmol) in methanol (2 ml) to react for 4 hours at 60° C. Dry it through rotation. Then add water (5 ml) and dichloromethane (10 ml) into the reaction system. Extract the aqueous layer with dichloromethane (10 ml×3) and then dry the combined organic layers with Na$_2$SO$_4$ before filter and evaporate to obtain the title compound (colorless solid, 40 mg, yield of 75%). LCMS(ESI) m/z: 407 (M+1).

Embodiment 73G 2-(2-amino-pyridin-4-yl)-5-(2-(1-(2-(4-(2-ethyl-2H-tetrazol-5-yl)-phenoxy)-ethyl)-cyclic propyl)-ethyl)-1,2,5-thiadiazolidine-1,1-dioxide

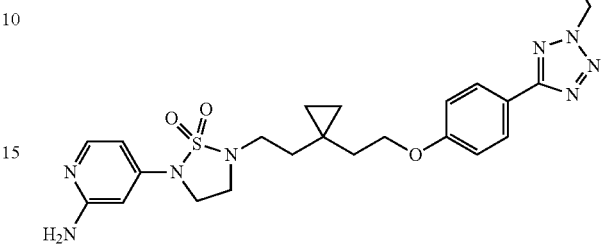

Under the protection of N$_2$ gas, add 8-hydroxyquinoline (14 mg, 98 μmol) and CuI (2 mg, 9.8 μmol) into the solution of Embodiment 73F (40 mg, 988 μmol), K$_2$CO$_3$ (27 mg, 0.2 mmol) and 2-amino-4-bromopyridine (26 mg, 148 μmol) in N,N-dimethylformamide (2 ml). Allow the mixture solution to react 12 hours at 120° C. Dry it through rotation. Then add water (5 ml) into the reaction system. Extract the aqueous layer with dichloromethane (10 ml×3) and then dry the combined organic layers with Na$_2$SO$_4$ before filter and evaporate. Then separate and purify the residue with the preparative chromatography (dichloromethane:methanol=20:1, dichloromethane:ethyl acetate=1:2) to obtain the title compound (colorless solid, 20 mg, yield of 39%). $^1$H NMR (400 MHz, CDCl$_3$) 8.05-8.08 (m, 2H), 7.91 (d, J=6.0 Hz, 1H), 6.99-7.02 (m, 2H), 6.45-6.47 (m, 1H), 6.28 (br.s., 1H), 5.00 (br.s., 2H), 4.66-4.69 (m, 2H), 4.11-4.17 (m, 2H), 3.76-3.80 (m, 2H), 3.50 (t, J=6.5 Hz, 2H), 3.26-3.34 (m, 2H), 1.80 (t, J=6.3 Hz, 2H), 1.71-1.76 (m, 2H), 1.68 (s, 3H), 0.25-0.62 (m, 4H). LCMS(ESI) m/z: 499 (M+1).

Procedure U

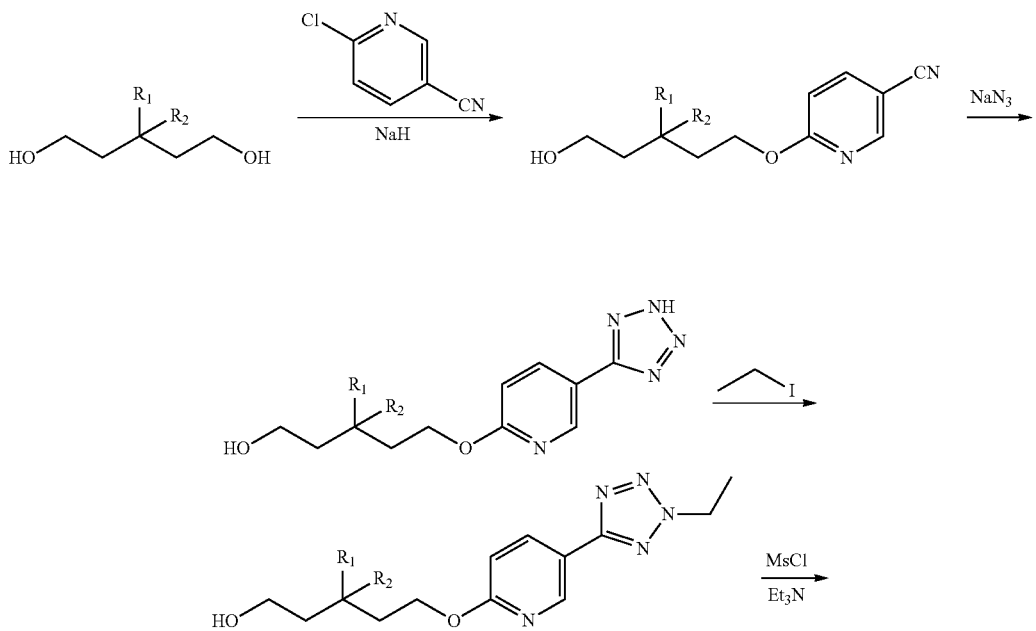

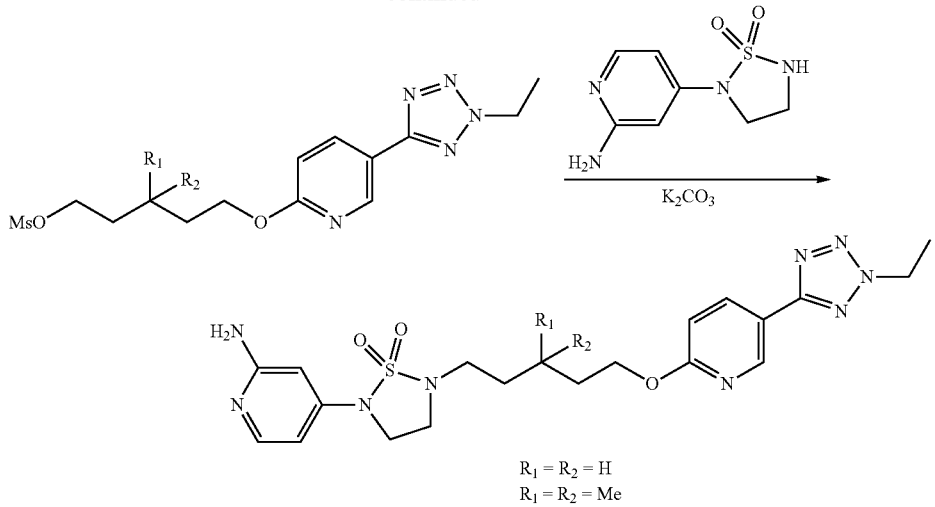

Embodiment 74

4-(5-(5-((5-(2-ethyl-tetrazol-5-yl)-2-pyridinyl)-oxy)-pentyl)-1,1-dioxo-1,2,5-thiadiazolidine-2-yl)-pyridin-2-amine

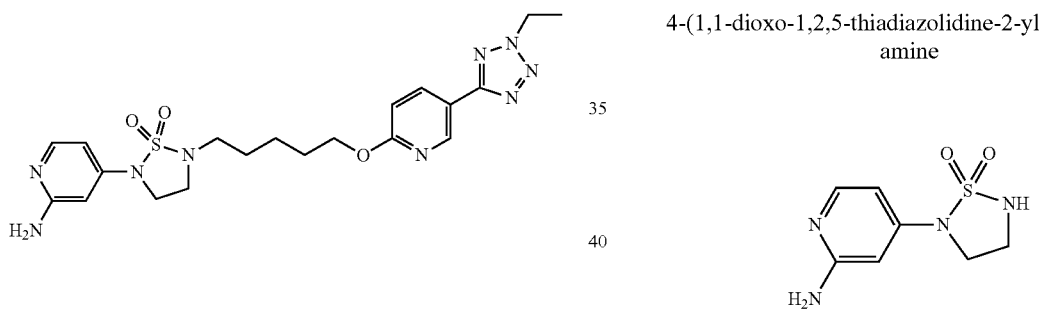

Embodiment 74A 5-(2-amino-4-pyridyl)-1,1-dioxo-1,2,5-thiadiazolidine-2-tert-butyl formate

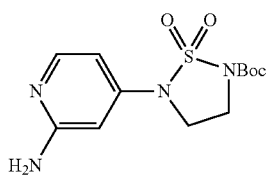

Dissolve 4-bromo-2-aminopyridine (10 g, 57.8 mmol), Embodiment 32B (25.7 g, 115.6 mmol), (1S,2S)—N₁,N₂-dimethyl-cyclohexanediamine (1.64 g, 11.6 mmol), K₂CO₃ (24 g, 173 mmol) and CuI (16.5 g, 86.7 mmol) in N,N-dimethylformamide (150 ml). Agitate the mixture 12 hours at 100° C. under the protection of N₂ gas. Pour the reaction solution into the mixture solution stirred continuously of ice water (300 ml), ammonia (100 ml) and ethyl acetate (200 ml). Extract it with ethyl acetate and dry the combined organic phases with anhydrous Na₂SO₄. Then filter and evaporate before recrystallize the residue with methanol. Then filter it to obtain the title compound (7.5 g, yield of 70%). $^1$H NMR (400 MHz, DMSO-d6) 7.87 (d, J=5.0 Hz, 1H), 6.40 (d, J=4.0 Hz, 1H), 6.30 (s, 1H), 6.09 (br.s., 2H), 3.99-3.89 (m, 2H), 3.87-3.75 (m, 2H), 1.50 (s, 9H).

Embodiment 74B 4-(1,1-dioxo-1,2,5-thiadiazolidine-2-yl)-pyridin-2-amine

At 0° C., add the solution of hydrogen chloride in ethyl acetate (4 mol/L) (50 ml) into the solution of Embodiment 74A (5.0 g, 15.9 mmol) in ethyl acetate (20 ml). Allow the mixture to react for 2 hours at 25° C. Then dry through rotation to obtain the title compound of hydrochloride (3.95 g, yield of 97%). $^1$H NMR (400 MHz, DMSO-d6) 8.44 (t, J=7.8 Hz, 1H), 7.91 (d, J=7.3 Hz, 1H), 7.82 (br.s., 2H), 6.63 (dd, J=2.3, 7.3 Hz, 1H), 6.41 (d, J=2.3 Hz, 1H), 3.94 (t, J=6.3 Hz, 2H), 3.59 (q, J=6.5 Hz, 2H).

Embodiment 74C 6-(5-hydroxwentyl-oxy)-pyridine-3-carbonitrile

Under the protection of N₂ gas at 0° C., add sodium hydride (8.7 g, 216.5 mmol, 60%) in batch into the solution of Embodiment 1,5-pentanediol (11.3 g, 108.3 mmol) in N,N-dimethylformamide (50 ml). Agitate the reaction solution 0.5 hour at 0° C. Then add the solution of 2-chloro-5-cyano-pyridine (5 g, 36.1 mmol) in N,N-dimethylformamide (20 ml). Then agitate it 2 hours at 0° C. Add water to quench the reaction. Then extract it with ethyl acetate (100 ml×3) and dry the combined organic layer with Na$_2$SO$_4$ before filter and evaporate. Then purify the residue with column chromatography to obtain the title compound (4.7 g, yield of 63%). $^1$H NMR (400 MHz, CDCl$_3$) 68.49 (d, J=2.0 Hz, 1H), 7.78 (dd, J=2.3, 8.5 Hz, 1H), 6.81 (d, J=8.5 Hz, 1H), 4.46-4.33 (m, 2H), 3.79-3.61 (m, 2H), 1.84 (quin, J=7.2 Hz, 2H), 1.71-1.45 (m, 4H). LCMS(ESI) m/z: 207 (M+1).

Embodiment 74D 5-((5 (2H-tetrazol-5-yl)-2-pyridinyl)-oxy)-pentan-1-ol

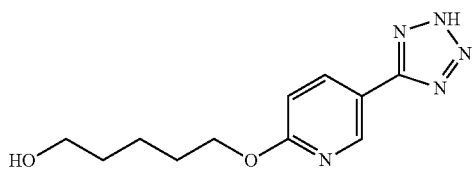 [SMILES: OCCCCCOc1ccc(-c2nn[nH]n2)cn1]

Add sodium azide (1.89 g, 29.09 mmol) and NH$_4$Cl (1.56 g, 29.09 mmol) into the solution of Embodiment 74C (2.00 g, 9.70 mmol) in N,N-dimethylformamide (20.00 ml). Agitate the mixture solution 12 hours at 110° C. Then add water to quench the reaction and adjust its pH value to 3 with dilute hydrochloric acid. Then dry the organic phase with anhydrous Na$_2$SO$_4$ before filter and evaporate to obtain the title compound (white solid, 2.3 g, yield of 90%). $^1$H NMR (400 MHz, CDCl$_3$) 8.81 (d, J=2.3 Hz, 1H), 8.27 (dd, J=2.4, 8.7 Hz, 1H), 6.99 (d, J=8.8 Hz, 1H), 4.52-4.29 (m, 2H), 3.68-3.50 (m, 2H), 1.86 (quin, J=7.0 Hz, 2H), 1.75-1.47 (m, 4H). LCMS(ESI) m/z: 250 (M+1).

Embodiment 74E 5-((5-(2-ethyl-tetrazol-5-yl)-2-pyridinyl)-oxy)-pentan-1-ol

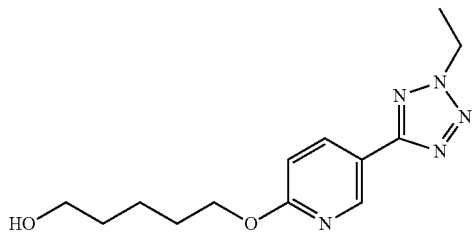 [SMILES: CCn1nnc(-c2ccc(OCCCCCO)nc2)n1]

Under the protection of N$_2$ gas, add iodoethane (93 mg, 2.32 mmol) into the solution of Embodiment 74D (1 g, 4.01 mmol) and K$_2$CO$_3$ (2.77 g, 20.05 mmol) in acetonitrile (15 ml). Agitate 4 hours at 25° C. Quench the reaction mixture with water (50 ml). Then extract with ethyl acetate (30 ml×3). Then wash the combined organic phases with saturated salt water. Then dry with anhydrous Na$_2$SO$_4$ before filter and dry through rotation. Then purify the residue with column chromatography (petroleum ether:ethyl acetate=3:1) to obtain the title compound (white solid, 700 mg, yield of 60%). $^1$H NMR (400 MHz, CDCl$_3$) 8.93 (d, J=2.0 Hz, 1H), 8.29 (dd, J=2.3, 8.8 Hz, 1H), 6.85 (d, J=8.5 Hz, 1H), 4.72 (q, J=7.3 Hz, 2H), 4.39 (t, J=6.7 Hz, 2H), 3.81-3.62 (m, 2H), 1.86 (quin, J=7.1 Hz, 2H), 1.75-1.50 (m, 7H). LCMS(ESI) m/z: 278 (M+1).

Embodiment 74F 5-((5-(2-ethyl-tetrazol-5-yl)-2-pyridinyl)-oxy)-pentyl methanesulfonate

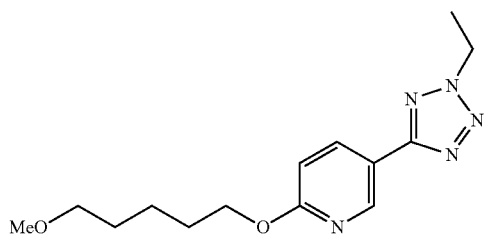 [SMILES: CCn1nnc(-c2ccc(OCCCCCOC)nc2)n1]

Under the protection of N$_2$ gas at 0° C., drop the solution of methanesulfonyl chloride (83 mg, 0.72 mmol) in THF (1 ml) into the solution of Embodiment 74E (0.1 g, 0.36 mmol) and triethylamine (146 mg, 1.44 mmol) in THF (8 ml). Agitate 2 hours at 0° C. Quench the reaction mixture with water (20 ml). Then extract with ethyl acetate (20 ml×3). Then wash the combined organic phases with saturated salt water. Then dry with anhydrous Na$_2$SO$_4$ before filter and dry through rotation to obtain the title compound (white solid, 120 mg, yield of 92.7%). $^1$H NMR (400 MHz, CDCl$_3$) 68.93 (d, J=2.3 Hz, 1H), 8.30 (dd, J=2.4, 8.7 Hz, 1H), 6.85 (d, J=8.8 Hz, 1H), 4.72 (q, J=7.3 Hz, 2H), 4.40 (t, J=6.5 Hz, 2H), 4.33-4.23 (m, 2H), 3.03 (s, 3H), 1.98-1.67 (m, 9H). LCMS(ESI) m/z: 356 (M+1).

Embodiment 74G 4-(5-(5-((5-(2-ethyl-tetrazol-5-yl)-2-pyridinyl)-oxy)-pentyl)-1,1-dioxo-1,2,5-thiadiazolidine-2-yl)-pyridin-2-amine

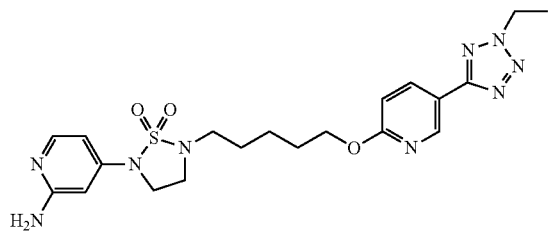 [SMILES: CCn1nnc(-c2ccc(OCCCCCN3CCN(c4ccnc(N)c4)S3(=O)=O)nc2)n1]

Under the protection of N$_2$ gas, add Embodiment 73F (422 mg, 1.97 mmol) into the solution of Embodiment 74B (0.7 g, 1.97 mmol) and K$_2$CO$_3$ (0.54 g, 3.94 mmol) in N,N-dimethylformamide (12 ml). Agitate for 12 hours at 60° C. Quench the reaction mixture with water (50 ml). Then extract with ethyl acetate (30 ml×3). Then wash the combined organic phases with saturated salt water. Then dry with anhydrous Na$_2$SO$_4$ before filter and dry through rotation.

Then purify the residue with column chromatography (petroleum ether:ethyl acetate=1:1) to obtain the title compound (white solid, 350 mg, yield of 36%). $^1$H NMR (400 MHz, CDCl$_3$) 8.86 (d, J=2.0 Hz, 1H), 8.32 (dd, J=2.3, 8.8 Hz, 1H), 7.80 (d, J=6.3 Hz, 1H), 6.95 (d, J=8.8 Hz, 1H), 6.52 (dd, J=2.0, 6.0 Hz, 1H), 6.31 (d, J=1.8 Hz, 1H), 4.76 (q, J=7.3 Hz, 2H), 4.41 (t, J=6.4 Hz, 2H), 3.84 (t, J=6.4 Hz, 2H), 3.56 (t, J=6.3 Hz, 2H), 3.22-3.10 (m, 2H), 1.97-1.76 (m, 4H), 1.75-1.58 (m, 5H). LCMS(ESI) m/z: 474 (M+1).

Embodiment 75

2-(2-amino-pyridin-4-yl)-5-(5-(4-(2-ethyl-2H-tetrazol-5-yl)-phenoxy)-3,3-dimethyl-pentyl)-1,2,5-thiadiazolidine-1,1-dioxide

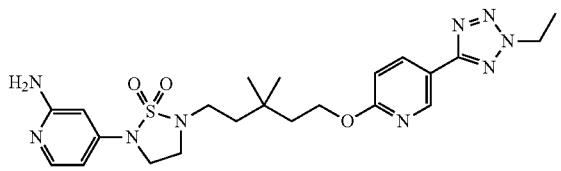 [SMILES: CCn1nnc(-c2ccc(OCCC(C)(C)CCN3CCN(c4ccnc(N)c4)S3(=O)=O)nc2)n1]

Embodiment 75A 3,3-dimethyl pentanediol

At 80° C., drop the solution of 3,3-dimethyl glutarate (50 g, 312 mmol) in THF (200 ml) into the solution of LiAlH$_4$ (50 g, 1.32 mol) in THF (1.3 L). After it is added, agitate the mixture solution 2 hours at 80° C. Add water (200 ml) into the reaction system. Extract the aqueous layer with ethyl acetate (300 ml×3) and then dry the combined organic layers with Na$_2$SO$_4$ before filter and evaporate to obtain the title compound (38 g, yield of 92%). $^1$H NMR (400 MHz, CDCl$_3$) 3.67 (t, J=7.03 Hz, 4H), 3.50 (br.s., 1H), 1.50-1.61 (m, 4H), 0.92 (s, 6H).

Embodiment 75B 6-((5-hydroxy-3,3-dimethyl-pentyl)-oxy)-nicotinonitrile

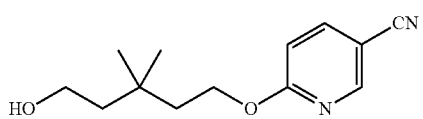 [SMILES: CC(C)(CCO)CCOc1ccc(C#N)cn1]

Please refer to the preparation method of Embodiment 74C for this embodiment. $^1$H NMR (400 MHz, CDCl$_3$) 8.47 (d, J=2.0 Hz, 1H), 7.76 (dd, J=8.5, 2.3 Hz, 1H), 6.78 (d, J=8.8 Hz, 1H), 4.44 (t, J=7.4 Hz, 2H), 3.75 (t, J=7.4 Hz, 2H), 1.75 (t, J=7.4 Hz, 2H), 1.61 (t, J=7.4 Hz, 2H), 1.01 (s, 6H).

Embodiment 75C 5-((5-(2H-tetrazol-5-yl)-pyridin-2-yl)-oxy)-3,3-dimethyl-1-ol

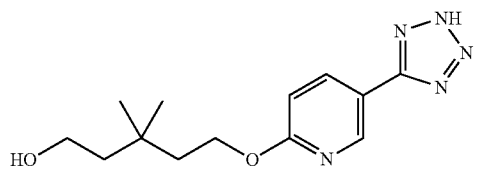 [SMILES: CC(C)(CCO)CCOc1ccc(-c2nn[nH]n2)cn1]

Please refer to the preparation method of Embodiment 74D for this embodiment. $^1$H NMR (400 MHz, CDCl$_3$) 8.81 (d, J=2.3 Hz, 1H), 8.26 (dd, J=8.8, 2.3 Hz, 1H), 7.00 (d, J=8.8 Hz, 1H), 4.39 (t, J=7.4 Hz, 2H), 3.49 (t, J=7.4 Hz, 2H), 1.68 (t, J=7.4 Hz, 2H), 1.45 (t, J=7.4 Hz, 2H), 0.92-0.97 (m, 6H).

Embodiment 75D 5-((4-(2-ethyl-tetrazol-5-yl)-phenoxy)-3,3-dimethyl-pentan-1-ol

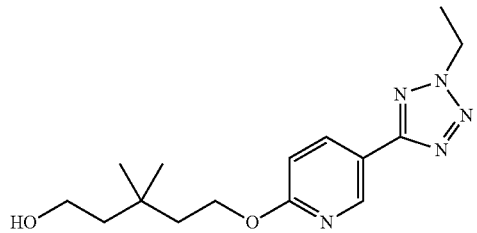 [SMILES: CCn1nnc(-c2ccc(OCCC(C)(C)CCO)nc2)n1]

Please refer to the preparation method of Embodiment 74E for this embodiment. $^1$H NMR (400 MHz, CDCl$_3$) 8.92 (d, J=2.0 Hz, 1H), 8.27 (dd, J=8.5, 2.3 Hz, 1H), 6.82 (d, J=8.8 Hz, 1H), 4.70 (q, J=7.4 Hz, 2H), 4.44 (t, J=7.4 Hz, 2H), 3.77 (t, J=7.4 Hz, 2H), 1.78 (s, 3H), 1.64-1.71 (m, 4H), 1.02 (s, 6H).

Embodiment 75E 5-(4-(2-ethyl-2H-tetrazol-5-yl)-phenoxy)-3,3-dimethyl-pentyl-methanesulfonate

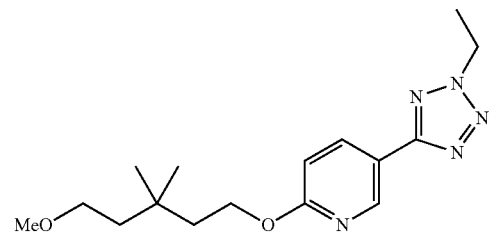 [SMILES: CCn1nnc(-c2ccc(OCCC(C)(C)CCOC)nc2)n1]

Please refer to the preparation method of Embodiment 74F for this embodiment. ¹H NMR (400 MHz, CDCl₃) 8.92 (d, J=2.0 Hz, 1H), 8.27 (dd, J=8.5, 2.0 Hz, 1H), 6.83 (d, J=9.0 Hz, 1H), 4.66-4.73 (m, 2H), 4.44 (t, J=7.0 Hz, 2H), 4.37 (t, J=7.3 Hz, 2H), 3.02 (s, 3H), 1.80 (dt, J=14.2, 7.2 Hz, 4H), 1.69 (t, J=7.5 Hz, 3H), 1.06 (s, 6H).

Embodiment 75F 2-(2-amino-pyridin-4-yl)-5-(5-(4-(2-ethyl-2H-tetrazol-5-yl)-phenoxy)-3,3-dimethyl-pentyl)-1,2,5-thiadiazolidine-1,1-dioxide

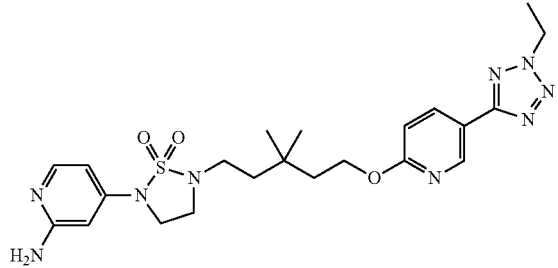 [SMILES: CCn1nnc(-c2ccc(OCCC(C)(C)CCN3CCN(c4ccnc(N)c4)S3(=O)=O)nc2)n1]

Please refer to the preparation method of Embodiment 74G for this embodiment. ¹H NMR (400 MHz, CDCl₃) 8.93 (d, J=2.0 Hz, 1H), 8.28 (dd, J=8.8, 2.3 Hz, 1H), 7.97 (d, J=6.0 Hz, 1H), 6.85 (d, J=8.5 Hz, 1H), 6.43 (dd, J=5.8, 2.3 Hz, 1H), 6.30 (d, J=2.0 Hz, 1H), 4.71 (q, J=7.4 Hz, 2H), 4.58 (br.s., 2H), 4.45 (t, J=7.0 Hz, 2H), 3.81 (t, J=6.5 Hz, 2H), 3.50-3.56 (m, 2H), 3.24 (d, J=8.5 Hz, 2H), 1.81 (t, J=7.0 Hz, 2H), 1.74 (d, J=8.5 Hz, 2H), 1.67-1.71 (m, 3H), 1.08 (s, 6H). LCMS(ESI) m/z: 501 (M+1).

Procedure V

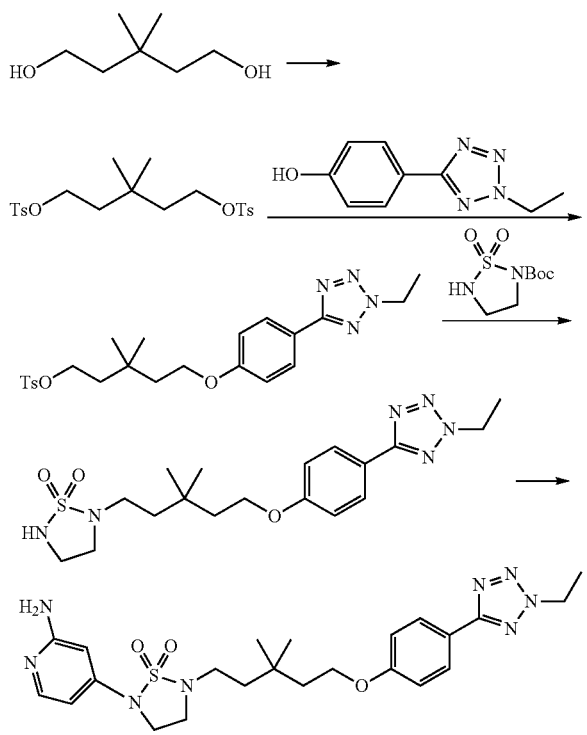

Embodiment 76

4-(5-(5-(4-(2-ethyl-tetrazol-5-yl)-phenoxy)-3,3-dimethyl-pentyl)-1,1-dioxo-1,2,5-thiadiazolidine-2-yl)-pyridin-2-amine

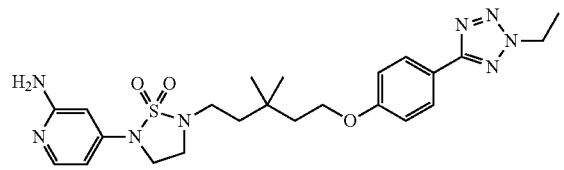 [SMILES: CCn1nnc(-c2ccc(OCCC(C)(C)CCN3CCN(c4ccnc(N)c4)S3(=O)=O)cc2)n1]

Embodiment 76A 3,3-dimethylpentyl-1,5-bis(4-methylbenzenesulfonate)

Please refer to the preparation method of Embodiment 14A for this embodiment. 1H NMR (400 MHz, CDCl₃) 7.77 (d, J=8.53 Hz, 2H), 7.35 (d, J=8.03 Hz, 2H), 4.02 (t, J=7.03 Hz, 2H), 2.45 (s, 3H), 1.55 (t, J=7.03 Hz, 2H), 0.84 (s, 3H).

Embodiment 76B 5-(4-(2-ethyl-2H-tetrazol-5-yl)-phenoxy)-3,3-dimethyl-pentyl-4-methylbenzenesulfonate

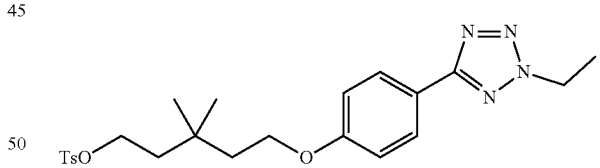

Add K₂CO₃ (8.72 g, 63.29 mmol) and KI (5.24 g, 31.55 mmol) into the solution of Embodiment 76A (6 g, 31.55 mmol) and Embodiment 11A (2.6 g, 31.55 mmol) in acetone solution (100 ml). Agitate the mixture solution 12 hours at 80° C. Then extract it with ethyl acetate. Dry the organic phase with anhydrous Na₂SO₄ before filter and evaporate. Then purify the residue with column chromatography (petroleum ether:ethyl acetate=10:1) to obtain the title compound (white solid, 8.0 g, yield of 56%). ¹H NMR (400 MHz, CDCl₃) 8.09 (d, J=8.5 Hz, 2H), 7.00 (d, J=8.8 Hz, 2H), 4.70 (q, J=7.3 Hz, 2H), 4.38 (t, J=7.4 Hz, 2H), 4.11 (t, J=6.8 Hz, 2H), 3.0-3.04 (m, 3H), 1.80-1.87 (m, 4H), 1.70 (t, J=7.4 Hz, 3H), 1.08 (s, 6H). LCMS(ESI) m/z: 459 (M+1).

Embodiment 76C 5-(4-(2-ethyl-2H-tetrazol-5-yl)-phenoxy)-3,3-dimethyl-pentyl-1,2,5-thiadiazolidine-1,1 dioxide

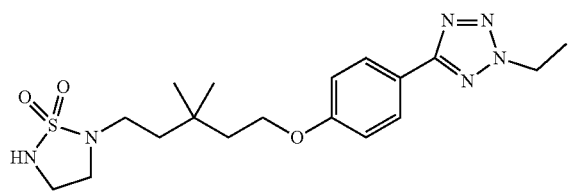 [SMILES: CCn1nnc(-c2ccc(OCCC(C)(C)CCN3CCNS3(=O)=O)cc2)n1]

At 0° C., add sodium hydride (41.9 mg, 1.7 mmol) into the solution of Embodiment 76B (969 mg, 4.4 mmol) in N,N-dimethylformamide (5 ml). Keep it still 30 minutes at 0° C. Then add the solution of Embodiment 32B (400 mg, 0.87 mmol) in N,N-dimethylformamide (1 ml) into the mixture solution above. After agitate it at 20° C. to react for 2 hours, add $K_2CO_3$ (0.24 mg, 1.7 mmol) into the reaction solution. Then add water to quench the reaction and extract the aqueous phase with ethyl acetate. Dry the combined organic phases with anhydrous $Na_1SO_4$. Then filter and evaporate it before separating it with column (petroleum ether:ethyl acetate=1:1) to obtain the title compound (yellow oily form, 100 mg, yield of 28%). $^1$H NMR (400 MHz, $CDCl_3$) 7.56 (d, J=8.5 Hz, 2H), 6.92 (d, J=9.0 Hz, 2H), 4.00 (t, J=6.5 Hz, 2H), 3.66-3.72 (m, 2H), 3.47-3.52 (m, 2H), 3.46 (s, 6H), 3.35-3.41 (m, 2H), 3.04 (t, J=7.3 Hz, 2H), 1.79-1.88 (m, 2H), 1.66-1.74 (m, 2H), 1.52-1.60 (m, 2H), 1.23 (t, J=7.0 Hz, 3H). LCMS(ESI) m/z: 409 (M+1).

Embodiment 76D 4-(5-(5-(4-(2-ethyl-tetrazol-5-yl)-phenoxy)-3,3-dimethyl-pentyl)-1,1-dioxo-1,2,5-thiadiazolidine-2-yl)-pyridin-2-amine

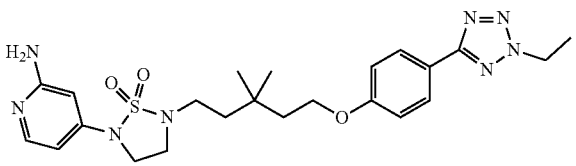 [SMILES: CCn1nnc(-c2ccc(OCCC(C)(C)CCN3CCN(c4ccnc(N)c4)S3(=O)=O)cc2)n1]

At 0° C., add $K_2CO_3$ (67 mg, 0.49 mmol), 2-amino-4-bromo-pyridine (85 mg, 0.489 mmol), 8-hydroxyquinoline (35 mg, 0.25 mmol) and CuI (23 mg, 0.12 mmol) into the solution of Embodiment 76C (100 mg, 0.24 mmol) in N,N-dimethylformamide (2 ml). After replace with $N_2$ gas, add cyclohexanediamine (14 mg, 0.12 mmol). Agitate it to react for 15 hours at 110° C. Then add water to quench the reaction and extract the aqueous phase with ethyl acetate. Dry the combined organic phases with anhydrous $Na_2SO_4$ before filter and evaporate to obtain the title compound (white solid, 35 mg, yield of 29%). $^1$H NMR (400 MHz, $CDCl_3$) 8.07 (d, J=8.5 Hz, 1H), 7.98 (d, J=5.5 Hz, 1H), 6.99 (d, J=8.5 Hz, 2H), 6.42 (d, J=4.5 Hz, 1H), 6.29 (s, 1H), 4.69 (q, J=7.5 Hz, 2H), 4.48 (br.s., 2H), 4.11 (t, J=6.5 Hz, 2H), 3.79 (t, J=6.0 Hz, 2H), 3.46-3.53 (m, 2H), 3.16-3.25 (m, 2H), 1.83 (t, J=6.5 Hz, 2H), 1.68-1.76 (m, 5H), 1.07 (s, 6H). LCMS(ESI) m/z: 501 (M+1).

Experimenal Example 1

Test of EV71 In-Vitro Cytopathic Effect (CPE)

Purpose of Experiment:
To test the in-vitro antiviral activity and cytotoxicity of a compound to HFMD virus EV71 by means of cytopathic effect (CPE) test.

Test Materials:
1. Virus strain: Shenzhen/120F1/09
2. Cell line: RD cells of human rhabdomyoma
3. Cell culture media: DMEM medium added with 10% serum, Penicillin/Streptomycin and L-Glutamine (1×)
4. Test reagent: cellular activity test reagent CCK8

Test Method:
1. Cell inoculation: digest off the RD cells from the attached state, then dilute them with culture medium to a density of 80000/ml and inoculate 100 µl into the micro wells the 96-well plate.
2. Dilution of compound:
    Step 1: prepare the dry powder of a compound to test into a 10 mM solution in DMSO. Then dilute the compound by three times to eight concentration points. Dilute the reference compounds with the same method.
    Step 2: further dilute the diluted solution of the compound in DMSO with cell culture medium. Add 10 µl DMSO solution for each well into 240 µl culture medium.
3. Add the diluted compound solution by 50 µl each well into the 96-well plate inoculated with cells (double holes, final concentration of DMSO is 1%).
4. Dilution of virus: dilute EV71 virus solution by 10000 times to a concentration of 100 $TCID_{50}$/50 µl/. Add the diluted virus solution by 50 µl each well into the 96-well plate. Prepare another 96-well plate to replace the virus with culture medium and similarly inoculate the cells. Add the compound to test the toxicity of compound on cells.
5. Cultivate the 96-well plate 3 days at the conditions of 37° C. and 5% $CO_2$.
6. EC50 and CC50 tests: add the cellular activity test reagent CCK8 into the micro-wells by 20 µl/well. Use ELIASA to read the absorbancy at the wavelength of 450 nm and 630 nm.
7. Analysis of data: analyze the data with Prism5.0 and calculate the antiviral activity of EC50 and the cellular toxicity of C50 of the compound.

The result is as shown in Table 1:

TABLE 1

| Result of $EC_{50}$ by EC71_CPE test | |
|---|---|
| Test sample (Title compound) | EV71 |
| Embodiment 1 | D |
| Embodiment 2 | A |
| Embodiment 6 | B |
| Embodiment 7 | A |
| Embodiment 8 | B |
| Embodiment 10 | B |
| Embodiment 11 | B |
| Embodiment 12 | A |
| Embodiment 13 | C |
| Embodiment 14 | A |
| Embodiment 15 | A |
| Embodiment 16 | A |
| Embodiment 17 | A |
| Embodiment 18 | A |
| Embodiment 19 | C |

TABLE 1-continued

Result of $EC_{50}$ by EC71_CPE test

| Test sample (Title compound) | EV71 |
|---|---|
| Embodiment 21 | A |
| Embodiment 22a | A |
| Embodiment 22b | D |
| Embodiment 23 | A |
| Embodiment 24 | D |
| Embodiment 25 | A |
| Embodiment 26 | C |
| Embodiment 27 | A |
| Embodiment 28 | A |
| Embodiment 29 | A |
| Embodiment 30 | A |
| Embodiment 31 | C |
| Embodiment 32 | A |
| Embodiment 33 | C |
| Embodiment 34 | D |
| Embodiment 35 | C |
| Embodiment 36 | A |
| Embodiment 37 | D |
| Embodiment 38 | A |
| Embodiment 39 | B |
| Embodiment 40 | A |
| Embodiment 41 | A |
| Embodiment 42 | C |
| Embodiment 43 | C |
| Embodiment 44 | B |
| Embodiment 45 | A |
| Embodiment 46 | C |
| Embodiment 47 | D |
| Embodiment 48 | C |
| Embodiment 49 | C |
| Embodiment 50 | A |
| Embodiment 51 | A |
| Embodiment 52 | A |
| Embodiment 53 | A |
| Embodiment 54 | D |
| Embodiment 55 | C |
| Embodiment 56 | B |
| Embodiment 57 | A |
| Embodiment 58 | A |
| Embodiment 59 | A |
| Embodiment 60 | A |
| Embodiment 61 | A |
| Embodiment 62 | C |
| Embodiment 63 | C |
| Embodiment 64 | A |
| Embodiment 65 | C |
| Embodiment 66 | B |
| Embodiment 67 | A |
| Embodiment 68 | D |
| Embodiment 69 | A |
| Embodiment 70 | C |
| Embodiment 71 | C |
| Embodiment 72 | B |
| Embodiment 73 | A |
| Embodiment 74 | A |
| Embodiment 75 | A |
| Embodiment 76 | A |

Note:
$A \leq 50$ nM; $50$ nM $< B \leq 100$ nM; $100$ nM $< C \leq 500$ nM; $500$ nM $< D \leq 1000$ nM.
Conclusion: the compounds according to the present invention have an obvious inhibitory effect to EV71 virus at a cell level.

The invention claimed is:

1. A compound(s) or its pharmaceutically-acceptable salt(s) as shown by Formula (II),

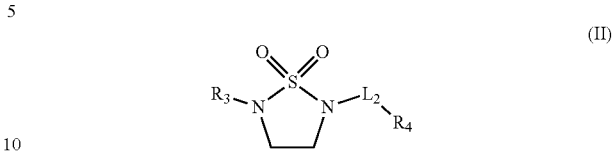

$R_3$ is selected from 5-membered aromatic heterocycles, $C_{6-12}$ aryl groups, and $C_{5-12}$ heteroaromatic rings, wherein $R_3$ is optionally substituted with from 1 to 3 $R_{01}$ groups;

$L_2$ is independently selected respectively from

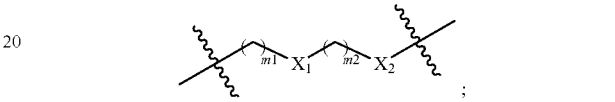

$m_1$ and $m_2$ are independently selected respectively from 1 or 2;

$X_1$ and $X_2$ are independently selected from —C($R_{d1}$)($R_{d2}$)—, —N($R_{d4}$)—, —C(=N$R_{d5}$)—, —O—, —S—, —C(=O)—, —C(=S)—, —S(=O)— or —S(=O)$_2$—;

$R_4$ is selected from 5-14-membered cycloalkyl, heterocycloalkyl, aryl, heteroaryl, bicyclic, or biaryl groups, wherein $R_4$ is substituted with $R_{01}$;

$R_{d1}$, $R_{d2}$, $R_{d4}$, and $R_{d5}$ are independently selected respectively from H, F, Cl, Br, I, CN, OH, SH, NH$_2$, CHO, and COOH;

$R_{01}$ is selected from H, F, Cl, Br, I, CN, OH, SH, NH2, CHO, COOH, $R_{02}$;

$R_{02}$ is selected from $C_{1-10}$ alkyl groups, $C_{1-10}$ alkylamino groups, N,N—($C_{1-10}$ alkyl) amino groups, $C_{1-10}$ alkoxy groups, $C_{1-10}$ alkanoyl groups, $C_{1-10}$ alkoxycarbonyl groups, $C_{1-10}$ alkylsulfonyl groups, $C_{1-10}$ alkylsulfinyl groups, $C_{3-10}$ cycloalkyl groups, $C_{3-10}$ cycloalkylamino groups, $C_{3-10}$ heterocyclic alkyl amino groups, $C_{3-10}$ cycloalkoxy groups, $C_{3-10}$ cycloalkyl acyl groups, $C_{3-10}$ cycloalkoxy-carbonyl groups, $C_{3-10}$ cycloalkylsulfonyl groups, $C_{3-10}$ cycloalkylsulfinyl groups, $C_3H_7$—O—N=, $CH_3ON$=, $C_2H_5ON$=, $C_2H_5ON$=CH—, $C_3H_5C$—O—N=CH—, and $C_3H_7$—O—N=CH—;

is optionally substituted by 1 to 3 $R_{001}$ groups;

$R_{001}$ is selected from F, Cl, Br, I, CN, OH, N(CH$_3$)$_2$, NH(CH$_3$), NH$_2$, CHO, COOH, trifluoromethyl group, aminomethyl group, hydroxymethyl group, methyl group, methoxy group, formyl group, methoxycarbonyl group, methylsulfonyl group and methylsulfinyl group;

optionally, $R_{d1}$ and $R_{d2}$ interconnect together to form a 3 or 4-membered carbocyclic or heterocyclic ring.

2. The compound(s) or its pharmaceutically-acceptable salt(s) according to claim 1, wherein Formula (II) is further defined as follows:

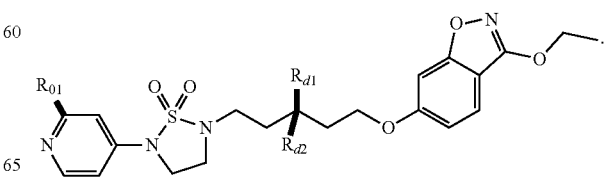

3. The compound(s) or its pharmaceutically-acceptable salt(s) according to claim 1, wherein Formula (II) is further defined as follows:

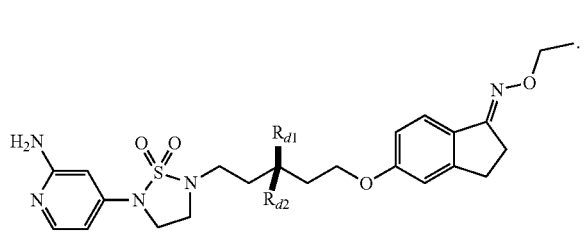

4. The compound(s) or its pharmaceutically-acceptable salt(s) according to claim 1, wherein Formula (II) is further defined as follows:

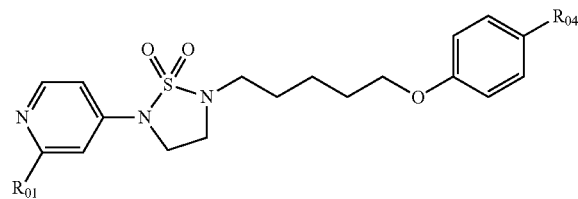

wherein $R_{01}$ is selected from —H, $CH_3$, $CH_3CONH$—, $NH_2$, $HOCH_2CH_2NH$—, and $CH_3NH$—;

$R_{04}$ is selected from $C_2H_5$=O—N=CH—, $C_3H_5CH_2$—O—N=CH—, and $C_3H_7$—O—N=CH—.

5. The compound(s) or its pharmaceutically-acceptable salt(s) according to claim 1, wherein Formula (II) is further defined as follows:

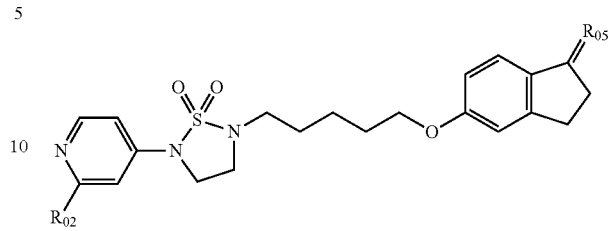

Wherein $R_{01}$ is selected from H, $NH_2$—, $HOCH_2CH_2NH$—, and $CH_3NH$—;

$R_{05}$ is selected from $C_3H_7$—O—N=, $CH_3$=O—N=, and $C_2H_5$—O—N=.

6. The compound(s) or its pharmaceutically-acceptable salt(s) according to claim 1, wherein Formula (II) is further defined as follows:

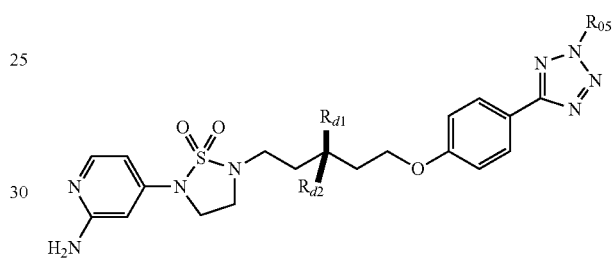

wherein $R_{05}$ is selected from $CH_3$, $C_2H_5$, and $C_3H_7$.

7. The compound(s) or its pharmaceutically-acceptable salt(s) according to claim 1, wherein Formula (II) is selected from the following

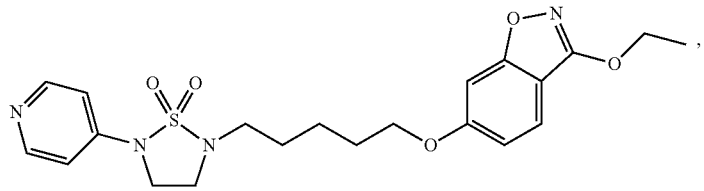

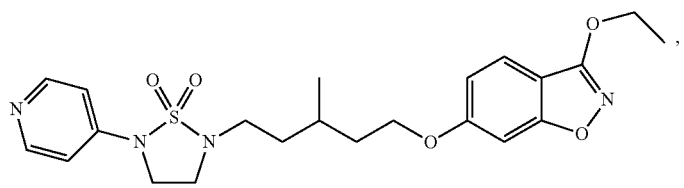

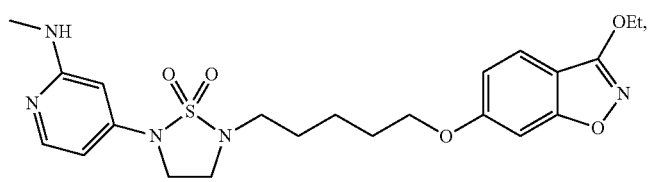

-continued
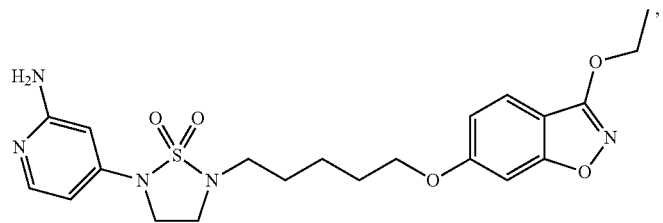
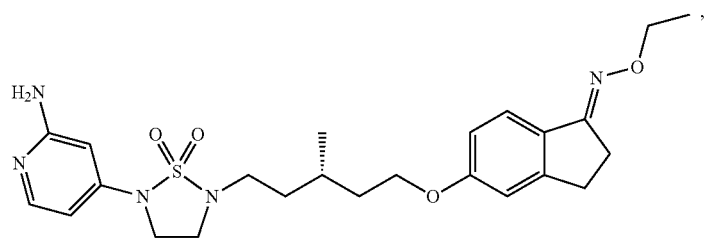
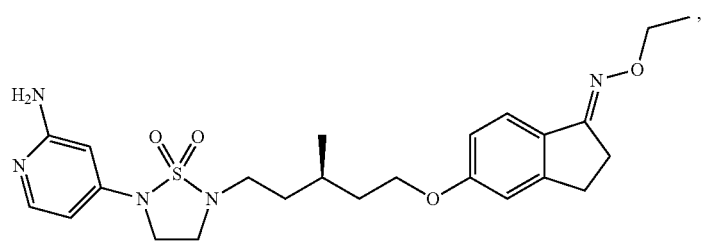
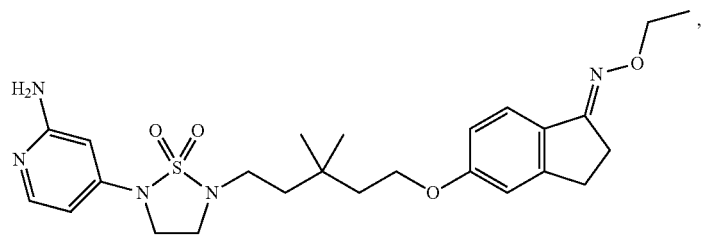
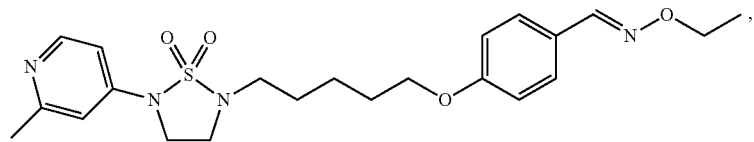
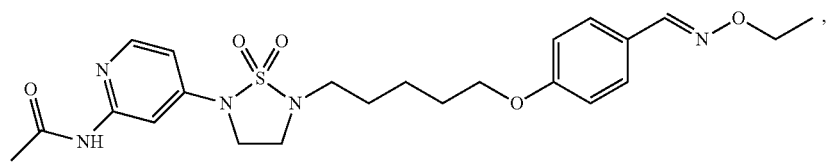
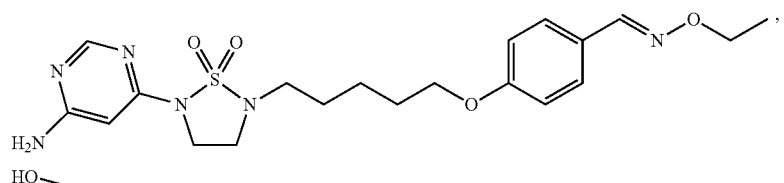
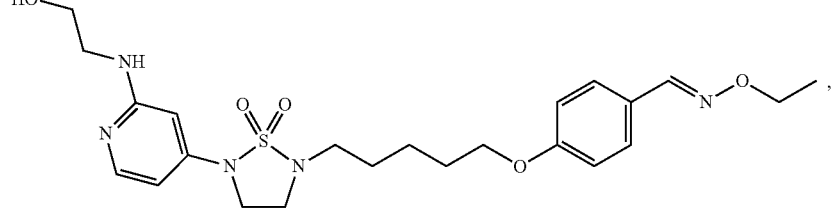

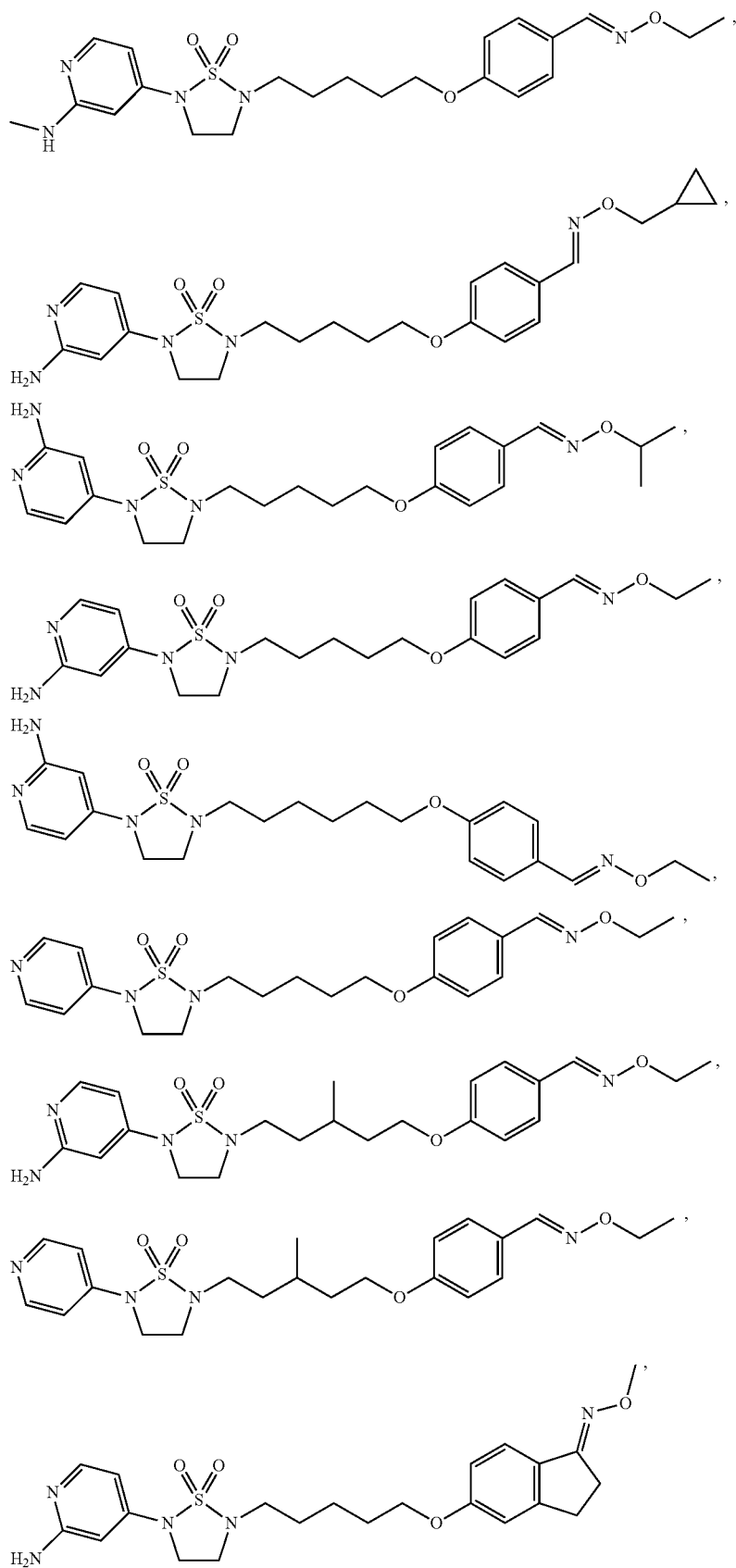

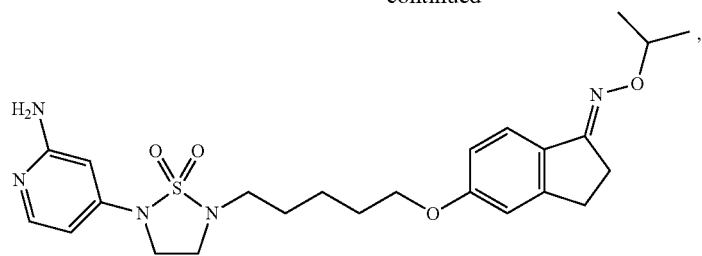
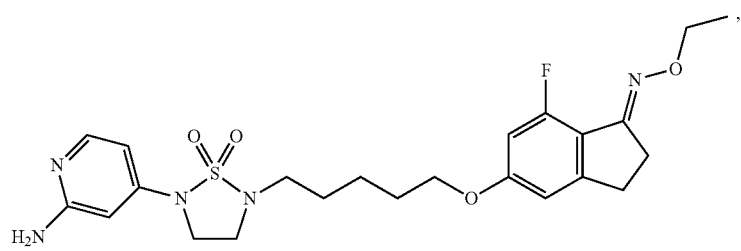
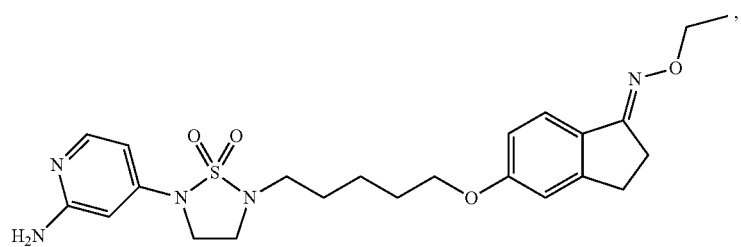
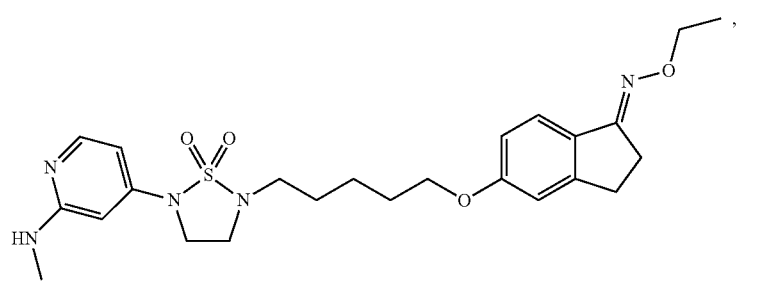
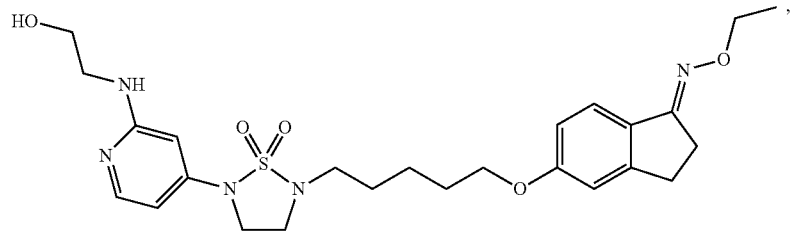
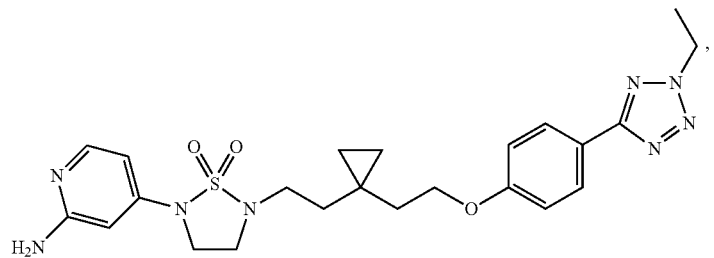

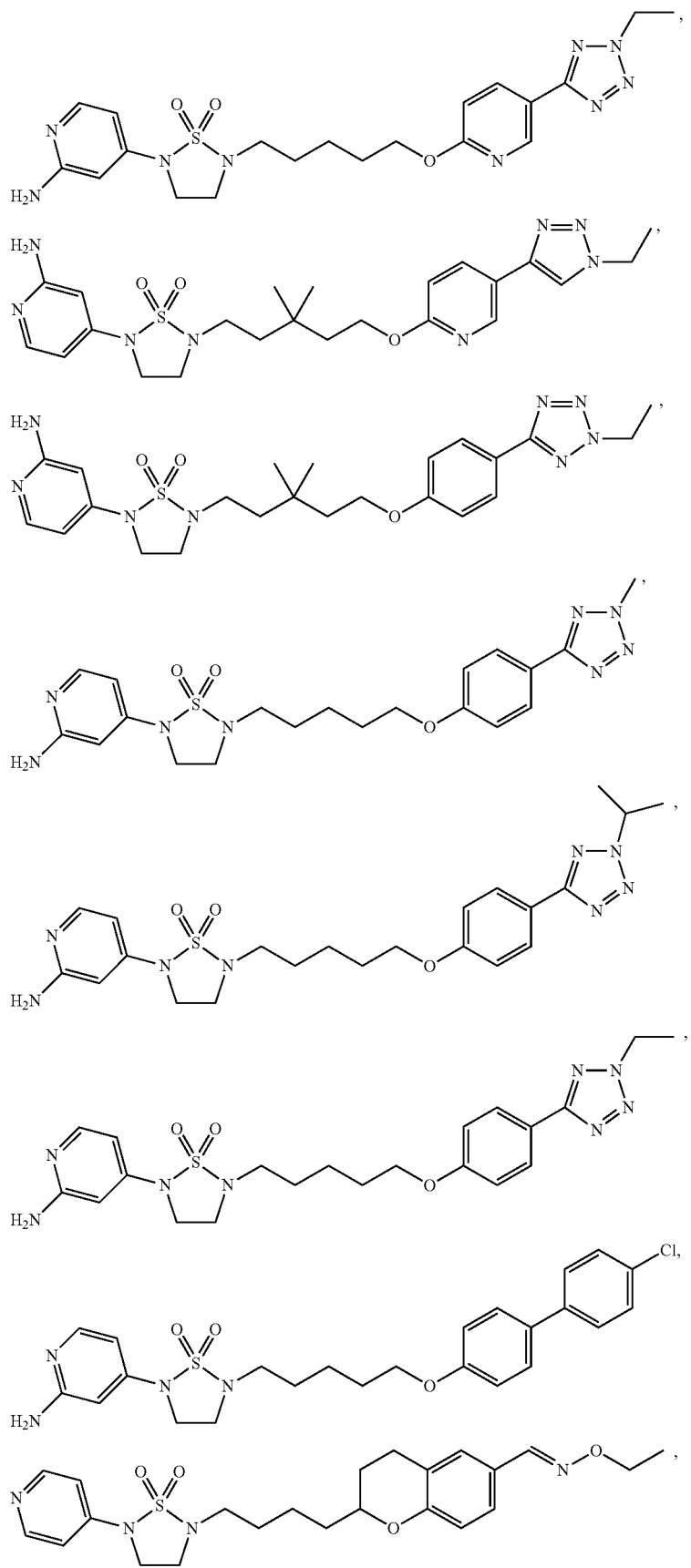

-continued
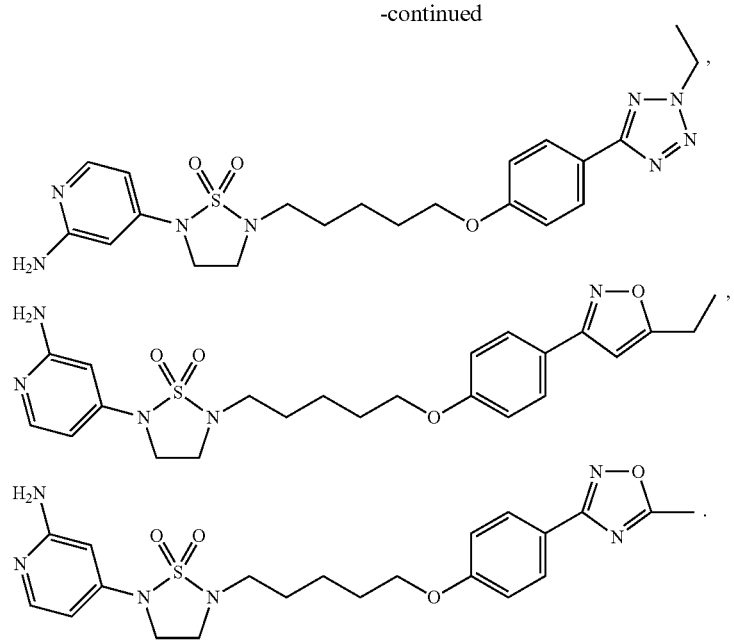
* * * * *